(12) United States Patent
Kuroda

(10) Patent No.: US 7,728,191 B2
(45) Date of Patent: Jun. 1, 2010

(54) NUCLEIC ACID FOR REDUCING PROTEIN CONTENT IN RICE SEED

(75) Inventor: Masaharu Kuroda, Niigata (JP)

(73) Assignee: Incorporated Administrative Agency National Agriculture and Bio-oriented Research Organization, Ibaraki (JP)

( * ) Notice: Subject to any disclaimer, the term of this patent is extended or adjusted under 35 U.S.C. 154(b) by 934 days.

(21) Appl. No.: 10/539,992

(22) PCT Filed: Dec. 9, 2003

(86) PCT No.: PCT/JP03/15753

§ 371 (c)(1),
(2), (4) Date: Apr. 12, 2006

(87) PCT Pub. No.: WO2004/056993

PCT Pub. Date: Jul. 8, 2004

(65) Prior Publication Data

US 2008/0096277 A1    Apr. 24, 2008

(30) Foreign Application Priority Data

Dec. 20, 2002    (JP) ................ 2002-369700

(51) Int. Cl.
*A01H 5/00*    (2006.01)
*C12N 15/82*    (2006.01)
*C07H 21/04*    (2006.01)

(52) U.S. Cl. ............ 800/285; 800/278; 800/288; 800/287; 800/295; 800/320.2; 536/24.5; 536/23.6; 435/468; 435/419; 435/320.1

(58) Field of Classification Search ............ None
See application file for complete search history.

(56) References Cited

U.S. PATENT DOCUMENTS 5,516,668 A * 5/1996 Maruta .............. 800/286
6,326,527 B1 * 12/2001 Kirihara et al. ........ 800/278

FOREIGN PATENT DOCUMENTS

| EP | 1 210 869 A1 | 6/2002 |
|---|---|---|
| WO | WO 93/18643 A1 | 9/1993 |
| WO | WO98/40489 A1 | 9/1998 |
| WO | WO 02/16604 A1 | 2/2002 |
| WO | WO03/078629 A1 | 9/2003 |

OTHER PUBLICATIONS

Mitsukawa et al. Amino acid sequencing and cDNA cloning of major rice seed storage proteins, the 13 kDa prolamins, extracted from PB-I protein bodies. (1999) GenBank Accession AB016505, pp. 1-2.*
Shewry et al., *The Plant Cell*, 7:945-956 (1995).
Mitsukawa et al., *Plant Biotechnology*, 16(2):103-113 (1999).
Database EMBL "*Oryza sativa* mRNA for prolamin, complete cds, clone:lambda RM9" retrieved from EBI Accession No. AB016505 (1999).
Database EMBL "*Oryza sativa* mRNA for prolamin, complete cds, strain:lambda RM1" retrieved from EBI Accession No. AB016503 (1999).
Huang, et al., *Plant Biology*, 2002: p. 106, Abstract #410, Annual Meeting of the American Society of Plant Biologists (2002).
Tada et al., *Breeding Science*, 53:61-67 (2003).
Goosens, A. et al., *FEBS Letters* 456:160-164, 1999.
Kim. W. and Okita, T., *FEB Letters*, 231(2):308-310, 1988.
Wesley, S. et al., *The Plant Journal* 27(6):581-590, 2001.
Maruta, Y. et al., *Molecular Breeding* 8:273-284, 2001.
Iida, S. et al., *Theor. Appl. Genet.* 94:177-183, 1997.
Smith, N.A. et al., "Total silencing by intron-spliced hairpin RNAs", 407:319-320 (2000).

* cited by examiner

*Primary Examiner*—Cathy Kingdon Worley
(74) *Attorney, Agent, or Firm*—King & Spalding LLP; Susan J. Myers Fitch; Peter J. Dehlinger

(57) ABSTRACT

It is intended to provide a method of reducing the total amount of stored protein, to develop a technique required therefor, and to provide a plant and its seeds developed by the above method and a method of using such a plant and seeds. More specifically, a nucleic acid molecule containing a consecutive nucleic acid sequence of at least 15 in length which is complementary with a nucleic acid sequence encoding prolamin polypeptide or a nucleic acid sequence having a homology of at least about 70% to the complementary nucleic acid sequence having at least 15 nucleotide length. A method of reducing the expression dose of a protein in a seed of a plant which comprises: A) the step of providing the above-described nucleic acid molecule; B) the step of transferring the nucleic acid molecule into the cells of the plant; C) the step of re-differentiating the cells to construct a transgenic plant; and D) the step of obtaining seeds from the transgenic plant.

64 Claims, 19 Drawing Sheets

Fig.3 Exemplary SDS-PAGE results of 13kDa prolamin reduced lineage (LP13K)

Fig.5

| | | | | | | |
|---|---|---|---|---|---|---|
| a) SDS-PAGE 13kDa prolamin | | | | | | |
| b) Western analysis using anti-13kDa prolamin antibody 13kDa prolamin | | | | | | |
| lane | 1 | 2 | 3 | 4 | 5 | 6 |
| variety | Nipponbare | Nihonmasari | LGC-1 | Nipponbare | Nipponbare | LGC-1 |
| antisense promoter | / | / | / | Seq. 47 | Seq. 47 | Seq. 47 |
| Sequence used for antisense | / | / | / | Seq. 1 | Seq. 51 | Seq. 1 |
| relative values of band concentration in Western analysis | 100 | 100 | 243 | 10 | 25 | 11 |

Fig.6a a-1) a variety having 13 KDa prolamin antisense gene
a-2) a standard variety (Nipponbare)
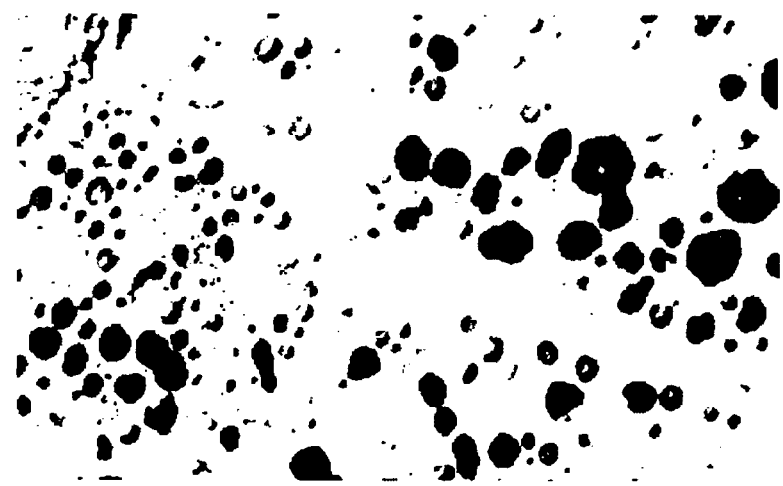
a-3) a variety having reduced glutelin and increased prolamin (LGC-1)
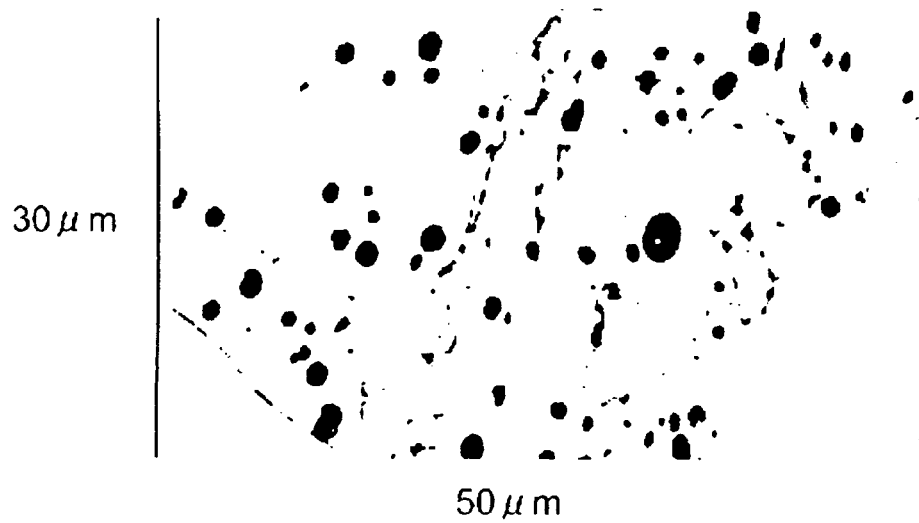
30 μm
50 μm Fig.6b  b-1) a variety having 13 KDa prolamin antisense gene
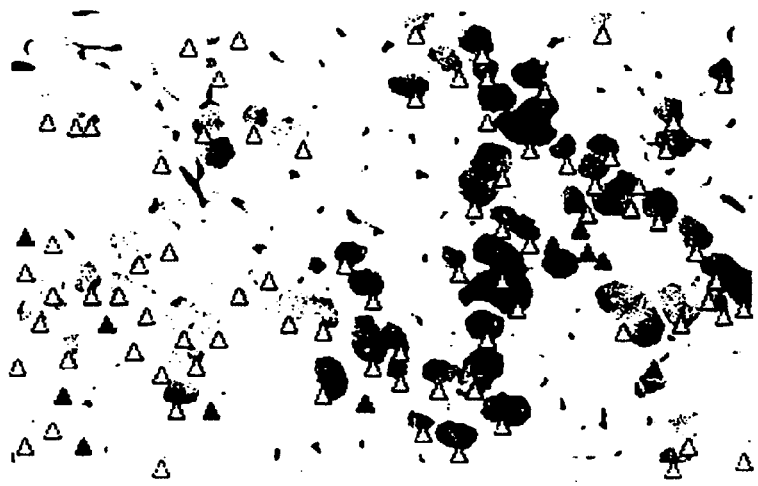
b-2) a standard variety (Nipponbare)
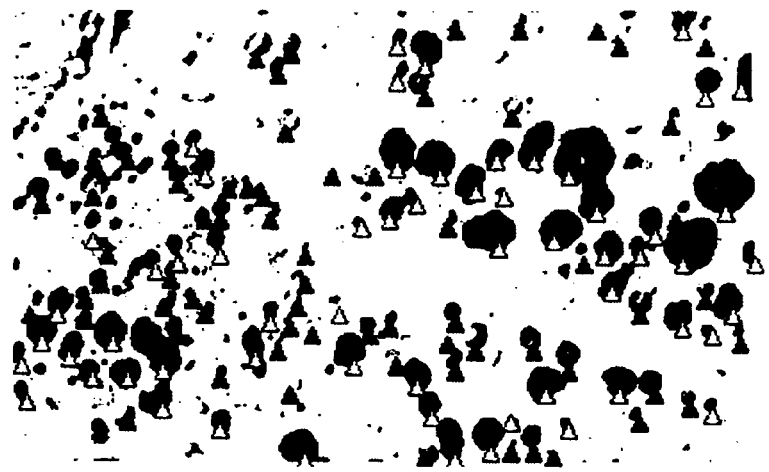
b-3) a variety having reduced glutelin and increased prolamin (LGC-1)
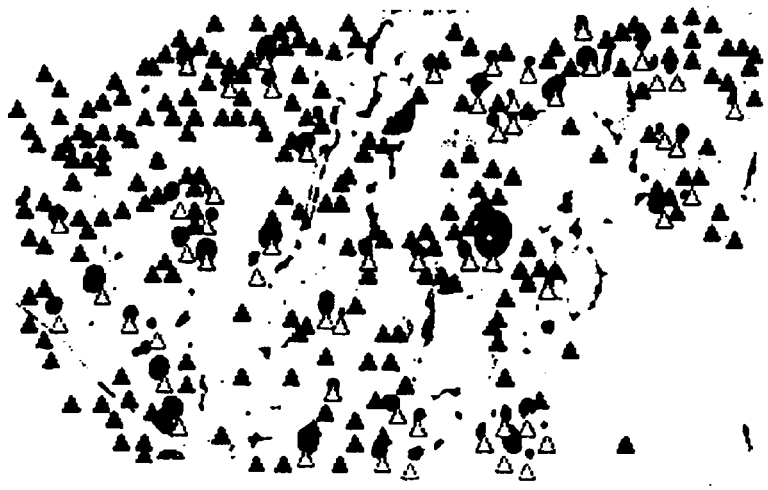

Fig. 9a

Comparative figure of 13K prolamin sequences

```
RM1.(SEQ ID.3)    1:---------------AG--GAAGCATAGTAGTAGAATCCTACAAAAATGAAGATCATTTT
RM4.(SEQ ID.94)   1:--G--CAAA-ATAGAA--AG-ATC-------TAGTGTCCCGCAGCAATGAAGATCATTTT
RM5.(SEQ ID.95)   1:CAATTCAAACATTATAGTTGAAGCATAGTAGTAGAATCCTACAAAAATGAAGATCATTTT
RM7.(SEQ ID.96)   1:--------------------GAAGCATAGTAGTAGAATCCAACAACAATGAAGATCATTTT
RM9.(SEQ ID.1)    1:--G--CAAA-AGCATA--AG-AAC-------TAGAAACCCACCACAATGAAGATCATTTT
                            * * *        *** ** *    ****************

RM1.(SEQ ID.3)   61:CGTATTTGCTCTCCTTGCTATTGTTGCATGCAA-CGCTTCTGCACGGTTTGATGCTCTTA
RM4.(SEQ ID.94)  61:CGTCTTTGCTCTCCTTGCTATTGCTGCATGCAG-CGCCTCTGCGCAGTTTGATGTTTTAG
RM5.(SEQ ID.95)  61:CGTATTTGCTCTCCTTGCTATTGTTGCATGCAA-CGCTTCTGCACGGTTTGATGCTCTTA
RM7.(SEQ ID.96)  61:CGTATTTGCTCTCCTTGCTATTGTTGCATGCAATCGC-TCTGCGCGGTTTGATCCTCTTA
RM9.(SEQ ID.1)   61:CTTCTTTGCTCTCCTTGCTATTGCTGCATGCAG-TGCCTCTGCGCAGTTTGATGCTGTTA
                    * * ******************* *******   ** ***** * ******  ** *

RM1.(SEQ ID.3)  121:GTCAAAGTTATAGACAATATCAACTACAATCGCATCTCCTGCTACAGCAACAAGTGCTCA
RM4.(SEQ ID.94) 121:GTCAAAGTTATAGGCAATATCAGCTGCAGTCGCCTGTCCTGCTACAGCAACAGGTGCTTA
RM5.(SEQ ID.95) 121:GTCAAAGTTATAGACAATATCAACTACAATCGCATCTCCTGCTACAGCAACAAGTGCTCA
RM7.(SEQ ID.96) 121:GTCAAAGTTATAGGCAATATCAACTACAGTCGCATCTCCTACTACAGCAACAAGTGCTCA
RM9.(SEQ ID.1)  121:CTCAAGTTTACAGGCAATATCAGCTGCAGCCGCATCTCATGCTGCAGCAACAGATGCTTA
                    ****  *** ** ********   **  **   *** * ** * **  ******  **** *

RM1.(SEQ ID.3)  181:GCCCATGCAGTGAGTTCGTAAGGCAACAGCATAGCATAGTGGCAACCCCCTTCTGGCAAC
RM4.(SEQ ID.94) 181:GCCCATATAATGAGTTCGTAAGGCAGCAGTATGGCATAGCGGCAAGCCCCTTCTTGCAAT
RM5.(SEQ ID.95) 181:GCCCATGCAGTGAGTTCGTAAGGCAACAGCATAGCATAGTGGCAACCCCCTTCTGGCAAC
RM7.(SEQ ID.96) 181:GCCCATGCAGTGAGTTCGTAAGGCAACAGTATAGCATAGTGGCAACCCCCTTCTGGCAAC
RM9.(SEQ ID.1)  181:GCCCATGCGGTGAGTTCGTAAGGCAGCAGTGCAGCACAGTGGCAACCCCCTTCTTCCAAT
                    ******   ************** *** ***  ***  ** *****  *******  ***

RM1.(SEQ ID.3)  241:CAGCTACGTTTCAATTGATAAACAACCAAGTCATGCAGCAACAGTGTTGCCAACAGCTCA
RM4.(SEQ ID.94) 241:CAGCTGCGTTTCAACTGAGAAACAACCAAGTC-TG--GCAACA--GCT--C-GC-GCT--
RM5.(SEQ ID.95) 241:CAGCTACGTTTCAATTGATAAACAACCAAGTCATGCAGCAACAGTGTTGCCAACAGCTCA
RM7.(SEQ ID.96) 241:CAGCTACGTTTCAATTCATAAACAACCAAGTCATGCAGCAGCAGTGTTGCCAACAGCTCA
RM9.(SEQ ID.1)  241:CACCCGTGTTTCAACTGAGAAACTGCCAAGTCATGCAGCAGCAGTGCTGCCAACAGCTCA
                    **  ******* *** **** ******** ****  ***     *   * *** *
```

Fig. 9b

```
RM1.(SEQ ID.3)   301:GGCTGGTAGCGCAACAATCTCACTACCAGGCCATTAGTAGCGTTCAGGCGATTGTGCAGC
RM4.(SEQ ID.94)  301:GG-TG---GCGCAACAATCTCACTATCAGGACATTAACATTGTTCAGGCCATAGCGCAGC
RM5.(SEQ ID.95)  301:GGCTGGTAGCGCAACAATCTCACTACCAGGCCATTAGTAGCGTTCAGGCGATTGTGCAGC
RM7.(SEQ ID.96)  301:GGCTGGTAGCACAACAATCTCACTACCAGGCCATTAGTATTGTTCAAGCGATTGTGCAAC
RM9.(SEQ ID.1)   301:GGATGATCGCACAACAGTCTCACTGCCAGGCCATTAGCAGTGTTCAGGCTATTGTGCAGC
                     ** **    ** ***** ****** **** *****  ***** ** **  *** *

RM1.(SEQ ID.3)   361:AACTACAGCTGCAGCAGGTCGGTGTT-GTCTACTTTGATCAGACTCAAGCTCAAGCTCAA
RM4.(SEQ ID.94)  361:AGCTACAACTCCAGCAGTTTGGTGATC-TCTACTTTGATCGGAATCTGGCTCAAGCTCAA
RM5.(SEQ ID.95)  361:AACTACAGCTGCAGCAGGTCGGTGTT-GTCTACTTTGATCAGACTCAAGCTCAAGCTCAA
RM7.(SEQ ID.96)  361:AGCTACAACTGCAGCAATTTAGTGGT-GTCTACTTTGATCAGACTCAAGCTCAAGCCCAA
RM9.(SEQ ID.1)   361:AGCTACGGCTACAACAGTTTGCT-AGCGTCTACTTCGATCAGAGTCAAGCTCAAGCCCAA
                     * ****  ** ** **  *   *      ******* **** ** ******** ***

RM1.(SEQ ID.3)   421:GCTTTGCTGGCCTTAAAACTTGCCATCCATATGTGGTATCTATCCTAACTACTACATTGCT
RM4.(SEQ ID.94)  421:GCTCTGTTGGCTTTTTAACGTGCCATCTAGATATGGTATCTACCCTAGGTACTATGGTGCA
RM5.(SEQ ID.95)  421:GCTTTGCTGGCCTTAAAACTTGCCATCCATATGTGGTATCTATCCTAACTACTACATTGCT
RM7.(SEQ ID.96)  421:ACTCTGTTGACCTTCAACTTGCCATCCATATGTGGTATCTACCCTAACTACTATAGTGCT
RM9.(SEQ ID.1)   421:GCTATGTTGGCCCTAAACATGCCGTCAATATGCGGTATCTACCCAAGCTACAACACTGCT
                     ** ** ** *  * *** **** ** * ** ******** ** * *** *   ***

Rm1.(SEQ ID.3)   481:CCGAGGAGCATTCCCACCGTTGGTGGTGTCTGGTACTGAATTGTAATAGTATAATGGTTC
Rm4.(SEQ ID.94)  481:CCCAGTACCATTACCACCCTTGGCGGTGTCTTGTAATGAGTTTTAACAGTATAGTGGTTC
RM5.(SEQ ID.95)  481:CCGAGGAGCATTCCCACCGTTGGTGGTGTCTGGTACTGAATTGTAATAGTATAATGGTTC
RM7.(SEQ ID.96)  481:CCCAGGAGCATTGCCACTGTTGGTGGTGTCTGGTACTGAATTGTAACAATATAATAGTTC
RM9.(SEQ ID.1)   481:CCCTGTAGCATTCCCACCGTCGGTGGTATCTGGTATTGAATTGTAGCAGTATAGTAGTAC
                     **   * **** **** ** * ** ***  ** *** ** *** ** ** *  ** *

RM1.(SEQ ID.3)   541:AAATGTTAAAAATAAAGTCATGCATCATCATGCGTGAC-AGTTGAAACTTGATGTC-ATA
RM4.(SEQ ID.94)  541:GGAAGTTAAAAATAAGCTCAGATATCAT-ATATGTGACATG-TGAAACTT-TGGGTGATA
RM5.(SEQ ID.95)  541:AAATGTTAAAAATAAAGTCATGCATCATCATGCGTGAC-AGTTGAAA-AAAAAAA--AAA
RM7.(SEQ ID.96)  541:GTATGTTAAAAATAAAGTCATACATCATCATGTGTGAC-TGTTGAAACTTAGGGTC-ATA
RM9.(SEQ ID.1)   541:AGGAGAGAAAAATAAAGTCATGCATCATCGTGTGTGACAAGTTGAAACATCGGGGTGATA
                      * ********  ***  *****  ***** * *****  *****

RM1.(SEQ ID.3)   601:TAAATCTAAAT-AAA-C-TCGTGC-C--------
RM4.(SEQ ID.94)  601:TAAATAGAAAAAAAGTTGTCTTTCATATTTA---
RM5.(SEQ ID.95)  601:AAA-----------------------------
RM7.(SEQ ID.96)  601:TAAATCTAAATAAAATCATCTTAC-CTAAAAAA-
RM9.(SEQ ID.1)   601:CAAATCTGAATAAAAATGTCATGCAAGTTTAAAC
                     **
```

Fig.10

| | 10-1 | 10-2 | 10-3 | 10-4 | 10-6 | 10-6 |
|---|---|---|---|---|---|---|
| Introduction of prolamin expression suppression gene | − + | − + | − + | − + | − + | − + |
| variety | Nipponbare | Nipponbare | Nipponbare | Koshihikari | Dontokoi | Basmati |
| 13kDa prolamin (relative amount) | 100 : 32 | 100 : 50 | 100 : 38 | 100 : 50 | 100 : 35 | 100 : 42 |
| promoter used for expression suppression | Seq.58 | Seq.58 | Seq.58 | Seq.47 | Seq.47 | Seq.47 |
| Sequences suppression and vector types used for expression | RNAi type 45bp(Seq.65) | RNAi type 23bp(Seq.72) | RNAi type (Seq.31) | Seq.1 | Seq.1 | Seq.1 |

Bands corresponding to 13 kDa prolamin, indicated by boxes

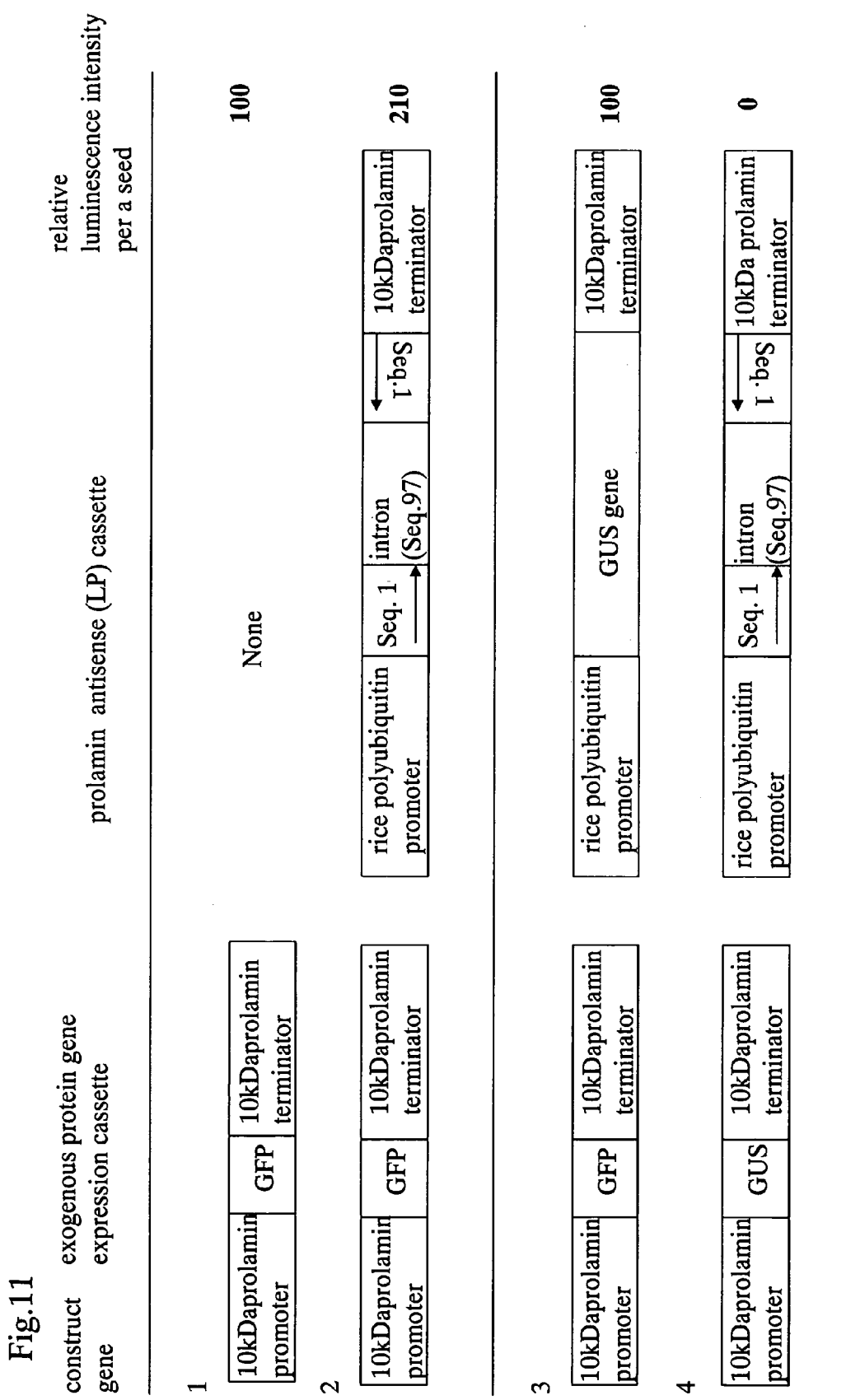

Fig. 14A (SEQ ID.108)
ATGGCAGCATACACCAGCAAGAGATCTTTGCCCTGTTTGCCTTAATTGCTCTCTTTCTGCAAGTGCCACTACTGCA
MetAlaAlaTyrThrSerLysIlePheAlaLeuPheAlaLeuIleAlaLeuSerAlaSerAlaThrThrAla (SEQ ID.119)
ATGGCAGCATACACCAGCAAGAGATCTTTGCCCTGTTTGCCTTAATTGCTCTCTTTCTGCAAGTGCCACTACTGCATCTAGAGCAATGGTGAGCAAGGGCGAGGAG
MetAlaAlaTyrThrSerLysIlePheAlaLeuPheAlaLeuIleAlaLeuSerAlaSerAlaThrThrAlaSerArgAlaMetValSerLysGlyGluGlu 10 kDa prolamin signal sequence    ligation sequence site (restriction enzyme site)    GFP protein

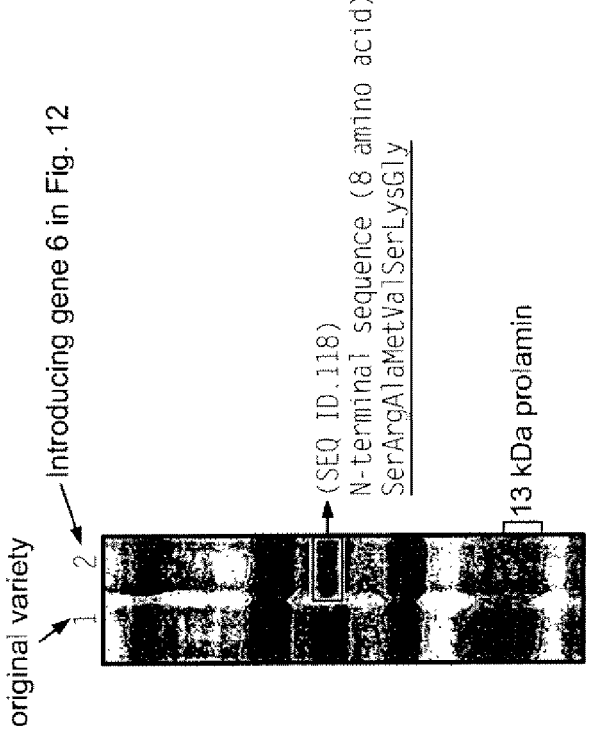

Fig. 14B original variety → introducing gene 6 in Fig. 12

(SEQ ID.118)
N-terminal sequence (8 amino acid)
SerArgAlaMetValSerLysGly 13 kDa prolamin

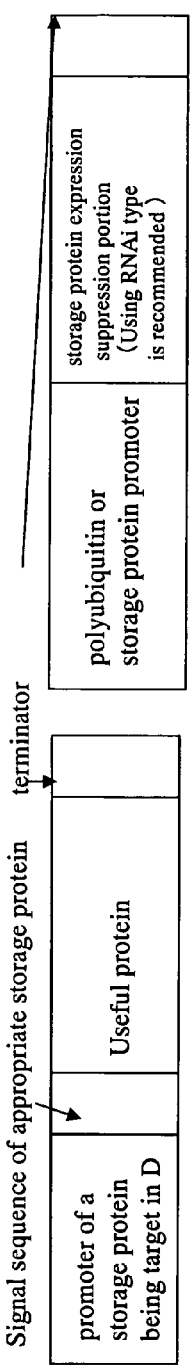
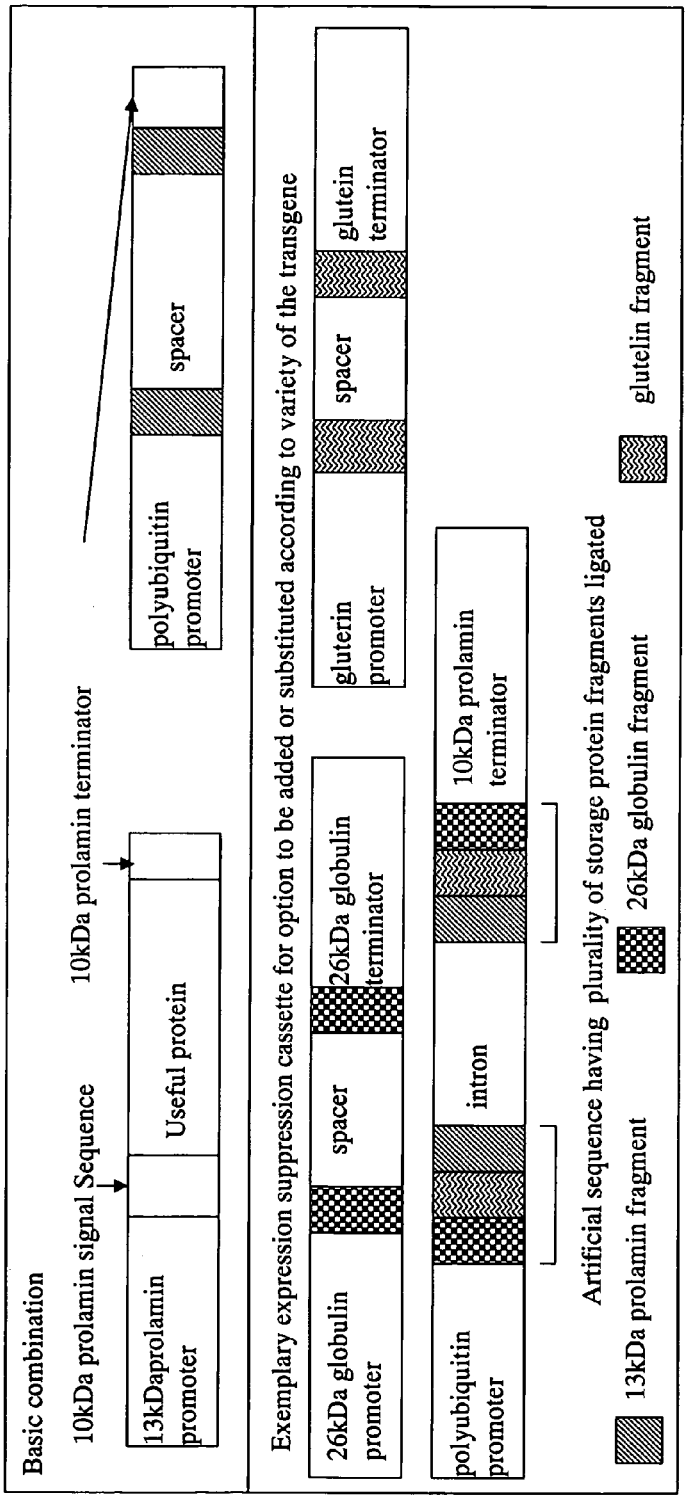
Fig 17 Exemplary structure of expected optimal transgene in using a seed as a bioreactor
Ideally, two or more cassettes are on a fundamental vector

SEQUENCE LISTING

```
<160> NUMBER OF SEQ ID NOS: 119

<210> SEQ ID NO 1
<211> LENGTH: 617
<212> TYPE: DNA
<213> ORGANISM: Oryza sativa
```

<220> FEATURE:
<223> OTHER INFORMATION: 13kD prolamin RM9

<400> SEQUENCE: 1

| | | | | | |
|---|---|---|---|---|---|
| gcaaaagcat | aagaactaga | aacccaccac | aatgaagatc | attttcttct | ttgctctcct | 60 |
| tgctattgct | gcatgcagtg | cctctgcgca | gtttgatgct | gttactcaag | tttacaggca | 120 |
| atatcagctg | cagccgcatc | tcatgctgca | gcaacagatg | cttagcccat | gcggtgagtt | 180 |
| cgtaaggcag | cagtgcagca | cagtggcaac | ccccttcttc | caatcacccg | tgtttcaact | 240 |
| gagaaactgc | caagtcatgc | agcagcagtg | ctgccaacag | ctcaggatga | tcgcacaaca | 300 |
| gtctcactgc | caggccatta | gcagtgttca | ggctattgtg | cagcagctac | ggctacaaca | 360 |
| gtttgctagc | gtctacttcg | atcagagtca | agctcaagcc | caagctatgt | tggccctaaa | 420 |
| catgccgtca | atatgcggta | tctacccaag | ctacaacact | gctccctgta | gcattcccac | 480 |
| cgtcggtggt | atctggtatt | gaattgtagc | agtatagtag | tacaggagag | aaaaataaag | 540 |
| tcatgcatca | tcgtgtgtga | caagttgaaa | catcggggtg | atacaaatct | gaataaaaat | 600 |
| gtcatgcaag | tttaaac | | | | | 617 |

<210> SEQ ID NO 2
<211> LENGTH: 156
<212> TYPE: PRT
<213> ORGANISM: Oryza sativa
<220> FEATURE:
<223> OTHER INFORMATION: 13kD prolamin RM9

<400> SEQUENCE: 2

```
Met Lys Ile Ile Phe Phe Phe Ala Leu Leu Ala Ile Ala Ala Cys Ser
1               5                   10                  15

Ala Ser Ala Gln Phe Asp Ala Val Thr Gln Val Tyr Arg Gln Tyr Gln
            20                  25                  30

Leu Gln Pro His Leu Met Leu Gln Gln Gln Met Leu Ser Pro Cys Gly
        35                  40                  45

Glu Phe Val Arg Gln Gln Cys Ser Thr Val Ala Thr Pro Phe Phe Gln
    50                  55                  60

Ser Pro Val Phe Gln Leu Arg Asn Cys Gln Val Met Gln Gln Gln Cys
65                  70                  75                  80

Cys Gln Gln Leu Arg Met Ile Ala Gln Gln Ser His Cys Gln Ala Ile
                85                  90                  95

Ser Ser Val Gln Ala Ile Val Gln Gln Leu Arg Leu Gln Gln Phe Ala
            100                 105                 110

Ser Val Tyr Phe Asp Gln Ser Gln Ala Gln Ala Gln Ala Met Leu Ala
        115                 120                 125

Leu Asn Met Pro Ser Ile Cys Gly Ile Tyr Pro Ser Tyr Asn Thr Ala
    130                 135                 140

Pro Cys Ser Ile Pro Thr Val Gly Gly Ile Trp Tyr
145                 150                 155
```

<210> SEQ ID NO 3
<211> LENGTH: 601
<212> TYPE: DNA
<213> ORGANISM: Oryza sativa
<220> FEATURE:
<223> OTHER INFORMATION: 13kD prolamin RM1

-continued

<400> SEQUENCE: 3

```
aggaagcata gtagtagaat cctacaaaaa tgaagatcat tttcgtattt gctctccttg    60
ctattgttgc atgcaacgct tctgcacggt tgatgctct tagtcaaagt tatagacaat   120
atcaactaca atcgcatctc ctgctacagc aacaagtgct cagcccatgc agtgagttcg   180
taaggcaaca gcatagcata gtggcaaccc ccttctggca accagctacg tttcaattga   240
taaacaacca agtcatgcag caacagtgtt gccaacagct caggctggta gcgcaacaat   300
ctcactacca ggccattagt agcgttcagg cgattgtgca gcaactacag ctgcagcagg   360
tcggtgttgt ctactttgat cagactcaag ctcaagctca agctttgctg gccttaaact   420
tgccatccat atgtggtatc tatcctaact actacattgc tccgaggagc attcccaccg   480
ttggtggtgt ctggtactga attgtaatag tataatggtt caaatgttaa aaataaagtc   540
atgcatcatc atgcgtgaca gttgaaactt gatgtcatat aaatctaaat aaactcgtgc   600
c                                                                   601
```

<210> SEQ ID NO 4
<211> LENGTH: 156
<212> TYPE: PRT
<213> ORGANISM: Oryza sativa
<220> FEATURE:
<223> OTHER INFORMATION: 13kD prolamin RM1

<400> SEQUENCE: 4

```
Met Lys Ile Ile Phe Val Phe Ala Leu Leu Ala Ile Val Ala Cys Asn
1               5                   10                  15

Ala Ser Ala Arg Phe Asp Ala Leu Ser Gln Ser Tyr Arg Gln Tyr Gln
            20                  25                  30

Leu Gln Ser His Leu Leu Gln Gln Gln Val Leu Ser Pro Cys Ser
        35                  40                  45

Glu Phe Val Arg Gln Gln His Ser Ile Val Ala Thr Pro Phe Trp Gln
    50                  55                  60

Pro Ala Thr Phe Gln Leu Ile Asn Asn Gln Val Met Gln Gln Gln Cys
65                  70                  75                  80

Cys Gln Gln Leu Arg Leu Val Ala Gln Gln Ser His Tyr Gln Ala Ile
                85                  90                  95

Ser Ser Val Gln Ala Ile Val Gln Gln Leu Gln Leu Gln Gln Val Gly
            100                 105                 110

Val Val Tyr Phe Asp Gln Thr Gln Ala Gln Ala Gln Ala Leu Leu Ala
        115                 120                 125

Leu Asn Leu Pro Ser Ile Cys Gly Ile Tyr Pro Asn Tyr Tyr Ile Ala
    130                 135                 140

Pro Arg Ser Ile Pro Thr Val Gly Gly Val Trp Tyr
145                 150                 155
```

<210> SEQ ID NO 5
<211> LENGTH: 766
<212> TYPE: DNA
<213> ORGANISM: Oryza sativa
<220> FEATURE:
<223> OTHER INFORMATION: 13kD prolamin

<400> SEQUENCE: 5

```
ttgcttcttc ccgtcctccc cgcttgggct cttgggcgcc cgttccgggc gccccctccc    60
tcctccctcc gcggtacccg gccgcctcac tcctctgctg accccccggc cgccccgggc   120
cgcgccccat cccggtgcgc gacccatcgt tcacacagtt caagcattat acagaaaaat   180
```

```
agaaagatct agtgtcccgc agcaatgaag atcattttcg tctttgctct ccttgctatt      240
gctgcatgca ggcctctgcc gagtttgatg tttttaggtc aaagttatag gcaatatcag      300
ctgcagtcgc ctgtcctgct acagcaacag gtgcttagcc catataatga gttcgtaagg      360
cagcagtatg gcatagcggc aagccccttc ttgcaatcag ctgcatttca actgagaaat      420
aaccaagtct ggcaacatca ggctggtggc aacaatctc gctatcagga cattaacatt      480
gttcaggcca tagcgtacga gctacaactc agcaatttg tgatctcta cttgatcgg        540 aatcaggctc aagctcaagc tctattggct tttaacgtgc catctagata tggtatctac      600
cctaggtact atggtgcacc cagtaccatt accaccttg gcggtgtctt gtaatgtgtt       660
ttaacagtat agtggttcgg aagttaaaaa taagctcaga tatcatcata tgtgacatgt      720
gaaactttgg gtgatataaa tagaaataaa gttgcctttc atattt                    766
```

```
<210> SEQ ID NO 6
<211> LENGTH: 149
<212> TYPE: PRT
<213> ORGANISM: Oryza sativa
<220> FEATURE:
<223> OTHER INFORMATION: 13kD prolamin

<400> SEQUENCE: 6

Met Lys Ile Ile Phe Val Phe Ala Leu Leu Ala Ile Ala Ala Cys Arg
1               5                   10                  15

Pro Leu Pro Ser Leu Met Phe Leu Gly Gln Ser Tyr Arg Gln Tyr Gln
                20                  25                  30

Leu Gln Ser Pro Val Leu Leu Gln Gln Gln Val Leu Ser Pro Tyr Asn
            35                  40                  45

Glu Phe Val Arg Gln Gln Tyr Gly Ile Ala Ala Ser Pro Phe Leu Gln
        50                  55                  60

Ser Ala Ala Phe Gln Leu Arg Asn Asn Gln Val Trp Gln His Gln Ala
65                  70                  75                  80

Gly Gly Gln Gln Ser Arg Tyr Gln Asp Ile Asn Ile Val Gln Ala Ile
                85                  90                  95

Ala Tyr Glu Leu Gln Leu Gln Gln Phe Gly Asp Leu Tyr Phe Asp Arg
            100                 105                 110

Asn Gln Ala Gln Ala Gln Ala Leu Leu Ala Phe Asn Val Pro Ser Arg
        115                 120                 125

Tyr Gly Ile Tyr Pro Arg Tyr Tyr Gly Ala Pro Ser Thr Ile Thr Thr
    130                 135                 140

Leu Gly Gly Val Leu
145
```

```
<210> SEQ ID NO 7
<211> LENGTH: 717
<212> TYPE: DNA
<213> ORGANISM: Oryza sativa
<220> FEATURE:
<223> OTHER INFORMATION: 13kD prolamin

<400> SEQUENCE: 7
gttccgggcg cccccctccc tcctccctcc gcggtacccg gccgcctcac tcctctgctg       60 gaccccggc cgcccggcc gcgcccccat cccggtgcgc gccccatcgt tcacacagtt       120
caagtattat acagaaaaat agaaagatct agtgtcccgc agcaatgaag atcattttcg      180
tctttgctct ccttgctatt gctgcatgca gcgcctctgc gcagtttgat gtttaggac       240 aaagttatag gcaatatcag ctgcagtcgc ctgtcctgct acagcaacag gtgcttagcc      300
```

| | |
|---|---|
| catataatga gttcgtaagg cagcagtatg gcatagcggc aagcccttc ttgcaatcag | 360 |
| ctgcatttca actgagaaac aaccaagtct ggcaacagct cgcgctggtg gcgcaacaat | 420 |
| ctcactatca ggacattaac attgttcagg ccatagcgca gcagctacaa ctccagcagt | 480 |
| ttggtgatct ctactttgat cggaatctgg ctcaagctca gttggctttt aacgtgccat | 540 |
| ctagatatgg tatctaccct aggtactatg gtgcacccag taccattacc acccttggcg | 600 |
| gtgtcttgta atgtgtttta acaaggtata gtggttcgga agttaaaaat aagctcagat | 660 |
| atcatcatat gtgacatgtg aaactttggg tgatataaat agaaataaag ttgtctt | 717 |

<210> SEQ ID NO 8
<211> LENGTH: 148
<212> TYPE: PRT
<213> ORGANISM: Oryza sativa
<220> FEATURE:
<223> OTHER INFORMATION: 13kD prolamin

<400> SEQUENCE: 8

Met Lys Ile Ile Phe Val Phe Ala Leu Leu Ala Ile Ala Ala Cys Ser
1               5                   10                  15

Ala Ser Ala Gln Phe Asp Val Leu Gly Gln Ser Tyr Arg Gln Tyr Gln
            20                  25                  30

Leu Gln Ser Pro Val Leu Leu Gln Gln Gln Val Leu Ser Pro Tyr Asn
        35                  40                  45

Glu Phe Val Arg Gln Gln Tyr Gly Ile Ala Ala Ser Pro Phe Leu Gln
    50                  55                  60

Ser Ala Ala Phe Gln Leu Arg Asn Asn Gln Val Trp Gln Gln Leu Ala
65                  70                  75                  80

Leu Val Ala Gln Gln Ser His Tyr Gln Asp Ile Asn Ile Val Gln Ala
                85                  90                  95

Ile Ala Gln Gln Leu Gln Leu Gln Gln Phe Gly Asp Leu Tyr Phe Asp
            100                 105                 110

Arg Asn Leu Ala Gln Ala Gln Leu Ala Phe Asn Val Pro Ser Arg Tyr
        115                 120                 125

Gly Ile Tyr Pro Arg Tyr Tyr Gly Ala Pro Ser Thr Ile Thr Thr Leu
    130                 135                 140

Gly Gly Val Leu
145

<210> SEQ ID NO 9
<211> LENGTH: 650
<212> TYPE: DNA
<213> ORGANISM: Oryza sativa
<220> FEATURE:
<223> OTHER INFORMATION: 13kD prolamin

<400> SEQUENCE: 9

| | |
|---|---|
| cttccccgtc gggcccggcc ccggccctcg cctatccgcc tcctccccc gcgcccttca | 60 |
| ccactcccaa cccagctccc tttctccacc taccggcccc atccttctca caactcaaac | 120 |
| attacagcga aagcataaca actagaatcc taccacaatg aagatcattt tcttctttgc | 180 |
| tctccttgct gaagctgcat gtagcgcctc tgcgcagttt gatgctgtta ctcaagttta | 240 |
| caggcaatat cagctgcagc aacagatgct tagcccatgc ggtgagttcg taaggcagca | 300 |
| gtgcagcaca gtggcaaccc ccttcttcca atcacccgtg tttcaactga gaaactgcca | 360 |
| agtcatgcag cagcagtgct gccaacagct caggatgatc gcgcaacagt ctcactgcca | 420 |
| ggccattagc agtgttcagg cgattgtgca gcagctacag ctacaacagt tttctggcgt | 480 |

```
ctacttcgat caggctcaag ctcaagccca agctatgttg ggcctaaaact tgccgtcaat    540 atgcggtatc tacccaagct acaacactgt ccctgagatt cctaccgtcg gtggtatctg    600
gtactgattg acgagataga gacagggaaa taagcatgat catcggggct               650

<210> SEQ ID NO 10
<211> LENGTH: 149
<212> TYPE: PRT
<213> ORGANISM: Oryza sativa
<220> FEATURE:
<223> OTHER INFORMATION: 13kD prolamin

<400> SEQUENCE: 10

Met Lys Ile Ile Phe Phe Phe Ala Leu Leu Ala Glu Ala Ala Cys Ser
1               5                   10                  15

Ala Ser Ala Gln Phe Asp Ala Val Thr Gln Val Tyr Arg Gln Tyr Gln
                20                  25                  30

Leu Gln Gln Gln Met Leu Ser Pro Cys Gly Glu Phe Val Arg Gln Gln
            35                  40                  45

Cys Ser Thr Val Ala Thr Pro Phe Phe Gln Ser Pro Val Phe Gln Leu
    50                  55                  60

Arg Asn Cys Gln Val Met Gln Gln Gln Cys Cys Gln Gln Leu Arg Met
65                  70                  75                  80

Ile Ala Gln Gln Ser His Cys Gln Ala Ile Ser Ser Val Gln Ala Ile
                85                  90                  95

Val Gln Gln Leu Gln Leu Gln Gln Phe Ser Gly Val Tyr Phe Asp Gln
            100                 105                 110

Ala Gln Ala Gln Ala Gln Ala Met Leu Gly Leu Asn Leu Pro Ser Ile
        115                 120                 125

Cys Gly Ile Tyr Pro Ser Tyr Asn Thr Val Pro Glu Ile Pro Thr Val
    130                 135                 140

Gly Gly Ile Trp Tyr
145

<210> SEQ ID NO 11
<211> LENGTH: 629
<212> TYPE: DNA
<213> ORGANISM: Oryza sativa
<220> FEATURE:
<223> OTHER INFORMATION: 13kD prolamin

<400> SEQUENCE: 11
cgttgaagca tagtagtaga atcctacaaa aatgaagatc attttcgtat ttgctctcct     60
tgctattgtt gcatgcaacg cttctgcacg gtttgatgct cttagtcaaa gttatagaca    120
atatcaacta caatcgcatc tccagctaca gcaacaagtg ctcagcccat gcagtgagtt    180
cgtaaggcaa cagcatagca tagtggcaac ccccttctgg caaccagcta cgtttcaatt    240
gataaacaac caagtcatgc agcaacagtg ttgccaacag ctcaggctgg tagcgcaaca    300
atctcactac caggccatta gtagcgttca ggcgattgtg cagcaactac agctgcagca    360
ggtcggtgtt gtctactttg atcagactca agctcaagct caagctttgc tggccttaaa    420
cttgccatcc atatgtggta tctatcctaa ctactacatt gctccgagga gcattcccac    480
cgttggtgtg tctggtactg aattgtaata gtataatggt tcaaatgtta aaaataaagt    540
catgcatcat catgcgtgac agttgaaact tgatgtcata taaatctaaa taaaatcacc    600
tatttaaata gcaaaaaaaa aaaaaaaaa                                      629
```

<210> SEQ ID NO 12
<211> LENGTH: 158
<212> TYPE: PRT
<213> ORGANISM: Oryza sativa
<220> FEATURE:
<223> OTHER INFORMATION: 13kD prolamin

<400> SEQUENCE: 12

```
Met Lys Ile Ile Phe Val Phe Ala Leu Leu Ala Ile Val Ala Cys Asn
1               5                   10                  15

Ala Ser Ala Arg Phe Asp Ala Leu Ser Gln Ser Tyr Arg Gln Tyr Gln
            20                  25                  30

Leu Gln Ser His Leu Gln Leu Gln Gln Val Leu Ser Pro Cys Ser
        35                  40                  45

Glu Phe Val Arg Gln Gln His Ser Ile Val Ala Thr Pro Phe Trp Gln
    50                  55                  60

Pro Ala Thr Phe Gln Leu Ile Asn Asn Gln Val Met Gln Gln Cys
65                  70                  75                  80

Cys Gln Gln Leu Arg Leu Val Ala Gln Ser His Tyr Gln Ala Ile
                85                  90                  95

Ser Ser Val Gln Ala Ile Val Gln Gln Leu Gln Leu Gln Val Gly
                100                 105                 110

Val Val Tyr Phe Asp Gln Thr Gln Ala Gln Ala Gln Ala Leu Leu Ala
            115                 120                 125

Leu Asn Leu Pro Ser Ile Cys Gly Ile Tyr Pro Asn Tyr Tyr Ile Ala
        130                 135                 140

Pro Arg Ser Ile Pro Thr Val Gly Val Ser Gly Thr Glu Leu
145                 150                 155
```

<210> SEQ ID NO 13
<211> LENGTH: 603
<212> TYPE: DNA
<213> ORGANISM: Oryza sativa
<220> FEATURE:
<223> OTHER INFORMATION: 13kD prolamin

<400> SEQUENCE: 13

```
gaagcatagt agtagaatcc aacaacaatg aagatcattt tcgtatttgc tctccttgct     60
attgttgcat gcaatcgctc tgcgcggttt gatcctctta gtcaaagtta taggcaatat    120
caactacagt cgcatctcct actacagcaa caagtgctca gcccatgcag tgagttcgta    180
aggcaacagt atagcatagt ggcaaccccc ttctggcaac cagctacgtt tcaattgata    240
aacaaccaag tcatgcagca gcagtgttgc aacagctca ggctggtagc acaacaatct    300
cactaccagg ccattagtat tgttcaagcg attgtgcaac agctacaact gcagcaattt    360
agtggtgtct actttgatca gactcaagct caagcccaaa ctctgttgac cttcaacttg    420
ccatccatat gtggtatcta ccctaactac tatagtgctc ccaggagcat tgccactgtt    480
ggtggtgtct ggtactgaat tgtaacaata taatagttcg tatgttaaaa ataaagtcat    540
acatcatcat gtgtgactgt tgaaacttag ggtcatataa atctaaataa aatcatctta    600
cct                                                                  603
```

<210> SEQ ID NO 14
<211> LENGTH: 156
<212> TYPE: PRT
<213> ORGANISM: Oryza sativa
<220> FEATURE:
<223> OTHER INFORMATION: 13kD prolamin

<400> SEQUENCE: 14

Met Lys Ile Ile Phe Val Phe Ala Leu Leu Ala Ile Val Ala Cys Asn
1               5                   10                  15

Arg Ser Ala Arg Phe Asp Pro Leu Ser Gln Ser Tyr Arg Gln Tyr Gln
            20                  25                  30

Leu Gln Ser His Leu Leu Gln Gln Gln Val Leu Ser Pro Cys Ser
        35                  40                  45

Glu Phe Val Arg Gln Gln Tyr Ser Ile Val Ala Thr Pro Phe Trp Gln
    50                  55                  60

Pro Ala Thr Phe Gln Leu Ile Asn Asn Gln Val Met Gln Gln Cys
65                  70                  75                  80

Cys Gln Gln Leu Arg Leu Val Ala Gln Ser His Tyr Gln Ala Ile
                85                  90                  95

Ser Ile Val Gln Ala Ile Val Gln Gln Leu Gln Leu Gln Gln Phe Ser
            100                 105                 110

Gly Val Tyr Phe Asp Gln Thr Gln Ala Gln Ala Gln Thr Leu Leu Thr
            115                 120                 125

Phe Asn Leu Pro Ser Ile Cys Gly Ile Tyr Pro Asn Tyr Tyr Ser Ala
        130                 135                 140

Pro Arg Ser Ile Ala Thr Val Gly Gly Val Trp Tyr
145                 150                 155

<210> SEQ ID NO 15
<211> LENGTH: 601
<212> TYPE: DNA
<213> ORGANISM: Oryza sativa
<220> FEATURE:
<223> OTHER INFORMATION: 13kD prolamin

<400> SEQUENCE: 15
attatacaac aaaaatttaa agaactagt gtcctgcaac aatgaagatc attttcgtct      60
ttgctctcct tgctattgct gcatgcagcg ccactgcgca gtttgatgtt ttaggtcaaa    120
atattaggca atatcaggtg cagtcgcctc tcctgctaca gcaacaggtg cttagcccat    180
ataatgagtt cgtaaggcag cagtatagca ttgcggcaag caccttcttg caatcagctg    240
cgtttcaact gagaaacaac caagtcttgc aacagctcag gctggtggcg caacaatctc    300
actaccagga cattaacgtt gtccaggcca tagcgcacca gctacacctc cagcagtttg    360
gcaatctcta cattgaccgg aatctggctc aagctcaagc actgttggct tttaacttgc    420
catctacata tggtatctac ccttggtcct atagtgcacc cgatagcatt accacccttg    480
gcggtgtctt gtactgaatt ttcacaatat tgtagttcgg aagtgaaaat ataagctcag    540
gtatcatcgt atgtgacatg tgaaacttga ggtgatataa atagaaataa aattatcttt    600
c                                                                    601

<210> SEQ ID NO 16
<211> LENGTH: 151
<212> TYPE: PRT
<213> ORGANISM: Oryza sativa
<220> FEATURE:
<223> OTHER INFORMATION: 13kD prolamin

<400> SEQUENCE: 16

Met Lys Ile Ile Phe Val Phe Ala Leu Leu Ala Ile Ala Ala Cys Ser
1               5                   10                  15

Ala Thr Ala Gln Phe Asp Val Leu Gly Gln Asn Ile Arg Gln Tyr Gln
            20                  25                  30

Val Gln Ser Pro Leu Leu Gln Gln Gln Val Leu Ser Pro Tyr Asn
         35                  40                  45

Glu Phe Val Arg Gln Gln Tyr Ser Ile Ala Ala Ser Thr Phe Leu Gln
 50                  55                  60

Ser Ala Ala Phe Gln Leu Arg Asn Asn Gln Val Leu Gln Gln Leu Arg
 65                  70                  75                  80

Leu Val Ala Gln Gln Ser His Tyr Gln Asp Ile Asn Val Val Gln Ala
                 85                  90                  95

Ile Ala His Gln Leu His Leu Gln Gln Phe Gly Asn Leu Tyr Ile Asp
                100                 105                 110

Arg Asn Leu Ala Gln Ala Gln Ala Leu Leu Ala Phe Asn Leu Pro Ser
                115                 120                 125

Thr Tyr Gly Ile Tyr Pro Trp Ser Tyr Ser Ala Pro Asp Ser Ile Thr
                130                 135                 140

Thr Leu Gly Gly Val Leu Tyr
145                 150

<210> SEQ ID NO 17
<211> LENGTH: 596
<212> TYPE: DNA
<213> ORGANISM: Oryza sativa
<220> FEATURE:
<223> OTHER INFORMATION: 13kD prolamin

<400> SEQUENCE: 17
gcaaaataga aagatctagt gtcccgcagc aatgaagatc atttctgtct ttgctctcct      60
tgctattgct gcatgcagcg cctctgcgca gtttgatgtt ttaggtcaaa gttataggca     120
atatcagctg cagtcgcctg tcctgctaca gcaacaggtg cttagcccat ataatgagtt     180
cgtaaggcag cagtatggca tagcggcaag ccccttcttg caatcagctg cgtttcaact     240
gagaaacaac caagtctggc aacagctcgc gctggtggcg caacaatctc actatcagga     300
cattaacatt gttcaggcca tagcgcagca gctacaactc cagcagtttg gtgatctcta     360 cttttgatcgg aatctggctc aagctcaagc tctgttggct tttaacgtgc catctagata     420
tggtatctac cctaggtact atggtgcacc cagtaccatt accaccctg gcggtgtctt     480 gtaatgagtt ttaacagtat agtggttcgg aagttaaaaa taagctcaga tatcatatat     540
gtgacatgtg aaactttggg tgatataaat agaaaaaaag ttgtctttca tattta         596

<210> SEQ ID NO 18
<211> LENGTH: 150
<212> TYPE: PRT
<213> ORGANISM: Oryza sativa
<220> FEATURE:
<223> OTHER INFORMATION: 13kD prolamin

<400> SEQUENCE: 18

Met Lys Ile Ile Phe Val Phe Ala Leu Leu Ala Ile Ala Ala Cys Ser
 1               5                  10                  15

Ala Ser Ala Gln Phe Asp Val Leu Gly Gln Ser Tyr Arg Gln Tyr Gln
                 20                  25                  30

Leu Gln Ser Pro Val Leu Leu Gln Gln Gln Val Leu Ser Pro Tyr Asn
                 35                  40                  45

Glu Phe Val Arg Gln Gln Tyr Gly Ile Ala Ala Ser Pro Phe Leu Gln
 50                  55                  60

Ser Ala Ala Phe Gln Leu Arg Asn Asn Gln Val Trp Gln Gln Leu Ala
 65                  70                  75                  80

```
Leu Val Ala Gln Gln Ser His Tyr Gln Asp Ile Asn Ile Val Gln Ala
                85                  90                  95

Ile Ala Gln Gln Leu Gln Leu Gln Gln Phe Gly Asp Leu Tyr Phe Asp
            100                 105                 110

Arg Asn Leu Ala Gln Ala Gln Ala Leu Leu Ala Phe Asn Val Pro Ser
        115                 120                 125

Arg Tyr Gly Ile Tyr Pro Arg Tyr Tyr Gly Ala Pro Ser Thr Ile Thr
    130                 135                 140

Thr Leu Gly Gly Val Leu
145             150

<210> SEQ ID NO 19
<211> LENGTH: 616
<212> TYPE: DNA
<213> ORGANISM: Oryza sativa
<220> FEATURE:
<223> OTHER INFORMATION: 13kD prolamin

<400> SEQUENCE: 19
cagttcaagc attatacagc aaaatagaaa gatctagtgt cccgcagcaa tgaagatcat      60
tttcgtcttt gctctccttg ctattgctgc atgcagcgcc tctcgcagtt tgattttagg     120
tcaaagttat aggcaatatc agctgcagtc gcctgtcctg ctacagcaac aggtgcttag     180
cccatataat gagttcgtaa gcagcagtat ggcatacggc aaccccttct tgcaatcagc     240
tgcgtttcaa ctgagaaaca accaagtctg gcaacagctc gcgctggtgg cgcaacaatc     300
tcactatcag gacattaaca ttgttcaggc catagcgcag cagctacaac tccagcagtt     360
tggtgatctc tactttgatc ggaatctggc tcaagctcaa gctctgttgg cttttaacgt     420
gccacctaaa tatggtatct accctaggta ctatggtgca cccagtacca ttaccaccct     480
tggcggtgtc ttgtaatgaa tttaacagta taatggtcgg aagttaaaaa taagctcaga     540
tatcctcata tgtgacatgt gaaactttgg gtgatataaa taaaaaaaaa attgtctttc     600
ctatttaaaa aaaaaa                                                     616

<210> SEQ ID NO 20
<211> LENGTH: 148
<212> TYPE: PRT
<213> ORGANISM: Oryza sativa
<220> FEATURE:
<223> OTHER INFORMATION: 13kD prolamin

<400> SEQUENCE: 20

Met Lys Ile Ile Phe Val Phe Ala Leu Leu Ala Ile Ala Ala Cys Ser
1               5                   10                  15

Ala Ser Arg Ser Leu Ile Leu Gly Gln Ser Tyr Arg Gln Tyr Gln Leu
            20                  25                  30

Gln Ser Pro Val Leu Leu Gln Gln Gln Val Leu Ser Pro Tyr Asn Glu
        35                  40                  45

Phe Val Ser Ser Ser Met Ala Tyr Gly Asn Pro Phe Leu Gln Ser Ala
    50                  55                  60

Ala Phe Gln Leu Arg Asn Asn Gln Val Trp Gln Gln Leu Ala Leu Val
65                  70                  75                  80

Ala Gln Gln Ser His Tyr Gln Asp Ile Asn Ile Val Gln Ala Ile Ala
                85                  90                  95

Gln Gln Leu Gln Leu Gln Gln Phe Gly Asp Leu Tyr Phe Asp Arg Asn
            100                 105                 110
```

Leu Ala Gln Ala Gln Ala Leu Leu Ala Phe Asn Val Pro Pro Lys Tyr
              115                 120                 125

Gly Ile Tyr Pro Arg Tyr Tyr Gly Ala Pro Ser Thr Ile Thr Thr Leu
        130                 135                 140

Gly Gly Val Leu
145

<210> SEQ ID NO 21
<211> LENGTH: 769
<212> TYPE: DNA
<213> ORGANISM: Oryza sativa
<220> FEATURE:
<223> OTHER INFORMATION: 13kD prolamin
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t

<400> SEQUENCE: 21
ttgctccttc nccgtcctcc ccgcttgggc tcttgggcgc ccgttccggg cgccccctcc      60
ctcctccctc cgcggtaccc ggccgcctca ctcctctgct ggaccccncg gccgccccgg     120
gccgcgcccc atcccggtgc gcgacccatc gttcacacag ttcaagcatt atacagaaaa     180
atagaaagat ctagtgtccc gcagcanatg aagatcattt tcgtctttgc tctccttgct     240
attgctgcat gcaggcctct gccgagtttg atgtttttag gtcaaagtta taggcaatat     300
cagctgcagt cgcctgtcct gctacagcaa caggtgctta gcccatataa tgagttcgta     360
aggcagcagt atggcatagc ggcaagcccc ttcttgcaat cagctgcatt caactgaga      420 aataaccaag tctggcaaca tcaggctggt ggccaacaat ctcgctatca ggacattaac     480
attgttcagg ccatagcgta cgagctacaa ctccagcaat tggtgatct ctactttgat      540 cggaatcagg ctcaagctca agctctattg cttttaacg tgccatctag atatggtatc      600
taccctaggt actatggtgc acccagtacc attaccaccc ttggcggtgt cttgtaatgt    660
gttttaacag tatagtggtt cggaagttaa aaataagctc agatatcatc atatgtgaca    720
tgtgaaactt tgggtgatat aaatagaaat aaagttgcct ttcatattt                769

<210> SEQ ID NO 22
<211> LENGTH: 149
<212> TYPE: PRT
<213> ORGANISM: Oryza sativa
<220> FEATURE:
<223> OTHER INFORMATION: 13kD prolamin

<400> SEQUENCE: 22

Met Lys Ile Ile Phe Val Phe Ala Leu Leu Ala Ile Ala Ala Cys Arg
1               5                  10                  15

Pro Leu Pro Ser Leu Met Phe Leu Gly Gln Ser Tyr Arg Gln Tyr Gln
            20                  25                  30

Leu Gln Ser Pro Val Leu Leu Gln Gln Gln Val Leu Ser Pro Tyr Asn
        35                  40                  45

Glu Phe Val Arg Gln Gln Tyr Gly Ile Ala Ala Ser Pro Phe Leu Gln
    50                  55                  60

Ser Ala Ala Phe Gln Leu Arg Asn Asn Gln Val Trp Gln His Gln Ala
65                  70                  75                  80

Gly Gly Gln Gln Ser Arg Tyr Gln Asp Ile Asn Ile Val Gln Ala Ile
                85                  90                  95

Ala Tyr Glu Leu Gln Leu Gln Gln Phe Gly Asp Leu Tyr Phe Asp Arg
            100                 105                 110

Asn Gln Ala Gln Ala Gln Ala Leu Leu Ala Phe Asn Val Pro Ser Arg
        115                 120                 125

Tyr Gly Ile Tyr Pro Arg Tyr Tyr Gly Ala Pro Ser Thr Ile Thr Thr
    130                 135                 140

Leu Gly Gly Val Leu
145

<210> SEQ ID NO 23
<211> LENGTH: 609
<212> TYPE: DNA
<213> ORGANISM: Oryza sativa
<220> FEATURE:
<223> OTHER INFORMATION: 13kD prolamin

<400> SEQUENCE: 23
aagcattata caacaaaaat ttaaaagaac tagtgtcctg caacaatgaa gatcattttc      60
gtctttgctc tccttgctat tgctgcatgc gccacagcgc agtttgatgt tttaggtcaa     120
aatattaggc aatatcaggt gcagtcgcct ctcctgctac agcaacaggt gcttagccta     180
tataatgagt tcgtaaggca gcagtatagc attgcggcaa gccccttctt gcaatcagct     240
gtgtttcaac tgagaaacaa ccaagtcttg caacagctca ggctggtggc gcaacaatct     300
cactaccagg acattaacgt tgtccaggcc atagcgcagc agctacacct ccagcagttt     360
ggcgatctct acattgaccg gaatctggct caagcgcaac gactgttggc ttttaacttg     420
ccatctacat atggtatcta ccctaggtac tatagagcac cgggtagtat taccacccct     480
ggcggtgtct tgtactgaat tttcacaata ttgtagttcg gaagtgaaaa tataagcctc     540
aggtatcatc gtatgtgaca tgtgaaactt aaggtgatat aaatagaaat aaaattatct     600
ttcatattt                                                            609

<210> SEQ ID NO 24
<211> LENGTH: 150
<212> TYPE: PRT
<213> ORGANISM: Oryza sativa
<220> FEATURE:
<223> OTHER INFORMATION: 13kD prolamin

<400> SEQUENCE: 24

Met Lys Ile Ile Phe Val Phe Ala Leu Leu Ala Ile Ala Ala Cys Ala
1               5                   10                  15

Thr Ala Gln Phe Asp Val Leu Gly Gln Asn Ile Arg Gln Tyr Gln Val
            20                  25                  30

Gln Ser Pro Leu Leu Leu Gln Gln Val Leu Ser Leu Tyr Asn Glu
        35                  40                  45

Phe Val Arg Gln Gln Tyr Ser Ile Ala Ala Ser Pro Phe Leu Gln Ser
    50                  55                  60

Ala Val Phe Gln Leu Arg Asn Asn Gln Val Leu Gln Gln Leu Arg Leu
65                  70                  75                  80

Val Ala Gln Gln Ser His Tyr Gln Asp Ile Asn Val Val Ala Ile
                85                  90                  95

Ala Gln Gln Leu His Leu Gln Phe Gly Asp Leu Tyr Ile Asp Arg
            100                 105                 110

Asn Leu Ala Gln Ala Gln Arg Leu Leu Ala Phe Asn Leu Pro Ser Thr
        115                 120                 125

Tyr Gly Ile Tyr Pro Arg Tyr Tyr Arg Ala Pro Gly Ser Ile Thr Thr
    130                 135                 140

Leu Gly Gly Val Leu Tyr
145             150

<210> SEQ ID NO 25
<211> LENGTH: 596
<212> TYPE: DNA
<213> ORGANISM: Oryza sativa
<220> FEATURE:
<223> OTHER INFORMATION: 13kD prolamin

<400> SEQUENCE: 25
ccagcaaaat agaaagatct agtgtcccgc agcaatgaag atcatttcg tctttgctct      60
ccttgctatt gctgcatgca ggcctctgca gtttgatgtt ttaggtcaaa gttataggca   120
atatcagctg cagtcgcctg tcctgctaca gcaacatgtg cttagcccat ataatgagtt   180
cgtaaggcag cagtatggca tagcggcaag ccccttcttg caatcagctg cgtttcaact   240
gagaaacaac caagtctggc aacagctcgc gctggtggcg caacaatctc actatcagga   300
cattaacatt gttcaggcca tagcgcagca gctacaactc cagcagtttg gtgatctcta   360
ctttgatcgg aatctggctc aagctcaagc tctgttggct tttaacgtgc catctagata   420
tggtatctac cctaggtact atggtgcacc cagtaccatt accacccttg gcggtgtctt   480
gtaatgagtt ttaacagtat agtggttcgg aagataaaaa taagctcaga tatcatcata   540
tgtgacatgt gaaactttgg gtgatataaa tagaaaaaaa gttgtctttc atattt         596

<210> SEQ ID NO 26
<211> LENGTH: 149
<212> TYPE: PRT
<213> ORGANISM: Oryza sativa
<220> FEATURE:
<223> OTHER INFORMATION: 13kD prolamin

<400> SEQUENCE: 26

Met Lys Ile Ile Phe Val Phe Ala Leu Leu Ala Ile Ala Ala Cys Arg
1               5                   10                  15

Pro Leu Gln Phe Asp Val Leu Gly Gln Ser Tyr Arg Gln Tyr Gln Leu
            20                  25                  30

Gln Ser Pro Val Leu Leu Gln Gln His Val Leu Ser Pro Tyr Asn Glu
        35                  40                  45

Phe Val Arg Gln Gln Tyr Gly Ile Ala Ala Ser Pro Phe Leu Gln Ser
    50                  55                  60

Ala Ala Phe Gln Leu Arg Asn Asn Gln Val Trp Gln Gln Leu Ala Leu
65                  70                  75                  80

Val Ala Gln Gln Ser His Tyr Gln Asp Ile Asn Ile Val Gln Ala Ile
                85                  90                  95

Ala Gln Gln Leu Gln Leu Gln Gln Phe Gly Asp Leu Tyr Phe Asp Arg
            100                 105                 110

Asn Leu Ala Gln Ala Gln Ala Leu Leu Ala Phe Asn Val Pro Ser Arg
        115                 120                 125

Tyr Gly Ile Tyr Pro Arg Tyr Tyr Gly Ala Pro Ser Thr Ile Thr Thr
            130                 135                 140

Leu Gly Gly Val Leu
145

<210> SEQ ID NO 27
<211> LENGTH: 285
<212> TYPE: DNA
<213> ORGANISM: Oryza sativa
<220> FEATURE:
<223> OTHER INFORMATION: 13kD prolamin

<400> SEQUENCE: 27
gttcgtaagg caacagtata gcatagtggc aaccccttc tggcaaccag ctacgtttca      60
tttgataaac aaccaagtca tgcagcagca gttttgccaa cagctcaggc tggtagcaca     120
acattctcac taccaggcca ttagtattgt tcaagcgatt gtgcaacagc tacaactgca     180
gcattttagt ggtgtctact ttgatcagac tcaagctcaa gcccaaactt ttttgacctt     240
caactttccc atccatatgt ggtatctacc ttaacttact attgt                    285

<210> SEQ ID NO 28
<211> LENGTH: 94
<212> TYPE: PRT
<213> ORGANISM: Oryza sativa
<220> FEATURE:
<223> OTHER INFORMATION: 13kD prolamin

<400> SEQUENCE: 28

Phe Val Arg Gln Gln Tyr Ser Ile Val Ala Thr Pro Phe Trp Gln Pro
1               5                   10                  15

Ala Thr Phe His Leu Ile Asn Asn Gln Val Met Gln Gln Gln Phe Cys
            20                  25                  30

Gln Gln Leu Arg Leu Val Ala Gln His Ser His Tyr Gln Ala Ile Ser
        35                  40                  45

Ile Val Gln Ala Ile Val Gln Gln Leu Gln Leu Gln His Phe Ser Gly
    50                  55                  60

Val Tyr Phe Asp Gln Thr Gln Ala Gln Ala Gln Thr Phe Leu Thr Phe
65                  70                  75                  80

Asn Phe Pro Ser Ile Cys Gly Ile Tyr Leu Asn Leu Leu Leu
                85                  90

<210> SEQ ID NO 29
<211> LENGTH: 1836
<212> TYPE: DNA
<213> ORGANISM: Oryza sativa
<220> FEATURE:
<223> OTHER INFORMATION: 13kD prolamin

<400> SEQUENCE: 29
tccacatggg acggggccaa ggtgaggaaa gcaagctgca caaaggatta agttcttgt       60 aaacttgaaa ctcaatttga gtgtttatcc tagctaatat gatcccttca tcctagaata    120
taacaatcta gaattagatg tgctatctaa acacattgta gtaggtaatg tgtcatctaa    180
tcttagatat aatctaaaac ggaaggtgaa acggagggag tacctacata gtaatggcat    240
gcctatgttg cttaatttga cccgtgcagc tgagtatatg tgatgagac aaaagttact     300 ttcatgatgg caccaaagga gatttgttgg ggtgcctaat agaacatcga tccaaatgac    360
acgacacact tagattctaa taggacatcc aagcaaaaca acacttagat cctaatagga    420
catccaagca aaactaacac tctagagcaa ccgataagga attgaaaaag tttgtccatc    480

```
attcttgaca agaggtagtg tacaaaaaaa atatttagtt gagctctcgc tcactacgca    540
tcacagaagt ataacctaga tataattaat tcagtataga agcaaaaatt cagcagcaac    600
aatgagggta aaaactagaa agaaggattt atgatgttcc tcagtttatt cagtcgcaaa    660
agatagttta ctgtaaacaa aatggataat aaacctgatg tttcaacaaa actagaggaa    720
ctctgtaaat tgtccaggtt catccctaga agttggtttc tccttacggg aggagggagt    780
atatgtgatg gacacaaaag ttactttcat gatgaaacca aagggtattt gttggggcac    840
ctaacagaac atctatctaa atgacatgac tcacttagat cctaatagga catccaagca    900
aaactaacac tctaaagcaa ccgatgagga attgaaagaa aatatatgcc atcgcatcta    960
taaatagaca agcccaatga aaaccctcct catcgtttac acagttcaag cattatacag   1020
aaaagaagat ctagtgtccc gcagcaatga agatcatttt ccgtctttgc tctccttgct   1080
attgctgcat gcaacacctc tgcgtagttg atgttttagg tcaaagttat aggcaatatc   1140
agctacagtc gcctctccta caacaacaac aggtgcttag cccatataat gacttcgtaa   1200
ggcagcgata tggcatagcg gcaagcccct tcttgcaatc agctgcgttt aaactgagaa   1260
ataaccaagt ctggcaacag ctcgggctgg tggcgcaaca atctcactat caggacatta   1320
acattgttca ggccatagcg cagcagctat aactccagca gtttggtgat ctctactttg   1380
atcggaatcc ggctcaagct caagctctgt tggcttttaa cgtgccatct agatatggta   1440
tctaccctag gtactatagt acacccagta ccattaccac ccttggcggt gtcttgtaat   1500
gagttttaac agtatagtgg ttcggaagtt aaaaataagc tcatatatta tcatatgtga   1560
catgtgaaat ttggggtgaa ataaatcgaa ataaagttgt ctttcatatt taaataccat   1620
gcctctataa ggatatatcc tagtacattg tcgtaactaa ttaccatcat cggtactcta   1680
caattttact gtgttcttac attcgatccg aagctacttt gttttttaaga tataaatgga   1740 gcgtataaag gatgtccgtc ctttcattcc aataagaaca atgtaacatc ctgaaaatgt   1800
gtcatttcct aatcctgcat catgccgact cttatg                             1836
```

<210> SEQ ID NO 30
<211> LENGTH: 101
<212> TYPE: PRT
<213> ORGANISM: Oryza sativa
<220> FEATURE:
<223> OTHER INFORMATION: 13kD prolamin

<400> SEQUENCE: 30

```
Met Lys Ile Ile Phe Arg Leu Cys Ser Pro Cys Tyr Cys Cys Met Gln
1               5                   10                  15

His Leu Cys Val Val Asp Val Leu Gly Gln Ser Tyr Arg Gln Tyr Gln
            20                  25                  30

Leu Gln Ser Pro Leu Leu Gln Gln Gln Val Leu Ser Pro Tyr Asn
        35                  40                  45

Asp Phe Val Arg Gln Arg Tyr Gly Ile Ala Ala Ser Pro Phe Leu Gln
    50                  55                  60

Ser Ala Ala Phe Lys Leu Arg Asn Asn Gln Val Trp Gln Gln Leu Gly
65                  70                  75                  80

Leu Val Ala Gln Gln Ser His Tyr Gln Asp Ile Asn Ile Val Gln Ala
                85                  90                  95

Ile Ala Gln Gln Leu
            100
```

<210> SEQ ID NO 31
<211> LENGTH: 622
<212> TYPE: DNA
<213> ORGANISM: Oryza sativa
<220> FEATURE:
<223> OTHER INFORMATION: 16kD prolamin

<400> SEQUENCE: 31

```
aaacatcaaa acgttataag agttctctag catccatcac atagccatga agatctttgt      60
catcctctct ctcctcgccc tcgcagcgag cagcgcctcg gcacagtttg atgcttgcac     120
ctatgggcaa tgccagcagc agccgtttat gcaaccgatc atgaacccgt gcaatgagtt     180
cgtgaggcaa cagtgcagcc cgatgagcct accttggaag cagtcacgca ggctacaact     240
gagcagctgc caggtgatgc ggcagcaatg ctgtcagcag atgaggttga tgcgcaaca      300
atatcattgc caggctattt gcaccatggt gcagtctatc atgcagcaag tgcagtttga     360
tgctggctt gttggcgagc ccaagctca ggcccaggcc caggtggctc tcaatttgcc       420
ctccatgtgt ggagtctacc ctaggtactg cagcactcca tgcaaagttg ctactggtca     480
ttgcggttct tggtagtgtg taccatcata tatatatagt tggataaata agtgtcaca     540
catcatcgtg tgtgtcatgt aataaaattt ggaatagtct ttggctgttc gtatgaataa    600
atgaaaatta taacaaaaaa aa                                            622
```

<210> SEQ ID NO 32
<211> LENGTH: 149
<212> TYPE: PRT
<213> ORGANISM: Oryza sativa
<220> FEATURE:
<223> OTHER INFORMATION: 16kD prolamin

<400> SEQUENCE: 32

```
Met Lys Ile Phe Val Ile Leu Ser Leu Leu Ala Leu Ala Ala Ser Ser
1               5                   10                  15

Ala Ser Ala Gln Phe Asp Ala Cys Thr Tyr Gly Gln Cys Gln Gln Gln
            20                  25                  30

Pro Phe Met Gln Pro Ile Met Asn Pro Cys Asn Glu Phe Val Arg Gln
        35                  40                  45

Gln Cys Ser Pro Met Ser Leu Pro Trp Lys Gln Ser Arg Arg Leu Gln
    50                  55                  60

Leu Ser Ser Cys Gln Val Met Arg Gln Gln Cys Cys Gln Gln Met Arg
65                  70                  75                  80

Leu Met Ala Gln Gln Tyr His Cys Gln Ala Ile Cys Thr Met Val Gln
                85                  90                  95

Ser Ile Met Gln Gln Val Gln Phe Asp Ala Gly Phe Val Gly Glu Pro
            100                 105                 110

Gln Ala Gln Ala Gln Ala Gln Val Ala Leu Asn Leu Pro Ser Met Cys
        115                 120                 125

Gly Val Tyr Pro Arg Tyr Cys Ser Thr Pro Cys Lys Val Ala Thr Gly
    130                 135                 140

His Cys Gly Ser Trp
145
```

<210> SEQ ID NO 33
<211> LENGTH: 562
<212> TYPE: DNA
<213> ORGANISM: Oryza sativa
<220> FEATURE:
<223> OTHER INFORMATION: 10kD prolamin -continued

```
<400> SEQUENCE: 33
cgtctacacc atctggaatc ttgtttaaca ctagtattgt agaatcagca atggcagcat      60
acaccagcaa gatctttgcc ctgtttgcct taattgctct ttctgcaagt gccactactg     120
caatcaccac tatgcagtat ttcccaccaa cattagccat gggcaccatg gatccgtgta     180
ggcagtacat gatgcaaacg ttgggcatgg gtagctccac agccatgttc atgtcgcagc     240
caatggcgct cctgcagcag caatgttgca tgcagctaca aggcatgatg cctcagtgcc     300
actgtggcac cagttgccag atgatgcaga gcatgcaaca agttatttgt gctggactcg     360
ggcagcagca gatgatgaag atggcgatgc agatgccata catgtgcaac atggcccctg     420
tcaacttcca actctcttcc tgtggttgtt gttgatcaaa cgttggttac atgtactcta     480
gtaataaggt gttgcatact atcgtgtgca aacactagaa ataagaacca ttgaataaaa     540
tatcaatcat tttcagactt gc                                              562

<210> SEQ ID NO 34
<211> LENGTH: 134
<212> TYPE: PRT
<213> ORGANISM: Oryza sativa
<220> FEATURE:
<223> OTHER INFORMATION: 10kD prolamin

<400> SEQUENCE: 34

Met Ala Ala Tyr Thr Ser Lys Ile Phe Ala Leu Phe Ala Leu Ile Ala
1               5                   10                  15

Leu Ser Ala Ser Ala Thr Thr Ala Ile Thr Thr Met Gln Tyr Phe Pro
            20                  25                  30

Pro Thr Leu Ala Met Gly Thr Met Asp Pro Cys Arg Gln Tyr Met Met
        35                  40                  45

Gln Thr Leu Gly Met Gly Ser Ser Thr Ala Met Phe Met Ser Gln Pro
    50                  55                  60

Met Ala Leu Leu Gln Gln Gln Cys Cys Met Gln Leu Gln Gly Met Met
65                  70                  75                  80

Pro Gln Cys His Cys Gly Thr Ser Cys Gln Met Met Gln Ser Met Gln
                85                  90                  95

Gln Val Ile Cys Ala Gly Leu Gly Gln Gln Gln Met Met Lys Met Ala
            100                 105                 110

Met Gln Met Pro Tyr Met Cys Asn Met Ala Pro Val Asn Phe Gln Leu
        115                 120                 125

Ser Ser Cys Gly Cys Cys
    130

<210> SEQ ID NO 35
<211> LENGTH: 332
<212> TYPE: DNA
<213> ORGANISM: Oryza rufipogon
<220> FEATURE:
<223> OTHER INFORMATION: 10kD prolamin

<400> SEQUENCE: 35
aattgctctt tctgcaagtg ccactactgc aatcaccact atgcagtatt tcccaccaac      60
attagccatg ggcaccatgg atccgtgtag gcagtacatg atgcaaacgt tgggcatggg    120
tagctccaca gccatgttca tgtcgcagcc aatggcgctc ctgcagcagc aatgttgcat    180
gcagctacaa ggcatgatgc ctcagtgcca ctgtggcacc agttgccaga tgatgcagag    240
```

```
catgcaacaa gttatttgtg ctggactcgg gcagcagcag atgatgaaga tggcgatgca    300
gatgccatac atgtgcaaca tggcccctgt ca                                  332
```

<210> SEQ ID NO 36
<211> LENGTH: 110
<212> TYPE: PRT
<213> ORGANISM: Oryza rufipogon
<220> FEATURE:
<223> OTHER INFORMATION: 10kD prolamin

<400> SEQUENCE: 36

```
Ile Ala Leu Ser Ala Ser Ala Thr Thr Ala Ile Thr Thr Met Gln Tyr
1               5                   10                  15

Phe Pro Pro Thr Leu Ala Met Gly Thr Met Asp Pro Cys Arg Gln Tyr
            20                  25                  30

Met Met Gln Thr Leu Gly Met Gly Ser Ser Thr Ala Met Phe Met Ser
        35                  40                  45

Gln Pro Met Ala Leu Leu Gln Gln Gln Cys Cys Met Gln Leu Gln Gly
    50                  55                  60

Met Met Pro Gln Cys His Cys Gly Thr Ser Cys Gln Met Met Gln Ser
65                  70                  75                  80

Met Gln Gln Val Ile Cys Ala Gly Leu Gly Gln Gln Met Met Lys
                85                  90                  95

Met Ala Met Gln Met Pro Tyr Met Cys Asn Met Ala Pro Val
            100                 105                 110
```

<210> SEQ ID NO 37
<211> LENGTH: 349
<212> TYPE: DNA
<213> ORGANISM: Oryza longistaminata
<220> FEATURE:
<223> OTHER INFORMATION: 10kD prolamin
<220> FEATURE:
<221> NAME/KEY: misc_feature
<222> LOCATION: (18)..(19)
<223> OTHER INFORMATION: n is a, c, g, or t

<400> SEQUENCE: 37

```
ccctgtttgc cttaattnnt cttctttctg caagtgccac tactgcaatc actactatgc    60
agtatttccc accaacatta gccatgggca ccatggatcc gtgtaggcag tacatgatgc    120
aaacgttggg catgggtagc tccacaacca tgttcatgtc gcagccaatg gcgctcctgc    180
agcagcaatg ttgcatgcag ctacaaggca tgatgcctca gtgccactgt ggcaccagtt    240
gccagatgat gcagagcatg caacaagttg tttgtgctgg actcgggcag cagcagatga    300
tgatgaagat ggcaatgcag atgccataca tgtgcaacat ggcccctgt              349
```

<210> SEQ ID NO 38
<211> LENGTH: 116
<212> TYPE: PRT
<213> ORGANISM: Oryza longistaminata
<220> FEATURE:
<223> OTHER INFORMATION: 10kD prolamin
<220> FEATURE:
<221> NAME/KEY: misc_feature
<222> LOCATION: (6)..(6)
<223> OTHER INFORMATION: Xaa can be any naturally occurring amino acid

```
<400> SEQUENCE: 38

Leu Phe Ala Leu Ile Xaa Leu Leu Ser Ala Ser Ala Thr Thr Ala Ile
1               5                   10                  15

Thr Thr Met Gln Tyr Phe Pro Pro Thr Leu Ala Met Gly Thr Met Asp
            20                  25                  30

Pro Cys Arg Gln Tyr Met Met Gln Thr Leu Gly Met Gly Ser Ser Thr
        35                  40                  45

Thr Met Phe Met Ser Gln Pro Met Ala Leu Leu Gln Gln Cys Cys
    50                  55                      60

Met Gln Leu Gln Gly Met Met Pro Gln Cys His Cys Gly Thr Ser Cys
65                  70                  75                  80

Gln Met Met Gln Ser Met Gln Val Val Cys Ala Gly Leu Gly Gln
                85                  90                  95

Gln Gln Met Met Met Lys Met Ala Met Gln Met Pro Tyr Met Cys Asn
            100                 105                 110

Met Ala Pro Val
        115

<210> SEQ ID NO 39
<211> LENGTH: 343
<212> TYPE: DNA
<213> ORGANISM: Oryza rufipogon
<220> FEATURE:
<223> OTHER INFORMATION: 10kD prolamin

<400> SEQUENCE: 39
ctgtttgcct taattgctct ttctgcaagt gccactactg caatcaccac tatgcagtat      60
ttcccaccaa cattagccat gggcaccatg gatccgtgta ggcagtacat gatgcaaacg     120
ttgggcatgg gtagctccac agccatgttc atgtcgcagc caatggcgct cctgcagcag     180
caatgttgca tgcagctaca aggcatgatg cctcagtgcc actgtggcac cagttgccag     240
atgatgcaga gcatgcaaca agttatttgt gctggactcg gcagcagca tgatgaag       300 atggcgatgc agatgccata catgtgcaac atggcccctg tca                      343

<210> SEQ ID NO 40
<211> LENGTH: 113
<212> TYPE: PRT
<213> ORGANISM: Oryza rufipogon
<220> FEATURE:
<223> OTHER INFORMATION: 10kD prolamin

<400> SEQUENCE: 40

Leu Phe Ala Leu Ile Ala Leu Ser Ala Ser Ala Thr Thr Ala Ile Thr
1               5                   10                  15

Thr Met Gln Tyr Phe Pro Pro Thr Leu Ala Met Gly Thr Met Asp Pro
            20                  25                  30

Cys Arg Gln Tyr Met Met Gln Thr Leu Gly Met Gly Ser Ser Thr Ala
        35                  40                  45

Met Phe Met Ser Gln Pro Met Ala Leu Leu Gln Gln Cys Cys Met
    50                  55                      60

Gln Leu Gln Gly Met Met Pro Gln Cys His Cys Gly Thr Ser Cys Gln
65                  70                  75                  80

Met Met Gln Ser Met Gln Val Ile Cys Ala Gly Leu Gly Gln Gln
                85                  90                  95
```

Gln Met Met Lys Met Ala Met Gln Met Pro Tyr Met Cys Asn Met Ala
            100                 105                 110

Pro

<210> SEQ ID NO 41
<211> LENGTH: 339
<212> TYPE: DNA
<213> ORGANISM: Oryza rufipogon
<220> FEATURE:
<223> OTHER INFORMATION: 10kD prolamin

<400> SEQUENCE: 41
tttgccttaa ttgctctttc tgcaagtgcc actactgcaa tcaccactat gcagtatttc      60
ccaccaacat tagccatggg caccatggat ccgtgtaggc agtacatgat gcaaacgttg     120
ggcatgggta gctccacagc catgttcatg tcgcagccaa tggcgctcct gcagcagcaa     180
tgttgcatgc agctacaagg catgatgcct cagtgccact gtggcaccag ttgccagatg     240
atgcagagca tgcaacaagt tatttgtgct ggactcgggc agcagcagat gatgaagatg     300
gcgatgcaga tgccatacat gtgcaacatg gcccctgtc                            339

<210> SEQ ID NO 42
<211> LENGTH: 113
<212> TYPE: PRT
<213> ORGANISM: Oryza rufipogon
<220> FEATURE:
<223> OTHER INFORMATION: 10kD prolamin

<400> SEQUENCE: 42

Phe Ala Leu Ile Ala Leu Ser Ala Ser Ala Thr Thr Ala Ile Thr Thr
1               5                   10                  15

Met Gln Tyr Phe Pro Pro Thr Leu Ala Met Gly Thr Met Asp Pro Cys
            20                  25                  30

Arg Gln Tyr Met Met Gln Thr Leu Gly Met Gly Ser Ser Thr Ala Met
        35                  40                  45

Phe Met Ser Gln Pro Met Ala Leu Leu Gln Gln Gln Cys Cys Met Gln
    50                  55                  60

Leu Gln Gly Met Met Pro Gln Cys His Cys Gly Thr Ser Cys Gln Met
65                  70                  75                  80

Met Gln Ser Met Gln Gln Val Ile Cys Ala Gly Leu Gly Gln Gln Gln
                85                  90                  95

Met Met Lys Met Ala Met Gln Met Pro Tyr Met Cys Asn Met Ala Pro
            100                 105                 110

Val

<210> SEQ ID NO 43
<211> LENGTH: 343
<212> TYPE: DNA
<213> ORGANISM: Oryza rufipogon
<220> FEATURE:
<223> OTHER INFORMATION: 10kD prolamin
<220> FEATURE:
<221> NAME/KEY: misc_feature
<222> LOCATION: (19)..(19)
<223> OTHER INFORMATION: n is a, c, g, or t

<400> SEQUENCE: 43
ccctgtttgc cttaattgnt ctttctgcaa gtgccactac tgcaatcacc actatgcagt      60
atttcccacc aacattagcc atgggcacca tggatccgtg taggcagtac atgatgcaaa     120
cgttgggcat gggtagctcc acagccatgt tcatgtcgca gccaatggcg ctcctgcagc     180

-continued

```
agcaatgttg catgcagcta caaggcatga tgcctcagtg ccactgtggc accagttgcc    240
agatgatgca gagcatgcaa caagttattt gtgctggact cgggcagcag cagatgatga    300
agatggcgat gcagatgcca tacatgtgca acatggcccc tgt                      343
```

<210> SEQ ID NO 44
<211> LENGTH: 114
<212> TYPE: PRT
<213> ORGANISM: Oryza rufipogon
<220> FEATURE:
<223> OTHER INFORMATION: 10kD prolamin
<220> FEATURE:
<221> NAME/KEY: misc_feature
<222> LOCATION: (6)..(6)
<223> OTHER INFORMATION: Xaa can be any naturally occurring amino acid

<400> SEQUENCE: 44

```
Leu Phe Ala Leu Ile Xaa Leu Ser Ala Ser Ala Thr Thr Ala Ile Thr
1               5                   10                  15

Thr Met Gln Tyr Phe Pro Pro Thr Leu Ala Met Gly Thr Met Asp Pro
            20                  25                  30

Cys Arg Gln Tyr Met Met Gln Thr Leu Gly Met Gly Ser Ser Thr Ala
        35                  40                  45

Met Phe Met Ser Gln Pro Met Ala Leu Leu Gln Gln Gln Cys Cys Met
    50                  55                  60

Gln Leu Gln Gly Met Met Pro Gln Cys His Cys Gly Thr Ser Cys Gln
65                  70                  75                  80

Met Met Gln Ser Met Gln Gln Val Ile Cys Ala Gly Leu Gly Gln Gln
                85                  90                  95

Gln Met Met Lys Met Ala Met Gln Met Pro Tyr Met Cys Asn Met Ala
            100                 105                 110

Pro Val
```

<210> SEQ ID NO 45
<211> LENGTH: 533
<212> TYPE: DNA
<213> ORGANISM: Oryza sativa
<220> FEATURE:
<223> OTHER INFORMATION: 10kD prolamin

<400> SEQUENCE: 45

```
atggcagcat acaccagcaa gatctttgcc ctgtttgcct taattgctct ttctgcaagt    60
gccactactg caatcaccac tatgcagtat ttcccaccaa cattagccat gggcaccatg    120
gatccgtgta ggcagtacat gatgcaaacg ttgggcatgg gtagctccac agccatgttc    180
atgtcgcagc caatggcgct cctgctgcag caatgttgca tgcagctaca aggcatgatg    240
cctcagtgcc actgtggcac cagttgccag atgatgcaga gcatgcaaca agttatttgt    300
gctggactcg ggcagcagca gatgatgaag atggcgatgc agatgccata catgtgcaac    360
atggcccctg tcaacttcca actctcttcc tgtggttgtt gttgatgaaa cgttggttac    420
atgtactcta gtaataaggt gttgcatact atcgtgtgca aacactagaa ataagtacca    480
ttgaataaaa tatcaaacat tttcagactt gcaaaaaaaa aaaaaaaaa aaa            533
```

<210> SEQ ID NO 46
<211> LENGTH: 134
<212> TYPE: PRT
<213> ORGANISM: Oryza sativa
<220> FEATURE:
<223> OTHER INFORMATION: 10kD prolamin

```
<400> SEQUENCE: 46

Met Ala Ala Tyr Thr Ser Lys Ile Phe Ala Leu Phe Ala Leu Ile Ala
1               5                   10                  15

Leu Ser Ala Ser Ala Thr Thr Ala Ile Thr Thr Met Gln Tyr Phe Pro
            20                  25                  30

Pro Thr Leu Ala Met Gly Thr Met Asp Pro Cys Arg Gln Tyr Met Met
            35                  40                  45

Gln Thr Leu Gly Met Gly Ser Ser Thr Ala Met Phe Met Ser Gln Pro
    50                  55                  60

Met Ala Leu Leu Leu Gln Gln Cys Cys Met Gln Leu Gln Gly Met Met
65                  70                  75                  80

Pro Gln Cys His Cys Gly Thr Ser Cys Gln Met Met Gln Ser Met Gln
                85                  90                  95

Gln Val Ile Cys Ala Gly Leu Gly Gln Gln Met Met Lys Met Ala
                100                 105                 110

Met Gln Met Pro Tyr Met Cys Asn Met Ala Pro Val Asn Phe Gln Leu
            115                 120                 125

Ser Ser Cys Gly Cys Cys
        130

<210> SEQ ID NO 47
<211> LENGTH: 940
<212> TYPE: DNA
<213> ORGANISM: Oryza sativa
<220> FEATURE:
<223> OTHER INFORMATION: 10kDa prolamin promoter

<400> SEQUENCE: 47
aatttagatc tatacatccg ttggtacatc tctactactc tagtactaaa aacatgagat      60
ctgaacatgg ctgcataggt tctccatccc aattcaccct gcagtgatcg ctgcactgga    120
taattataat atcagttaaa attgaaaata atgcaacttc atacttgcat ggtgtcagta    180
gtgcctgcct aagaaatgtg tcttgtcata atatgattac atgaaatatg tttacttcct    240
tcgtttctct ttatttgtaa gataaagaac tagatatgtg gaaagtagga tagcaaagag    300
tatggccaaa ctctaatctt tgctttattt tttgggatgg acccaaaatt tgtttctcct    360
ttacttcttt cccttacaa caatgttctt tacttccaat tcttattaac aaaactccaa     420
atacatgcca aactgcatat gtatgtatgc tattaaggca catttacaaa gctccaagtt    480
tacctactca atcattcaca tatggcgatg actcaaactc ttaattgtta tctgtgtaag    540
ctgtgacttg tgtaacacat tctacaagtc ccatacgaat tctgttcaca aaagtttctt    600
tgtccagctc ataatttaca aaactgcaaa atgccaaagc aatctggcac aaccttatca    660
tcatattttc tttccacgca ttaaagcact ggcagaatta tctttgtgta gatattccaa    720
aagtattggt tgaataaatg tccaaataaa ttccatgcct catgatttcc agcttatgtg    780
gcctccacta ggtggttttg caaaggccaa actctttcct ggcttacaca gctaccagca    840
tgtataaata ggcccctagg caaccattat tccatcatcc tcaacaatat tgtctacacc    900
atctggaatc ttgtttaaca ctagtattgt agaatcagca                          940

<210> SEQ ID NO 48
<211> LENGTH: 1351
<212> TYPE: DNA
<213> ORGANISM: Oryza sativa
<220> FEATURE:
<223> OTHER INFORMATION: GLUTELIN-B1 promoter
```

<400> SEQUENCE: 48

```
gatctcgatt tttgaggaat tttagaagtt gaacagagtc aatcgaacag acagttgaag      60
agatatggat tttctaagat taattgattc tctgtctaaa gaaaaaaagt attattgaat     120
taaatggaaa aagaaaaagg aaaaagggga tggcttctgc tttttgggct gaaggcggcg     180
tgtggccagc gtgctgcgtg cggacagcga gcgaacacac gacggagcag ctacgacgaa     240
cgggggaccg agtggaccgg acgaggatgt ggcctaggac gagtgcacaa ggctagtgga     300
ctcggtcccc gcgcggtatc ccgagtggtc cactgtctgc aaacgcgatt cacatagagc     360
gggcagacgc gggagccgtc ctaggtgcac cggaagcaaa tccgtcgcct gggtggattt     420
gagtgacacg gcccacgtgt agcctcacag ctctccgtgg tcagatgtgt aaaattatca     480
taatatgtgt ttttcaaata gttaaataat atatataggc aagttatatg ggtcaataag     540
cagtaaaaag gcttatgaca tggtaaaatt acttacacca atatgcctta ctgtctgata     600
tattttacat gacaacaaag ttacaagtac gtcatttaaa aatacaagtt acttatcaat     660
tgtagtgtat caagtaaatg acaacaaacc tacaaatttg ctattttgaa ggaacactta     720
aaaaaatcaa taggcaagtt atatagtcaa taaactgcaa gaaggcttat gacatggaaa     780
aattacatac accaatatgc tttattgtcc ggtatatttt acaagacaac aaagttataa     840
gtatgtcatt taaaaataca agttacttat caattgtcaa gtaaatgaaa acaaacctac     900
aaatttgtta ttttgaagga acacctaaat tatcaaatat agcttgctac gcaaaatgac     960
aacatgctta caagttatta tcatcttaaa gttagactca tcttctcaag cataagagct    1020
ttatggtgca aaaacaaata taatgacaag gcaaagatac atacatatta agagtatgga    1080
cagacatttc tttaacaaac tccatttgta ttactccaaa agcaccagaa gtttgtcatg    1140
gctgagtcat gaaatgtata gttcaatctt gcaaagttgc ctttcctttt gtactgtgtt    1200
ttaacactac aagccatata ttgtctgtac gtgcaacaaa ctatatcacc atgtatccca    1260
agatgctttt ttattgctat ataaactagc ttggtctgtc tttgaactca catcaattag    1320
cttaagtttc cataagcaag tacaaatagc t                                   1351
```

<210> SEQ ID NO 49
<211> LENGTH: 852
<212> TYPE: DNA
<213> ORGANISM: Unknown
<220> FEATURE:
<223> OTHER INFORMATION: CaMV 35S gene promoter

<400> SEQUENCE: 49

```
ccccagatta gccttttcaa tttcagaaag aatgctaacc cacagatggt tagagaggct      60
tacgcagcag gtctcatcaa gacgatctac ccgagcaata atctccagga aatcaaatac     120
cttcccaaga aggttaaaga tgcagtcaaa agattcagga ctaactgcat caagaacaca     180
gagaaagata tatttctcaa gatcagaagt actattccag tatggacgat tcaaggcttg     240
cttcacaaac caaggcaagt aatagagatt ggagtctcta aaaaggtagt tcccactgaa     300
tcaaaggcca tggagtcaaa gattcaaata gaggacctaa cagaactcgc cgtaaagact     360
ggcgaacagt tcatacagag tctcttacga ctcaatgaca agaagaaaat cttcgtcaac     420
atggtggagc acgacacact tgtctactcc aaaaatatca aagatacagt ctcagaagac     480
caaagggcaa ttgagacttt tcaacaaagg gtaatatccg gaaacctcct cggattccat     540
tgcccagcta tctgtcactt tattgtgaag atagtggaaa aggaaggtgg ctcctacaaa     600
tgccatcatt gcgataaagg aaaggccatc gttgaagatg cctctgccga cagtggtccc     660
```

```
aaagatggac ccccacccac gaggagcatc gtggaaaaag aagacgttcc aaccacgtct      720
tcaaagcaag tggattgatg tgatatctcc actgacgtaa gggatgacgc acaatcccac      780
tatccttcgc aagacccttc ctctatataa ggaagttcat ttcatttgga gagaacacgg      840
gggactgtcg ag                                                          852

<210> SEQ ID NO 50
<211> LENGTH: 1047
<212> TYPE: DNA
<213> ORGANISM: Artificial Sequence
<220> FEATURE:
<223> OTHER INFORMATION: recombinant construct

<400> SEQUENCE: 50
actagacggt cggcatctac tctattcctt tgccctcgga cgagtgctgg ggcgtcggtt       60
tccactatcg gcgagtactt ctacacagcc atcggtccag acggccgcgc ttctgcgggc      120
gatttgtgta cgcccgacag tcccggctcc ggatcggacg attgcgtcgc atcgaccctg      180
cgcccaagct gcatcatcga aattgccgtc aaccaagctc tgatagagtt ggtcaagacc      240
aatgcggagc atatacgccc ggagccgcgg cgatcctgca agctccggat gcctccgctc      300
gaagtagcgc gtctgctgct ccatacaagc caaccacggc ctccagaaga agatgttggc      360
gacctcgtat tgggaatccc cgaacatcgc ctcgctccag tcaatgaccg ctgttatgcg      420
gccattgtcc gtcaggacat tgttggagcc gaaatccgcg tgcacgaggt gccggacttc      480
ggggcagtcc tcggcccaaa gcatcagctc atcgagagcc tgcgcgacgg acgcactgac      540
ggtgtcgtcc atcacagttt gccagtgata cacatgggga tcagcaatcg cgcatatgaa      600
atcacgccat gtagtgtatt gaccgattcc ttgcggtccg aatgggccga acccgctcgt      660
ctggctaaga tcgccgcag cgatcgcatc catgacctcc gcgaccggct gaagaacagc      720
gggcagttcg gtttcaggca ggtcttgcaa cgtgacaccc tgtgcacggc gggagatgca      780
ataggtcagg ctctcgctga actcccaat gtcaagcact tccggaatcg ggagcgcggc      840
cgatgcaaag tgccgataaa cataacgatc tttgtagaaa ccatcggcgc agctatttac      900
ccgcaggaca tatccacgcc ctcctacatc gaagctgaaa gcacgagatt cttcgccctc      960
cgagagctgc atcaggtcgg agacgctgtc gaacttttcg atcagaaact tctcgacaga     1020
cgtcgcggtg agttcaggct ttttcat                                         1047

<210> SEQ ID NO 51
<211> LENGTH: 67
<212> TYPE: DNA
<213> ORGANISM: Artificial Sequence
<220> FEATURE:
<223> OTHER INFORMATION: recombinant construct

<400> SEQUENCE: 51
aatgaagatc attttcgtat ttgctctcct tgctattgtt gcatgcaacg cttctgcacg       60
gtttgat                                                                67

<210> SEQ ID NO 52
<211> LENGTH: 15
<212> TYPE: DNA
<213> ORGANISM: Artificial Sequence
<220> FEATURE:
<223> OTHER INFORMATION: recombinant construct
```

<400> SEQUENCE: 52

| atgaagatca ttttc | 15 |

<210> SEQ ID NO 53
<211> LENGTH: 15
<212> TYPE: DNA
<213> ORGANISM: Artificial Sequence
<220> FEATURE:
<223> OTHER INFORMATION: recombinant construct

<400> SEQUENCE: 53

| ggatcccggg gtacc | 15 |

<210> SEQ ID NO 54
<211> LENGTH: 1047
<212> TYPE: DNA
<213> ORGANISM: Unknown
<220> FEATURE:
<223> OTHER INFORMATION: hygromycin phosphotransferase gene

<400> SEQUENCE: 54

| atgaaaaagc ctgaactcac cgcgacgtct gtcgagaagt ttctgatcga aaagttcgac | 60 |
| agcgtctccg acctgatgca gctctcggag ggcgaagaat ctcgtgcttt cagcttcgat | 120 |
| gtaggagggc gtggatatgt cctgcgggta aatagctgcg ccgatggttt ctacaaagat | 180 |
| cgttatgttt atcggcactt tgcatcggcc gcgctcccga ttccggaagt gcttgacatt | 240 |
| ggggagttca gcgagagcct gacctattgc atctcccgcc gtgcacaggg tgtcacgttg | 300 |
| caagacctgc ctgaaaccga actgcccgct gttcttcagc cggtcgcgga ggtcatggat | 360 |
| gcgatcgctg cggccgatct tagccagacg agcgggttcg gcccattcgg accgcaagga | 420 |
| atcggtcaat acactacatg gcgtgatttc atatgcgcga ttgctgatcc ccatgtgtat | 480 |
| cactggcaaa ctgtgatgga cgacaccgtc agtgcgtccg tcgcgcaggc tctcgatgag | 540 |
| ctgatgcttt gggccgagga ctgccccgaa gtccggcacc tcgtgcacgc ggatttcggc | 600 |
| tccaacaatg tcctgacgga caatggccgc ataacagcgg tcattgactg gagcgaggcg | 660 |
| atgttcgggg attcccaata cgaggtcgcc aacatcttct tctggaggcc gtggttggct | 720 |
| tgtatggagc agcagacgcg ctacttcgag cggaggcatc cggagcttgc aggatcgccg | 780 |
| cggctccggg cgtatatgct ccgcattggt cttgaccaac tctatcagag cttggttgac | 840 |
| ggcaatttcg atgatgcagc ttgggcgcag gtcgatgcg acgcaatcgt ccgatccgga | 900 |
| gccgggactg tcgggcgtac acaaatcgcc cgcagaagcg cggccgtctg gaccgatggc | 960 |
| tgtgtagaag tactcgccga tagtggaaac cgacgcccca gcactcgtcc gagggcaaag | 1020 |
| gaatagagta gatgccgacc gtctagt | 1047 |

<210> SEQ ID NO 55
<211> LENGTH: 265
<212> TYPE: DNA
<213> ORGANISM: Unknown
<220> FEATURE:
<223> OTHER INFORMATION: Nos terminator

<400> SEQUENCE: 55

| gaatttcccc gatcgttcaa acatttggca ataaagtttc ttaagattga atcctgttgc | 60 |
| cggtcttgcg atgattatca tataatttct gttgaattac gttaagcatg taataattaa | 120 |
| catgtaatgc atgacgttat ttatgagatg ggtttttatg attagagtcc gcaattata | 180 |

```
catttaatac gcgatagaaa acaaaatata gcgcgcaaac taggataaat tatcgcgcgc    240
ggtgtcatct atgttactag atcgg                                          265
```

<210> SEQ ID NO 56
<211> LENGTH: 341
<212> TYPE: PRT
<213> ORGANISM: Artificial Sequence
<220> FEATURE:
<223> OTHER INFORMATION: recombinant construct HPT

<400> SEQUENCE: 56

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Val Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340
```

<210> SEQ ID NO 57
<211> LENGTH: 2158
<212> TYPE: DNA
<213> ORGANISM: Artificial Sequence
<220> FEATURE:
<223> OTHER INFORMATION: recombinant construct CAMV35S-Modified HPT-NOS

<400> SEQUENCE: 57

| | | | | |
|---|---|---|---|---|
| ccccagatta | gccttttcaa | tttcagaaag | aatgctaacc | cacagatggt | tagagaggct | 60 |
| tacgcagcag | gtctcatcaa | gacgatctac | ccgagcaata | atctccagga | aatcaaatac | 120 |
| cttcccaaga | aggttaaaga | tgcagtcaaa | agattcagga | ctaactgcat | caagaacaca | 180 |
| gagaaagata | tatttctcaa | gatcagaagt | actattccag | tatggacgat | tcaaggcttg | 240 |
| cttcacaaac | caaggcaagt | aatagagatt | ggagtctcta | aaaaggtagt | tcccactgaa | 300 |
| tcaaaggcca | tggagtcaaa | gattcaaata | gaggacctaa | cagaactcgc | cgtaaagact | 360 |
| ggcgaacagt | tcatacagag | tctcttacga | ctcaatgaca | agaagaaaat | cttcgtcaac | 420 |
| atggtggagc | acgacacact | tgtctactcc | aaaaatatca | aagatacagt | ctcagaagac | 480 |
| caaagggcaa | ttgagacttt | tcaacaaagg | gtaatatccg | gaaacctcct | cggattccat | 540 |
| tgcccagcta | tctgtcactt | tattgtgaag | atagtggaaa | aggaaggtgg | ctcctacaaa | 600 |
| tgccatcatt | gcgataaagg | aaaggccatc | gttgaagatg | cctctgccga | cagtggtccc | 660 |
| aaagatggac | ccccacccac | gaggagcatc | gtggaaaaag | aagacgttcc | aaccacgtct | 720 |
| tcaaagcaag | tggattgatg | tgatatctcc | actgacgtaa | gggatgacgc | acaatcccac | 780 |
| tatccttcgc | aagacccttc | ctctatataa | ggaagttcat | ttcatttgga | gagaacacgg | 840 |
| gggactgtcg | agatgaaaaa | gcctgaactc | accgcgacgt | ctgtcgagaa | gtttctgatc | 900 |
| gaaaagttcg | acagcgtctc | cgacctgatg | cagctctcgg | agggcgaaga | atctcgtgct | 960 |
| ttcagcttcg | atgtaggagg | gcgtggatat | gtcctgcggg | taaatagctg | cgccgatggt | 1020 |
| ttctacaaag | atcgttatgt | ttatcggcac | tttgcatcgg | ccgcgctccc | gattccggaa | 1080 |
| gtgcttgaca | ttggggagtt | cagcgagagc | ctgacctatt | gcatctcccg | ccgtgcacag | 1140 |
| ggtgtcacgt | tgcaagacct | gcctgaaacc | gaactgcccg | ctgttcttca | gccggtcgcg | 1200 |
| gaggtcatgg | atgcgatcgc | tgcggccgat | cttagccaga | cgagcgggtt | cggcccattc | 1260 |
| ggaccgcaag | gaatcggtca | atacactaca | tggcgtgatt | tcatatgcgc | gattgctgat | 1320 |
| ccccatgtgt | atcactggca | aactgtgatg | gacgacaccg | tcagtgcgtc | cgtcgcgcag | 1380 |
| gctctcgatg | agctgatgct | ttgggccgag | gactgccccg | aagtccggca | cctcgtgcac | 1440 |
| gcggatttcg | gctccaacaa | tgtcctgacg | gacaatggcc | gcataacagc | ggtcattgac | 1500 |
| tggagcgagg | cgatgttcgg | ggattcccaa | tacgaggtcg | ccaacatctt | cttctggagg | 1560 |
| ccgtggttgg | cttgtatgga | gcagcagacg | cgctacttcg | agcggaggca | tccggagctt | 1620 |
| gcaggatcgc | cgcggctccg | ggcgtatatg | ctccgcattg | gtcttgacca | actctatcag | 1680 |
| agcttggttg | acggcaattt | cgatgatgca | gcttgggcgc | agggtcgatg | cgacgcaatc | 1740 |
| gtccgatccg | gagccgggac | tgtcgggcgt | acacaaatcg | cccgcagaag | cgcggccgtc | 1800 |
| tggaccgatg | gctgtgtaga | agtactcgcc | gatagtggaa | accgacgccc | cagcactcgt | 1860 |
| ccgagggcaa | aggaatagag | tagatgccga | ccgtctagtg | aatttcccg | atcgttcaaa | 1920 |
| catttggcaa | taaagtttct | taagattgaa | tcctgttgcc | ggtcttgcga | tgattatcat | 1980 |
| ataatttctg | ttgaattacg | ttaagcatgt | aataattaac | atgtaatgca | tgacgttatt | 2040 |

-continued

```
tatgagatgg gttttttatga ttagagtccc gcaattatac atttaatacg cgatagaaaa    2100
caaaatatag cgcgcaaact aggataaatt atcgcgcgcg gtgtcatcta tgttacta       2158
```

<210> SEQ ID NO 58
<211> LENGTH: 1757
<212> TYPE: DNA
<213> ORGANISM: Artificial Sequence
<220> FEATURE:
<223> OTHER INFORMATION: Synthetic promoter sequence

<400> SEQUENCE: 58

```
ctgatgatta ttttgttgat catgattttc ttttggctat ttgattttt  gaaagatatt      60
tttttccctg ggaagacacc tatgggacga agatattatg tttcttatat agcaccaaac    120
aaatttaata tatatatata tatatatata tatatatata tatatatata tatatatata    180
tatatatata tatatatata tatatatata tatcacatca gtctctgcac aaagtgcatc    240
ctgggctgct tcaattataa agccccattc accacatttg ctagatagtc gaaaagcacc    300
atcaatattg agcttcaggt atttttggtt gtgttgtggt tggattgatt ctaatatata    360
ccaaatcaat ataattcact accaaaatat accatagcca tcacaacttt attaattttg    420
gtagcttaag atggtatata taataaccaa ttaacaactg attctaattt tactacggcc    480
cagtatgtac caatacaaaa caacgagtat gtttttcttcc atcgtaatcg tacacagtac    540
aaaaaaacct ggccagcctt tcttgggctg gggctctctt tcgaaaggtc acaaaacgta    600
cacggcagta acgccgcttc gctgcgtgtt aacggccacc aacccgccg  tgagcaaacg    660
gcatcagctt ccacctcct  cgatatctcc gcggcgccgt ctggacccgc ccccttccg     720
ttcctttctt tccttctcgc gtttgcgtgg tggggacgga ctccccaaac cgcctctccc    780
tctctccttt ctttatttgt ctatattctc actgggcccc acccaccgca cccctgggcc    840
cactcacgag tccccccctc cccacctata aataccccac cccctcctcg cctcttcctc    900
cgtcaatcga accccaaaat cgcagagaaa aaaaaatctc ccctcgaagc gaagcgtcga    960
atcgccttct caaggtatgc gatttctga  tcctctccgt tcctcgcgtt tgatttgatt   1020
tcccggcctg ttcgtgattg tgagatgttg tggttagtct ccgttttgcg atctgtggta   1080
gatttgaaca ggtttagatg gggttcgcgt ggtatgctgg atctgtgatt atgagcgatg   1140
ctgttcgtgg tccaagtatt gattggttcg gatctagtag tagaactgtg ctagggttgt   1200
gattcgttcc gatctgttca attagtagga tttagtctct gtttttctcg ttgatccaag   1260
tagcagcttc aggtatattt tgcttaggtt gttttttgatt cagtccctct agttgcatag   1320
attctactct gttcatgttt aatctaaggg ctgcgtcttg ttgattagtg attacatagc   1380
atagctttca ggatattta  cttgcttatg cctatcttat caactgttgc acctgtaaat   1440
tctagcctat gttataacct gccttatgtg ctctcgggat agtgctagta gttattgaat   1500
cagtttgccg atggatttct agtagttcat agacctgcat attattttg  tgaacacgag   1560
cacggtgcgt ctctctatttt tgttaggtca ctgttggtgt tgataggtac actgatgtta   1620
ttgtggttta ggtcgtgtat ctaacatatt ggaataattt gattgactga tttctgctgt   1680
acttgcttgg tattgttata atttcatgtt catagttgct gaccatgctt cggtaattgt   1740
gtgtgcagat ctctaga                                                   1757
```

<210> SEQ ID NO 59
<211> LENGTH: 926
<212> TYPE: DNA
<213> ORGANISM: Unknown

<220> FEATURE:
<223> OTHER INFORMATION: GUS gene partial fragment

<400> SEQUENCE: 59

```
gatatctacc cgcttcgcgt cggcatccgg tcagtggcag tgaagggcga acagttcctg      60
attaaccaca aaccgttcta ctttactggc tttggtcgtc atgaagatgc ggacttacgt     120
ggcaaaggat tcgataacgt gctgatggtg cacgaccacg cattaatgga ctggattggg     180
gccaactcct accgtacctc gcattaccct tacgctgaag agatgctcga ctgggcagat     240
gaacatggca tcgtggtgat tgatgaaact gctgctgtcg gctttaacct ctctttaggc     300
attggtttcg aagcgggcaa caagccgaaa gaactgtaca gcgaagaggc agtcaacggg     360
gaaactcagc aagcgcactt acaggcgatt aaagagctga tagcgcgtga caaaaaccac     420
ccaagcgtgg tgatgtggag tattgccaac gaaccggata cccgtccgca agtgcacggg     480
aatatttcgc cactggcgga agcaacgcgt aaactcgacc cgacgcgtcc gatcaccctg     540
gtcaatgtaa tgttctgcga cgctcacacc gataccatca gcgatctctt tgatgtgctg     600
tgcctgaacc gttattacgg atggtatgtc caaagcggcg atttggaaac ggcagagaag     660
gtactggaaa aagaacttct ggcctggcag agaaactgc atcagccgat tatcatcacc     720
gaatacggcg tggatacgtt agccgggctg cactcaatgt acaccgacat gtggagtgaa     780
gagtatcagt gtgcatggct ggatatgtat caccgcgtct tgatcgcgt cagcgccgtc     840
gtcggtgaac aggtatggaa tttcgccgat tttgcgacct cgcaaggcat attgcgcgtt     900
ggcggtaaca agaaagggat cttcac                                          926
```

<210> SEQ ID NO 60
<211> LENGTH: 1198
<212> TYPE: DNA
<213> ORGANISM: Oryza sativa

<400> SEQUENCE: 60

```
cctctagctc atggcttgaa tgtgtgagaa tcatagatta tttatttcta atctataaca      60
tgatggcttt agtctaaaat gatcacccta attctaatgc ggaattggat aatggacggt     120
gttttgttga cagacatgga gatgttgttg atgctatgaa tagtcgatag ttttaagttg     180
gttatttaat ttggatatag actgacaaat gattatattc ttctaattga ttaaattcta     240
cttttggatg gttgatagga ttatttacaa gttattggaa gaacttgcag catgtggggt     300
atatggttat actacgtgac atatattcat gagtggagtt cagagttttg gcttgtctcc     360
aggcatacat ataacctaggc acaagtccag cgcaaaagca tacaaggaag atcataacaa     420
catgtttccc cttctctgga aaattttgtt ggcaacagat gccttctcct tctttcagct     480
tctgcttctt tagtcagttt ggaggaagca gcaaatagtt gatgatatga aatcctcta      540
catcggctag gtgtaccaca cgactttatt attattatta ttattattat tattatttta     600
caaaatataa atagatcagt ccctcaccaa caagtagagc aagttggtga ttattgtaa     660
agttctacaa agctaattta aaagttattg cattaactta tttcatatta caaacaagag     720
tgtcaatgga acaatgaaaa ccatatgaca tactataatt ttgtttttat tattgaaatt     780
atataattca aagagaataa atccacatag ccgtaaagtt ctacatgtgg tgcattacca     840
aaatatatat agcttacaaa acatgacaag cttagtttga aaattgcaa tccttatcac      900
attgacacat aaagtgagtg atgagtcata atattatttt tcttgctacc catcatgtat     960
atatgatagc cacaaagtta ctttgatgat gataccaaag aacatttta ggtgcaccta    1020
```

| acagaatatc caaataatat gactcactta gatcataata gagcatcaag taaaactaac | 1080 |
| actctaaagc aaccgatggg aaagcatcta taaatagaca agcacaatga aaatcctcat | 1140 |
| catccttcac cacaattcaa atattatagt tgaagcatag tagtagaatc caacaaca | 1198 |

<210> SEQ ID NO 61
<211> LENGTH: 163
<212> TYPE: DNA
<213> ORGANISM: Oryza sativa
<220> FEATURE:
<223> OTHER INFORMATION: 10kDa prolamin terminator

<400> SEQUENCE: 61

| tcaaacgttg gttacatgta ctctagtaat aaggtgttgc atactatcgt gtgcaaacac | 60 |
| tagaaataag aaccattgaa taaaatatca atcattttca gacttgcaaa tattgggtat | 120 |
| ttggatttct gtcccatgtc cctcttgaaa gccatgctgt aca | 163 |

<210> SEQ ID NO 62
<211> LENGTH: 984
<212> TYPE: DNA
<213> ORGANISM: Oryza sativa
<220> FEATURE:
<223> OTHER INFORMATION: GLUTELIN-A3 promoter

<400> SEQUENCE: 62

| agaagaaaga taaataaccg aaactatttg gagagcattc aggttacatg gttagtccat | 60 |
| ggtgctagat attgctatat aatactcaat gcaatgctca atagatataa gtttcaaagc | 120 |
| tgtataagaa ttttaggtta gtgtgcaatg taagtgtagc ttcttatagc ttagtgcttt | 180 |
| actatcttca caagcacatg ctatagtatt gttccaagat gaaagaataa ttcatccttg | 240 |
| ctaccaactt gcatgatatt atatttgtga atatcctatc tcttggctta taatgaaatg | 300 |
| tgctgctggg ttatacctga ccatggtatt tgagagacct ttgtatagct gaaaccaacg | 360 |
| tatatgcgag catggaacaa gagaacaaaa tgcaaggatt tttttatact ggttcatgcc | 420 |
| cctggatggg ttaatatcgt gatcatcaaa aaagatatgc ataaaattaa agtaataaat | 480 |
| ttgctcataa gaaaccaaaa ccaaaagcac atatgtccta acaaactgc attttgtttg | 540 |
| tcatgtagca atacaagaga taatatatga cgtggttatg acttattcac ttttttgtgac | 600 |
| tccaaaatgt agtaggtcta actgattgtt taaagtgatg tgcttactgt agaagtttca | 660 |
| tcccaaaagc aatcactaaa gcaacacaca acgtatagtc caccttgcac gtaattcttt | 720 |
| gtggaagata acaagaaggc tcactgaaaa ataaaagcaa agaaaggat atcaaacaga | 780 |
| ccattgtgta tcccattgat acttgtatgt ctatttatct atccacctt tgtgtaccctt | 840 |
| acttctatct agtgagtcac ttcatatgtg gacattaaca aactctatct taacatctag | 900 |
| tcgatcacta ctttacttca ctataaaagg accaacatat atcaccatttt ctcacaaaag | 960 |
| cattgagttc agtcccacaa aaac | 984 |

<210> SEQ ID NO 63
<211> LENGTH: 30
<212> TYPE: DNA
<213> ORGANISM: Artificial Sequence
<220> FEATURE:
<223> OTHER INFORMATION: recombinant construct

<400> SEQUENCE: 63

| atgaagatca ttttcgtatt tgctctcctt | 30 |

<210> SEQ ID NO 64
<211> LENGTH: 45
<212> TYPE: DNA
<213> ORGANISM: Artificial Sequence
<220> FEATURE:
<223> OTHER INFORMATION: recombinant construct

<400> SEQUENCE: 64
atgaagatca ttttcgtatt tgctctcctt gctattgttg catgc                45

<210> SEQ ID NO 65
<211> LENGTH: 30
<212> TYPE: DNA
<213> ORGANISM: Artificial Sequence
<220> FEATURE:
<223> OTHER INFORMATION: recombinant construct

<400> SEQUENCE: 65
caaagttata gacaatatca actacaatcg                30

<210> SEQ ID NO 66
<211> LENGTH: 15
<212> TYPE: DNA
<213> ORGANISM: Artificial Sequence
<220> FEATURE:
<223> OTHER INFORMATION: recombinant construct

<400> SEQUENCE: 66
gagttcgtaa ttcaa                15

<210> SEQ ID NO 67
<211> LENGTH: 45
<212> TYPE: DNA
<213> ORGANISM: Artificial Sequence
<220> FEATURE:
<223> OTHER INFORMATION: recombinant construct

<400> SEQUENCE: 67
gagttcgtaa ttcaacagca tagcatagtg gcaaccccct tctgg                45

<210> SEQ ID NO 68
<211> LENGTH: 45
<212> TYPE: DNA
<213> ORGANISM: Artificial Sequence
<220> FEATURE:
<223> OTHER INFORMATION: recombinant construct

<400> SEQUENCE: 68
caacaatctc actaccaggc cattagtagc gttcaggcga ttgtg                45

<210> SEQ ID NO 69
<211> LENGTH: 15
<212> TYPE: DNA
<213> ORGANISM: Artificial Sequence
<220> FEATURE:
<223> OTHER INFORMATION: recombinant construct

<400> SEQUENCE: 69
gctcaagctc aagct                15

<210> SEQ ID NO 70
<211> LENGTH: 30
<212> TYPE: DNA
<213> ORGANISM: Artificial Sequence
<220> FEATURE:
<223> OTHER INFORMATION: recombinant construct

```
<400> SEQUENCE: 70
tactttgatc agactcaagc tcaagctcaa                                       30

<210> SEQ ID NO 71
<211> LENGTH: 16
<212> TYPE: DNA
<213> ORGANISM: Artificial Sequence
<220> FEATURE:
<223> OTHER INFORMATION: recombinant construct

<400> SEQUENCE: 71
tgcagcagca gtgttg                                                      16

<210> SEQ ID NO 72
<211> LENGTH: 23
<212> TYPE: DNA
<213> ORGANISM: Artificial Sequence
<220> FEATURE:
<223> OTHER INFORMATION: recombinant construct

<400> SEQUENCE: 72
tgcagcagca gtgttgccaa cag                                              23

<210> SEQ ID NO 73
<211> LENGTH: 22
<212> TYPE: PRT
<213> ORGANISM: Artificial Sequence
<220> FEATURE:
<223> OTHER INFORMATION: recombinant construct

<400> SEQUENCE: 73

Met Lys Ile Ile Phe Val Phe Ala Leu Leu Ala Ile Val Ala Cys Asn
1               5                   10                  15

Ala Ser Ala Arg Phe Asp
            20

<210> SEQ ID NO 74
<211> LENGTH: 5
<212> TYPE: PRT
<213> ORGANISM: Artificial Sequence
<220> FEATURE:
<223> OTHER INFORMATION: recombinant construct

<400> SEQUENCE: 74

Met Lys Ile Ile Phe
1               5

<210> SEQ ID NO 75
<211> LENGTH: 10
<212> TYPE: PRT
<213> ORGANISM: Artificial Sequence
<220> FEATURE:
<223> OTHER INFORMATION: recombinant construct

<400> SEQUENCE: 75

Met Lys Ile Ile Phe Val Phe Ala Leu Leu
1               5                   10

<210> SEQ ID NO 76
<211> LENGTH: 14
<212> TYPE: PRT
<213> ORGANISM: Artificial Sequence
<220> FEATURE:
<223> OTHER INFORMATION: recombinant construct
```

```
<400> SEQUENCE: 76

Met Lys Ile Ile Phe Val Phe Ala Leu Leu Ala Ile Val Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: recombinant construct

<400> SEQUENCE: 77

Gln Ser Tyr Arg Gln Tyr Gln Leu Gln Ser
1               5                   10

<210> SEQ ID NO 78
<211> LENGTH: 5
<212> TYPE: PRT
<213> ORGANISM: Artificial Sequence
<220> FEATURE:
<223> OTHER INFORMATION: recombinant construct

<400> SEQUENCE: 78

Glu Phe Val Arg Gln
1               5

<210> SEQ ID NO 79
<211> LENGTH: 15
<212> TYPE: PRT
<213> ORGANISM: Artificial Sequence
<220> FEATURE:
<223> OTHER INFORMATION: recombinant construct

<400> SEQUENCE: 79

Glu Phe Val Arg Gln Gln His Ser Ile Val Ala Thr Pro Phe Trp
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: recombinant construct

<400> SEQUENCE: 80

Gln Gln Ser His Tyr Gln Ala Ile Ser Ser Val Gln Ala Ile Val
1               5                   10                  15

<210> SEQ ID NO 81
<211> LENGTH: 5
<212> TYPE: PRT
<213> ORGANISM: Artificial Sequence
<220> FEATURE:
<223> OTHER INFORMATION: recombinant construct

<400> SEQUENCE: 81

Ala Gln Ala Gln Ala
1               5

<210> SEQ ID NO 82
<211> LENGTH: 10
<212> TYPE: PRT
<213> ORGANISM: Artificial Sequence
<220> FEATURE:
<223> OTHER INFORMATION: recombinant construct
```

```
<400> SEQUENCE: 82

Tyr Phe Asp Gln Thr Gln Ala Gln Ala Gln
1               5                   10

<210> SEQ ID NO 83
<211> LENGTH: 5
<212> TYPE: PRT
<213> ORGANISM: Artificial Sequence
<220> FEATURE:
<223> OTHER INFORMATION: recombinant construct

<400> SEQUENCE: 83

Gln Gln Gln Cys Cys
1               5

<210> SEQ ID NO 84
<211> LENGTH: 7
<212> TYPE: PRT
<213> ORGANISM: Artificial Sequence
<220> FEATURE:
<223> OTHER INFORMATION: recombinant construct

<400> SEQUENCE: 84

Gln Gln Gln Cys Cys Gln Gln
1               5

<210> SEQ ID NO 85
<211> LENGTH: 9
<212> TYPE: PRT
<213> ORGANISM: Artificial Sequence
<220> FEATURE:
<223> OTHER INFORMATION: recombinant construct

<400> SEQUENCE: 85

Glu Phe Val Arg Gln Gln Cys Ser Pro
1               5

<210> SEQ ID NO 86
<211> LENGTH: 11
<212> TYPE: PRT
<213> ORGANISM: Artificial Sequence
<220> FEATURE:
<223> OTHER INFORMATION: recombinant construct

<400> SEQUENCE: 86

Cys Gln Val Met Gln Gln Cys Cys Gln Gln
1               5                   10

<210> SEQ ID NO 87
<211> LENGTH: 6
<212> TYPE: PRT
<213> ORGANISM: Artificial Sequence
<220> FEATURE:
<223> OTHER INFORMATION: recombinant construct

<400> SEQUENCE: 87

Gln Gln Cys Cys Gln Gln
1               5

<210> SEQ ID NO 88
<211> LENGTH: 6
<212> TYPE: PRT
<213> ORGANISM: Artificial Sequence
<220> FEATURE:
<223> OTHER INFORMATION: recombinant construct
```

```
<400> SEQUENCE: 88

Glu Phe Val Arg Gln Gln
1               5

<210> SEQ ID NO 89
<211> LENGTH: 144
<212> TYPE: PRT
<213> ORGANISM: Oryza sativa
<220> FEATURE:
<223> OTHER INFORMATION: RM4

<400> SEQUENCE: 89

Met Lys Ile Ile Phe Val Phe Ala Leu Leu Ala Ile Ala Ala Cys Ser
1               5                   10                  15

Ala Ser Ala Gln Phe Asp Val Leu Gly Gln Ser Tyr Arg Gln Tyr Gln
            20                  25                  30

Leu Gln Ser Pro Val Leu Leu Gln Gln Val Leu Ser Pro Tyr Asn
        35                  40                  45

Glu Phe Val Arg Gln Gln Tyr Gly Ile Ala Ala Ser Pro Phe Leu Gln
    50                  55                  60

Ser Ala Ala Phe Gln Leu Gln Gln Leu Ala Leu Val Ala Gln Gln Ser
65                  70                  75                  80

His Tyr Gln Asp Ile Asn Ile Val Gln Ala Ile Ala Gln Gln Leu Gln
                85                  90                  95

Leu Gln Gln Phe Gly Asp Leu Tyr Phe Asp Arg Asn Leu Ala Gln Ala
            100                 105                 110

Gln Ala Leu Leu Ala Phe Asn Val Pro Ser Arg Tyr Gly Ile Tyr Pro
        115                 120                 125

Arg Tyr Tyr Gly Ala Pro Ser Thr Ile Thr Thr Leu Gly Gly Val Leu
    130                 135                 140

<210> SEQ ID NO 90
<211> LENGTH: 156
<212> TYPE: PRT
<213> ORGANISM: Oryza sativa
<220> FEATURE:
<223> OTHER INFORMATION: RM5

<400> SEQUENCE: 90

Met Lys Ile Ile Phe Val Phe Ala Leu Leu Ala Ile Val Ala Cys Asn
1               5                   10                  15

Ala Ser Ala Arg Phe Asp Ala Leu Ser Gln Ser Tyr Arg Gln Tyr Gln
            20                  25                  30

Leu Gln Ser His Leu Leu Leu Gln Gln Gln Val Leu Ser Pro Cys Ser
        35                  40                  45

Glu Phe Val Arg Gln Gln His Ser Ile Val Ala Thr Pro Phe Trp Gln
    50                  55                  60

Pro Ala Thr Phe Gln Leu Ile Asn Asn Gln Val Met Gln Gln Gln Cys
65                  70                  75                  80

Cys Gln Gln Leu Arg Leu Val Ala Gln Gln Ser His Tyr Gln Ala Ile
                85                  90                  95

Ser Ser Val Gln Ala Ile Val Gln Gln Leu Gln Leu Gln Gln Val Gly
            100                 105                 110

Val Val Tyr Phe Asp Gln Thr Gln Ala Gln Ala Gln Ala Leu Leu Ala
        115                 120                 125
```

Leu Asn Leu Pro Ser Ile Cys Gly Ile Tyr Pro Asn Tyr Tyr Ile Ala
    130                 135                 140

Pro Arg Ser Ile Pro Thr Val Gly Gly Val Trp Tyr
145                 150                 155

<210> SEQ ID NO 91
<211> LENGTH: 158
<212> TYPE: PRT
<213> ORGANISM: Oryza sativa
<220> FEATURE:
<223> OTHER INFORMATION: RM7

<400> SEQUENCE: 91

Met Lys Ile Ile Phe Val Phe Ala Leu Leu Ala Ile Val Ala Cys Asn
1               5                   10                  15

Arg Ser Ala Arg Phe Asp Pro Leu Ser Gln Ser Tyr Arg Gln Tyr Gln
            20                  25                  30

Leu Gln Ser His Leu Leu Gln Gln Gln Val Leu Ser Pro Cys Ser
        35                  40                  45

Glu Phe Val Arg Gln Gln Tyr Ser Ile Val Ala Thr Pro Phe Trp Gln
50                  55                  60

Pro Ala Thr Phe Gln Leu Ile Asn Asn Gln Val Met Gln Gln Gln Arg
65                  70                  75                  80

Met Cys Cys Gln Gln Leu Arg Leu Val Ala Gln Gln Ser His Tyr Gln
                85                  90                  95

Ala Ile Ser Ile Val Gln Ala Ile Val Gln Gln Leu Gln Leu Gln Gln
            100                 105                 110

Phe Ser Gly Val Tyr Phe Asp Gln Thr Gln Ala Gln Ala Gln Thr Leu
        115                 120                 125

Leu Thr Phe Asn Leu Pro Ser Ile Cys Gly Ile Tyr Pro Asn Tyr Tyr
    130                 135                 140

Ser Ala Pro Arg Ser Ile Ala Thr Val Gly Gly Val Trp Tyr
145                 150                 155

<210> SEQ ID NO 92
<211> LENGTH: 134
<212> TYPE: PRT
<213> ORGANISM: Oryza sativa
<220> FEATURE:
<223> OTHER INFORMATION: RM10

<400> SEQUENCE: 92

Met Ala Ala Tyr Thr Ser Lys Ile Phe Ala Leu Phe Ala Leu Ile Ala
1               5                   10                  15

Leu Ser Ala Ser Ala Thr Thr Ala Ile Thr Thr Met Gln Tyr Phe Pro
            20                  25                  30

Pro Thr Leu Ala Met Gly Thr Met Asp Pro Cys Arg Gln Tyr Met Met
        35                  40                  45

Gln Thr Leu Gly Met Gly Ser Ser Thr Ala Met Phe Met Ser Gln Pro
50                  55                  60

Met Ala Leu Leu Gln Gln Gln Cys Cys Met Gln Leu Gln Gly Met Met
65                  70                  75                  80

Pro Gln Cys His Cys Gly Thr Ser Cys Gln Met Met Gln Ser Met Gln
                85                  90                  95

Gln Val Ile Cys Ala Gly Leu Gly Gln Gln Gln Met Met Lys Met Ala
            100                 105                 110

```
Met Gln Met Pro Tyr Met Cys Asn Met Ala Pro Val Asn Phe Gln Leu
        115                 120                 125

Ser Ser Cys Gly Cys Cys
    130

<210> SEQ ID NO 93
<211> LENGTH: 149
<212> TYPE: PRT
<213> ORGANISM: Oryza sativa
<220> FEATURE:
<223> OTHER INFORMATION: RM16

<400> SEQUENCE: 93

Met Lys Ile Phe Val Ile Leu Ser Leu Leu Ala Leu Ala Ala Ser Ser
1               5                   10                  15

Ala Ser Ala Gln Phe Asp Ala Cys Thr Tyr Gly Gln Cys Gln Gln Gln
            20                  25                  30

Pro Phe Met Gln Pro Ile Met Asn Pro Cys Asn Glu Phe Val Arg Gln
        35                  40                  45

Gln Cys Ser Pro Met Ser Leu Pro Trp Lys Ser Arg Arg Leu Gln
    50                  55                  60

Leu Ser Ser Cys Gln Val Met Arg Gln Gln Cys Cys Gln Gln Met Arg
65                  70                  75                  80

Leu Met Ala Gln Gln Tyr His Cys Gln Ala Ile Cys Thr Met Val Gln
                85                  90                  95

Ser Ile Met Gln Gln Val Gln Phe Asp Ala Gly Phe Val Gly Glu Pro
            100                 105                 110

Gln Ala Gln Ala Gln Ala Gln Val Ala Leu Asn Leu Pro Ser Met Cys
        115                 120                 125

Gly Val Tyr Pro Arg Tyr Cys Ser Thr Pro Cys Lys Val Ala Thr Gly
    130                 135                 140

His Cys Gly Ser Trp
145

<210> SEQ ID NO 94
<211> LENGTH: 596
<212> TYPE: DNA
<213> ORGANISM: Oryza sativa
<220> FEATURE:
<223> OTHER INFORMATION: RM4

<400> SEQUENCE: 94
gcaaaataga aagatctagt gtcccgcagc aatgaagatc attttcgtct ttgctctcct      60
tgctattgct gcatgcagcg cctctgcgca gtttgatgtt ttaggtcaaa gttataggca     120
atatcagctg cagtcgcctg tcctgctaca gcaacaggtg cttagcccat ataatgagtt     180
cgtaaggcag cagtatggca tagcggcaag ccccttcttg caatcagctg cgtttcaact     240
gagaaacaac caagtctggc aacagctcgc gctggtggcg caacaatctc actatcagga     300
cattaacatt gttcaggcca tagcgcagca gctacaactc cagcagtttg gtgatctcta     360
ctttgatcgg aatctggctc aagctcaagc tctgttggct tttaacgtgc catctagata     420
tggtatctac cctaggtact atggtgcacc cagtaccatt accacccttg gcggtgtctt     480
gtaatgagtt ttaacagtat agtggttcgg aagttaaaaa taagctcaga tatcatatat     540
gtgacatgtg aaactttggg tgatataaat agaaaaaaag ttgtctttca tattta          596
```

```
<210> SEQ ID NO 95
<211> LENGTH: 597
<212> TYPE: DNA
<213> ORGANISM: Oryza sativa
<220> FEATURE:
<223> OTHER INFORMATION: RM5

<400> SEQUENCE: 95
caattcaaac attatagttg aagcatagta gtagaatcct acaaaaatga agatcatttt      60
cgtatttgct ctccttgcta ttgttgcatg caacgcttct gcacggtttg atgctcttag     120
tcaaagttat agacaatatc aactacaatg catctcctg ctacagcaac aagtgctcag      180
cccatgcagt gagttcgtaa ggcaacagca tagcatagtg gcaacccct tctggcaacc      240 agctacgttt caattgataa acaaccaagt catgcagcaa cagtgttgcc aacagctcag     300
gctggtagcg caacaatctc actaccaggc cattagtagc gttcaggcga ttgtgcagca     360
actacagctg cagcaggtcg gtgttgtcta ctttgatcag actcaagctc aagctcaagc     420
tttgctggcc ttaaacttgc catccatatg tggtatctat cctaactact acattgctcc     480
gaggagcatt cccaccgttg gtggtgtctg gtactgaatt gtaatagtat aatggttcaa     540
atgttaaaaa taaagtcatg catcatcatg cgtgacagtt gaaaaaaaaa aaaaaaa        597

<210> SEQ ID NO 96
<211> LENGTH: 609
<212> TYPE: DNA
<213> ORGANISM: Oryza sativa
<220> FEATURE:
<223> OTHER INFORMATION: RM7

<400> SEQUENCE: 96
gaagcatagt agtagaatcc aacaacaatg aagatcattt tcgtatttgc tctccttgct      60
attgttgcat gcaatcgctc tgcgcggttt gatcctctta gtcaaagtta taggcaatat     120
caactacagt cgcatctcct actacagcaa caagtgctca gcccatgcag tgagttcgta     180
aggcaacagt atagcatagt ggcaaccccc ttctggcaac cagctacgtt tcaattgata     240
aacaaccaag tcatgcagca gcagtgttgc caacagctca ggctggtagc acaacaatct     300
cactaccagg ccattagtat tgttcaagcg attgtgcaac agctacaact gcagcaattt     360
agtggtgtct actttgatca gactcaagct caagcccaaa ctctgttgac cttcaacttg     420
ccatccatat gtggtatcta ccctaactac tatagtgctc ccaggagcat tgccactgtt     480
ggtggtgtct ggtactgaat tgtaacaata taatagttcg tatgttaaaa ataaagtcat     540
acatcatcat gtgtgactgt tgaaacttag ggtcatataa atctaaataa aatcatctta     600
cctaaaaaa                                                              609

<210> SEQ ID NO 97
<211> LENGTH: 1002
<212> TYPE: DNA
<213> ORGANISM: Oryza sativa
<220> FEATURE:
<223> OTHER INFORMATION: intron sequence

<400> SEQUENCE: 97
tctagatcta agaatggtcc gtgccttaaa actttcccca accgtgctag tttatgttgt      60
gactgtctgc ctctctcagt ttacttggat gcattgacaa catcctttt tgctattact      120 cgtatttgct ctatagctgg tggcatatct catgttgaaa tttgcccttt taatccaaaa     180
ttggatgtaa ttgaaagaat cctacgtggt agttatttgg attttggtgt gaaaaaaaat     240
```

```
agccttgtta gaagaagcaa aattggattt agttaaaagg atactagatg gtgttatttg    300
gattttggtg caaatcaaat taggaggttg gtttttattca agttaaagtt tgttttaaaa    360
aaattctcct aaaagatag atactagatt tgcatatatg cattgaaaat tacatcttcg    420
cttggcggtt atactttag tccctctaaa ttgttcaatc atttatgatg aaaaggaaaa    480
tcatttata tcacaaagta tttatgatga aagggaaaa atattctgca tgggtttgaa    540
caaaatacgt ggattggtgt agccttaaca tacttgaaaa gggtatgatg ttgatgtagt    600
gcccacatgg tgtcgcttga cattaaaacg atatgcagtc aggattgagg aacattgctg    660
acaatttact atcgctgtct gtgttgacca caataattca gatgtaccat cctatcttct    720
aactagaaag atgcatggaa gtttcttaca ttatttccag cacttgaaat tttagtgaaa    780
tatcattaaa acataaccac ttactttgct gtgatatgaa ataaatgttt tatttcttgg    840
aaagtggtat attcatatat tcttacagta aatttattga ttttcttttc atttatttct    900
aaatttaac caccctttg gtagcttaag gaaaattgta tgtttgacag tcctgttttc    960
tgttgtttca tccctccagg aaaaccagct actagtggat cc                      1002
```

<210> SEQ ID NO 98
<211> LENGTH: 37
<212> TYPE: PRT
<213> ORGANISM: Oryza sativa

<400> SEQUENCE: 98

Gln Val Met Gln Gln Cys Cys Gln Gln Leu Arg Leu Val Ala Gln
1               5                   10                  15

Gln Ser His Tyr Gln Ala Ile Ser Ser Val Gln Ala Ile Val Gln Gln
            20                  25                  30

Leu Gln Leu Gln Gln
        35

<210> SEQ ID NO 99
<211> LENGTH: 34
<212> TYPE: PRT
<213> ORGANISM: Oryza sativa

<400> SEQUENCE: 99

Met Lys Ile Ile Phe Val Phe Ala Leu Leu Ala Ile Val Ala Cys Asn
1               5                   10                  15

Ala Ser Ala Arg Phe Asp Ala Leu Ser Gln Ser Tyr Arg Gln Tyr Gln
            20                  25                  30

Leu Gln

<210> SEQ ID NO 100
<211> LENGTH: 26
<212> TYPE: PRT
<213> ORGANISM: Oryza sativa

<400> SEQUENCE: 100

Glu Phe Val Arg Gln Gln His Ser Ile Val Ala Thr Pro Phe Trp Gln
1               5                   10                  15

Pro Ala Thr Phe Gln Leu Ile Asn Asn Gln
            20                  25

<210> SEQ ID NO 101
<211> LENGTH: 31
<212> TYPE: PRT
<213> ORGANISM: Oryza sativa

<400> SEQUENCE: 101

Tyr Phe Asp Gln Thr Gln Ala Gln Ala Gln Ala Leu Leu Ala Leu Asn
1               5                   10                  15

Leu Gln Ser Ile Cys Gly Ile Tyr Pro Asn Tyr Tyr Ile Ala Pro
            20                  25                  30

<210> SEQ ID NO 102
<211> LENGTH: 111
<212> TYPE: DNA
<213> ORGANISM: Oryza sativa
<220> FEATURE:
<221> NAME/KEY: CDS
<222> LOCATION: (1)..(111)
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (31)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (70)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (97)..(99)
<223> OTHER INFORMATION: n is a, c, g, or t
<220> FEATURE:
<221> NAME/KEY: misc_feature
<222> LOCATION: (103)..(105)
<223> OTHER INFORMATION: n is a, c, g, or t

<400> SEQUENCE: 102 car gtn atg car car car tgy tgy car car nnn nnn nnn gtn gcn car      48
Gln Val Met Gln Gln Gln Cys Cys Gln Gln Xaa Xaa Xaa Val Ala Gln
1               5                   10                  15 car nnn cay tay car gcn atg nnn nnn gtn car gcn atg gtn car car      96
Gln Xaa His Tyr Gln Ala Met Xaa Xaa Val Gln Ala Met Val Gln Gln
            20                  25                  30 nnn car nnn car car                                                  111
Xaa Gln Xaa Gln Gln
        35

```
<210> SEQ ID NO 103
<211> LENGTH: 102
<212> TYPE: DNA
<213> ORGANISM: Oryza sativa
<220> FEATURE:
<221> NAME/KEY: CDS
<222> LOCATION: (1)..(102)
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(54)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t
<220> FEATURE:
<221> NAME/KEY: misc_feature
<222> LOCATION: (69)..(75)
<223> OTHER INFORMATION: n is a, c, g, or t
<220> FEATURE:
<221> NAME/KEY: misc_feature
<222> LOCATION: (79)..(81)
<223> OTHER INFORMATION: n is a, c, g, or t
<220> FEATURE:
<221> NAME/KEY: misc_feature
<222> LOCATION: (85)..(87)
<223> OTHER INFORMATION: n is a, c, g, or t
<220> FEATURE:
<221> NAME/KEY: misc_feature
<222> LOCATION: (97)..(99)
<223> OTHER INFORMATION: n is a, c, g, or t

<400> SEQUENCE: 103 atg aar atg atg tty gtn tty gcn nnn nnn gcn atg gtn gcn tgy aay      48
Met Lys Met Met Phe Val Phe Ala Xaa Xaa Ala Met Val Ala Cys Asn
 1               5                  10                  15 gcn nnn gcn nnn tty gay gcn nnn nnn car nnn tay nnn car tay car      96
Ala Xaa Ala Xaa Phe Asp Ala Xaa Xaa Gln Xaa Tyr Xaa Gln Tyr Gln
             20                  25                  30 nnn car                                                              102
Xaa Gln <210> SEQ ID NO 104
<211> LENGTH: 78
<212> TYPE: DNA
<213> ORGANISM: Oryza sativa
<220> FEATURE:
<221> NAME/KEY: CDS
<222> LOCATION: (1)..(78)
<220> FEATURE:
<221> NAME/KEY: misc_feature
<222> LOCATION: (9)..(12)
<223> OTHER INFORMATION: n is a, c, g, or t
```

```
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (64)..(66)
<223> OTHER INFORMATION: n is a, c, g, or t

<400> SEQUENCE: 104 gar tty gtn nnn car car cay nnn atg gtn gcn acn ccn tty tgg car      48
Glu Phe Val Xaa Gln Gln His Xaa Met Val Ala Thr Pro Phe Trp Gln
1               5                   10                  15 ccn gcn acn tty car nnn atg aay aay car                              78
Pro Ala Thr Phe Gln Xaa Met Asn Asn Gln
            20                  25

<210> SEQ ID NO 105
<211> LENGTH: 93
<212> TYPE: DNA
<213> ORGANISM: Oryza sativa
<220> FEATURE:
<221> NAME/KEY: CDS
<222> LOCATION: (1)..(93)

<400> SEQUENCE: 105 tac ttt gat cag act caa gct caa gct caa gct ttg ctg gcc tta aac      48
Tyr Phe Asp Gln Thr Gln Ala Gln Ala Gln Ala Leu Leu Ala Leu Asn
1               5                   10                  15 ttg caa tcc ata tgt ggt atc tat cct aac tac tac att gct ccg          93
Leu Gln Ser Ile Cys Gly Ile Tyr Pro Asn Tyr Tyr Ile Ala Pro
            20                  25                  30

<210> SEQ ID NO 106
<211> LENGTH: 1426
<212> TYPE: DNA
<213> ORGANISM: Oryza sativa

<400> SEQUENCE: 106
ttagcattaa tatttataga gtgataaagt catactacaa taaatcctta tatattaatt    60
gggggtcata ctagaagccc catattaatc ctacgagagg tagaaaacta gaaattatcg   120
cactagtcaa gttgcacttg gcctagagtc tcaattgtag tataaatgat ataataattc   180
```

```
taaaattaaa attagcaaat aacaagttca attaggtttg aagccgtaat tctattttta      240
taatttaatc attcttaaat ttagaattac taaaaaataa ttattaatac agcgttgtac      300
ttgctgtaga gactcatata gttttttacga cgatttaata atttcaaaaa taaatacagg     360
aaattgctaa gtttgtaatc taaaatataa tattgtcata atataataat tctaaaattc     420
aaattaataa ataccaagtt gatgttttat ttaaaatata tagtatgtgc cgcacagctt     480
gatgcttagt ctagatcttt taaccgtgct acgctgggtt aattagcgat ggtgcaggtc     540
acgtacccaa atttcttcac tgttggatca actagagtag ttaaacgagg catgtgatg     600 aaggctagct atttgaaatt ttccaattat ccctgcataa gtcaggctac aatagcacct     660
ggactacatg cagggattac aaaataggtg gtaaccacat ttaccgcgtt aaccctatca     720
aattcaaata aattttaaaa gtaatttgat ttttttaata aattttgtat ggttctcaa     780 gctttatttt ggttaccgtg cttactgccg gaggcaatgg gaaaccctca ctagaagttg     840
cacctgttct tgtctgtgca ccatatcatg ttgaatcatg tgcgttgtgt cctttcggaa     900
gaaccgattt actacatgac tcatcaattc cactttacgt atcaaaaggt ttgttatggg     960
ggcaatgctt ttgtgaaatt aaattttat tttgcgtcac gttgtatcta gttaaacact    1020
acctacctac cattacaaaa cctcattcca caaaacgatg catctagata aaaaatatga    1080
catgtaaagt gagtaatgac tcatgtttat tatcaaaaat cgataacaat caaatgatat    1140
aggtagtaaa gtacctttga aatggcatgt ccaagtatgt gtagctccac ctagcacaat    1200
atcccaagtg atcatcataa aaggcataca aatacaagca gccgatgatg cacacaagaa    1260
acaacacaaa ttgcacaaaa ccaaaagcaa ccgatgcctt gagcatagag atcatgctat    1320
tcccactata aatacaaatg caccatatca agatgctcct cacccttact gaaaaatcac    1380
aaacatcaaa acgttataag agttctctag catccatcac atagcc                    1426

<210> SEQ ID NO 107
<211> LENGTH: 1008
<212> TYPE: DNA
<213> ORGANISM: Oryza sativa

<400> SEQUENCE: 107 gcccccgcc ggacctcccg tgcccgtggc gcctggaggg aggagagggg agagatggtg       60
agagaggagg aagaagagga ggggtgacaa tgatatgtgg gccatgtggc ccccaccatt     120
ttttaattca ttcttttgtt gaaactgaca tgtgggtccc atgagaatta ttattttcg     180 gatcgaattg ccacgtaagc gctacgtcaa tgctacgtca gatgaagacc gagtcaaatt    240
agccacgtaa gcgccacgtc agccaaaacc accatccaaa ccgccgaggg acctcatctg    300
cactggtttt gatagttgag ggaccegttg tatctggttt ttcgattgaa ggacgaaaat    360
caaatttgtt gacaagttaa gggaccttaa atgaacttat tccatttcaa aatattctgt    420
gagccatata tccgtgggct tccaatcctc tcaaattaa agggcctttt taaaatagat    480
aattgccttc tttcagtcac ccataaaagt acaaaactac taccaacaag caacatgcgc    540
agttacacac atttctgca catttccacc acgtcacaaa gagctaagag ttatccctag    600
gacaatctca ttagtgtaga tacatccatt aatctttat cagaggcaaa cgtaaagccg     660
ctctttatga caaaaatagg tgacacaaaa gtgttatctg ccacatacat aacttcagaa    720
attacccaac accaagagaa aaataaaaaa aaatcttttt gcaagctcca aatcttggaa    780
acctttttca ctcttgcag cattgtactc ttgctctttt tccaaccgat ccatgtcacc     840
ctcaagcttc tacttgatct acacgaagct caccgtgcac acaaccatgg ccacaaaaac    900
```

```
cctataaaac cccatccgat cgccatcatc tcatcatcag ttcatcacca acaaacaaaa    960
gaggaaaaaa aacatataca cttctagtga ttgtctgatt gatcatca                1008
```

<210> SEQ ID NO 108
<211> LENGTH: 72
<212> TYPE: DNA
<213> ORGANISM: Oryza sativa
<220> FEATURE:
<221> NAME/KEY: CDS
<222> LOCATION: (1)..(72)

<400> SEQUENCE: 108

```
atg gca gca tac acc agc aag atc ttt gcc ctg ttt gcc tta att gct    48
Met Ala Ala Tyr Thr Ser Lys Ile Phe Ala Leu Phe Ala Leu Ile Ala
1               5                   10                  15 ctt tct gca agt gcc act act gca                                    72
Leu Ser Ala Ser Ala Thr Thr Ala
            20
```

<210> SEQ ID NO 109
<211> LENGTH: 24
<212> TYPE: PRT
<213> ORGANISM: Oryza sativa

<400> SEQUENCE: 109

```
Met Ala Ala Tyr Thr Ser Lys Ile Phe Ala Leu Phe Ala Leu Ile Ala
1               5                   10                  15

Leu Ser Ala Ser Ala Thr Thr Ala
            20
```

<210> SEQ ID NO 110
<211> LENGTH: 66
<212> TYPE: DNA
<213> ORGANISM: Oryza sativa
<220> FEATURE:
<221> NAME/KEY: CDS
<222> LOCATION: (1)..(66)

<400> SEQUENCE: 110

```
atg aag atc att ttc gta ttt gct ctc ctt gct att gtt gca tgc aat    48
Met Lys Ile Ile Phe Val Phe Ala Leu Leu Ala Ile Val Ala Cys Asn
1               5                   10                  15 gct tct gca cgg ttt gat                                            66
Ala Ser Ala Arg Phe Asp
            20
```

<210> SEQ ID NO 111
<211> LENGTH: 22
<212> TYPE: PRT
<213> ORGANISM: Oryza sativa

<400> SEQUENCE: 111

```
Met Lys Ile Ile Phe Val Phe Ala Leu Leu Ala Ile Val Ala Cys Asn
1               5                   10                  15

Ala Ser Ala Arg Phe Asp
            20
```

<210> SEQ ID NO 112
<211> LENGTH: 57
<212> TYPE: DNA
<213> ORGANISM: Oryza sativa
<220> FEATURE:
<221> NAME/KEY: CDS
<222> LOCATION: (1)..(57)

-continued

```
<400> SEQUENCE: 112 atg aag atc ttt gtc atc ctc tct ctc ctc gcc ctc gca gcg agc agc    48
Met Lys Ile Phe Val Ile Leu Ser Leu Leu Ala Leu Ala Ala Ser Ser
1               5                   10                  15 gcc tcg gca                                                        57
Ala Ser Ala <210> SEQ ID NO 113
<211> LENGTH: 19
<212> TYPE: PRT
<213> ORGANISM: Oryza sativa

<400> SEQUENCE: 113

Met Lys Ile Phe Val Ile Leu Ser Leu Leu Ala Leu Ala Ala Ser Ser
1               5                   10                  15

Ala Ser Ala

<210> SEQ ID NO 114
<211> LENGTH: 72
<212> TYPE: DNA
<213> ORGANISM: Oryza sativa
<220> FEATURE:
<221> NAME/KEY: CDS
<222> LOCATION: (1)..(72)

<400> SEQUENCE: 114 atg gcg agt tcc gtt ttc tct cgg ttt tct ata tac ttt tgt gtt ctt    48
Met Ala Ser Ser Val Phe Ser Arg Phe Ser Ile Tyr Phe Cys Val Leu
1               5                   10                  15 cta tta tgc cat ggt tct atg gcc                                    72
Leu Leu Cys His Gly Ser Met Ala
            20

<210> SEQ ID NO 115
<211> LENGTH: 24
<212> TYPE: PRT
<213> ORGANISM: Oryza sativa

<400> SEQUENCE: 115

Met Ala Ser Ser Val Phe Ser Arg Phe Ser Ile Tyr Phe Cys Val Leu
1               5                   10                  15

Leu Leu Cys His Gly Ser Met Ala
            20

<210> SEQ ID NO 116
<211> LENGTH: 66
<212> TYPE: DNA
<213> ORGANISM: Oryza sativa
<220> FEATURE:
<221> NAME/KEY: CDS
<222> LOCATION: (1)..(66)

<400> SEQUENCE: 116 atg gct agc aag gtc gtc ttc ttc gcg gcg gcg ctc atg gcg gcc atg    48
Met Ala Ser Lys Val Val Phe Phe Ala Ala Ala Leu Met Ala Ala Met
1               5                   10                  15 gtg gcc atc tcc ggc gcg                                            66
Val Ala Ile Ser Gly Ala
            20

<210> SEQ ID NO 117
<211> LENGTH: 22
<212> TYPE: PRT
<213> ORGANISM: Oryza sativa
```

-continued

```
<400> SEQUENCE: 117

Met Ala Ser Lys Val Val Phe Phe Ala Ala Ala Leu Met Ala Ala Met
1               5                   10                  15

Val Ala Ile Ser Gly Ala
            20

<210> SEQ ID NO 118
<211> LENGTH: 8
<212> TYPE: PRT
<213> ORGANISM: Oryza sativa

<400> SEQUENCE: 118

Ser Arg Ala Met Val Ser Leu Gly
1               5

<210> SEQ ID NO 119
<211> LENGTH: 102
<212> TYPE: DNA
<213> ORGANISM: Artificial Sequence
<220> FEATURE:
<223> OTHER INFORMATION: recombinant construct

<400> SEQUENCE: 119
atggcagcat acaccagcaa gatctttgcc ctgtttgcct taattgctct ttctgcaagt        60
gccactactg catctagagc aatggtgagc aagggcgagg ag                         102
```

NUCLEIC ACID FOR REDUCING PROTEIN CONTENT IN RICE SEED

REFERENCE TO SEQUENCE LISTING, TABLE OR COMPUTER PROGRAM

A "Sequence Listing" is submitted with this application in the form of a text file, created 26 Aug. 2009, and named "591508035Seqlist.txt" (95,709 bytes), the contents of which are incorporated herein by reference in their entirety.

TECHNICAL FIELD

The present invention relates to functional modification of a plant. More specifically, the present invention is related to a method for reducing expression of a storage protein and for efficiently expressing a foreign protein, and an antisense construct, RNAi construct, composition, device therefor and the like. In another aspect, the present invention is related to a method for expressing a protein of interest instead of a native protein.

BACKGROUND ART

The functional improvement of plants including grains such as rice, has seen a significant development together with genetic engineering technology for plants. At first, improvements or plant breeding were directed to culture mainly targeting farmers, such as resistance against diseases, insects, herbicide and the like. Recently, targets have been changed to be directed to transformation of edible portions which can mainly appeal to consumers. Studies of expression in a plant of a variety foreign functional proteins, such as physiologically functional peptides and antibodies, have been performed worldwide, and in particular, seeds are of note as a producing machine of such a foreign functional protein, as seeds can preserve the protein for a long period of time in a stable manner (Japanese Laid-Open Publication No. 2002-58492; Molecular Breeding 9:149-158 (2002)). Further, studies for expression in seeds by the use of promoters have been reported (Plant Cell Physiol. 39:885-889 (1998)).

In grain seeds such as rice, the protein content thereof is said to be about several to about 10 percent, and most of the proteins are present as a storage protein. Storage proteins are believed to be a source for nitrogen nutrient in germination, but no physiological functions are believed to exist therein. Generally, proteins are classified into four categories depending on the solubility thereof, including glutelin, prolamin, globulin, and albumin. Types of storage proteins are unique for each protein species.

In seeds of Leguminosae plants, globulin is the major storage protein, whereas monocotyledonous seeds such as cereals, prolamin is the major storage protein with some exceptions (J. Exp. Botany 53:947-958 (2002)).

Rice exceptionally contains glutelin as a main storage protein amongst cereals, and the content thereof is 60-70% of the seed protein. The glutelin gene group consists of about ten genes per haploid genome, and these genes are classified into two subfamilies GluA and GluB, which have 60-65% homology at the amino acid level in the coding regions to each other. Further, each subfamily contains about five genes presenting 80% or greater homology in the amino acid level. Glutelin has evolutionary relationships with globulin of beans, a storage protein, and the amino acid composition thereof is relatively rich in essential amino acids and has high nutritional value. On the other hand, prolamin shares 20-30% of rice seed proteins, and thus the content thereof follows that of glutelin. Prolamin is characterized by a large amount of glutamin, and a relatively high content of proline. Prolamin is poor in lysine, an essential amino acid, and is poor in nutritive value. There are multiple genes for prolamins in the genome, with similar structures with slightly altered amino acid sequences, and it is estimated that the total number thereof is between 25 and 100. Another storage protein includes globulin having a molecular weight of 26 kDa, which shares sequence homologies at a few percent level of the storage proteins. In seeds, storage proteins are intracellularly accumulated in a granular cellular structure, called a protein body. If seeds are likened to a factory of protein production, the protein body plays a role as a protein warehouse. Rice is characterized in that two types of protein bodies co-exist in albumen, which have completely different origins and purpose, and are called, Protein Body 1 (in which prolamin is accumulated), and Protein Body 2 (in which glutelin and globulin are accumulated), respectively (Plant Cell Physiol. 28: 1517-1527 (1987); Plant Physiol. 88: 649-655 (1988); Plant Biotechnology, 16: 103-113 (1999); Jokyo (1993) 414-420; Inegakutaisei Vol 3., 32-39 (1990), and Inegakutaisei Vol. 3 317-325 (1990)).

An attempt to modify a storage protein has been made for a variety of cereals, and these attempts were mainly directed to improve nutritional value or processing characteristics. In the case of rice, low-protein content is preferred as raw material for sake production or rice processed foods, and extensive search has been conducted to find variant lineages with reduced main seed storage protein content or composition amongst rice variant pools which were subjected to radiation or mutagen treatment (Iida, S. et al. (1997) Theor. Appl. Genet. 94, 177-183; Iida, S. et al. (1993) Theor. Appl. Genet. 87, 374-378; Crop Sci. 39: 825-831 (1999); Ikushugaku Kenkyu 4 (Suppl. 1) 66 (2002); Ikushugaku zasshi 47 (Suppl. 2) 632 (1997); Ikushugaku Zasshi 47 (Suppl. 2) 176 (1997); Ikushugaku Zasshi 45 (Suppl. 2) 502 (1995); and Ikushugaku Zasshi 45 (Suppl. 1) 508 (1995)). To date, variant rice which lack specific glutelin gene or which shows reduced glutelin content have been subjected to extensive research, due to the fact that glutelin is the major storage protein of rice and the major target thereof. Typical low glutelin rice lineages include mutant LGC-1 and recombinant glutelin rice lineages by antisense technology as known in Japanese Patent No. 3149951; Ikushugaku Kenkyu 3 (2001) and Molecular Breeding 8: 273-284 (2001)). Amongst these, LGC-1 has been analyzed to prove that the causative gene of variation is dominantly inherited by one gene, and the gene has been recently isolated (The Plant Cell 15, 1455-1467, (2003)). The structure thereof lacks both terminator regions between two glutelin genes (GluB4 and GluB5) in the genome regions, which originally are to be transcribed to each other, thereby the transcription of GluB4 promoter was transcribed in an antisense direction beyond its original termination point to the GluB5 gene, resulting in double-stranded RNA formation of homologous regions of GluB4 and GluB5, and expression suppression of the entire storage protein glutelins by RNAi phenomenon. Mutations per se may be used for crossing or breeding species, and the variety per se or its progeny are registered as a novel plant variety (Nogyogijutsu 55 (10), 26-29 (2000) and Ikushugakukenkyu 4: 33-42 (2002)). The LGC-1 gene, however, is not recognized to have an optimum structure for suppressing glutelin expression, and thus LGC-1 still retains glutalin at about 30-50% of its original content. The present invention is significantly superior, in terms of technology, in that the RNAi phenomenon is used for suppressing expression of a storage protein by means of an optimum structure gene construct, whereby significant improvement in efficiency of expression inhibition has been achieved.

A common problem shared by low-glutelin rice lineages is that the glutelin content is significantly reduced compared to the original content, but a significant increase in prolamins has been observed. This is due to the regulatory machinery in plants to maintain protein content in the seed at a certain level, and a plant senses that the lack of glutelin to induce an increase in the prolamin synthesis. In this sense, low-glutelin lineages have not been fully successful in protein reduction, even with a variant rice in which storage protein composition has been altered.

On the other hand, prolamins are low in nutrition, have poor digestibility, and lower working characteristics or taste of rice, and thus are desired to be lowered. Although some rice variants are already known in the art (Iida, S. et al. (1997) Theor. Appl. Genet. 94, 177-183; Iida, S. et al. (1993) Theor. Appl. Genet. 87, 374-378; Ikushugaku kenkyu (Supple. 1) 66 (2002); Ikushugaku zasshi 47 (Suppl. 2) 632 (1997); Ikushugaku zasshi 47 (Supple. 2) 176 (1997); Ikushugaku zasshi 45 (Supple. 2) 502 (1995); and Ikushugaku zasshi 45 (Supple. 1) 508 (1995) 15~19), the degree of reduction in prolamins is small, or other variation had also occurred and thus the plants became infertile, and therefore selection of promising lineages has not yet been done. Therefore, there cannot be any clue to date to solve problems where prolamins are significantly increased which is accompanied by the reduction of a group of glutelin lineages. As such, development of low prolamin rice is a problem that has yet to be solved.

As mentioned in the introduction, research has focused using seed production machinery (bioreactor) for production of useful proteins. Seeds have been used throughout history as a food eaten by human beings. There is little risk in which toxic substances contaminate seeds, and also such seeds have merits in that they can be eaten without specific purification or operation. If seeds with reduced storage proteins are used, remaining amino acids are efficiently used for synthesizing foreign protein synthesis, and thus there is a possibility in which expression thereof increases. Even if storage proteins are reduced, and the same amount are replaced with useful proteins, function as a nitrogen source is fulfilled and thus it is believed that there is no problem in terms of seed physiology. It is therefore, contemplated that as, glutelin and prolamin are accumulated in separate granules in a strict manner in rice, and such machinery can be successfully used to increase expression of a useful protein by accumulating the protein into the protein body, or facilitating purification of a useful protein. For example, a signal sequence of the storage protein prolamin has high homology not only within the same species, but also between species, for example, wheat, barley or maize storage proteins, and thus these sequences may be used to accumulate proteins in Protein Body 1.

However, research to date in which a foreign protein is expressed in seeds for creating a functional crop (Japanese Laid-Open Publication No.: 2002-17187; Japanese Laid-Open Publication No.: 7-213185; and Japanese PCT National Phase Laid-Open Publication No.: 2001-518305; Ikushugaku kenkyu 5 (Suppln. 2), 294 (2003)), usually uses normal varieties for expression thereof. In such cases, most of amino acid pool in the seeds is consumed for rice storage protein synthesis, and thus the amount that can be used for useful protein production is very limited. As a result, useful protein expression level is limited and thus efficiency of functional modification is not good. Further, in the example where storage protein variant rice is used for foreign protein expression (Japanese Laid-Open Publication No.: 2002-58492), the total amount of seed protein of glutelin-reduced rice is equal to that in the original, and thus the problem of competition between useful protein and storage protein in the seeds is not solved.

As such, conventional technology is not recognized to use an efficient expression system for a foreign protein.

Low-protein rice is useful when rice is used for removing proteins thereof in any manner since it reduces labor-intensity for removing proteins. In general, rice as food or a raw material for rice-based processed food, low-protein rice would be preferable as a raw material for allergen-reduced food, which has become increasingly required in recent years ("Bioscience of seeds", Shushi Seirikagaku kenkyukai (Seed physiochemical research association) ed. Gakkai center 2., Rice, 251-257 (1995); ("Bioscience of seeds", Shushi Seirikagaku kenkyukai (Seed physiochemical research association) ed. Gakkai center 4, Processed food product of rice 359-365 (1995), and ("Bioscience of seeds", Shushi Seirikagaku kenkyukai (Seed physiochemical research association) ed. Gakkai center 5, Sake, 366-371, (1995)). Some one third of Japanese people have an allergy, and amongst these people, rice allergies, for which few problems had been reported to date, are being increasingly reported. In such cases, nutritional replacement food substitutes are required; however, physiological problem is significant as conventionally consumed rice cannot be eaten. As such, there is an increasing need and demand for processed rice based on allergen reduced for rice allergy patients. Globulin protein is the major allergen in rice. Japanese Laid-Open Publication No. 2-167040 attempts degradation and removal of globulin protein by reacting rice with proteinase in order to remove allergen removal. Further, Japanese Patent No. 3055729 describes a method for solubilizing and removing allergen by alkaline washing "low-protein rice" as a raw material. In either case, protein removal is the major object, and the protein extract and removal efficiency would be higher if rice with lower protein content is used. However, rice lineages actually used are normal lineages, or those in which the storage protein composition has been altered but the protein amount per se is not reduced, and thus it is not efficient. Japanese patent No. 3055729 attempts a variety of known variant rice, and does not attempt to develop functional crops in a strategic manner. Further, low-glutelin or low-prolamin contents, which have a large range of molecular weights in a single variety, have not been established in a single variety, which is considered to be preferable, and thus the removal of all allergens has not been successful to date.

As described above, there is high demand for providing a low-protein content seed, and improving foreign protein expression in a seed in the field of high utility rice and rice processed foods, production of functional plant and seed and the like.

It is thereof an object of the present invention to provide a method for reduce protein content in seeds and development of necessary technology therefore, and thus developed plants and seeds thereof, and method of using such plants and seeds.

DISCLOSURE OF INVENTION

The present inventor has identified that antisense molecules complementary to at least a portion (at least 15 bases in length are sufficient) of a gene sequence encoding a certain prolamin, significantly reduces the entire expression of the prolamin multiple gene group, resulting in the reduction of protein content in seeds, thereby solved the above-mentioned problems.

Accordingly, the present invention provides the following:

1. A nucleic acid molecule comprising a nucleic acid sequence having at least a 15 contiguous nucleotide length complementary to a nucleic acid sequence encoding a prolamin polypeptide, or a nucleic acid sequence having at least about 70% homology to the complementary nucleic acid sequence having at least a 15 contiguous nucleotide length.

2. The nucleic acid molecule according to Item 1 comprising said nucleic acid sequence having at least a 15 contiguous nucleotide length complementary to a nucleic acid sequence encoding a prolamin polypeptide.

3. The nucleic acid molecule according to Item 1, wherein the prolamin is rice prolamin.

4. The nucleic acid molecule according to Item 1, wherein the prolamin is *japonica* rice prolamin.

5. The nucleic acid molecule according to Item 1, wherein the complementary nucleic acid sequence having at least a 15 contiguous nucleotide length has at least a 50 contiguous nucleotide length.

6. The nucleic acid molecule according to Item 1, wherein the complementary nucleic acid sequence having at least a 15 contiguous nucleotide length comprises a full length sequence encoding the prolamin polypeptide.

7. The nucleic acid molecule according to Item 1, wherein the complementary nucleic acid sequence having at least a 15 contiguous nucleotide length is a 5' terminal nucleic acid sequence encoding the prolamin polypeptide.

8. The nucleic acid molecule according to Item 1, wherein the complementary at least a 15 contiguous nucleotide length, is a nucleotide length of 50 nucleotides or less.

9. The nucleic acid molecule according to Item 1, wherein the complementary at least a 15 contiguous nucleotide length, is a nucleotide length of 30 nucleotides or less.

10. The nucleic acid molecule according to Item 1, wherein the complementary at least a 15 contiguous nucleotide length, comprises a sequence having at least a 15 nucleotide length of a nucleic acid sequence encoding an amino acid sequence selected from the group consisting of SEQ ID NOs: 98-101.

11. The nucleic acid molecule according to Item 1, wherein the prolamin is a 13 kDa prolamin.

12. The nucleic acid molecule according to Item 1, comprising a nucleic acid sequence of at least a 15 contiguous nucleotide length, complementary to:

(a) a polynucleotide having a nucleic acid sequence set forth in a SEQ ID NO: selected from the group consisting of SEQ ID NOs: 1, 3, 5, 7, 9, 11, 13, 15, 17, 19, 21, 23, 25, 27, 29, 31, 33, 35, 37, 39, 41, 43 and 45, or a fragment sequence thereof;

(b) a polynucleotide encoding a polypeptide having an amino acid sequence set forth in a SEQ ID NO: selected from the group consisting of SEQ ID NO: 2, 4, 6, 8, 10, 12, 14, 16, 18, 20, 22, 24, 26, 28, 30, 32, 34, 36, 38, 40, 42, 44 and 46, or a fragment sequence thereof;

(c) a polynucleotide encoding a polypeptide variant having at least one mutation selected from the group consisting of one or more amino acid substitution, addition and deletion in an amino acid sequence set forth in a SEQ ID NO: selected from the group consisting of SEQ ID NO: 2, 4, 6, 8, 10, 12, 14, 16, 18, 20, 22, 24, 26, 28, 30, 32, 34, 36, 38, 40, 42, 44 and 46, and having a biological activity;

(d) a polynucleotide of an allelic variant of a DNA consisting of a nucleic acid sequence set forth in a SEQ ID NO: selected from the group consisting of SEQ ID NOs: 1, 3, 5, 7, 9, 11, 13, 15, 17, 19, 21, 23, 25, 27, 29, 31, 33, 35, 37, 39, 41, 43 and 45;

(e) a polynucleotide encoding a species homolog or an ortholog of a polypeptide consisting of an amino acid sequence set forth in a SEQ ID NO: selected from the group consisting of SEQ ID NO: 2, 4, 6, 8, 10, 12, 14, 16, 18, 20, 22, 24, 26, 28, 30, 32, 34, 36, 38, 40, 42, 44 and 46;

(f) a polynucleotide hybridizing to at least one polynucleotide of any of (a)-(e), and encoding a polypeptide having a biological activity; or (g) a polynucleotide consisting of a base sequence having at least about 70% identity with at least one polynucleotide of (a)-(e) or a complementary sequence thereof, and encoding a polypeptide having a biological activity.

13. The nucleic acid molecule according to Item 1, having antisense activity.

14. The nucleic acid molecule according to Item 13, wherein the antisense activity reduces expression of the prolamin polypeptide.

15. A nucleic acid molecule comprising a nucleic acid sequence having at least a 15 contiguous nucleotide length of a nucleic acid sequence encoding a prolamin polypeptide, or a nucleic acid sequence having at least about 70% homology to the nucleic acid sequence having at least a 15 contiguous nucleotide length.

16. A nucleic acid molecule comprising:

A nucleic acid sequence A comprising a nucleic acid sequence having at least a 15 contiguous nucleotide length of a nucleic acid sequence encoding a prolamin polypeptide, or a nucleic acid sequence having at least about 70% homology to the nucleic acid sequence having at least a 15 contiguous nucleotide length; and (B) a nucleic acid sequence B comprising a nucleic acid sequence having at least a 15 contiguous nucleotide length complementary to a nucleic acid sequence encoding a prolamin polypeptide, or a nucleic acid sequence having at least about 70% homology to the complementary nucleic acid sequence having at least a 15 contiguous nucleotide length 17. The nucleic acid molecule according to Item 16, wherein the nucleic acid sequence A and the nucleic acid sequence B have a portion substantially complementary to each other.

18. The nucleic acid molecule according to Item 16, wherein the nucleic acid sequence A and the nucleic acid sequence B are substantially complementary to each other.

19. The nucleic acid molecule according to Item 16, further comprising a spacer sequence.

20. The nucleic acid molecule according to Item 19, wherein the spacer sequence comprises an intron sequence.

21. The nucleic acid molecule according to Item 19, wherein the spacer sequence is comprised between the nucleic acid sequence A and the nucleic acid sequence B.

22. An agent causing RNA interference (RNAi) against a gene sequence encoding a prolamin polypeptide.

23. A nucleic acid cassette comprising a nucleic acid sequence B comprising a nucleic acid sequence having at least a 15 contiguous nucleotide length complementary to a nucleic acid sequence encoding a prolamin polypeptide, or a nucleic acid sequence having at least about 70% homology to the complementary nucleic acid sequence having at least a 15 contiguous nucleotide length.

24. The nucleic acid cassette according to Item 23, further comprising a nucleic acid sequence encoding a foreign gene.

25. The nucleic acid cassette according to Item 23, further comprising a nucleic acid sequence A comprising a nucleic acid sequence having at least a 15 contiguous nucleotide length of a nucleic acid sequence encoding a prolamin polypeptide, or a nucleic acid sequence having at least about 70% homology to the nucleic acid sequence having at least a 15 contiguous nucleotide length.

26. The nucleic acid cassette according to Item 25, further comprising a spacer sequence.

27. The nucleic acid cassette according to Item 26, wherein the spacer sequence comprises an intron sequence.

28. The nucleic acid cassette according to Item 26, wherein the spacer sequence is comprised between the nucleic acid sequence A and the nucleic acid sequence B.

29. The nucleic acid cassette according to Item 25, further comprising a signal sequence region.

30. The nucleic acid cassette according to Item 29, wherein the signal sequence is located upstream of the foreign gene.

31. The nucleic acid cassette according to Item 29, wherein the signal sequence is a signal sequence of a storage protein.

32. The nucleic acid sequence according to Item 29, wherein the signal sequence is a prolamin signal sequence.

33. The nucleic acid cassette according to Item 24, further comprising a promoter sequence.

34. The nucleic acid cassette according to Item 33, wherein the promoter sequence is operably linked to both the foreign gene and the nucleic acid sequence B.

35. The nucleic acid cassette according to Item 24, wherein separate promoters are independently operably linked to the foreign gene and the nucleic acid B.

36. The nucleic acid cassette according to Item 35, wherein a promoter sequence operably linked to the foreign gene (promoter sequence A), and a promoter sequence operably linked to the nucleic acid sequence B (promoter sequence B), are different to each other.

37. The nucleic acid cassette according to Item 36, wherein the promoter sequence B is a promoter promoting expression in a high level in seeds.

38. The nucleic acid cassette according to Item 36, wherein the promoter sequence B is derived from a storage protein promoter.

39. The nucleic acid cassette according to Item 36, wherein the promoter sequence B is derived from a storage protein promoter, and is different from the promoter sequence A.

40. The nucleic acid cassette according to Item 36 wherein the promoter sequence B is derived from a promoter selected from the group consisting of a polyubiquitin promoter, 26 kD globulin promoter, glutelin A promoter, glutelin B promoter, 16 kD prolamin promoter, 13 kD prolamin promoter and 10 kD prolamin promoter.

41. The nucleic acid cassette according to Item 36 wherein the promoter sequence A is derived from a storage protein promoter.

42. The nucleic acid cassette according to Item 36, wherein the promoter sequence A is a promoter sequence naturally associated with the nucleic acid sequence B.

43. The nucleic acid cassette according to Item 36 wherein the promoter sequence A is derived from a promoter selected from the group consisting of 26 kD globulin promoter, glutelin A promoter, glutelin B promoter, 16 kD prolamin promoter, 13 kD prolamin promoter and 10 kD prolamin promoter.

44. The nucleic acid cassette according to Item 36, wherein the promoter sequence A is a prolamin promoter.

45. The nucleic acid cassette according to Item 36, wherein the promoter sequence A is derived from a prolamin promoter, and the promoter sequence B is derived from a promoter other than the prolamin promoter.

46. The nucleic acid cassette according to Item 33, comprising a signal sequence between the foreign gene and the promoter sequence in frame.

47. The nucleic acid cassette according to Item 25, further comprising a terminator sequence.

48. The nucleic acid cassette according to Item 47, wherein the terminator sequence is a terminator sequence of 10 kD prolamin.

49. The nucleic acid cassette according to Item 25, further comprising a foreign gene, and the foreign gene is located upstream of both the nucleic acid sequence A and the nucleic acid sequence B.

50. The nucleic acid cassette according to Item 49, comprising a spacer sequence between the nucleic acid sequence A and the nucleic acid sequence B.

51. The nucleic acid cassette according to Item 49, comprising an intron sequence between the nucleic acid sequence A and the nucleic acid sequence B.

52. A method for producing a nucleic acid cassette comprising the steps of:
   A) providing a nucleic acid cassette comprising a set of a nucleic acid cassette comprising a nucleic acid sequence B comprising a nucleic acid sequence having at least a 15 contiguous nucleotide length complementary to a nucleic acid sequence encoding a prolamin polypeptide, or a nucleic acid sequence having at least about 70% homology to the complementary nucleic acid sequence having at least a 15 contiguous nucleotide length, and a nucleic acid sequence A comprising a nucleic acid sequence having at least a 15 contiguous nucleotide length of a nucleic acid sequence encoding a prolamin polypeptide, or a nucleic acid sequence having at least about 70% homology to the nucleic acid sequence having at least a 15 contiguous nucleotide length, a promoter sequence B upstream of the set, a foreign gene located upstream or downstream of the promoter sequence B, and a promoter sequence A operably linked to the foreign gene;
   B) transforming a plant with the nucleic acid cassette; and
   C) selecting a nucleic acid cassette having the expression amount of prolamin is partially reduced with respect to the transformed plant.

53. A vector comprising the nucleic acid molecule according to Item 1.

54. The vector according to Item 53, further comprising a sequence having a promoter activity.

55. The vector according to Item 54, wherein the sequence having the promoter activity is a storage protein promoter.

56. The vector according to Item 53 wherein the sequence having the promoter activity is a promoter of the prolamin.

57. The vector according to Item 53, further comprising a terminator.

58. The vector according to Item 53, further comprising a sequence encoding a selectable marker.

59. The vector according to Item 53, further comprising a sequence encoding a foreign gene different from the nucleic acid molecule according to Item 1.

60. A plant cell comprising the nucleic acid molecule according to Item 1.

61. The plant cell according to Item 60, further comprising a nucleic acid molecule encoding a foreign gene different from the nucleic acid molecule according to Item 1.

62. The plant cell according to Item 60, wherein the plant species from which the prolamin is derived, and the species of the plant are of the same species.

63. The plant cell according to Item 60 wherein the plant species from which the prolamin is derived, and the species of the plant are of the same variant.

64. The plant cell according to Item 60, wherein the species from which the prolamin is derived and the species of the plant are rice.

65. The plant cell according to Item 60, wherein the species from which the prolamin is derived and the species of the plant are a *japonica* rice.

66. The plant cell according to Item 60, having the nucleic acid molecule of Item 1 introduced in both alleles thereof.

67. A plant tissue comprising the plant cell according to Item 60.

68. A plant body comprising the nucleic acid molecule of Item 1.

69. The plant body according to Item 68, further comprising a nucleic acid molecule encoding a foreign gene different from the nucleic acid molecule according to Item 1.

70. The plant body according to Item 68, which is of the same species as that from which the prolamin is derived.

71. The plant body according to Item 68, which is of the same variant as that from which the prolamin is derived.

72. The plant body according to Item 68, wherein the plant species from which the prolamin and the plant body are derived, are rice.

72. The plant body according to Item 68, wherein the plant species from which the prolamin and the plant body are derived, are *japonica* rice.

74. The plant body according to Item 68, having the nucleic acid molecule of Item 1 introduced in both alleles thereof.

75. A plant seed produced from the plant body according to Item 68.

76. A plant seed produced from the plant body according to Item 69.

77. A starch preparation produced from the plant body according to Item 68, or the plant seed according to Item 75.

78. A composition comprising a gene product of the foreign gene produced from the plant body according to Item 69 or the plant seed according to Item 76.

79. A method for reducing expression of a protein in a seed in a plant, comprising the steps of:

providing the nucleic acid molecule according to Item 1; introducing the nucleic acid molecule into the plant; redifferentiating the cell to produce a transgenic plant; and obtaining a seed from the transgenic plant.

80. The method according to Item 79, wherein the step of introducing is performed by *Agrobacterium* method.

81. The method according to Item 79, further comprising the step of E) selecting a plant cell with the nucleic acid introduced therein.

82. The method according to Item 81, wherein the step of selecting is performed by determining resistance against an antibiotic.

83. A method for expressing a foreign gene in a plant seed, comprising the steps of:

providing the nucleic acid molecule according to Item 1;

providing a nucleic acid encoding the foreign gene;

introducing the nucleic acid molecule according to Item 1 and the nucleic acid encoding the foreign gene, into a cell of the plant;

redifferentiating the cell to produce a transgenic plant; and obtaining a seed from the transgenic plant.

84. The method according to Item 83, wherein the step of introducing is performed by a *Agrobacterium* method.

85. The method according to Item 83, further comprising the step of F) selecting a plant cell with the nucleic acid molecule introduced.

86. The method according to Item 85, wherein the step of selecting is carried out by determining resistance of the plant cell against an antibiotic.

87. The method according to Item 83, further comprising the step of G) separating a gene product of the foreign gene from the seed.

88. A composition comprising a gene product of the foreign gene produced by the method according to Item 83.

89. Use of a nucleic acid molecule according to Item 1 for reducing expression of a protein in a seed of a plant.

90. Use of a nucleic acid molecule according to Item 1 for expressing a foreign gene in a seed of a plant.

91. Use according to Item 90, wherein the expression of native proteins of the plant in the seed is reduced.

Hereinafter preferable embodiments of the invention will be described. It should be appreciated that those skilled in the art will readily carry out other embodiments thereof from the disclosure of the present application in view of common general knowledge of the art and well known and routine technology of the art, and thus will understand the actions and effects attained by the present invention.

BRIEF DESCRIPTION OF DRAWINGS

FIG. 5 depicts results of Western blotting analysis of prolamin reduction phenotypes, using an anti-13 kDa prolamin antibody (Nipponbare), by randomly selecting seeds from lineages which exhibited significant reduction effects amongst rice with a variety of prolamin antisense gene expression cassette constructs introduced therein. In the Figure: (a), Coommassie Brilliant blue staining was carried out after SDS-PAGE (15 μl of seed extracted protein was used); (b), blotting was carried out onto a PVDF membrane after SDS-PAGE, and Western blotting was carried out with anti-13 kDa prolamin (Nipponbare) polyclonal antibody (0.5 μl of seed extracted protein was used). Relative ratio of absorbance of a band is presented under the lanes.

FIGS. 6 (a and b) describes a photograph of an albumen surface cell layer of LP13K observed by transmission electron microscopy. a) depicts the observed photograph without processing, and b) depicts overlapping image of the protein body type. Protein Body 1 is a gray globular granule (in which prolamin accumulates) which is shown as a solid triangle in b). Protein Body 2 is a relatively larger granule which appears black (dense) in which glutelin and globulin accumulate, which is shown as a white triangle.

Usually, comparing with the observed image (b2) in the variety, Protein Body 1 in which prolamin should accumulate, has reduced its number in LP13K (b1). In LGC-1 (b3), Protein Body 2 numbers have decreased, whereas the number of Protein Body 1 has greatly increased. As such, it has been shown that control of prolamin can results in the formation of protein bodies, and can vary the state of the inside of the surface layer of cells to a greater extent.

Figure 7:
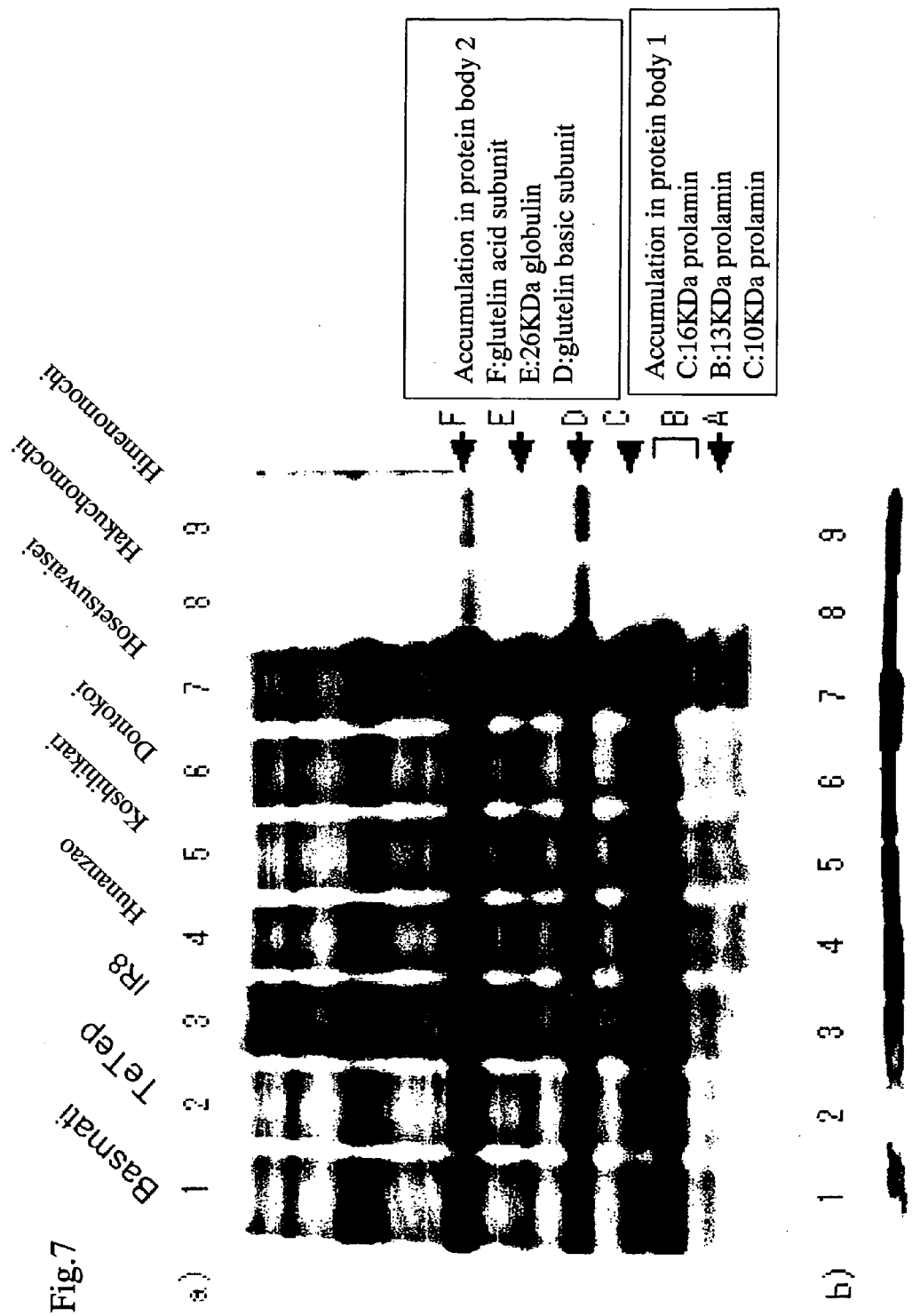

FIG. 7 depicts results of SDS-PAGE of seed proteins from a variety of variants, and Western blotting analysis with anti-13 kDa prolamin polyclonal antibody. 13 kDa prolamins having good reactivity with the antibody were detected both from *japonica* and *indica* variants, and thus the structures thereof are highly conserved.

Figure 8:
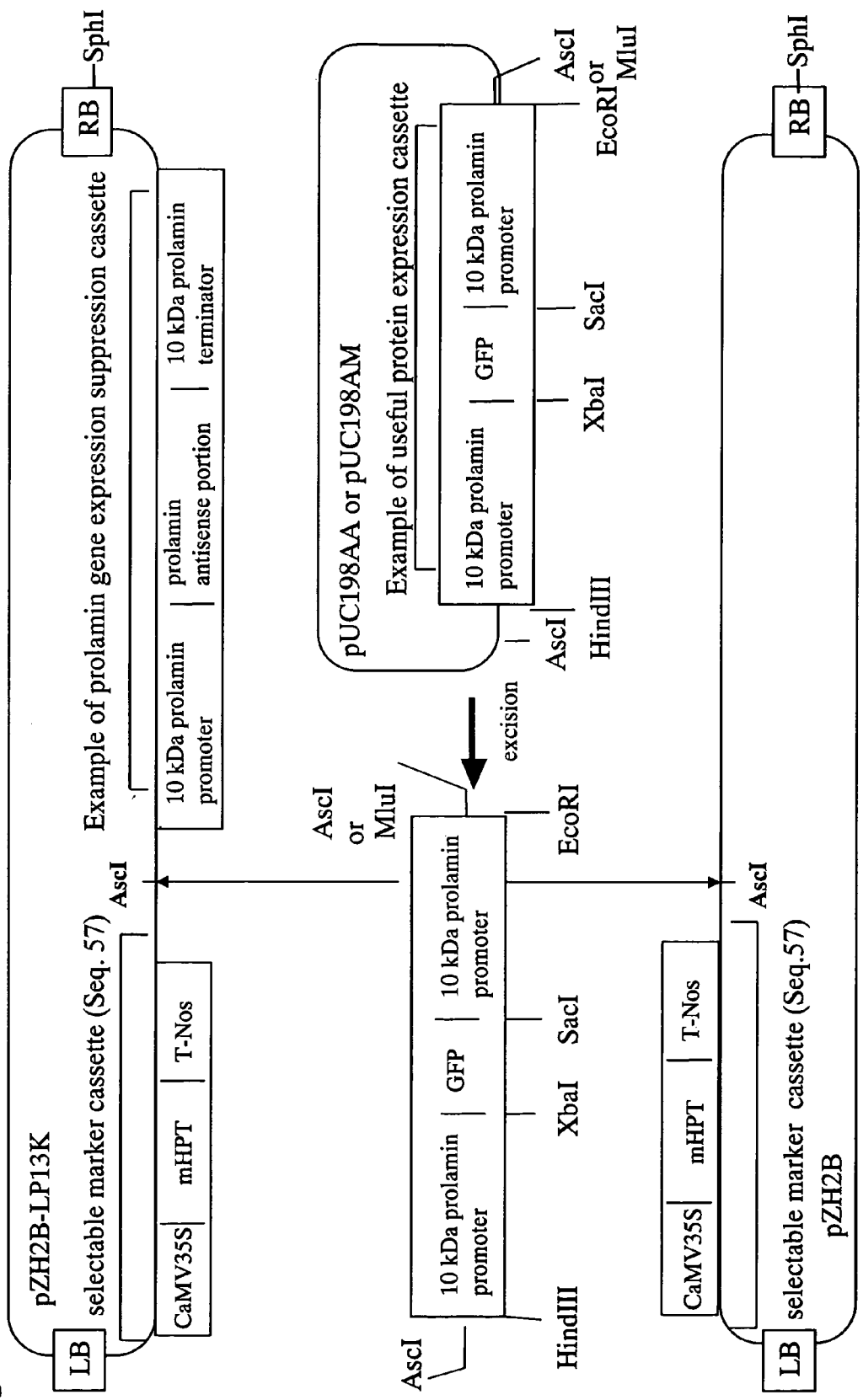

FIG. 8 depicts an example of expression vector structure used for confirming the possibility of the present invention for application as a useful protein expression system.

FIG. 9 (A-B) is a comparative figure of representative prolamin sequences.

FIG. 10 shows a result of an experimental example of electrogram of Example 8.

FIG. 11 shows a structure of the structural gene used in a foreign gene expression experiment in a rice seed, using GFP as a model protein in Example 11. It was shown that the simultaneous introduction of a 13 kDa prolamin expression-suppression cassette, i.e., the reduction of storage protein, results in the augmentation of GFP expression levels.

Figure 12:
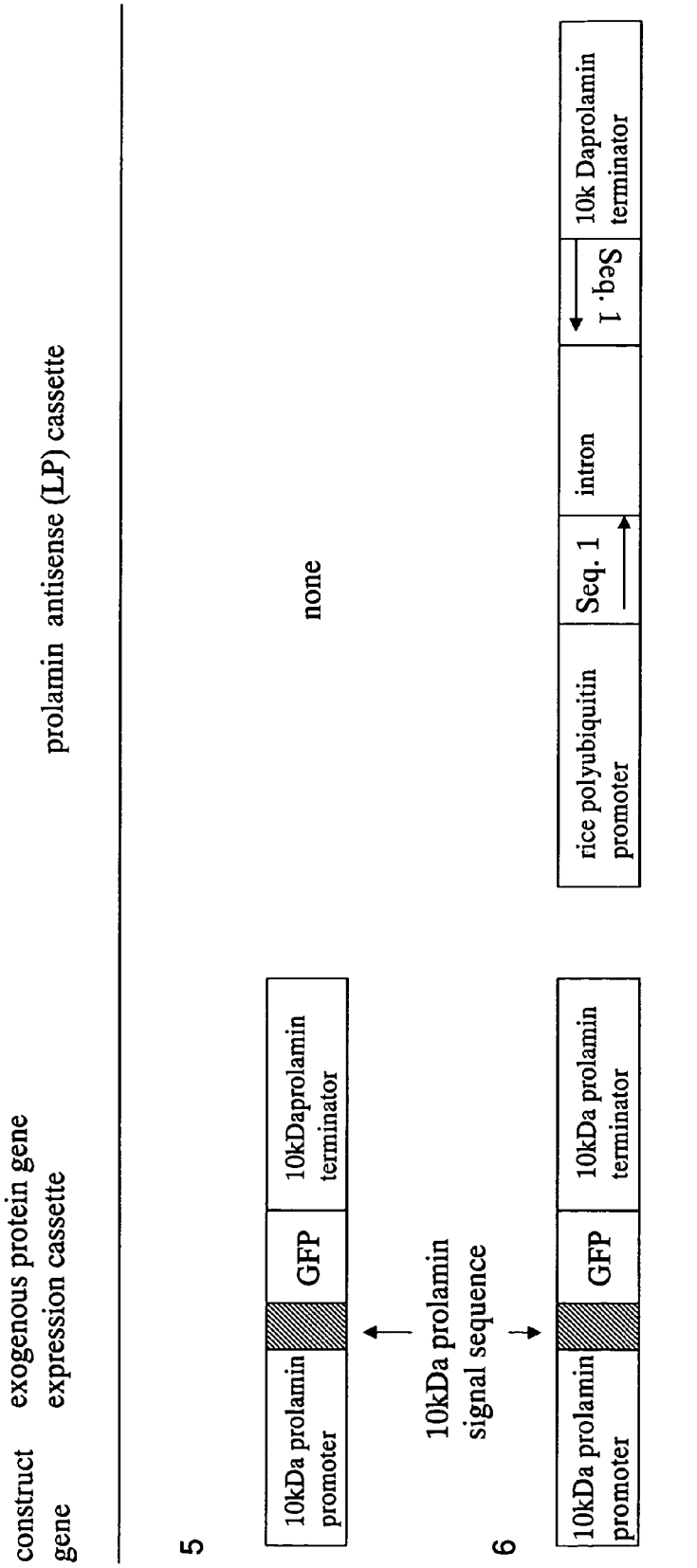

FIG. 12 shows a structure of the structural gene used in Example 12, in view of the result of Example 11.

Figure 13:
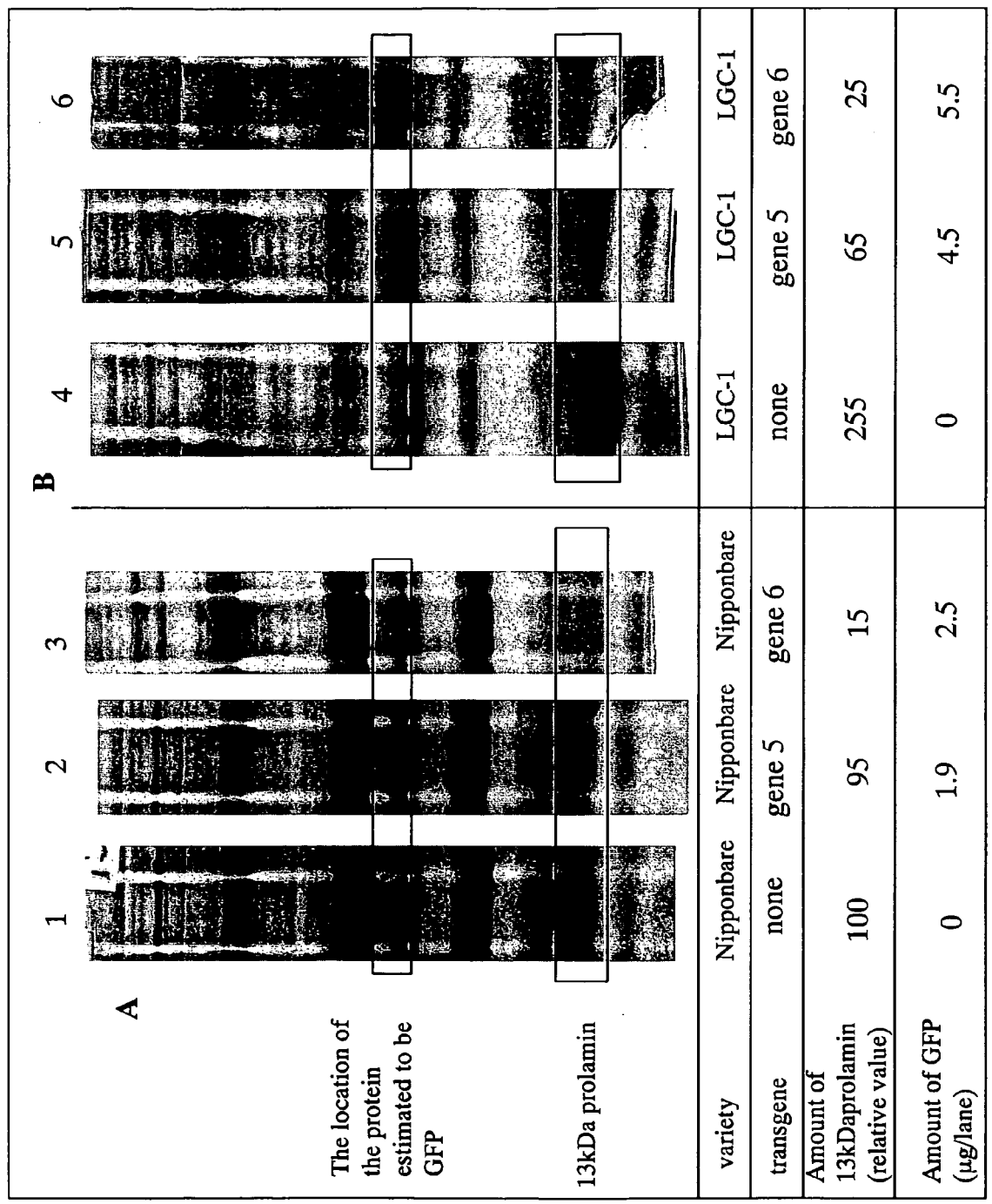

FIG. 13 shows results of an electrogram diagram of a protein of a rice seed with genes 5 and 6 introduced therein and quantification of the amount of GFP expression thereof in FIG. 12. A more superior level of GFP expression is produced when comparing the conventional technology and the use of the technology of the present invention. Further, an electrogram pattern of the seed proteins are very different from those of normal variants, and thus showing that a novel rice seed has been successfully created.

FIG. 14 shows a result in which it was confirmed that the signal sequence has been deleted from the structural gene of Example 12, as shown therein, and a correct GFP protein has been expressed as designed, by directly sequencing the N-terminus of the protein. This proves a significant effect of the structure of the structural gene of the present invention.

Figure 15:
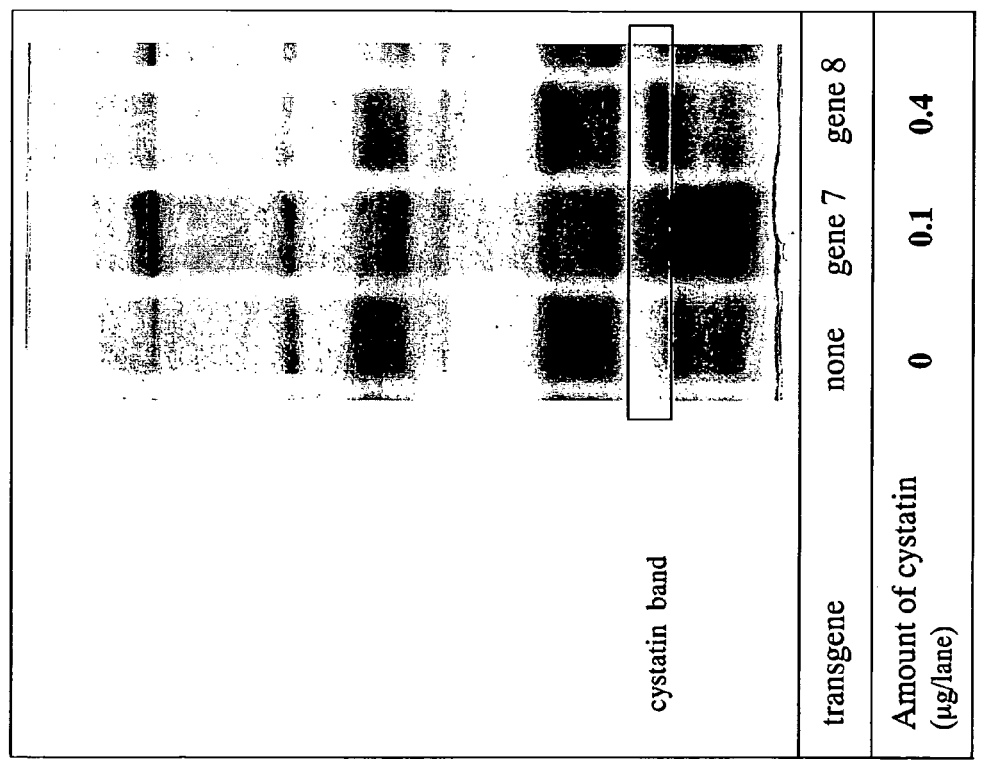

FIG. 15 shows an example of production of Cystatin, which is a useful protein, using the technology of the present invention in Example 13. As seen, Cystatin expression was achieved at a much greater level than using the conventional technology.

Figure 16:
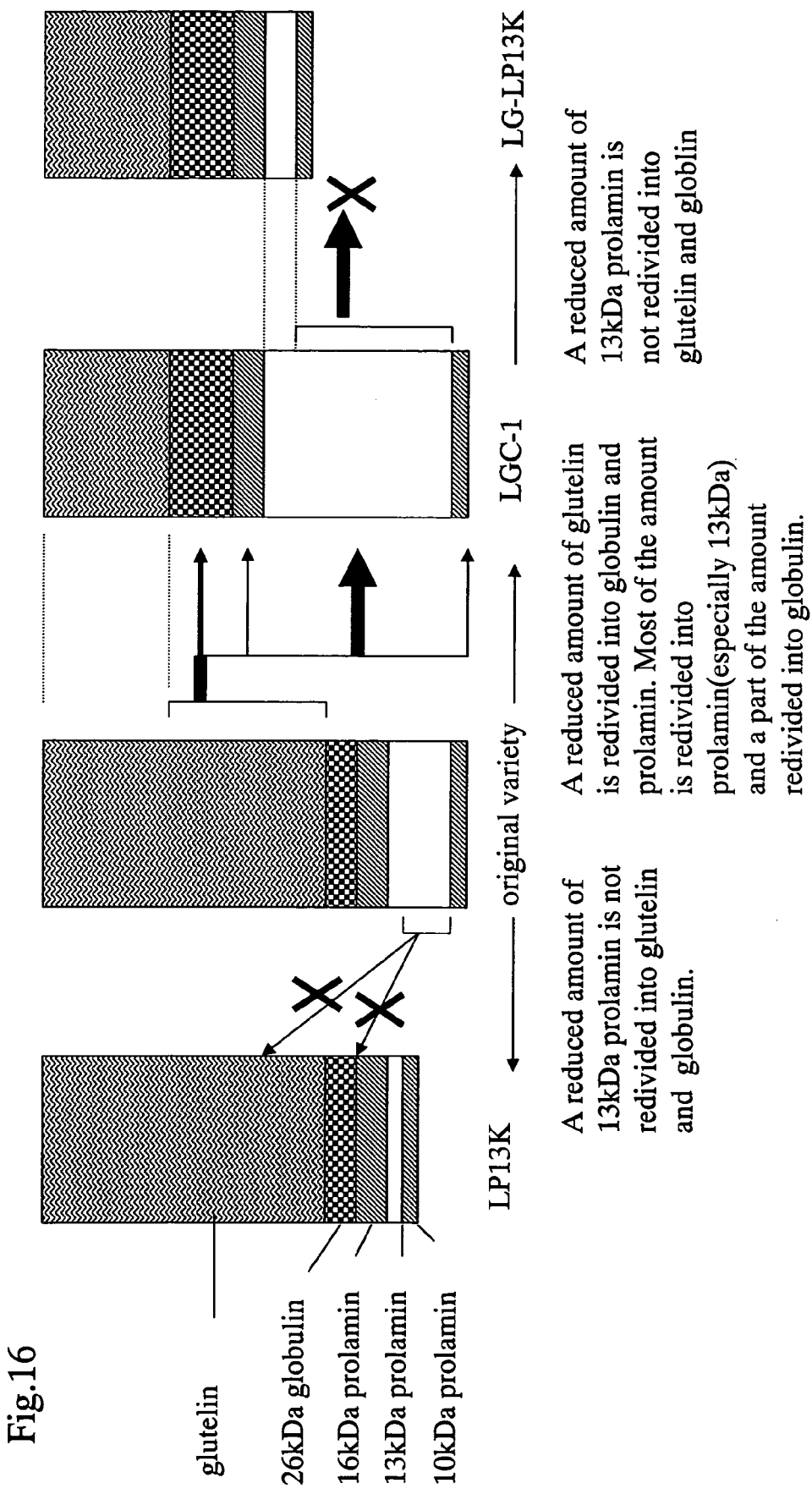

FIG. 16 shows a summary of the regulation pattern of storage protein compositions in a rice seed, which was expounded in the process of the present invention. This clarified a method for efficiently diverting amino acids used for storage proteins to the foreign protein, on which the present invention is based.

FIG. 17 shows a concept of construct genes generally useful for efficient expression of a foreign protein in a seed.

DESCRIPTION OF SEQUENCE LISTING

SEQ ID NO: 1: nucleic acid sequence of 13 kDa prolamin (RM9)

SEQ ID NO: 2: amino acid sequence of 13 kDa prolamin (RM9)

SEQ ID NO: 3: nucleic acid sequence of 13 kDa prolamin (RM1)

SEQ ID NO: 4: amino acid sequence of 13 kDa prolamin (RM1)

SEQ ID NO: 5-30: sequences of other typical 13 kDa prolamin

SEQ ID NO: 31-32: sequences of typical 16 kDa prolamin

SEQ ID NO: 33-46: sequences of typical 10 kDa prolamin

SEQ ID NO: 47: promoter sequence derived from rice 10 kDa prolamin gene

SEQ ID NO: 48: promoter sequence derived from rice glutelin B1 gene

SEQ ID NO: 49: promoter sequence derived from CaMV35S gene

SEQ ID NO: 50: antisense of the full length of cDNA encoding 13 kDa prolamin (SEQ ID NO: 1)

SEQ ID NO: 51: antisense of the N-terminal 67 bp of cDNA encoding 13 kDa prolamin SEQ ID NO: 52: antisense of the N-terminal 15 bp of cDNA encoding 13 kDa prolamin SEQ ID NO: 53: sequence of negative control SEQ ID NO: 54: hygromycin phosphotransferase SEQ ID NO: 55: NOS terminator SEQ ID NO: 56: Variant gene mHPT amino acid sequence SEQ ID NO: 57: Selective marker expression cassette with CMV35S promoter and NOS terminator processed not to be cleaved by restriction enzymes SEQ ID NO: 58: mRUbiP promoter sequence SEQ ID NO: 59: GUS gene fragment SEQ ID NO: 60: 13 kDa prolamin promoter sequence SEQ ID NO: 61: 10 kDa prolamin terminator sequence SEQ ID NO: 62: glutelin A3 promoter sequence SEQ ID NOs: 63-72: other exemplified antisense sequences.

SEQ ID NOs: 73-84: corresponding amino acid sequences of the other exemplified antisense sequences.

SEQ ID NOs: 85-88: Characteristic motives of prolamin

SEQ ID NO: 89: RM4 amino acid sequence

SEQ ID NO: 90: RM5 amino acid sequence

SEQ ID NO: 91: RM7 amino acid sequence

SEQ ID NO: 92: RM10 amino acid sequence

SEQ ID NO: 93: RM16 amino acid sequence

SEQ ID NO: 94: RM4 nucleic acid sequence

SEQ ID NO: 95: RM5 nucleic acid sequence

SEQ ID NO: 96: RM7 nucleic acid sequence

SEQ ID NO: 97: intron sequence of rice aspartate protease gene

SEQ ID NO: 98: consensus sequence example 1 of 13 kDa prolamin

SEQ ID NO: 99: consensus sequence example 2 of 13 kDa prolamin

SEQ ID NO: 100: consensus sequence example 3 of 13 kDa prolamin

SEQ ID NO: 101: coding nucleic acid sequence of consensus sequence example 4 of 13 kDa prolamin SEQ ID NO: 102: coding nucleic acid sequence of consensus sequence example 1 of 13 kDa prolamin SEQ ID NO: 103: coding nucleic acid sequence of consensus sequence example 2 of 13 kDa prolamin SEQ ID NO: 104: coding nucleic acid sequence of consensus sequence example 3 of 13 kDa prolamin SEQ ID NO: 105: coding nucleic acid sequence of consensus sequence example 4 of 13 kDa prolamin SEQ ID NO: 106: 16 kDa prolamin promoter sequence SEQ ID NO: 107: 26 kDa globulin promoter sequence SEQ ID NO: 108: 10 kDa prolamin signal sequence (nucleic acid)

SEQ ID NO: 109: 10 kDa prolamin signal sequence (amino acid)

SEQ ID NO: 110: 13 kDa prolamin signal sequence (nucleic acid)

SEQ ID NO: 111: 13 kDa prolamin signal sequence (amino acid)

SEQ ID NO: 112: 16 kDa prolamin signal sequence (nucleic acid)

SEQ ID NO: 113: 16 kDa prolamin signal sequence (amino acid)

SEQ ID NO: 114: glutelin B1 signal sequence (nucleic acid)

SEQ ID NO: 115: glutelin B1 signal sequence (amino acid)

SEQ ID NO: 116: 26 kDa globulin signal sequence (nucleic acid)

SEQ ID NO: 117: 26 kDa globulin signal sequence (amino acid)

SEQ ID NO: 118: Determination sequence of SEQ ID NO:11

BEST MODE FOR CARRYING OUT THE INVENTION

Hereinafter, the present invention will be described. It should be understood throughout the present specification that articles for singular forms (e.g., "a", "an", "the", etc. in English; "ein", "der", "das", "die", etc. and their inflections in German; "un", "une", "le", "la", etc. in French; "un", "una", "el", "la", etc. in Spanish, and articles, adjectives, etc. in other languages) include plural referents unless the context clearly dictates otherwise. It should be also understood that the terms as used herein have definitions typically used in the art unless otherwise mentioned. Accordingly, unless otherwise defined, all terminology and technical terms used herein will have the same meanings as those generally understood by those skilled in the art belonging to the file of the present invention. If there is contradiction, the present specification (including the definition) takes precedence.

Terms particularly used herein are defined as follows.

(Terms)

As used herein the term "seed protein" refers to a protein stored in a plant seed. Seed proteins are classified based on difference in solubility in solvent, and classified into water-soluble albumins, salt-solution soluble globulins, water-containing alcohol soluble prolamins, glutelins which are soluble in weak acid or weak alkali solution.

As used herein "prolamin" collectively refers to proteins which are soluble in water-based solution containing 50%-90% alcohol. Cereal seeds contain typically this prolamin type of proteins as major storage proteins. Depending on each type of cereals, each species has its own unique name for prolamin, including wheat glutenin, barley hordin, maize zein, oat avenin and the like, and in rice it is simply called prolamin. In the case of rice, glutelin comprises 60-70% of the seed proteins, and thus is a major protein, whereas prolamin comprises 20-30% in its content next thereto, and globulin comprises a small percentage. Molecular weights of prolamins vary depending on the plant species, and the common features thereof include that the amino acid sequences thereof are rich in glutamine, and the region having consecutive glutamines (for example, Gln-Gln, Gln-Gln-Gln and the like) or region having glutamines at a predetermined space (for example, Gln-Xaa-Gln-Xaa-Gln). Further, it is also unique that motives (for example Glu-Phe-Val-Arg-Gln-Gln-Cys-Ser-Pro (SEQ ID NO: 85) or Cys-Gln-Val-Met-Gln-Gln-Gln-Cys-Cys-Gln-Gln (SEQ ID NO: 86), and variant sequences with one or more substitutions, additions or deletions thereof)

comprising several amino acids including prolines and cysteines in addition to glutamines, are well and commonly conserved in the prolamin gene amino acid genes. Cysteine residues involved in S—S bonds are also well conserved. Moreover, these motifs are often conserved not only in the prolamin genes in the same plant species, but also between different plant species, and thus is evolutionarily said to form the prolamin gene superfamily having common ancestors (Shewry, P E et al., Plant Cell 7, 945-956, 1995). As in the other storage proteins, prolamin genes have multiple copies in the genome, and is known to be a multigene family. Seeds have a variety of prolamins with slightly different amino acid sequences derived from each gene present in a mixed state.

Rice prolamin has been efficiently extracted by using 55-60% 1-propanol (Sugimoto, T. et al., Agric. Biol. Chem. 50, 2409-2410, 1986). Further, the number of the genes is estimated to be between 25-100 based on genomic Southern analysis, cDNA cloning and isoelectric focusing and the like. These are classified into several subfamilies, and the classification and designations thereof vary depending on researchers, varieties used in the experiments, and the most common classification is based on the molecular weight from first-dimensional SDS electrophoresis. In this classification, there are 10 kDa, 13 kDa (in *indica* species, it may be described as 14 kDa, and as used herein, "13 kDa prolamin" encompasses this 14 kDa type), 16 kDa (in *indica* species, it may be described as 18 kDa, and as used herein, "13 kDa prolamin" encompasses this 18 kDa type) and the like. The band of each prolamin may be a mixture of a variety of proteins even if it appears as one single band, and there is at least one type for the 10 kDa prolamin, at least three species for the 16 kDa prolamin, and there are at least 12 types for the 13 kDa prolamin, which is the most multiple gene amongst them, and it has been shown that there exists more than that. As for the 13 kDa prolamins, there is a study in which the detailed classification was made based on the correspondence between the protein spot and the cDNA thereof (Mitsukawa, N et al., Plant Biotech. 16, 103-113, 1999), which further classifies the 13 kDa prolamins into four types depending on the property of varying solubility with or without reduction between S—S bond, amino acid homology thereof, and the number of cysteine residues. In addition, in analogy to the classification example of wheat, there is also an example of the classification depending on the sulphur content (mainly, cysteine residue content) into sulphur-rich and sulphur-poor types, and sulphur-poor types which have no cysteine. All the prolamins have a blocked N-terminus and thus it is difficult to analyze by protein sequencing analysis. Therefore, there are still believed to be a number of prolamins which are unidentified with respect to either protein or cDNA levels, or unclear as to their homology with identified cDNAs. However, regardless of its classification or designation, whether or not a protein belongs to prolamins may be readily determined by those skilled in the art by (1) dissolving in a water-containing alcohol, (2) being rich in glutamines (at least 10%), or poor (3% or less) in lysines or no lysine, (3) having a glutamine residue per one or more amino acids, or a plurality of sites having two or more consecutive glutamines, (4) there are motifs comprising amino acids such as prolines, cysteines and the like having glutamine as the core (Glu-Phe-Val-Arg-Gln-Gln-Cys-Ser-Pro (SEQ ID NO: 85), or Cys-Gln-Val-Met-Gln-Gln-Gln-Cys-Cys-Gln-Gln (SEQ ID NO: 86) or motif having 50% or more homology thereto) are conserved, as common features. As for (4), the motif of Gln-Gln-Cys-Cys-Gln-Gln (SEQ ID NO: 87) is highly conserved in rice prolamins and wheat glutenins, and Glu-Phe-Val-Arg-Gln-Gln (SEQ ID NO: 88) is conserve in rice prolamins, maize gliadins, oat avenins and the like. As such, there are some cases where molecular weight thereof is different or the entire homology of the proteins is low, cereal prolamins are recognized to be the prolamin gene superfamily which have the same ancestral genes (Shewry, P E et al., Plant Cell 7, 945-956, 1995). What have been reported in the literature as rice prolamins include, but are not limited to, in the cDNA level, λRM1, λRM2, λRM4, λRM7, λRM9, 1pS18, pS23, pX24, pPro17, pPro114, pPro117, λRP16, λRP10 and the like. Such prolamins include, but are not limited to, for example, a polynucleotide having nucleic acid sequence as set forth in a SEQ ID NO selected from the group consisting of SEQ ID NOs: 1, 3, 5, 7, 9, 11, 13, 15, 17, 19, 21, 23, 25, 27, 29 (13 kDa prolamin), 31 (16 kDa prolamin), 33, 35, 37, 39, 41, 43 and 45 (10 kDa prolamin) or a fragment sequence thereof, and a polypeptide having an amino acid sequence selected from the group consisting of SEQ ID NOs: 2, 4, 6, 8, 10, 12, 14, 16, 18, 20, 22, 24, 26, 28, 30 (13 kDa prolamin), 32 (16 kDa prolamin), 34, 36, 38, 40, 42, 44 and 46 (10 kDa prolamin), or a fragment thereof, or a polynucleotide sequence encoding the same. Any prolamin genes other than described above may be used as long as they are registered in a gene bank such as GenBank, NCBI, EMBL, DDBJ or the like.

As used herein the term "13 kDa prolamin" refers to a prolamin which is generally electrophoresed at a molecular weight of around 13 kDa by SDS-PAGE from *japonica* rice, and it is mostly contained in rice in terms of content. This the most abundant gene present in the genome, and as a result of analysis such as cDNA cloning or electrofocusing, it has been confirmed that there are at least 12 different genes having different amino acid sequences to each other, and it is assumed that there are actually more than that number of such 13 kDa prolamins. Typical 13 kDa prolamins include, but are not limited to, prolamins comprising nucleic acid sequence selected from the group consisting of SEQ ID NOs: 1, 3, 5, 7, 9, 11, 13, 15, 17, 19, 21, 23, 25, 27 and 29, or amino acid sequence selected from the group consisting of SEQ ID NOs: 2, 4, 6, 8, 10, 12, 14, 16, 18, 20, 22, 24, 26, 28 and 30, and other prolamin gene superfamily members from different plants.

As used herein the term "storage protein" is a protein which specifically highly accumulates in a plant seed, and has no specific other physiological function such as enzymatic activity in plants, and are usually accumulated in the protein body.

As used herein the term "protein body" refers to a granular intracellular structure in which storage proteins accumulate. There is usually one type in a plant, but in rice and oats, there are two types of protein bodies in which outlooks and forms thereof are apparently distinct from each other. In rice, there are two types: Protein Body Type 1 in which prolamins accumulate, and Protein Body Type 2 in which glutelin and globulin accumulate. Both are apparently distinct from each other in terms of outlook, forms, size, derivation and the like, and the correspondence between protein bodies and storage proteins are strictly controlled.

Prolamin conservative sequences useful in the present invention include the following. The present invention exemplifies antisense sequences encoding such a conservative sequence as a preferable sequence:

```
SEQ 1:
                                           (SEQ ID NO: 98)
Gln Val Met Gln Gln Gln Cys Cys Gln Gln Leu Arg

Leu Val Ala Gln Gln Ser His Tyr Gln Ala Ile Ser

Ser Val Gln Ala Ile Val Gln Gln Leu Gln Leu Gln

Gln
```

```
                          -continued
SEQ 2:
                                              (SEQ ID NO: 99)
Met Lys Ile Ile Phe Val Phe Ala Leu Leu Ala Ile Val Ala Cys Asn Ala Ser Ala Arg Phe Asp Ala Leu Ser Gln Ser Tyr Arg Gln Tyr Gln Leu Gln SEQ 3:
                                             (SEQ ID NO: 100)
Glu Phe Val Arg Gln Gln His Ser Ile Val Ala Thr Pro Phe Trp Gln Pro Ala Thr Phe Gln Leu Ile Asn Asn Gln SEQ 4:
                                             (SEQ ID NO: 101)
Tyr Phe Asp Gln Thr Gln Ala Gln Ala Gln Ala Leu Leu Ala Leu Asn Leu Pro Ser Ile Cys Gly Ile Tyr Pro Asn Tyr Tyr Ile Ala Pro
```

In the present invention, it was shown that a sequence which is antisense to a sequence encoding at least five amino acids of the above-mentioned sequences, can actually be used to suppress the prolamin gene expression.

The terms "protein", "polypeptide", "oligopeptide" and "peptide" as used herein have the same meaning and refer to an amino acid polymer having any length. This polymer may be a straight, branched or cyclic chain. An amino acid may be a naturally-occurring or non-naturally-occurring amino acid, or a variant amino acid. The term may include those assembled into a composite of a plurality of polypeptide chains. The term also includes a naturally-occurring or artificially modified amino acid polymer. Such modification includes, for example, disulfide bond formation, glycosylation, lipidation (acylation), acetylation, phosphorylation, or any other manipulation or modification (e.g., conjugation with a labeling moiety). This definition encompasses a polypeptide containing at least one amino acid analog (e.g., non-naturally-occurring amino acid, etc.), a peptide-like compound (e.g., peptoid), and other variants known in the art.

The terms "polynucleotide", "oligonucleotide", "nucleic acid molecule" and "nucleic acid" as used herein have the same meaning and refer to a nucleotide polymer having any length. This term also includes an "oligonucleotide derivative" or a "polynucleotide derivative". An "oligonucleotide derivative" or a "polynucleotide derivative" includes a nucleotide derivative, or refers to an oligonucleotide or a polynucleotide having linkages between nucleotides different from typical linkages, which are interchangeably used. Examples of such an oligonucleotide specifically include 2'-O-methyl-ribonucleotide, an oligonucleotide derivative in which a phosphodiester bond in an oligonucleotide is converted to a phosphorothioate bond, an oligonucleotide derivative in which a phosphodiester bond in an oligonucleotide is converted to a N3'-P5' phosphoroamidate bond, an oligonucleotide derivative in which a ribose and a phosphodiester bond in an oligonucleotide are converted to a peptide-nucleic acid bond, an oligonucleotide derivative in which uracil in an oligonucleotide is substituted with C-5 propynyl uracil, an oligonucleotide derivative in which uracil in an oligonucleotide is substituted with C-5 thiazole uracil, an oligonucleotide derivative in which cytosine in an oligonucleotide is substituted with C-5 propynyl cytosine, an oligonucleotide derivative in which cytosine in an oligonucleotide is substituted with phenoxazine-modified cytosine, an oligonucleotide derivative in which ribose in DNA is substituted with 2'-O-propyl ribose, and an oligonucleotide derivative in which ribose in an oligonucleotide is substituted with 2'-methoxyethoxy ribose. Unless otherwise indicated, a particular nucleic acid sequence also implicitly encompasses conservatively-modified variants thereof (e.g. degenerate codon substitutions) and complementary sequences as well as the sequence explicitly indicated. Specifically, degenerate codon substitutions may be produced by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

As used herein, the term "nucleic acid molecule" is interchangeably used with nucleic acid, oligonucleotide and polynucleotide, and includes cDNA, mRNA, genomic DNA and the like. As used herein, nucleic acids and nucleic acid molecules may be encompassed by the term "gene". A nucleic acid molecule encoding a gene sequence encompasses "splicing variant". Similarly, a specific protein encoded by a nucleic acid includes any proteins encoded by splicing variants encoded thereby. As the designation indicates, the term "splicing variant" refers to a product of an alternative splicing event. After transcription, the first nucleic acid transcript may be spliced into those encoding different polypeptides as different (distinct) nucleic acid splicing products. Although production mechanism of splicing variants varies, it includes exon alternative splicing. Different polypeptides derived from the same nucleic acid by incorrect transcription are also encompassed in this definition. Any products of a splicing reaction (including splicing products in a form of recombinantation) are also encompassed in the definition.

As used herein, the term "isolated" biological agent (e.g., nucleic acid, protein or the like) refers to a biological agent that is substantially separated or purified from other biological agents in cells of a naturally-occurring organism (e.g., in the case of nucleic acids, agents other than nucleic acids and a nucleic acid having nucleic acid sequences other than an intended nucleic acid; and in the case of proteins, agents other than proteins and proteins having an amino acid sequence other than an intended protein). The "isolated" nucleic acids and proteins include nucleic acids and proteins purified by a standard purification method. The isolated nucleic acids and proteins also include chemically synthesized nucleic acids and proteins.

As used herein, the term "purified" biological agent (e.g., nucleic acids, proteins, and the like) refers to one from which at least a part of naturally accompanying agents are removed. Therefore, ordinarily, the purity of a purified biological agent is higher than that of the biological agent in a normal state (i.e., concentrated).

As used herein, "gene" refers to an element defining a genetic trait. A gene is typically arranged in a given sequence on a chromosome. A gene which defines the primary structure of a protein is called a structural gene. A gene which regulates the expression of a structural gene is called a regulatory gene.

As used herein, "gene" may refer to "polynucleotide", "oligonucleotide", "nucleic acid", and "nucleic acid molecule" and/or "protein", "polypeptide", "oligopeptide" and "peptide". As used herein the term "gene product" refers also to "polynucleotide", "oligonucleotide", and "nucleic acid" and/or "protein", "polypeptide", "oligopeptide" and "peptide" expressed by the gene. Those skilled in the art would readily understand what such a gene product is depending on the situation and context used.

As used herein the term "homology" of a gene (nucleic acid sequence or amino acid sequence) refers to the magnitude of identity between two or more gene sequences. Therefore, the greater the homology between two genes, the greater the identity or similarity between their sequences. Whether or not two genes have homology is determined by comparing their sequences directly or by a hybridization method under stringent conditions. When two gene sequences are directly compared with each other, the genes have homology if representatively at least 50%, preferably at least 70%, more preferably at least 80%, 90%, 95%, 96%, 97%, 98%, or 99% of the DNA sequence of the genes are identical. As used herein, "similarity" of genes (for example, nucleic acid sequence, amino acid sequence or the like) refers to a degree of identity to each other of two or more gene sequences when conservative substitutions are considered to be positive (i.e. identical) in the above mentioned homology. Accordingly, when conservative substitutions exist, identity and similarity are different depending on the existence of the conservative substitutions. Further, when no conservative substitution exists, the identity and similarity will be of identical value.

As used herein, comparison of similarity, identity and homology of base sequences is calculated using BLAST, a tool for analyzing sequences with default parameters.

As used herein the term "foreign gene" refers to a gene which does not exist in a native plant. Such a foreign gene may be those which are modified from a naturally occurring gene, or genes which exist in a different plant, and may be artificially synthesized or a complex thereof such as a fusion of two or more genes. A plant comprising such a foreign gene may be expressed in a gene product which is not expressed in nature.

In order to produce an artificially synthesized gene, DNA synthesis technologies and nucleic acid chemistry are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994) Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press and the like, which are hereby incorporated by reference herein for the pertinent portions thereof.

As used herein the term "foreign gene" may be any gene that is capable of being expressed in a plant. Accordingly, in one embodiment, "foreign gene" may be any gene encoding a useful protein which is contemplated to be expressed in large amounts, which are also within the scope of the present invention. Such a gene includes, but is not limited to, for example: peptides having pharmaceutical activity (for example, cytokines (interleukins, chemokines, granular macrophage colony stimulating factor (GM-CSF), macrophage colony stimulating factor (M-CSF), granular colony stimulating factor (G-CSF), multi-CSF (IL-3), erythropoietin (EPO), leukemia inhibitory factor (LIF), hematopoietic factors such as c-kit ligand (SCF), tumor necrosis factors, interferons, platelet derived growth factor (PDGF), epidermal growth factor (EGF), fibroblast growth factor (FGF), hepatocyte growth factor (HGF), vascular endothelial growth factor (VEGF) or the like); hormones (for example, insulin, growth hormones, thyroid stimulating hormone or the like)), vaccine antigens, blood products, agriculturally useful peptides such as antibacterial proteins, a variety of enzymes capable of synthesizing secondary metabolites having physiological or pharmacological action or hydrolytic enzymes, inhibitors regulating enzymatic reaction, soybean glycinin having blood pressure lowering action, or artificial proteins designed so that physiologically active peptides are cleaved due to enzymatic degradation in digestive tracts and the like. Further, substances significant in terms of nutrition, include but are not limited to, for example, caseins, albumins or globulins of beans, or synthesizing enzymes of vitamins, sugars, lipids or the like. Proteins involved in the food processing process as raw materials include, for example, wheat glutenin (bakery), soybean globulins (tofu), milk caseins (cheese), or proteins enhancing palatability or functionality of a food, for example, specific synthetic enzymes of sugars or amino acids including cyclodextrin, oligosaccharides, γ-amino acetate or the like, dye synthesizing enzymes for improving appearance, or proteins involved in the synthesis of a taste component, or peptides which are designed that will have physiological actions by enzymatic digestion in the digestive tracts (for example, angiotensin converting enzyme inhibitory peptides or the like, having blood pressure lowering action, and the like), and the like.

As used herein the term "sugar chain" refers to a compound in which at least one sugar unit/saccharide (a monosaccharide and/or derivative thereof) is associated in series. When two or more sugar units are associated together, such association is mediated by binding via dehydration-condensation of glycoside linkage. Such sugar chains include, but are not limited to, for example, a wide variety of polysaccharides such as those found in living organisms such as glucose, galactose, mannose, fucose, xylose, N-acetylglucosamine, N-acetylgalactosamine, sialic acid and the complexes and derivatives thereof, degraded polysaccharides, glycoproteins, proteoglycans, glycosaminoglycans, glycolipids, and complexed biomolecules thereof, degraded or derivatized sugar chains derived wherefrom, and the like. Accordingly, as used herein, the term "sugar chain" may be interchangeably used with "polysaccharide", "carbohydrate", and "sugar". Further, unless otherwise specified, as used herein, the term "sugar chain" may include sugar chains and sugar chain containing substances.

As used herein the term "monosaccharide" refers to a polyhydroxyaldehyde or polyhydroxy ketone containing at least one hydroxy group and at least one aldehyde or ketone group which is not hydrolysed into similar molecules, and derivatives thereof. Usually, monosaccharides may be represented by the formula: $C_nH_{2n}O_n$, however, the formula is not limited to this, and includes fucose (deoxy hexose), N-acetylglucosamine and the like. As used herein in the above mentioned formula, the molecules where n=2, 3, 4, 5, 6, 7, 8, 9 and 10, respectively refer to diose, triose, tetrose, pentose, hexose, heptose, octose, nonose, and decose. Generally, monosaccharides are aldehydes or ketones of chain type polyalcohols, and the aldehyde-type is also called "aldose", and the ketone-type is also called "ketose". As used herein and specifically mentioned, derivatives of monosaccharides refer to substances resulting from at least one hydroxy group on a non-derivatized monosaccharide being substituted with another substituent. Derivatives of such a monosaccharide include but are not limited to a sugar having a carboxyl group (for example, aldonic acid, a carboxylic acid resulting from oxidization of C-1 position of aldose such as D-gluconic acid which D-glucose is oxidized, an uronic acid, a carboxylic acid resulting from oxidization of C-atom at the terminus of an aldose such as D-glucuronic acid) resulting from oxidization of D-glucose, sugar having an amino group or a derivative thereof (for example, an acetylated amino group), such as N-acetyl D-glucosamine, N-acetyl D-galactosamine and the like, a sugar having both amino group and a carboxy group (for example, N-acetylneuraminic acid (sialic acid), N-acetyl muramic acid and the like, a deoxy sugar such as 2-deoxy-D-ribose, a sulfated sugar including a sulfate group, phosphorylated sugar having a phosphate group, and the like. As used herein when referring to monosaccharide, such derivatives are also encompassed unless otherwise specified. Alternatively, sugars in which a hemiacetal structure is formed and reacted with an alcohol to form an acetal structure, is also within the scope of monosaccharides.

As used herein, reference to aspargine-linked sugar chain structures, is in accordance with the nomenclature of Takahashi (http://www.gak.co.jp; see also Seikagaku Jikkenho (Experimental methods of Biochemistry, 23, Gakkai Shuppan Center, ed. N. Takahashi, 1989; Takahashi N, Tomiya N: Analysis of N-linked oligosaccharides: Application of glycoamidase A: in Handbook of endoglycosidases and glycoamidases (Takahashi N, Muramatsu T eds.). pp. 209-241, CRC Press, Boca Raton, Fla., 1992). According to Takahashi nomenclature, 1) N-acetyl lactosamine (complex type) sugar chain is represented by (A) indicating the number of branches in the first three digits; (B) indicating 1 when a fucose is bound to N-acetyl glucosamine of the reduced terminus by α1,6 linkage, and 0 when no linkage is found at the center of the three digits; (C) indicating 1 when N-acetyl glucosamine is linked to a β-mannose, which is a core pentose thereof, by β1,4, and 0 when no linkage is found, at the end of the three digits. 2) High mannose type sugar chain is represented by indicating M first, and the number of mannose residues in the following digits. Thereafter, "." is inserted and on the right hand side thereof is added an inherent number. When a fucose is linked to N-acetyl glucosamine at the reducing terminus by α1,6 linkage, F is inserted after "M". 3) Hybrid type sugar chain is represented by indicating H first, and the number of mannose residues in the following digits. Thereafter, "." is inserted and on the right hand side thereof is added an inherent number. When a fucose is linked to N-acetyl glucosamine at the reducing terminus by α1,6 linkage, F is inserted after "H". 4) When fucose is linked to N-acetyl glucosamine at the reducing terminus by α1,3 linkage, F is inserted, and when xylose is linked to β-mannose which is a core pentose by β1,2 linkage, X is inserted at the bottom. If both exist, FX is inserted in this order. 5) When having galactose instead of N-acetylgalactosamine, after giving the symbol for galactose, a lower case letter corresponding to the number is added to the bottom, such as if the number of N-acetylgalactosamine is one, then "a" is inserted, if two then "b" is inserted, if three then "c" is inserted, and the like. 6) When it can be classified into any of N-acetyl lactosamine type, and high mannose type or hybrid type such as core pentose, then the nomenclature of N-acetyl lactosamine type is precedent. 7) When having sialic acid, then the residue number of sialic acid is described, and then the species next to the sialic acid is N-acetyl neuraminic acid, then "A" is inserted, and the set of inherent number is given after inserting before the above-mentioned sugar chain structure. Such designation methods include the following: galactose β1,4-N-acetylglucosamine β1,2-mannose α1,3-(mannose α1,3-(mannose α1,6-)mannose α1,6-)mannose β1,4-N-acetylglucosamine β1,4-N-acetylglucosamine refers to H5.12 and the like.

The proteins produced by the present invention in the present specification are subjected to post-translational modification in plants and specific sugar chains bind thereto. Such sugar chains preferably are identical when utilized for animal use, and if the modifications in plants are identical to those of animals, such sugar chain may be used without problems as long as such sugar chain are substantially the same. Further, even in the case where modification pattern of sugar chains are different, those may be used without problem if those are effective in animals, and preferably without having side effects. If one wishes to alter the modification pattern, such alteration may be made by the use of means such as enzymatic measures or the like.

Foreign genes to be expressed may also be used having homology to an above-described naturally occurring foreign gene. Foreign genes having such a homology include but are not limited to, for example, nucleic acid molecules comprising nucleic acid sequence having identity or similarity of at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% to a naturally occurring gene; or polypeptide comprising amino acid sequence having identity or similarity of at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% to a naturally occurring gene.

As used herein, the term "expression" of a gene product, such as a gene, a polynucleotide, a polypeptide, or the like, indicates that the gene or the like is affected by a predetermined action in vivo to be changed into another form. Preferably, the term "expression" indicates that genes, polynucleotides, or the like are transcribed and translated into polypeptides. In one embodiment of the present invention, genes may be transcribed into mRNA. More preferably, these polypeptides may have post-translational processing modifications.

Accordingly, as used herein, "reduction" of "expression" of a gene, a polynucleotide, a polypeptide or the like refers to that when an agent of the present invention is subjected to an action, the amount of expression is significantly reduced compared to that when the agent is not subjected to an action. Preferably, the reduction of expression includes reduction of the amount of polypeptide expression. More specifically, the reduction of expression amount refers to at least about 10% reduction of expression when comparing post-action with pre-action of an agent, preferably at least about 20%, more preferably at least about 30%, still more preferably at least about 40%, still more preferably at least about 50%, still more preferably at least about 75%, still more preferably at least about 90%, still more preferably at least about 100%. As used herein, the "increase" of "expression" of a gene, a polynucleotide, a polypeptide or the like refers to that when an agent of the present invention is subjected to an action, the amount of expression is significantly increased compared to that when the agent is not subjected to an action. Preferably, the increase of an expression includes an increase the amount of polypeptide expression. More specifically, the increase in expression amount refers to at least about 10% increase of expression amount when comparing post-action with pre-action of an agent, preferably at least about 20%, more preferably at least about 30%, still more preferably at least about 40%, still more preferably at least about 50%, still more preferably at least about 75%, still more preferably at least about 90%, still more preferably at least about 100% or more, still more preferably at least about 200% or more, or that the expression occurs which has not expressed before the action of an agent in issue.

As used herein, the term "amino acid" may refer to a naturally-occurring or nonnaturally-occurring amino acid. The term "amino acid derivative" or "amino acid analog" refers to an amino acid which is different from a naturally-occurring amino acid and has a function similar to that of the original amino acid. Such amino acid derivatives and amino acid analogs are well known in the art.

The term "naturally-occurring amino acid" refers to an L-isomer of a naturally-occurring amino acid. The naturally-occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, and lysine. Unless otherwise indicated, all amino acids as used herein are L-isomers, however, embodiments using D-isomers are also within the scope of the present invention.

The term "non-naturally occurring amino acid" refers to an amino acid which is ordinarily not found in nature. Examples of non-naturally-occurring amino acids include D-form of amino acids as described above, norleucine, para-nitrophenylalanine, homophenylalanine, para-fluorophenylalanine, 3-amino-2-benzyl propionic acid, D- or L-homoarginine, and D-phenylalanine.

The term "amino acid analog" refers to a molecule having a physical property and/or function similar to that of amino acids, but is not an amino acid. Examples of amino acid analogs include, for example, ethionine, canavanine, 2-methylglutamine, and the like. An amino acid mimic refers to a compound which has a structure different from that of the general chemical structure of amino acids but which functions in a manner similar to that of naturally-occurring amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "corresponding" amino acid or nucleic acid refers to an amino acid or nucleotide in a given polypeptide or polynucleotide molecule, which has, or is anticipated to have, a function similar to that of a predetermined amino acid or nucleotide in a polypeptide or polynucleotide as a reference for comparison. Particularly, in the case of enzyme molecules, the term refers to an amino acid which is present at a similar position in an active site and similarly contributes to catalytic activity. For example, in the case of antisense molecules, the term refers to a similar portion in an ortholog corresponding to a particular portion of the antisense molecule. Such a "corresponding" amino acid or nucleic acid may extend over a region or domain having a certain range. Therefore, in this case, such a region or domain is herein referred to as a "corresponding" region or domain.

As used herein, the term "corresponding" gene (e.g., a polypeptide or polynucleotide molecule) refers to a gene (e.g., a polypeptide or polynucleotide molecule) in a given species, which has, or is anticipated to have, a function similar to that of a predetermined gene in a species as a reference for comparison. Between corresponding genes, a number of common amino acid sequences are found in a highly conserved manner. When there are a plurality of genes having such a function, the term refers to a gene having the same evolutionary origin. Therefore, a gene corresponding to a given gene may be an ortholog of the given gene. Genes encoding the rice prolamin may correspond to those encoding the glutenin of wheat. Such a corresponding gene can be identified by techniques well known in the art. Therefore, for example, a corresponding gene in a given organism can be found by searching a sequence database of the organism (e.g., wheat, maize) using the sequence of a reference gene (e.g., rice prolamin gene, and the like) as a query sequence.

As used herein, the term "nucleotide" may be either naturally-occurring or nonnaturally-occurring. The term "nucleotide derivative" or "nucleotide analog" refers to a nucleotide which is different from naturally-occurring nucleotides and has a function similar to that of the original nucleotide. Such nucleotide derivatives and nucleotide analogs are well known in the art. Examples of such nucleotide derivatives and nucleotide analogs include, but are not limited to, phosphorothioate, phosphoramidate, methylphosphonate, chiral-methylphosphonate, 2-O-methyl ribonucleotide, and peptide-nucleic acid (PNA).

As used herein, the term "fragment" refers to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more nucleotides. Lengths represented by integers which are not herein specified (e.g., 11 and the like) may be appropriate as a lower limit. For example, in the case of polynucleotides, the lower limit of the length of the fragment includes 5, 6, 7, 8, 9, 10, 15, 20, 25, 30, 40, 50, 75, 100 or more nucleotides. Lengths represented by integers which are not herein specified (e.g., 11 and the like) may be appropriate as a lower limit. As used herein, the length of polypeptides or polynucleotides can be represented by the number of amino acids or nucleic acids, respectively. However, the above-described numbers are not absolute. The above-described numbers, as the upper or lower limit, are intended to include some greater or smaller numbers (e.g., +10%), as long as the same function is maintained. For this purpose, "about" may be herein put ahead of the numbers. However, it should be understood that the interpretation of numbers is not affected by the presence or absence of "about" in the present specification.

As used herein, the term "biological activity" refers to activity possessed by an agent (e.g., a polynucleotide, a protein, etc.) within an organism, including activities exhibiting various functions. For example, when an agent is an antisense molecule, the biological activity thereof is binding to a target nucleic acid molecule, and expression suppression thereby and the like. In another example, when a certain factor is an enzyme, the biological activity thereof includes its enzyme activity. In still another example, when a certain factor is a ligand, the biological activity thereof includes the binding of the ligand to a receptor corresponding thereto. The above-described biological activity can be measured by techniques well-known in the art.

As used herein, the term "antisense (activity)" refers to activity which permits specific suppression or reduction of expression of a target gene. More specifically, it refers to an activity capable of reducing the expression levels of a protein by specifically reducing the mRNA amount of a gene having a nucleotide sequence region complementary to a nucleotide sequence which was introduced in to a cell. As technologies therefor, there are methods for directly introducing an RNA molecule complementary to the mRNA produced from the target gene into a cell, and a method for introducing a construct vector capable of expressing an RNA complementary to the desired gene into a cell, and the latter is more generally conducted in plants.

The antisense activity is ordinarily achieved by a nucleic acid sequence having a length of at least 8 contiguous nucleotides, which is complementary to the nucleic acid sequence of a target gene. A molecule having such antisense activity is called an antisense molecule. Such a nucleic acid sequence preferably has a length of at least 9 contiguous nucleotides, more preferably a length of at least 10 contiguous nucleotides, and even more preferably a length of at least 11 contiguous nucleotides, a length of at least 12 contiguous nucleotides, a length of at least 13 contiguous nucleotides, a length of at least 14 contiguous nucleotides, a length of at least 15 contiguous nucleotides, a length of at least 20 contiguous nucleotides, a length of at least 30 contiguous nucleotides, a length of at least 40 contiguous nucleotides, and a length of at least 50 contiguous nucleotides. These nucleic acid sequences include nucleic acid sequences having at least 70% homology thereto, more preferably at least 80%, even more preferably at least 90%, and still even more preferably at least 95%. The antisense activity is preferably complementary to a 5' terminal sequence of the nucleic acid sequence of a target gene. Such an antisense nucleic acid sequence includes the above-described sequences having one or several, or at least one, nucleotide substitutions, additions, and/or deletions. Therefore, "antisense activity" of the present application includes but is not limited to the reduction of expression of a gene.

General antisense techniques are described in textbooks (e.g., Murray, J. A. H. eds., Antisense RNA and DNA, Wiley-Liss Inc, 1992). Later research has revealed a phenomenon called RNA interference (RNAi), leading to the development of antisense techniques. RNAi is a phenomenon in which when double-stranded RNA (about 20 bases in length) having a sequence homologous to a target gene is introduced into a cell, mRNA of the target gene homologous to the RNA sequence is specifically decomposed to reduce the expression level thereof. The phenomenon which was originally found in nematodes has been revealed to be a universal phenomenon throughout organisms including plants. The molecular mechanism of the antisense technique suppressing the expression of target genes has been elucidated to have a process similar to that of RNAi. Conventionally, a certain DNA sequence complementary to the nucleotide sequence of a target gene is linked to an appropriate promoter to construct an expression vector which expresses artificial mRNA under the control of a promoter, and the vector is then introduced into cells. According to recent findings, an expression vector which is designed to construct double-stranded RNA in cells is used. The basic structure of the vector is such that a DNA sequence complementary to a certain target gene is linked downstream of a promoter and the same sequence is linked in the reverse direction. A single-stranded mRNA transcribed from the above-described constructed gene is paired with the reverse-directed, complementary nucleotide sequence portion into double-stranded RNA having a hair-pin, secondary structure. This structure elicits decomposition of mRNA of a target gene in accordance with the mechanism of RNAi. For plants, RNAi was found in *Arabidopsis thaliana* (Smith, N. A. et al., Nature, 407, 319-320, 2000). RNAi is reviewed in, for example, Morita and Yoshida, Tanpakushitsu•Kakusan•Koso [Protein/Nucleic acid/Enzyme], 47, 1939-1945, 2002). These documents are herein incorporated by reference in their entirety.

As used herein, the term "RNAi" is an abbreviation of RNA interference and refers to a phenomenon where an agent for causing RNAi, such as double-stranded RNA (also called dsRNA), is introduced into cells and the mRNA homologous thereto is specifically degraded, so that synthesis of gene products is suppressed. As used herein, RNAi may have the same meaning as that of an agent which causes RNAi.

As used herein, the term "an agent causing RNAi" refers to any agent capable of causing RNAi. As used herein, "an agent causing RNAi of a gene" indicates that the agent causes RNAi relating to the gene and the effect of RNAi is achieved (e.g., suppression of expression of the gene, and the like). Examples of such an agent causing RNAi include, but are not limited to, a sequence having at least about 70% homology to the nucleic acid sequence of a target gene or a sequence hybridizable under stringent conditions, RNA containing a double-stranded portion having a length of at least 10 nucleotides or variants thereof. Here, this agent may be preferably DNA containing a 3' protruding end, and more preferably the 3' protruding end has a length of 2 or more nucleotides (e.g., 2-4 nucleotides in length).

Alternatively, RNAi used in the present invention includes, but is not limited to a pair of short inverted complementary sequences (for example, at least 15 bp, such as 23 bp and the like).

As used herein the term "antisense gene" is a gene or a construct (e.g. expression cassette) capable of rendering antisense activity. Similarly, "RNAi gene" as used herein refers to a gene or a construct (e.g. expression cassette) capable of inducing the RNAi phenomenon. "Expression inhibitory gene" is used to collectively refer to both "antisense gene" and "RNAi gene".

A polypeptide of a foreign gene used in the present invention may be produced by, for example, cultivating primary culture cells producing the peptides or cell lines thereof, followed by separation or purification of the peptides from culture supernatant. Alternatively, genetic manipulation techniques can be used to incorporate a gene encoding a polypeptide of interest into an appropriate expression vector, transform an expression host with the vector, and collect recombinant polypeptides from the culture supernatant of the transformed cells. The above-described host cell may be any host cells conventionally used in genetic manipulation techniques as long as they can express a polypeptide of interest while keeping the physiological activity of the peptide (e.g., *E. coli*, yeast, an animal cell, etc. in addition to a plant cell). Polypeptides derived from the thus-obtained cells may have at least one amino acid substitution, addition, and/or deletion or at least one sugar chain substitution, addition, and/or deletion as long as they have substantially the same function as that of naturally-occurring polypeptides.

A given amino acid may be substituted with another amino acid in a protein structure, such as a cationic region or a substrate molecule binding site, without a clear reduction or loss of interactive binding ability. A given biological function of a protein is defined by the interactive ability or other property of the protein. Therefore, a particular amino acid substitution may be performed in an amino acid sequence, or at the DNA code sequence level, to produce a protein which maintains the original property after the substitution. Therefore, various modifications of peptides as disclosed herein and DNA encoding such peptides may be performed without clear losses of biological usefulness.

When the above-described modifications are designed, the hydrophobicity indices of amino acids may be taken into consideration. The hydrophobic amino acid indices play an important role in providing a protein with an interactive biological function, which is generally recognized in the art (Kyte, J. and Doolittle, R. F., J. Mol. Biol. 157(1):105-132, 1982). The hydrophobic property of an amino acid contributes to the secondary structure of a protein and then regulates interactions between the protein and other molecules (e.g., enzymes, substrates, receptors, DNA, antibodies, antigens, etc.). Each amino acid is given a hydrophobicity index based on the hydrophobicity and charge properties thereof as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well known that if a given amino acid is substituted with another amino acid having a similar hydrophobicity index, the resultant protein may still have a biological function similar to that of the original protein (e.g., a protein having an equivalent enzymatic activity). For such an amino acid substitution, the hydrophobicity index is preferably within ±2, more preferably within ±1, and even more preferably within ±0.5. It is understood in the art that such an amino acid substitution based on hydrophobicity is efficient.

A hydrophilicity index is also useful for modification of an amino acid sequence of the present invention. As described in U.S. Pat. No. 4,554,101, amino acid residues are given the following hydrophilicity indices: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent. For such an amino acid substitution, the hydrophilicity index is preferably within ±2, more preferably ±1, and even more preferably ±0.5.

The term "conservative substitution" as used herein refers to amino acid substitution in which a substituted amino acid and a substituting amino acid have similar hydrophilicity indices or/and hydrophobicity indices. For example, conservative substitution is carried out between amino acids having a hydrophilicity or hydrophobicity index of within ±2, preferably within ±1, and more preferably within 0.5. Examples of conservative substitution include, but are not limited to, substitutions within each of the following residue pairs: arginine and lysine; glutamic acid and aspartic acid; serine and threonine; glutamine and asparagine; and valine, leucine, and isoleucine, which are well known to those skilled in the art.

As used herein, the term "variant" refers to a substance, such as a polypeptide, polynucleotide, or the like, which differs partially from the original substance. Examples of such variants include a substitution variant, an addition variant, a deletion variant, a truncated variant, an allelic variant, and the like. Examples of such variants include, but are not limited to, a nucleotide or polypeptide having one or several substitutions, additions and/or deletions or a nucleotide or polypeptide having at least one substitution, addition and/or deletion. The term "allele" as used herein refers to a genetic variant located at a locus identical to a corresponding gene, where the two genes are distinguished from each other. Therefore, the term "allelic variant" as used herein refers to a variant which has an allelic relationship with a given gene. Such an allelic variant ordinarily has a sequence the same as or highly similar to that of the corresponding allele, and ordinarily has almost the same biological activity, though it occasionally has different biological activity. The term "species homolog" or "homolog" as used herein refers to one that has an amino acid or nucleotide homology with a given gene in a given species (preferably at least 60% homology, more preferably at least 80%, at least 85%, at least 90%, and at least 95% homology). A method for obtaining such a species homolog is clearly understood from the description of the present specification. The term "ortholog" (also called orthologous genes) refers to genes in different species derived from a common ancestry (due to speciation) For example, in the case of the hemoglobin gene family having multigene structure, human and mouse α-hemoglobin genes are orthologs, while the human α-hemoglobin gene and the human β-hemoglobin gene are paralogs (genes arising from gene duplication). Further, comparing human Cystatin A, a cysteine protease inhibitor, and rice Oryzacystatin, only three short amino acid motives are conserved which are believed to be critical for interaction with a protease of target, and the other portions have very low amino acid similarity. However, both belong to the superfamily of cystatin genes, and have genes of common origin, and thus, not only the cases where there are high amino acid homology, but also in cases where there are only a few common amino acids in a particular region of these protein structure, these may be called orthologs to each other. As such, orthologs usually play a similar role to that in the original species in another species. As such, orthologs from another species may be useful in the present invention. A prolamin targeted by the present invention may form a family having a number of members, and such may be appreciated as a conservatively modified variant.

As used herein, the term "conservative (or conservatively modified) variant" applies to both amino acid and nucleic acid sequences. With respect to particular nucleic acid sequences, conservatively modified variants refer to those nucleic acids which encode identical or essentially identical amino acid sequences. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" which represent one species of conservatively modified variation. Every nucleic acid sequence herein which encodes a polypeptide also describes every possible silent variation of the nucleic acid. Those skilled in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence. Preferably, such modification may be performed while avoiding substitution of cysteine, which is an amino acid capable of largely affecting the higher-order structure of a polypeptide. Examples of a method for such modification of a base sequence include cleavage using a restriction enzyme or the like; ligation or the like by treatment using DNA polymerase, Klenow fragments, DNA ligase, or the like; and a site specific base substitution method using synthesized oligonucleotides (specific-site directed mutagenesis; Mark Zoller and Michael Smith, Methods in Enzymology, 100, 468-500 (1983)). Modification can be performed using methods ordinarily used in the field of molecular biology.

In order to prepare functionally equivalent polypeptides, amino acid additions, deletions, or modifications can be performed in addition to amino acid substitutions. Amino acid substitution(s) refers to the replacement of at least one amino acid of an original peptide chain with different amino acids, such as the replacement of 1 to 10 amino acids, preferably 1 to 5 amino acids, and more preferably 1 to 3 amino acids with different amino acids. Amino acid addition(s) refers to the addition of at least one amino acid to an original peptide chain, such as the addition of 1 to 10 amino acids, preferably 1 to 5 amino acids, and more preferably 1 to 3 amino acids to an original peptide chain. Amino acid deletion(s) refers to the deletion of at least one amino acid, such as the deletion of 1 to 10 amino acids, preferably 1 to 5 amino acids, and more preferably 1 to 3 amino acids. Amino acid modification includes, but is not limited to, amidation, carboxylation, sulfation, halogenation, truncation, lipidation, alkylation, glycosylation, phosphorylation, hydroxylation, acylation (e.g., acetylation), and the like. Amino acids to be substituted or added may be naturally-occurring or nonnaturally-occurring amino acids, or amino acid analogs. Naturally-occurring amino acids are preferable.

As used herein, the term "peptide analog" refers to a compound which is different from a peptide but has at least one chemical or biological function equivalent to the peptide. Therefore, a peptide analog includes one that has at least one amino acid analog or amino acid derivative addition or substitution with respect to the original peptide. A peptide analog has the above-described addition or substitution so that the function thereof is substantially the same as the function of the original peptide (e.g., a similar pKa value, a similar functional group, a similar binding manner to other molecules, a similar water-solubility, and the like). Such a peptide analog can be prepared using a technique well known in the art. Therefore, a peptide analog may be a polymer containing an amino acid analog.

As used herein the terms "polynucleotide analog" and "nucleic acid analog" are interchangeably used to refer to a compound which is different from a polynucleotide or nucleic acid, but still equivalent in terms of at least one chemical or biological function with a polynucleotide or nucleic acid. Accordingly, polynucleotide analog or nucleic acid analog encompasses those having at least one nucleotide analog or nucleotide derivative added thereto or substituted therewith respect to its original polynucleotide or nucleic acid.

Nucleic acid molecules as used herein may be deleted or substituted with another base, or added with an additional nucleic acid sequence in a portion thereof as described above, as long as the polypeptide to be expressed has substantially identical activity to that of native polypeptide thereof. Alternatively, such a nucleic acid molecule may bind to another nucleic acid at its 5' and/or 3' terminus (i). Further, such a nucleic acid molecule may be a nucleic acid molecule hybridizing to a gene encoding a polypeptide under stringent conditions and encoding a polypeptide having substantially identical function to the polypeptide. Such a gene is known in the art and those skilled in the art can readily use such a known gene in the present invention.

The above-described nucleic acid can be obtained by a well-known PCR method, i.e., chemical synthesis. This method may be combined with, for example, site-specific mutagenesis, hybridization, or the like.

As used herein, the term "substitution, addition or deletion" for a polypeptide or a polynucleotide refers to the substitution, addition or deletion of an amino acid or its substitute, or a nucleotide or its substitute, with respect to the original polypeptide or polynucleotide, respectively. This is achieved by techniques well known in the art, including a site-specific mutagenesis technique and the like. A polypeptide or a polynucleotide may have any number (>0) of substitutions, additions, or deletions. The number can be as large as a variant having such a number of substitutions, additions or deletions which maintains an intended function (e.g., the information transfer function of hormones and cytokines, etc.). For example, such a number may be one or several, and preferably within 20% or 10% of the full length, or no more than 100, no more than 50, no more than 25, or the like.

As used herein, the term "specifically expressed" in relation to a gene indicates that the gene is expressed in a specific site or for a specific period of time, at a level different from (preferably higher than) that in other sites or for other periods of time. The term "specifically expressed" indicates that a gene may be expressed only in a given site (specific site) or may be expressed in other sites. Preferably, the term "specifically expressed" indicates that a gene is expressed only in a given site.

As used herein, a gene being "specifically suppressed" refers to that the gene is suppressed at a specific site of a plant or at a specific period, in a different manner than the other sites or periods, respectively, at a different (preferably higher) level. Specific suppression may include suppression only at a certain site (specific site), or may include suppression at different sites. Preferably, specific suppression refers to suppression only at a certain site.

When a gene is mentioned herein, the term "vector" refers to an entity capable of transferring a polynucleotide sequence of interest to a target cell. Such a vector is capable of self-replication or incorporation into a chromosome in a host cell (e.g., a prokaryotic cell, yeast, an animal cell, a plant cell, an insect cell, an individual animal, and an individual plant, etc.), and contains a promoter at a site suitable for transcription of a polynucleotide of the present invention. As used herein, a vector may be a expression vector, recombinant vector or the like.

Vectors as used herein include general bacteria (typically *E. coli* strains derived from *E. coli* K 12 strain) used in normal gene experiments which are replicable and can be isolated and purified. This is necessary for constructing a target gene that is to be introduced into a plant. Specifically, for example, *E. coli* pBR322, pUC18, pUC19, pBluescript, and pGEM-T plasmids, which are commercially available construct plasmids. In the cases where a gene fragment is directly introduced into a plant cell using methods such as electroporation method, polyethylene glycol method, particle gun method or the like, such a commercially available general plasmid may be used to introduce a gene of interest to prepare a construct including the same. In a specific case of such vectors, where *Agrobacterium*-base gene introduction method is used to transform a plant cell, it may be necessary to have a plasmid called a "binary vector", which includes nucleotide sequences corresponding to both *E. coli* and *Agrobacterium* replication origins, and border sequences from T-DNA presenting border regions that can be introduced into a plant (Left border and Right Border). It includes, but is not limited to, for example, pBI101 (available from Clontech), pBIN (Bevan, N., Nucleic Acid Research 12, 8711-8721, 1984), pBINPlus (van Engelen, F A et al., Transgenic Research 4, 288-290, 1995), pTN or pTH (Fukuoka H et. al., Plant Cell Reports 19, 2000), pPZP (Hajdukiewicz P. et al., Plant Molecular Biology 25, 989-994, 1994) and the like. In addition, vectors which are capable of being used in a plant may be exemplified by a tobacco mosaic virus vector, but such a type of vector does not introduce a desired gene into a plant chromosome, and thus it can still be used in the present invention, but is limited to be used for propagating plants with a gene introduced without need of a seed.

As used herein, the term "expression cassette" refers to a unit of an artificially constructed gene, in which a structural gene, and a promoter sequence or a regulatory element regulating the same, and a terminator sequence terminating the mRNA transcription thereof are linked in a manner such that the structural gene is operated in a host cell. Exemplary cassettes include, but are not limited to, an expression cassette with a selective marker for selecting only a host cell with a gene (for example, hygromycin resistant gene) introduced, or an expression cassette of a useful protein gene to be expressed in a host cell. Types, structure and number of such expression cassettes to be prepared are to be appropriately selected depending on the organism, host cell and purpose to be used, and such combinations thereof are well known to those skilled in the art.

As used herein the term "expression vector" refers to a "vector" which may comprise one or more "expression cassette(s)" as described above. Target gene expression cassettes to be introduced into plants may be located on separate vectors, or all such cassettes may be located on a single vector in a linked manner. Expression vectors for plants of the present invention may be a binary vector. Further, such a vector may include a selectable marker (for example, hygromycin resistance gene) expression cassette appropriately chosen for a host plant which is concurrently introduced with a target gene expression cassette.

Selectable markers used herein include but are not limited to, for example, hydromycin phosphotransferase, variant type acetoacetate synthase and the like. Promoters which may be used as a selectable marker expression cassette include but are not limited to, for example, CaMV35S promoter and variant promoters thereof, ubiquitin promoters and the like; terminators include but are not limited to Nos terminator, Tm1 terminator, 10 kDa prolamin terminator, 13 kDa prolamin terminator, 16 kDa prolamin terminator and the like.

As used herein, the term "terminator" refers to a sequence which is located downstream of a protein-encoding region of a gene and which is involved in the termination of transcription when DNA is transcribed into mRNA, and the addition of a poly A sequence. It is known that a terminator contributes to the stability of mRNA, and has an influence on the amount of gene expression. Examples of a terminator include, but are not limited to, the CaMV35S terminator, the terminator of the nopaline synthase gene (Tnos), the terminator of the tobacco PR1a gene, and the like. In the present invention, any of those presenting terminator activity in a plant, may be used.

As used herein, the term "promoter" refers to a base sequence which determines the initiation site of transcription of a gene and is a DNA region which directly regulates the frequency of transcription. Transcription is started by RNA polymerase binding to a promoter. A promoter region is usually located within about 2 kbp upstream of the first exon of a putative protein coding region. Therefore, it is possible to estimate a promoter region by predicting a protein coding region in a genomic base sequence using DNA analysis software. A putative promoter region is usually located upstream of a structural gene, but depending on the structural gene, i.e., a putative promoter region may be located downstream of a structural gene. Preferably, a putative promoter region is located within about 2 kbp upstream of the translation initiation site of the first exon. Preferably, in the present invention, promoters promoting specific expression may be used. Such specific promoters preferably include but are not limited to promoters driving such specific expression in storage proteins promoting activity. More preferably, in the present invention, promoters include preferably those derived from a storage protein (for example, prolamin), but are not limited thereto. In a preferred embodiment, promoters derived from 16 kDa prolamin, 13 kDa prolamin, 10 kDa prolamin and the like may be used. Selection of terminators sometimes gives an influence on expression intensity, and to date generally NOS terminators are mostly used, regardless of the promoter used, based on the past results. However, in a preferred embodiment, the present invention uses a terminator derived from a prolamin (in particular, 10 kDa prolamin). This terminator is shorter in base sequence thereof, and has no restriction enzyme sites, which often present in multicloning sites, and thus has now been shown to be used in combination with a variety of a storage protein promoters, ubiquitin promoter, actin promoter, or CaMV35S promoter. Therefore, it is to be noted that a general terminator derived from a novel plant (rice), which may replace Nos terminator, has now been obtained.

As used herein when used for gene expression, the term "site specificity" refers generally to expression specificity of the gene in a site (for example, in the case of plants, protein body, root, stem, stock, leaves, flowers, seed albumen, embryo, fruits and the like) of an organism (for example, plant). The term "periodic specificity" refers to expression specificity of the gene depending on a development stage (for example, in the case of plants, growth phase (for example, specific period of time for forming protein body, days after germination) of an organism (for example, a plant). Such specificity may be introduced to a desired organism by selecting an appropriate promoter.

"Constitutive" expression of a promoter as used herein refers to a trait in which expression is similarly carried out in a plant tissue during the juvenile period and the mature period in the course of the growth of a plant. Specifically, when northern blot analysis is carried out under conditions similar to those in the examples described herein, if expression is observed in the same or corresponding site on both day 5 and day 15, the expression is regarded as being constitutive by the definition in the present invention. Constitutive promoters are believed to play a role in the homeostasis of plants in a normal growth environment. "Responsiveness to stress or stimulus" expression of a promoter refers to a trait in which when at least one stress or stimulus is applied to a plant, the expression amount is changed. Particularly, a trait in which the expression amount is increased is called "stress inductivity", and a trait in which the expression amount is decreased is called "stress reducibility". "Stress reducible" expression is based on the assumption that expression can be observed in normal cases, and therefore overlaps the idea of "constitutive" expression. These traits can be determined by extracting RNA from an arbitrary portion and subjecting the RNA to Northern blot analysis to analyze expression amounts or subjecting the expressed protein to Western blot analysis. A plant or a portion thereof (for example, a specific cell, tissue or the like) transformed with a vector incorporating a stress (or stimulant) inducive promoter together with a nucleic acid encoding the polypeptide of the present invention, may reduce storage proteins and subsequently express a desired protein in a specific condition by using stimulant agent having inductive activity of the promoter.

An "enhancer" may be used so as to enhance the expression efficiency of a gene of interest. As such an enhancer, an enhancer region containing an upstream sequence within the CaMV35S promoter is preferable. A plurality of enhancers may be used, or only one enhancer may, or may not, be used.

As used herein the term "silencer" refers to a sequence having a function of inhibiting and resting gene expression. In the present invention, any silencer may be used as long as its silencing function is possessed, and may not be used.

As used herein the phrase "operably linked" refers to that expression (operation) of a desired sequence is located under the control of a transcription/translation regulatory sequence (for example, promoter, enhancer or the like), or under translation regulatory sequence. In order to link a promoter operably with a gene, the gene is usually located just upstream of the promoter, but is necessarily located next thereto.

Any technique may be used herein for introduction of a nucleic acid molecule into cells, including, for example, transformation, transduction, transfection, and the like. Such a nucleic acid molecule introduction technique is well known in the art and commonly used, and is described in, for example, Ausubel F. A. et al., editors, (1988), Current Protocols in Molecular Biology, Wiley, New York, N.Y.; Sambrook J. et al. (1987) Molecular Cloning: A Laboratory Manual, 2nd Ed. and its 3rd Ed., Cold Spring Harbor Laboratory Press, Cold Spring Harbor, N.Y.; Special issue, Jikken Igaku [Experimental Medicine] "Experimental Method for Gene Introduction & Expression Analysis", Yodo-sha, 1997; and the like. Gene introduction can be confirmed by methods as described herein, such as Northern blotting analysis and Western blotting analysis, or other well-known, common techniques.

Any of the above-described methods for introducing DNA into cells can be used as a vector introduction method, including, for example, transfection, transduction, transformation, and the like (e.g., a calcium phosphate method, a liposome method, a DEAE dextran method, an electroporation method, a particle gun (gene gun) method, and the like), lipofection method, spheroplast method [Proc. Natl. Acad. Sci. USA, 84, 1929 (1978)], lithium acetate method [J. Bacteriol., 153, 163 (1983)], and a method described in Proc. Natl. Acad. Sci. USA, 75, 1929 (1978).

As used herein the term "gene introduction reagent" refers to a reagent used for promoting introduction efficiency in a gene introduction method. Such gene introduction reagents include, but are not limited to cationic macromolecules, cationic lipids, polyamine reagents, polyimine reagents, phosphate calcium and the like. Specific examples of such reagents used for transfection include commercially available reagents from a variety of sources, and include but are not limited to, for example, Effectene Transfection Reagent (cat. no. 301425, Qiagen, CA), TransFast™ Transfection Reagent (E2431, Promega, WI), Tfx™-20 Reagent (E2391, Promega, WI), SuperFect Transfection Reagent (301305, Qiagen, CA), PolyFect Transfection Reagent (301105, Qiagen, CA), LipofectAMINE 2000 Reagent (11668-019, Invitrogen corporation, CA), JetPEI (×4) conc. (101-30, Polyplus-transfection, France) and ExGen 500 (R0511, Fermentas Inc., MD).

For the purpose of introduction of a plant expression vector into a plant cell, a method well known to those skilled in the art, such as an indirect method using *Agrobacterium*, and a method for directly introducing into cells, can be used. As such an indirect method using *Agrobacterium*, for example, a method of Nagel et al. (Nagel et al. (1990), Microbiol. Lett., 67, 325) may be used. In this method, initially *Agrobacterium* is transformed with a plant expression vector by electroporation, and then the transformed *Agrobacterium* is introduced into a plant cell with a method described in Gelvin et al. (Gelvin et al., ed. (1994), Plant Molecular Biology Manual (Kluwer Academic Press Publishers)). As a method for directly introducing a plant expression vector into a cell, an electroporation method (see Shimamoto et al., (1989), Nature, 338: 274-276; and Rhodes et al., (1989), Science, 240:204-207), a particle gun method (see Christou et al. (1991), Bio/Technology 9:957-962), and a polyethyleneglycol (PEG) method (see Datta et al. (1990), Bio/Technology 8: 736-740) are illustrated. These methods are well known in the art. A method suitable for a plant to be transformed can be appropriately selected by those skilled in the art.

Cells with a plant expression vector introduced therein may be firstly selected using drug resistance such as hygromycin-resistance, and kanamycin-resistance and the like. Thereafter, the cell may be regenerated to a plant tissue, a plant organ, and/or a plant using a well-known method in the art. Further, seeds may be obtained from the plant. The expression of introduced genes may be detected by a Northern method or a PCR method. The expression of proteins which are genetic products may be confirmed by, for example, a Western blot method.

The promoters of the present invention have been shown to be particularly useful, but can also be used for other organisms. Molecular biological technologies used in the present invention are well known and routine in the art, and include, for example, those described in Ausubel F. A. et al. (1988), Current Protocols in Molecular Biology, Wiley, New York, N.Y.; Sambrook J. et al. (1987) Molecular Cloning: A Laboratory Manual, 2nd Ed. and the third edition thereof, Cold Spring Harbor Laboratory Press, Cold Spring Harbor, N.Y., Suppl. Experimental Medicine "Gene introduction and Expression analysis Experimentals" Yodo-sha, 1997.

As used herein, the term "transformant" refers to the whole or a part of an organism, such as a cell, which is produced by transformation. Examples of a transformant include a prokaryotic cell, yeast, an animal cell, a plant cell, an insect cell, and the like. Transformants may be referred to as transformed cells, transformed tissue, transformed hosts, or the like, depending on the subject, and may refer to any specific form depending on the context.

In a method of transformation, physical methods include polyethylene glycol (PEG method), electroporation method, microinjection method, particle gun method and the like. These methods are highly useful in that they can be used for both monocotyledonous and dicotyledonous plant bodies. However, in the polyethylene glycol method and electroporation method, the cell wall will be an obstacle, and therefore protoplast should be used, and in addition, there is also a problem in which the probability of a gene to be introduced into chromosomal DNA of the target plant cell is very low. Further, microinjection methods using a callus or tissue without using a protoplast have a number of difficulties with respect to the size of needle used or immobilization of the targeted tissue or the like. Using a particle gun with tissues has problems in that mutations appear in the form of a chimera or the like. Further, these physical methodologies are generally likely to incorporate multiple copies of foreign genes to be introduced in an incomplete form into the nuclear genome. It is known that once such multiple copies of a foreign gene are introduced, such a gene is likely to be inactivated.

On the other hand, a method for introducing an isolated gene using an organism includes *Agrobacterium* method, viral vector method, and recently developed pollen-virus based method. These methods have advantages in which a plant callus, tissue or plant body is used for gene introduction without using a protoplast, and thus culture does not take too long, and somaclonal mutation or the like is rarely occurs. Amongst these, the pollen vector based method has less experience and thus have known portions as a transformation of plant. The viral vector method has advantages in which genes to be introduced are spread into the entire plant body infected with the virus used, however, the gene is merely amplified in each cell and expressed therein, and not guaranteed to be inherited to the next generation, and has the problem in which a longer DNA fragment cannot be introduced. The *Agrobacterium* method has many advantages, including allowing introduction of a DNA of more than about 20 kbp without significant rearrangement into the chromosome, and the number of gene copies to be introduced is few, and is highly reproducible and the like. *Agrobacterium* is out of the host range for monocotyledonous plants such as Gramineae plants, and thus foreign gene introduction into Gramineae plants has been conducted by the above-mentioned physical methods to date. However, *Agrobacterium* method may be applied to monocotyledonous plants such as rice or the like in which culture system has been established, and today, *Agrobacterium* method is preferably used.

In introduction of a foreign gene by *Agrobacterium* method, when low-molecular weight phenol compound such as acetosyringone synthesized by a plant into Ti plasmid vir region, T-DNA region is cleaved from a Ti plasmid, and through a number of processes, the T-DNA region is incorporated into the nuclear chromosomal DNA of a plant cell. In a dicotyledonous plant, the plant per se comprises synthetic machinery of such a phenol compound, and thus it is easy to introduce a foreign gene by leaf disc methods or the like, and is thus reproducible. On the other hand, in monocotyledonous plants, plants per se cannot synthesize such a phenol compound, it was difficult to produce a transformed plant by *Agrobacterium*. However, by adding acetosyringone in infection of *Agrobacterium*, it is now possible to introduce a foreign gene into a monocotyledonous plant.

In the present invention, in a transformant, a desired nucleic acid molecule (transgene) may or may not be introduced in to a chromosome. Preferably, such a desired nucleic acid molecule (transgene) is introduced into a chromosome, and more preferably, it is introduced into both alleles of the chromosome.

Plant cells, as used herein, include, for example, cells of rice, potato, tobacco, maize, *Brassica*, soybean, tomato, carrot, wheat, barley, rye, alfalfa, flax and the like, and woody plants (for example, poplar) and the like. Preferably, the plant cell may be of rice. Rice includes but is not limited to *japonica* variant, *indica* variant and the like. In one preferable embodiment, rice may be of *japonica* variant. As used herein, rice variants include, but are not limited to, for example, Nipponbare, Nihonmasari, Kinmaze, Norin No. 22, Chiseiasahi, Koshihikari, Akitakomachi, Dontokoi, Hinohikari, Mangetsumochi, Kaguramochi, Hakuchomochi, LGC-1, Shun'yo, Hosetsuwaisei, Tetep, Basmati, IR8, Hyokumochi, Himenomochi, Koganemochi, Kazenokomochi and the like. In other preferable embodiments, rice include *indica* variants. Types of *indica* variants include but are not limited to Tetep, Basmati, IR8, Hunanzao, and the like. Method for introducing recombinant vectors into a plant cell may be any method as long as it introduces a nucleic acid into a plant cell, and as described elsewhere herein in detail, and include, but are not limited to, for example, *Agrobacterium* (Japanese Laid-Open Publication Nos: 59-14088, 60-70080, and WO94/00977), electroporation method (Japanese Laid-Open Publication No: 60-251887), particle gun (gene gun) based method (Japanese Patent Nos: 2606856, 2517813) and the like.

As used herein the term "plant" collectively refers to an organism belonging to the kingdom of Plantae and is typically characterized by the presence of chlorophyll, a hard cell wall, the presence of abundant permanent embryonal cells, and incapability of movement or the like. Typically, "plant" refers to Phanerogamae having a cell wall formation and an anabolism action by chlorophyll. "Plant" encompasses both monocotyledonous plant and dicotyledonous plant. Preferably, plants include, but are not limited to, for example, monocotyledonous plants belonging to Gramineae such as rice, wheat, maize, barley, sorghum, and the like. Preferably, the plant may be rice. Rice includes but is not limited to *japonica* and *indica* variants. More preferably, rice may be *japonica* variant. As used herein, variants of rice include but are not limited to, for example, Nipponbare, Nihonmasari, Kinmaze, Norin No. 22, Chiseiasahi, Koshihikari, Akitakomachi, Dontokoi, Hinohikari, Mangetsumochi, Kaguramochi, Hakuchomochi, LGC-1, Shun'yo, Hosetsuwaisei, Tetep, Basmati, IR8, Hyokumochi, Himenomochi, Koganemochi, Kazenokomochi and the like. *Indica* variants include, but are not limited to Tetep, Basmati, IR8, Hunanzao, Kasalath and the like Most preferably, rice in which expression of other storage proteins (for example, glutelins, globulins and the like) have been reduced, such as for example LGC-1, is used in the present invention. Preferable plants are not limited to crops, but also flowers, trees, turfs, weeds and the like. Unless otherwise stated, plant refers to any of plant body, plant organ, plant tissue, plant cell, and seed. Examples of plant organs include root, leaf, stem and flower and the like. Examples of plant cells include a callus and suspended culture cells.

Examples of Gramicear plants include plants belonging to *Oryza, Hordenum, Secale, Scccharum, Echinochloa*, or *Zea*, and include rice, barley, rye, Japanese millet, sorghum, maize and the like.

Plants used for a method for production according to the present invention are preferably monocotyledonous plant, and more preferably Gramineae plant. More preferably, it may be rice. Still more preferably, the plants used in a method of production according to the present invention include, but are not limited to Nipponbare, Dontokoi, LGC-1, Hosetsuwaisei, Tetep, Basmati, Koshihikari, Gohyakumangoku, koganemochi, Kasalath. The genome sequence of Nipponbare is disclosed, and thus is preferable as the chromosomal site of a gene introduced can be readily identified. Dontokoi is preferable because it is tasty, and easy to produce as it is shorter than Koshihikari. LGC-1 is preferable because prolamin antisense is more effectively achieved. Hosetsuwaisei is preferable since it has a very small plant body (about 20 cm), but the seeds thereof are of normal size, and thus can be produced in an incubator. Koshihikari is preferable since it is a major Japanese variant, and reduction of protein improves its quality such as taste and the like. Gohyakumangoku is preferable, since there is a demand for low-protein variants thereof as raw material for sake. Koganemochi is preferable, since there is a demand for low-protein variants thereof as raw material for processed rice foods such as rice cookies or the like. Tetep, Basmati, and Kasalath are preferable in some embodiments, since they can be normally cultured to obtain seeds in the more temperate zone south of the Hokuriku area of Honshu island of Japan.

As used herein the term "tissue" of an organism refers to a collection of cells in which the cells have a determined similar function therein. Accordingly, tissue may be a portion of an organ. In an organ, cells often have the same functions, however, may there may be contamination with those having slightly different functions, and thus as used herein, a tissue may have a variety of cells as long as the tissue has a determined property in common.

As used herein the term "organ" refers to a construct formed to serve a determined function by combining one or more tissues, and having an independent form. In plants, organs include callus, root, stem, trunk, leaf, flower, seed, albumen, germ, fruit, embryo and the like.

As used herein the term "organism" (or called "plant body" in the case of plants) refers to the widest meaning used in the art to refer to those (or plants) performing life phenomenon, and typically having a variety of properties such as cellular structure, propagation (self-reproduction), growth, regulation, substance metabolism, repairing capability and the like. Usually, such an organism has heredity governed by nucleic acids, and propagation in which metabolism governed by proteins are involved, as basic attributes. Organisms include prokaryotic organisms, eukaryotic organisms (such as plants and animals), and the like. Preferably, organisms used in the invention may be plants. As used herein, preferably, such a plant body may be fertile. More preferably, such a plant body may produce seeds.

Gene constructs, agents, compositions and methods of the present invention are contemplated to function not only in monocotyledonous plants but also other organisms including dicotyledonous plants and animals and the like.

As used herein the term "transgenic" refers to incorporation of a specific gene into an organism, or an organism (for example, including plant (rice or the like)) with a specific gene incorporated therein.

Plants can be herein cultivated by any known method in the art. Methods of cultivating plants are illustrated in, for example, "Moderu-shokubutsu-no-Jikken-Purotokoru For Ine•Shiroinunazuna: Saibo-kogaku Bessatsu-shokubutsu-saibo-kogaku sirizu 4; Ine-no-saibaiho [Experimental Protocol for Model Plants For Rice and *Arabidopsis thaliana*: Cellular Engineering, Special Issue, Plant Cellular Engineering Series 4; Rice Cultivating Methods]" (Kazutoshi Okuno) pp. 28-32, and "Arabidopushisu-no-saibaiho [Cultivating Methods for *Arabidopsis*]" (Yasuo Niwa) pp. 33-40 (Supervised by Ko Shimamoto and Kiyotaka Okada), which are not herein described in detail. For example, *Arabidopsis thaliana* can be cultivated by any of soil culture, rock wool culture, and water culture. After dissemination, flowering is first observed in about 4 weeks if the plant is cultivated under constant light of a white color fluorescent lamp (about 6000 lux). After flowering, seeds are fully matured in about 16 days. 40 to 50 seeds are obtained from one pod. During 2 to 3 months from dissemination to death, about 10,000 seeds are obtained. The dormancy term of the seed is short. Full-matured seeds after about one week drying are germinated 2 to 3 days after absorbing water. Note that if the seeds are subjected to cryogenic processing at 4° C. for 2 to 4 days after water absorption and dissemination, the seeds are simultaneously germinated. Cultivation of rice is mainly performed on soil, and grown under light conditions of at least 10,000 lux. Head spout is induced by subjecting to shorter daylight conditions after day 40 of sowing. About 30 days after the induction of head spout, blooming is found, and thus mature seeds are obtained at around 40 days after flowering.

Known methodologies and media in the art are used for culture, differentiation and regeneration of plant cells, plant tissues and plant bodies. Such media include, but are not limited to, for example, Murashige-Skoog (MS) medium, GaMborg B5 (B) medium, White medium, Nitsch & Nitsch (Nitsch) medium and the like. These media are usually used with an appropriate addition of plant growth regulating substances (plant hormone).

As used herein, in the case of plants, the term "redifferentiation" of a plant refers to a phenomenon in which a portion of an individual is induced to form the entirety of the individual. For example, redifferentiation can form an organ or plant body from an explant such as cells (leaf, root and the like).

Methods for redifferentiating a transformant into a plant body are well known in the art. Such a method includes but is not limited to, those described in: Rogers et al., Methods in Enzymology 118:627-640 (1986); Tabata et al., Plant Cell Physiol., 28:73-82 (1987); Shaw, Plant Molecular Biology: A practical approach. IRL press (1988); Shimamoto et al., Nature 338:274 (1989); Maliga et al., Methods in Plant Molecular Biology: A laboratory course. Cold Spring Harbor Laboratory Press (1995) and the like. Accordingly, those skilled in the art can conduct redifferentiation depending on the desired transgenic plant using the above-mentioned well-known methodologies in an appropriate manner. Transgenic plants thus obtained have a target gene introduced, and the introduction of such a gene may be confirmed by using methods described herein such as Northern blotting, Western blotting, or the like or any other well-known and/or routine technologies.

Analysis of expression regulation of storage proteins by the present invention may be carried out by gene analysis methods using a DNA array. DNA arrays are fully reviewed in "DNA microarray and most recent PCR methods", Saibokogaku Suppl., ed. Shujun-sha). Further, analysis of plants using DNA arrays has also been recently conducted (see Schenk P. M. et al. (2000) Proc. Natl. Acad. Sci. (USA) 97: 11655-11660).

Microfabrication technologies used in DNA array technology include, but are not limited to, for example, those described in Campbell, S. A. (1996). The Science and Engineering of Microelectronic Fabrication, Oxford University Press; Zaut, P. V. (1996). Micromicroarray Fabrication: a Practical Guide to Semiconductor Processing, Semiconductor Services; Madou, M. J. (1997). Fundamentals of Microfabrication, CRC 15 Press; Rai-Choudhury, P. (1997). Handbook of Microlithography, Micromachining, & Microfabrication: Microlithography and the like, and the pertinent portion in the present specification is incorporated herein as reference.

Regulation of expression of a storage protein gene and its downstream genes according to the present invention may also be analyzed by gene analysis based on differential display technology.

As used herein the term "differential display (technology)" is a method for detecting or identifying a gene presenting a change in expression. In this method, cDNA is produced from each of two or more samples, and amplification is conducted by PCR using any primer set, and thereafter the resultant plurality of PCR products are separated by gel electrophoresis, and classified into patterns, and based on the change in relative signal strength in each band, an expression changing gene can be selected and cloned.

In the present invention, based on the disclosure of the present invention, it is also contemplated that a drug based on computer modeling is provided.

The present invention includes compounds obtained by using modeling quantitative structure activity relationship (QSAR) technology by computers as a tool screening validity with respect to regulating activity against the antisense construct of the present invention. As used herein, computer technologies include substrate templates produced by a number of computers, pharmacophore, and production of homologous models of the active site of the present invention. Generally, a method for modeling a usual property group of interactive agents against a substance data obtained in vitro has been presented using the recently developed CATALYST™ pharmacophore method (Ekins et al., Pharmacogenetics, 9: 477–489, 1999; Ekins et al., J. Pharmacol. & Exp. Ther., 288: 21-29, 1999; Ekins et al., J. Pharmacol. & Exp. Ther., 290: 429-438, 1999; Ekins et al., J. Pharmacol. & Exp. Ther., 291: 424-433, 1999) and comparative molecular field analysis (CoMFA) (Jones et al., Drug Metabolism & Disposition, 24: 1-6, 1996) and the like. In the present invention, computer modeling software (for example, CATALYST™ version 4 (Molecular Simulations, Inc., San Diego, Calif.) and the like) may be used.

In another aspect, the present invention provides a composition comprising the antisense composition of the present invention. Such a composition may be an agricultural composition. Such an agricultural composition is provided in a form according to provisions defined by the Ministry of Agriculture, Forestry and Fishery of Japan or any other corresponding authority of different countries. Such an agricultural composition is provided after solving any ethical issues.

When the present invention is formulated as an agricultural composition, such a composition may include an agriculturally acceptable carrier. Such a carrier includes any number of known substances in the art.

Such an appropriate agriculturally acceptable agent includes but is not limited to: antioxidant, preservative, coloring agent, flavoring agent, diluent, emulsifier, suspension agent, solvent, filler, bulk filler, buffer, delivery vehicle, excipient and/or agricultural adjuvant. Typically, the agricultural composition of the present invention may be administered with the agent of the present invention together with at least one physiologically acceptable carrier, excipient, or diluent. In the case of agricultural composition, such a carrier may be water appropriate for agricultural administration.

Exemplary appropriate carriers include neutral buffered saline or saline mixed with serum albumin. Preferably, such a product is formulated as a lyophilized agent using an appropriate excipient (for example sucrose). Other standard carriers, diluents and excipients may be included as desired. Other exemplary compositions include a Tris buffer of pH 7.0-8.5, or acetate buffer of pH 4.0-5.5, and may further include sorbitol or any other appropriate substitute. pH of such a solution should be selected based on the relative solubility of the agent of the present invention at a variety of pH levels.

The solvent in a composition may be any aqueous or non-aqueous solvent. Further, such a vehicle may include other formulation materials such as those for modifying or maintaining pH, volume osmolic concentration, viscosity, clarity, color, sterility, stability, isotonicity, degradation rate, or odor. Similarly, the composition of the present invention may include other formulation materials for modifying or maintaining the release rate of the effective ingredient or accelerating absorption or permeability of the effective ingredient.

BEST MODE FOR CARRYING OUT THE PRESENT INVENTION

Hereinafter, preferable embodiments for carrying out the present invention are described. The embodiments provided below are only intended for better understanding of the present invention, and thus it should be understood that the scope of the present invention should not be limited to the description of the following section. Accordingly, it should be clear that those skilled in the art can readily carry out any embodiment with an appropriate modification within the scope of the present invention in view of the description of the present specification.

In one aspect, the present invention provides an antisense molecule of a nucleic acid sequence encoding a prolamin polypeptide. Specifically, the present invention provides a nucleic acid molecule comprising a nucleic acid sequence having at least 15 contiguous nucleotide length complementary to a nucleic acid sequence encoding a prolamin polypeptide, or a nucleic acid sequence at least about 70%, preferably at least about 80%, more preferably at least about 90% homologous to the complementary nucleic acid sequence having at least 10, preferably at least 15 contiguous nucleotide length. Such a sequence may include at least one nucleotide substitution, addition, or deletion. Such a variant sequence may have a lower numerical value as long as the sequence achieves antisense activity. It was unexpectedly discovered that provision of such a nucleic acid can suppress expression of the entire prolamin gene group, which is a multigene family, including storage proteins, which are stored in plant seeds, and can achieve reduction of seed proteins. Although not wishing to be bound by any theory, it is generally an accepted theory that, in case expression of a seed protein is reduced, maintenance machinery of the homeostasis increases other protein expression in order to compensate for the reduction, and thus the total amount of seed protein is not altered. In fact, a lineage in which glutelin expression is suppressed has increased the expression of prolamins for the amount of the reduced glutelin, and as a result, it was confirmed that the total amount of seed protein has not been altered. On the other hand, in the present invention, even though expression suppression of prolamins is performed in a low-glutelin lineage, the property of low-glutelin has been maintained, and in addition, globulin has not significantly increased, and thus the results attained thereby are unexpectedly significant.

In another embodiment, antisense molecules used may have a partial sequence simply complementary to the objective sequence, but may have a hair-pin like RNA structure utilizing two partial sequences of similar complementary sequences to the objective sequence using the RNAi phenomenon. Such sequences may be completely identical or may be partially different to each other. Preferably, in order to promote expression of such an antisense molecule, 10 kDa prolamin promoter, 13 kDa prolamin promoter, glutelin B1 promoter, ubiquitin promoter or the like is used. Further, in order to regulate expression of such an antisense molecule, Nos terminator, 13 kDa prolamin terminator, 10 kDa prolamin and the like may be used.

In one embodiment, the above-described nucleic acid molecules have antisense activity. Specifically, such an antisense activity includes, but is not limited to, for example, the reduction of the mRNA expression amount of prolamin, the reduction of the expression amount of prolamin polypeptide and the like. It has now been unexpectedly found that the provision of the present inventive nucleic acid molecule with a plant has attained not only the reduction of expression amount of prolamin polypeptides, but also the reduction of the protein amount expressed in seeds. Such an event has never found to date, or even suggested, and thus it should be noted that the present invention has attained significant effects.

In one embodiment, the nucleic acid molecule comprises a nucleic acid sequence having at least a 15 contiguous nucleotide length complementary to a nucleic acid sequence encoding a prolamin polypeptide. More preferably, such a nucleic acid sequence may have at least a 20 contiguous nucleotide length complementary thereto, at least a 25 contiguous nucleotide length complementary thereto, at least a 30 contiguous nucleotide length complementary thereto, at least a 40 contiguous nucleotide length complementary thereto, at least a 50 contiguous nucleotide length complementary thereto, at least a 60 contiguous nucleotide length complementary thereto, at least a 70 contiguous nucleotide length complementary thereto, at least a 80 contiguous nucleotide length complementary thereto, at least a 90 contiguous nucleotide length complementary thereto, at least a 100 contiguous nucleotide length complementary thereto, or the like. More preferably, such a nucleic acid sequence may comprise the complementary sequence of the full length sequence encoding a prolamin polypeptide. Usually, it is sufficient to provide a 15 contiguous nucleotide length complementary to the objective sequence in order to attain the antisense effect. In order to certainly attain antisense activity, it is preferable to provide a nucleic acid molecule having longer contiguous sequence, for example, at least a 20 contiguous nucleotide length, or at least a 30 contiguous nucleotide length.

In another embodiment, the nucleic acid sequence comprised in the nucleic acid molecule of the present invention may be those complementary to the 5' terminus of the nucleic acid sequence encoding a prolamin polypeptide, because prolamin has often high homology at the 5' terminus thereof. Further, provision of a nucleic acid sequence complementary to such a 5' terminal sequence attains inhibition of transcription and/or translation of the gene from the reaction initiation thereof, and may therefore attain more efficient inhibition of gene expression. However, in the present invention, sequences other than those having complementary to the 5' terminal sequence of the nucleic acid sequence encoding the desired polypeptide may be used, as long as the sequence has an antisense effect.

The nucleic acid sequence comprised in the nucleic acid molecule of the present invention may be any sequence as long as it is derived from prolamin. Preferably, those derived from rice 13 kDa prolamin or those corresponding thereto in another orthologous variety. Prolamins used in the present invention may be of rice. Preferably, prolamin used herein may be of *japonica* variant of rice. More preferably, the prolamin used herein may be 13 kDa prolamin of *japonica* variant of rice. Most preferably, the prolamin used herein is RM9 or RM1 prolamin. 13 kDa prolamin is preferable because the amount of protein corresponding to 13 kDa prolamin is highest amongst the prolamins included in rice seeds, and thus the reduction effects of expression are expected to be more efficient.

In other preferred embodiments, nucleic acid molecules of the present invention may comprise a nucleic acid sequence of at least a 15 contiguous nucleotide length, complementary to:

(a) a polynucleotide having a nucleic acid sequence set forth in a SEQ ID NO, selected from the group consisting of SEQ ID NOs: 1, 3, 5, 7, 9, 11, 13, 15, 17, 19, 21, 23, 25, 27, 29, 31, 33, 35, 37, 39, 41, 43 and 45, or a fragment sequence thereof;

(b) a polynucleotide encoding a polypeptide having an amino acid sequence set forth in a SEQ ID NO: selected from the group consisting of SEQ ID NO: 2, 4, 6, 8, 10, 12, 14, 16, 18, 20, 22, 24, 26, 28, 30, 32, 34, 36, 38, 40, 42, 44 and 46, or a fragment sequence thereof;

(c) a polynucleotide encoding a polypeptide variant having at least one mutation selected from the group consisting of one or more amino acid substitutions, additions and deletions in an amino acid sequence set forth in a SEQ ID NO: selected from the group consisting of SEQ ID NO: 2, 4, 6, 8, 10, 12, 14, 16, 18, 20, 22, 24, 26, 28, 30, 32, 34, 36, 38, 40, 42, 44 and 46, and having a biological activity;

(d) a polynucleotide of an allelic variant of a DNA consisting of a nucleic acid sequence set forth in a SEQ ID NO, selected from the group consisting of SEQ ID NOs: 1, 3, 5, 7, 9, 11, 13, 15, 17, 19, 21, 23, 25, 27, 29, 31, 33, 35, 37, 39, 41, 43 and 45;

(e) a polynucleotide encoding a species homolog or an ortholog of a polypeptide consisting of an amino acid sequence set forth in a SEQ ID NO: selected from the group consisting of SEQ ID NO: 2, 4, 6, 8, 10, 12, 14, 16, 18, 20, 22, 24, 26, 28, 30, 32, 34, 36, 38, 40, 42, 44 and 46;

(f) a polynucleotide hybridizing to at least one polynucleotide of any of (a)-(e), and encoding a polypeptide having a biological activity; or (g) a polynucleotide consisting of a base sequence having at least 70% identity with at least one polynucleotide of (a)-(e) or a complementary sequence thereof, and encoding a polypeptide having a biological activity. More preferably, the nucleic acid sequence may be of at least 20 nucleotides in length, more preferably of at least 30 nucleotides in length, most preferably of at least 50 nucleotides in length of contiguous complementary portion of the objective sequence.

In another embodiment, the above-mentioned sequence may be of SEQ ID NO: 1 or 3, and of SEQ ID NO: 2 or 4 (corresponding to RM9 or RM 1, respectively).

In another aspect, the present invention provides a nucleic acid molecule comprising a nucleic acid sequence having at least a 15 contiguous nucleotide length of a nucleic acid sequence encoding a prolamin polypeptide, or a nucleic acid sequence having at least about 70% homology to the nucleic acid sequence having at least a 15 contiguous nucleotide length. Such a sequence is a sense sequence, and it is useful as an agent responsible for a part of RNAi. Such a sequence can attain an expression suppression effect with as short as a 15 nucleotide length.

In another aspect, the present invention provides a nucleic acid molecule comprising:

A nucleic acid sequence A comprising a nucleic acid sequence having at least a 15 contiguous nucleotide length of a nucleic acid sequence encoding a prolamin polypeptide, or a nucleic acid sequence having at least about 70% homology to the nucleic acid sequence having at least a 15 contiguous nucleotide length; and (B) a nucleic acid sequence B comprising a nucleic acid sequence having at least a 15 contiguous nucleotide length complementary to a nucleic acid sequence encoding a prolamin polypeptide, or a nucleic acid sequence having at least about 70% homology to the complementary nucleic acid sequence having at least a 15 contiguous nucleotide length. Such a nucleic acid molecule is also called an "RNAi nucleic acid molecule". As used herein, nucleic acid sequence A and nucleic acid sequence B can be called as the sense- and antisense-sequences, respectively. Such a nucleic acid molecule having two types of sequences serves as an agent causing RNAi, resulting in the global suppression of targeted prolamin expression, and as a result, reduction of the entire expression amount of seed proteins. This has not been achieved in any other seed proteins, and thus the effects attained by suppression of prolamin protein expression can be said to be unexpected, because suppression of glutelin expression, which is has been a target to date, has increased other seed proteins or any other proteins in seeds, and thus the global protein amount expression has not been altered. Accordingly, the effects attained by the present invention should be recognized to be unexpectedly significant by those skilled in the art. The RNAi nucleic acid molecule of the present invention have antisense- and sense-sequences of as short as 15 bp, preferably 23 bp, against the targeted prolamin sequence in order to achieve the inhibitory effects thereof.

In a preferable embodiment, nucleic acid A and nucleic acid B included in the RNAi nucleic acid molecule of the present invention comprise a part substantially complementary to each other, because the RNAi effect will be more efficiently attained by comprising a part complementary to each other in the nucleic acids A and B. More preferably, the nucleic acids A and B are substantially complementary to each other in their sequences, and still more preferably, they are completely complementary to each other at the sequence level. Although not wishing to be bound by any theory, this is because the effects of RNAi are improved by having substantial or complement complementarity to each other.

In one embodiment, the RNAi nucleic acid molecule of the present invention further comprises a spacer sequence, and preferably, such a spacer sequence is inserted between the nucleic acids A and B in the RNAi nucleic acid molecule of the present invention. Although not wishing to be bound by any theory, the effects of the RNAi are improved by having a spacer sequence at an appropriate location.

In a preferred embodiment, the spacer sequence is an intron sequence. Such an intron sequence includes but is not limited to, for example, those of gamma-globin, beta-actin and the like. Although not wishing to be bound by any theory, it is known that the expression is enhanced by inserting an intron into a coding region of a gene in plants, and it is also believed that when an intron portion of pre mRNA is cleaved, the formation of double-stranded RNA is promoted in terms of three-dimensional manner.

In another aspect, the present invention provides an agent causing RNA interference (RNAi) against a gene sequence encoding a prolamin polypeptide. The RNAi against the prolamin of the present invention has attained significant effects such as significant reduction in seed proteins and/or significant increase in forced expression of foreign proteins. RNAi agents may be in the form of siRNA or shRNA, but in the present invention, those including complementary chains in the nucleic acid construct are preferably used. Not wishing to be bound by any theory, nucleic acid constructs comprising a complementary chain are said to be more universal than siRNA or shRNA.

In another aspect, the present invention provides a nucleic acid cassette comprising a nucleic acid sequence B comprising a nucleic acid sequence having at least a 15 contiguous nucleotide length complementary to a nucleic acid sequence encoding a prolamin polypeptide, or a nucleic acid sequence having at least about 70% homology to the complementary nucleic acid sequence having at least a 15 contiguous nucleotide length. This nucleic acid cassette can be used as an antisense cassette.

In a preferably embodiment, the nucleic acid cassette of the present invention further comprises a nucleic acid sequence encoding a foreign gene.

Any foreign gene may be used when modifying a plant using the nucleic acid cassette of the present invention, as long as it is intended to express the foreign gene in lieu of prolamin or any other seed protein.

Such foreign genes include, but are not limited to, for example: markers (fluorescence, phosphorescence or the like), peptides having pharmaceutical activity (for example, cytokines (interleukins, chemokines, GM-CSF, M-CSF, G-CSF, multi-CSF (IL-3), hemopoietic factors such as EPO, LIF, SCF, TNFs, interferons, PDGF, EGF, FGF, HGF, VEGF and the like), hormones (for example, insulin, growth hormones, thyroid hormones), vaccine antigens, blood products, agriculturally useful peptides (for example, antibacterials, insecticides, antibiotic proteins), enzymes synthesizing secondary metabolites having physiological or pharmacological actions, inhibitors regulating enzymatic reactions, receptors, receptor ligands, artificial proteins, nutritionally significant substances (for example, casein, bean albumin, globulin, synthetases of vitamins, sugars, lipids, or the like), proteins involved in processability (for example, wheat glutenin (bakery), soybean globulins (tofu), milk caseins (cheese), or proteins enhancing the palatability or functionality of a food, for example, specific synthetic enzymes of sugars or amino acids including cyclodextrin, oligosaccharides, γ-amino acetate or the like, dye synthesizing enzymes for improving appearance, or proteins involved in the synthesis of a taste component, or peptides which are designed to have physiological actions after enzymatic cleavage in the digestive tracts (for example, angiotensin converting enzyme inhibitory peptides which have blood pressure lowering action, and the like), and the like.

In a preferable embodiment, the above-mentioned nucleic acid cassette of the present invention further comprises a nucleic acid sequence A, comprising a nucleic acid sequence having at least a 15 contiguous nucleotide length of a nucleic acid sequence encoding a prolamin polypeptide, or a nucleic acid sequence having at least about 70% homology to the nucleic acid sequence having at least 15 contiguous nucleotide length. By having such two types of nucleic acid sequences A and B, the nucleic acid cassette of the present invention can better attain RNAi.

The nucleic acid cassette of the present invention may further include, in addition to Nucleic Acid Sequence A and B, a spacer sequence. Although not wishing to be bound by any theory, this is because inclusion of a spacer sequence therein enhances RNAi. Selection of such a spacer sequence may be appropriately performed by those skilled in the art, and preferably, an intron sequence may be used as a space sequence. Such a spacer sequence, preferably an intron sequence, may be advantageously inserted between Nucleic Acid Sequences A and B. Although not wishing to be bound by any theory, this is because an appropriate location of an intron sequence renders more efficient alteration into a molecular structure leading to RNAi when such an intron portion of pre mRNA is cleaved in cells.

In another preferably embodiment, the nucleic acid cassette of the present invention may comprise a signal sequence. Such a signal sequence may be located upstream of a foreign gene, and preferably in an in frame manner. More preferably, such a location is advantageously just before a translation initiation site of such a foreign gene. Inclusion of such a signal sequence allows more efficient expression of such a foreign gene from a desired site.

In a preferable embodiment, a signal sequence used in the present invention is advantageously that of a storage protein. Storage proteins are transported into the endoplasmic reticulum as a consequence of the signal sequence, and then on into the protein body, accumulating therein in a stable manner and in a large amount. Accordingly, imitation of such a process allows the production of seeds having more efficient accumulation of a protein encoded by a foreign gene located downstream of a storage protein signal sequence.

More preferably, such a signal sequence is advantageously a prolamin signal sequence. As shown in the Examples of the present specification, it has been found that use of the prolamin promoter is more effective for expression of a foreign gene, and thus it is more desirable to use a prolamin signal sequence in combination therewith. Prolamin signal sequences include, but are not limited to, for example, signal sequences from 10 kDa prolamin, 13 kDa prolamin, 16 kDa prolamin and the like.

Location of such a signal sequence may be performed using a well-known technology in the art. For example, it is understood that if sequence information of such a signal sequence is known, PCR reactions may be used to include such a sequence. Alternatively, it is also understood that if such a nucleic acid molecule comprising a signal sequence is possessed, a target sequence may be isolated and inserted at a desired site to locate such a signal sequence at a desired location.

In another embodiment, the nucleic acid vector of the present invention further includes a promoter sequence. By having such a promoter sequence, prolamin suppression effects attained by the present invention are more efficiently, and/or expression of foreign gene is attained in a more efficient manner or with a desired specificity. Location of a promoter is performed by those skilled in the art using a well known technology in the art.

Preferably, a promoter sequence may be operably linked to both a foreign gene and the above mentioned nucleic acid sequence B. This is because the promoter can drive expression of both genes (foreign gene and antisense gene) or induce or enhance the same. Preferably, it is advantageous that both a foreign gene and nucleic acid sequence B are operably linked to separate promoter sequences in an independent manner. Such independent promoters are included to allow separate expression control.

In a more preferable embodiment, it is advantageous that a promoter sequence operably linked to the foreign gene (promoter sequence A), and a promoter sequence operably linked to the nucleic acid sequence B (promoter sequence B) used in the nucleic acid cassette of the present invention, are different to each other. Such a constitution arrangement avoids the risk of the efficiency of gene expression by one promoter being reduced due to breakup of promoter capability into prolamin expression suppression and high expression of foreign gene. Further, it also allows expression of foreign gene to be induced after the expression control of prolamin has been confirmed, thus increasing the number of possible variations of control and thus providing a more efficient foreign gene expression system.

In another embodiment, the promoter sequence B used in the present invention is a promoter sequence expressed in seeds, and preferably, a promoter sequence driving high level expression in seeds. It is thought that the higher the expression level of the promoter used is, the more efficiently or effectively the suppression of prolamin expression is achieved. Such high level expression promoters in seeds, include but are not limited to, for example: those derived from genes encoding storage proteins (for example, glutelin, globulin, prolamin), and genes essential for survival of a cell (polyubiquitin, actin or the like). Efficient suppression of prolamin, a storage protein, is not achieved necessarily by promoters of prolamin per se, but also achieved by any one of those promoters described above, which was unexpectedly found by the present invention for the first time.

In more preferable embodiments, the promoter sequence B is derived from a storage protein promoter, and is different from the promoter sequence A. Without wishing to be bound by any theory, by employing this arrangement, the nucleic acid cassette of the present invention can efficiently control foreign gene and prolamin suppression, and allow maximum expression.

The promoter sequence B used in the present invention may be a polyubiquitin promoter, a 26 kD globulin promoter, a glutelin A promoter, a glutelin B promoter, a 16 kD prolamin promoter, a 13 kD prolamin promoter and a 0 kD prolamin promoter, or variants or fusions thereof, and the like.

In another embodiment, the promoter sequence A used in the present invention is derived from a storage protein promoter. Expression specificity of storage protein promoters is limited to the seed, and their level of expression is high. Accordingly, as a promoter to be linked to a foreign gene, a particular storage protein promoter (for example, glutelin, globulin, prolamin) is used to avoid the risk of energy being consumed by unobjectively expressing a foreign protein at a different site of the plant body, whilst still efficiently and highly expressing it in the seed. Furthermore, a promoter to be linked with a foreign gene is preferably a promoter derived from a storage protein of the same type as a storage protein targeted for suppression (for example, 13 kDa prolamin), including for example SEQ ID NO: 60. This is because there are cases where the mRNA level of a storage protein targeted for expression suppression is increased, and thus the effects attained thereby are used for expression of a foreign gene. Accordingly, promoter sequence A may be a promoter naturally associated with nucleic acid sequence B. Preferably, as such a promoter, 13 kDa prolamin or 10 kDa prolamin derived promoters may be used. Although not wishing to be bound by any theory, content of 13 kDa prolamin is the largest amongst of prolamins of multigene family, and its expression increases significantly in the rice variant with low-glutelin character. On the other hand, 10 kDa prolamin is a single gene, and is expressed at a high level during stationary phase so that expression thereof can be confirmed by electrophoresis, and its expression increases significantly in the rice variant with low-glutelin character. Promoters derived from the above genes both have very high promoter activity, and thus are useful. Which of the 13 kDa prolamin or 10 kDa prolamin is advantageous promoter, should be determined by the characteristics of the original variant to be introduced, and the characteristics of a foreign gene to be expressed.

The promoter sequence A used in the present invention may be a 26 kD globulin promoter, a glutelin A promoter, a glutelin B promoter, a 16 kD prolamin promoter, a 13 kD prolamin promoter, a 10 kD prolamin promoter, or the like. Preferably, a prolamin promoter may be used as the promoter sequence A, and more preferably, 13 kDa prolamin promoter or 10 kDa prolamin promoter may be used.

In one embodiment of the nucleic acid cassette of the present invention, the promoter sequence A is derived from a prolamin promoter, and the promoter sequence B is derived from a promoter other than the prolamin promoter. Examples of such a combination include, but are not limited to the 13 kDa promoter and the 10 kDa promoter and the like.

In a preferable embodiment, the nucleic acid cassette of the present invention includes a signal sequence between the foreign gene and the promoter sequence in frame.

In another preferable embodiment, the nucleic acid cassette of the present invention includes a terminator. Appropriate location of a terminator allows appropriate control of expression. Preferably the terminator is a terminator sequence of 10 kDa prolamin. There have been no reports to date of utilization of the terminator sequence of a 10 kDa prolamin. However, the present invention has shown that a promoter of 10 kDa prolamin may be generally used to control expression of a gene in combination of a variety of promoters, and thus it is significant result. Such a promoter is derived from a plant (rice), and further is derived from a gene expressed in the seed of interest applied to the invention, and thus it is preferable to use this rather than the NOS terminator which is derived from a bacterium.

In one embodiment, the nucleic acid cassette of the present invention includes a foreign gene, and the foreign gene is preferably located upstream of both nucleic acid sequence A and nucleic acid sequence B. Although not wishing to be bound by any theory, using this construct, a number of advantages are contemplated but are not limited to such as that expression of foreign gene can be confirmed after confirming suppression of prolamin.

Accordingly, in a preferable embodiment of the present invention, it is advantageous that the cassette of the present invention comprises a spacer sequence, preferably an intron sequence, between the nucleic acid sequence A and the nucleic acid sequence B, because RNAi effects are promoted thereby.

In one aspect, the present invention provides a method for producing a nucleic acid cassette. The present method comprises the steps of: A) providing a nucleic acid cassette comprising a section of a nucleic acid cassette comprising a nucleic acid sequence B comprising a nucleic acid sequence having at least 15 contiguous nucleotide length complementary to a nucleic acid sequence encoding a prolamin polypeptide, or a nucleic acid sequence having at least about 70% homology to the complementary nucleic acid sequence having at least 15 contiguous nucleotide length, and a nucleic acid sequence A comprising a nucleic acid sequence having at least 15 contiguous nucleotide length of a nucleic acid sequence encoding a prolamin polypeptide, or a nucleic acid sequence having at least about 70% homology to the nucleic acid sequence having at least 15 contiguous nucleotide length, a promoter sequence B upstream of the section, a foreign gene located upstream or downstream (preferably upstream, but the present invention is not limited thereto) of the promoter sequence B, and a promoter sequence A operably linked to the foreign gene; B) transforming a plant with the nucleic acid cassette; and C) selecting a nucleic acid cassette having the a partially reduced expression level with respect to the transformed plant.

In such a production method, those cassettes having more efficient reduction activity of prolamin expression are preferentially selected, and thus the efficiency of the nucleic acid cassette of the present invention is greatly enhanced.

In another aspect, the present invention provides a vector comprising a nucleic acid molecule of the present invention. Accordingly, the vector of the present invention may be provided in a form of a vector comprising the above-mentioned nucleic acid cassette.

Preferably, the vector may comprise a regulatory sequence (element) such as a promoter sequence or the like. Such a regulatory sequence includes, but is not limited to, for example, enhancers, promoters, transcription termination sequences, translation termination sequences, transcription initiation sites, intron sequences and the like. Preferably, the vector further comprises a sequence having promoter activity.

Such a sequence having promoter activity may preferably be a promoter of a storage protein. Promoters of storage proteins are expected to promote transcription in seeds. In the present invention, regardless of the type of storage protein, any sequence derived from a sequence of promoter of a storage protein has been found to be useful for expressing an antisense sequence that suppresses prolamin activity. Simultaneously, it was also shown that sequences derived from prolamin promoters are more useful for antisense sequence activity expression than other storage protein derived promoters. Such a result has also been demonstrated in the present invention.

More preferably, the sequence having promoter activity may be a promoter derived from a structural gene to which the antisense sequence is operably linked to.

More preferably, promoters may be derived from the same plant species as that from which antisense sequence is derived. This is because it is expected that sequences derived from the same origin as the subject plant species will function more effectively.

The vector of the present invention may preferably further comprise a terminator. Vectors of the present invention may further comprise a selectable marker. Such a selectable marker may be any marker in the art, however, for convenience, genes conferring antibiotic resistance (for example, hygromycin phosphotransferase) are preferable. When using a vector comprising a selectable marker, selection of a plant cell transformed with an antisense construct according to the present invention will be extremely easy, but such a selectable marker is not always necessary.

In another embodiment, the vector of the present invention may comprise a sequence encoding a foreign gene different from an antisense sequence (for example, a marker gene such as a GFP gene or a useful gene). Such a foreign gene may be a structural gene. Such a foreign gene may be of a protein desired to be expressed in a large amount. Such a protein includes, but is not limited to, for example: peptides having pharmaceutical activity (for example, cytokines (interleukins, chemokines, granular macrophage colony stimulating factor (GM-CSF), macrophage colony stimulating factor (M-CSF), granular colony stimulating factor (G-CSF), multi-CSF (IL-3), erythropoietin (EPO), leukemia inhibitory factor (LIF), hematopoietic factors such as c-kit ligand (SCF), tumor necrosis factors, interferons, platelet derived growth factor (PDGF), epidermal growth factor (EGF), fibroblast growth factor (FGF), hepatocyte growth factor (HGF), vascular endothelial growth factor (VEGF) or the like); hormones (for example, insulin, growth hormones, thyroid stimulating hormone or the like)), vaccine antigens, blood products, agriculturally useful peptides such as antibacterial proteins, a variety of enzymes capable of synthesizing secondary metabolites having physiological or pharmacological action or hydrolytic enzymes, inhibitors regulating enzymatic reaction, soybean glycinin having blood pressure lowering action, or artificial proteins designed so that a physiologically active peptides are cleaved by enzymatic degradation in the digestive tract, and the like. Further, substances significant in terms of nutrition, include but are not limited to, for example, caseins, albumins or bean globulins, or synthesis enzymes of vitamins, sugars, lipids or the like. Proteins involved in processing the raw materials of a variety of processed foods include, for example, wheat glutenin (bakery), soybean globulins (tofu), milk caseins (cheese), or proteins enhancing the palatability or functionality of a food, for example, specific synthetic enzymes of sugars or amino acids including cyclodextrin, oligosaccharides, γ-amino acetate or the like, dye synthesizing enzymes for improving appearance, or proteins involved in the synthesis of a taste component, or peptides which are designed to be physiologically active after enzymatic cleavage in the digestive tracts (for example, angiotensin converting enzyme inhibitory peptides having blood pressure lowering activity, and the like), and the like.

Such a foreign gene is preferably operably linked to a promoter. In such a case, such a promoter used may be any promoter and preferably derived from a storage protein. More preferably, such a promoter used includes those derived from prolamin (10 kDa prolamin promoter, 13 kDa prolamin promoter, 16 kDa prolamin promoter and the like).

In another aspect, the present invention provides a plant cell comprising a nucleic acid of the present invention. Alternatively, the present invention also provides a plant cell transformed with a vector of the present invention. Such a plant cell may be transiently transduced with the vector of the present invention, or permanently transformed therewith. The plant cell of the present invention may include a nucleic acid molecule encoding a foreign gene different from the antisense construct of the present invention. Exemplification of such a foreign gene is described hereinabove.

Preferably, the plant species from which prolamin used in the present invention may be identical or different from the plant species of the plant cell of the present invention. Preferably, both plant species may be identical. Both plant species of the plants may be identical or different. Preferably, both plant species may be identical. Preferably, plant species and/or plant cell species from which the prolamin of the present invention is derived, may be of rice. More preferably, plant species and/or plant cell species from which the prolamin of the present invention is derived, may be of the *japonica* or *indica* variant of rice.

In a preferable embodiment, the nucleic acid molecule of the present invention may be introduced into both alleles of the chromosome of the plant cell of the present invention, but those with only one allele introduced may also be useful.

In another aspect, the present invention provides a plant tissue comprising the plant cells of the present invention. The present invention also provides plant tissue comprising the nucleic acid molecule of the present invention. Such a plant cell or nucleic acid molecule may be in a preferable format as described above.

Accordingly, the present invention provides a plant tissue (or a portion or a site of a living body) comprising the polynucleotide or vector of the present invention. Such a plant tissue includes a seed or a portion derived therefrom. Accordingly, any tissues capable of forming a protein body may be used. Preferably, the tissue of the present invention may be transformed with the polynucleotide or vector of the present invention. The tissue of the present invention may be transiently transformed or permanently transformed with the polynucleotide or vector of the present invention. The polynucleotide of the present invention introduced therein by such a transformation method, may be constitutively or specifically expressed.

In another aspect, the present invention provides a plant comprising the nucleic acid molecule of the present invention. Provision of such a plant body allows production of low-protein containing seeds. The plant body may preferably be rice. The plant body may further include a nucleic acid molecule encoding a foreign gene different from the antisense construct of the present invention. Such a plant is also herein referred to as transgenic plant, and may be obtained by conducting redifferentiation (regeneration) of the plant cell or tissue of the present invention using well known technologies in the art.

Once a cell (for example, a plant cell) transformed with a desired polynucleotide (for example, it is well known in the art that the polynucleotide or vector of the present invention) has been obtained, transgenic organisms (for example, plants) comprising the desired polynucleotide from such a transformed cell at a certain rate, may be obtained easily. Accordingly, an organism for which a cell thereof capable of being transformed is available, transgenic organisms of any organism can be produced to comprise the polynucleotide or vector of the present invention.

A method for producing such a transgenic organism was well known in the art. When the organism of the present invention is a plant, such a transgenic plant may be formed into a plant body by propagating a cell transformed with the polynucleotide or vector of the present invention to form a tissue or an organ and differentiating the same. Such a tissue or an organ may be any type, and includes but is not limited to, for example, a callus, a root, a stem or the like. Any organs of a plant generally have totipotency, and thus any types of an organ or tissue comprising the polynucleotide or vector of the present invention may be used for redifferentiation into a plant body. When the present invention is a tree, protocols such as those described herein may be used to produce a transgenic plant.

In the plant body of the present invention, plant species from which the prolamin is derived, and the species of the plant body may be identical or different. Preferably, both species may be identical. In this case, both species may be of the identical variant or of different variants. Preferably, both species may be of identical variant.

In a preferable embodiment, plant species from which the plant body of the present invention and/or prolamin is derived may be of rice. More preferably, both plant species may be *japonica* rice variant. The rice may be LGC-1 strain rice.

In a preferable embodiment, the plant body of the present invention may have the nucleic acid molecule of the present invention introduced into both alleles of the chromosome, but may be those with the nucleic acid molecule introduced into one allele may also be useful.

In another aspect, the present invention provides a seed produced by the plant body of the present invention. In this instance, when the plant body of the present invention comprises the antisense construct of the present invention, the protein content (particularly prolamin) in the seed is significantly reduced. Accordingly, when using such a seed for food, it is understood that the seed of the present invention is particularly useful in situations where low-protein food is preferable. When a plant body of the present invention further comprises a nucleic acid molecule encoding a foreign gene, it is recognized that the expression of the polypeptide encoded by such a foreign gene would be significant. Accordingly, the seed of the present invention may be used as a bioreactor for a useful protein.

The present invention provides a starch preparation prepared by the seed of the present invention. Such a protein preparation has a significantly reduced protein content comprising storage protein such as prolamin. Accordingly, such a starch preparation may be used for applications in which low protein is preferable.

Further, the starch preparation of the present invention comprises, when a plant produced by the seed of the present invention comprises a nucleic acid molecule encoding a foreign gene, a polypeptide encoded by the foreign gene. Since such a polypeptide is a useful protein, such a starch preparation is preferable and useful as a raw material of such a useful protein, or in order to provide a food with a useful protein or secondary metabolite product derived from the function of the added useful protein.

The present invention provides a composition comprising a gene product of a foreign gene produced from the plant body of the present invention or the seed of the present invention. The gene product of such a foreign gene, may be produced in an efficient manner into a edible portion thereof by means of the system of the present invention, therefore it is extremely useful as a food, nutritional additive, agricultural chemical, cosmetic, pharmaceutical or other applications.

In another aspect, the present invention provides a method for reducing the expression level of a protein in a seed in a plant. The present method comprises the steps of: A) providing the nucleic acid molecule of the present invention; B) introducing the nucleic acid molecule into the plant; C) redifferentiating the cell to produce a transgenic plant; and D) obtaining a seed from the transgenic seed. As used herein the technology for providing a nucleic acid molecule of the present invention is well known in the art, and it should be understood that any technology may be used to provide the nucleic acid molecule of the present invention. Technologies for introducing a nucleic acid molecule into a plant cell are well known in the art, and such technologies are well described in the literature cited herein or the like. Introduction of a nucleic acid molecule into a plant cell may be stable or transient.

Both transient and stable gene introduction technologies are well known in the art. It should be understood that technologies for producing transgenic plants by differentiating a cell used in the present invention, are well known in the art, and such technologies are well described in the literature cited herein. Technologies for obtaining seeds from a transgenic plant are also well known in the art, and such technologies are described in the literature cited herein.

Accordingly, as such, a method for reducing expression amount of proteins in the seed according to the present invention may be carried out by the means of well known technology.

Any known gene introduction technology may be used in the present invention. In a preferable embodiment, the gene introduction step of the present invention uses *Agrobacterium* method.

In a preferable embodiment, a method for reducing expression amount of a protein in a seed of a plant according to the present invention, further comprises the step of E) selecting a plant cell with the nucleic acid molecule of the present invention introduced therein. The present step is included to allow more efficient growth of such a transgenic plant, however, such a step is not always necessary in the practice of the present invention. Such a selection method varies depending on the properties of the nucleic acid molecule introduced, and for example, when an antibiotic resistance gene (for example, hygromycin, kanamycin or the like) is introduced, such a cell can be selected using such a particular antibiotic. Alternatively, a labeled gene (for example, green fluorescence gene or the like) may be used to select a desired cell using such a label as a guideline.

In another aspect, the present invention provides a method for expressing a foreign gene in a plant seed. The present method comprises the steps of: A) providing the nucleic acid molecule according to Item 1; B) providing a nucleic acid encoding the foreign gene; C) introducing the nucleic acid molecule according to Item 1 and the nucleic acid encoding the foreign gene, into a cell of the plant; D) redifferentiating the cell to produce a transgenic plant; and E) obtaining a seed from the transgenic plant.

Technologies for introducing a nucleic acid molecule in to a plant cell are well known in the art, and such technologies are fully described in the references cited herein and the like. Introduction of a nucleic acid molecule into a plant cell may be transient or stable. Transient or stable gene introduction technologies are well known in the art. It is well known in the art to produce transgenic plant by differentiating a cell used in the present invention, and it is understood that such technologies are well described in the literature cited herein. Technologies to obtain a seed from a transgenic plant are also well known in the art, and such technologies are also well described in the literature cited herein.

Any known gene introduction technology may be used in the method of expression of a foreign gene according to the present invention. In a preferable embodiment, the gene introduction step used in the present invention uses an *Agrobacterium* method. When an antisense construct of the present invention and a nucleic acid molecule encoding such a foreign gene are separately provided into a gene, such introduction into a cell may be conducted using the same method or different methods.

In a preferable embodiment, the method for expressing a foreign gene in a plant seed, further comprises the step of F) selecting a plant cell with the nucleic acid molecule introduced. By including this step, it is possible to grow transgenic plants in a more efficient manner, however, such a selection is not necessarily essential in practicing the present invention. Such selection may vary depending on the properties of the nucleic acid molecules introduced, and for example, when an antibiotic resistance gene (for example, hygromycin, kanamycin and the like) is introduced, such a specific antibiotic is used to select a target cell. Alternatively, labeling genes (for example, green fluorescence gene or the like) may be used to select a desired cell using such a label as a guideline. Alternatively, when such a foreign gene causes a distinguishing difference in phenotype, such a difference may be used as a guideline to select a gene-introduced cell. Such a distinguishing difference may be, for example, the presence and absence of a dye, but is not limited thereto.

The method of expressing a foreign gene of the present invention preferably further comprises the step of G) separating the gene product of the foreign gene from the seed.

Such separation technologies for gene products are well known in the art, any technologies capable of separating gene products (for example, protein or mRNA or the like) may be used therefor. Accordingly, well known or routine methods for isolating or purifying a protein such as a gene product of the foreign gene of the present invention, may be used to isolate or purify the same from a culture of the transformant of the present invention. For example, when the polypeptide of the present invention is secreted outside of the cell of the transformant of the present invention, such a culture is treated by means of centrifugation or the like to obtain soluble fractions. Purified product may be obtained from its soluble fraction by means of solvent extraction methods, salting out desalt methods such as using ammonium sulfate or the like, precipitation using an organic solvent, anionic exchange chromatography using a resin such as diethylaminoethyl (DEAE) Sepharose, DIAION HPA-75 (Mitsubishi Chemistry) or the like, cationic exchange chromatography using a resin such as S-Sepharose FF (Pharmacia) or the like, hydrophobic chromatography using a resin such as butyl Sepharose, Phenyl Sepharose or the like, gel filtration using a molecular sieve, electrophoresis such as isoelectric focusing or the like, or any other means.

When accumulating polypeptides such as the gene product of the foreign gene of the present invention in a cell of the transformant of the present invention are soluble, centrifugation of the culture is used to collect cells from the culture, the cells are washed, and the cells are broken down using a sonicator, a French press, a Manton-Gaulin homogenizer, a dienomill or the like to obtain cell-free extract. Supernatant which is obtained by centrifuging the cell-free extract, is treated with anionic exchange chromatography using a resin such as diethylaminoethyl (DEAR) Sepharose, DIAION HPA-75 (Mitsubishi Chemistry) or the like, cationic exchange chromatography using a resin such as S-Sepharose FF (Pharmacia) or the like, hydrophobic chromatography using a resins such as butyl Sepharose, Phenyl Sepharose or the like, gel filtration using a molecular sieve, electrophoresis such as isoelectric focusing or the like, or any other means, to obtain purified product.

Further, when a polypeptide such as a gene product of the foreign gene of the present invention is expressed to form an insoluble body inside the cell, cells are similarly collected and broken down, and centrifugation is used to obtain precipitate fractions, from which the polypeptide is collected by means of routine methods, and the insoluble body of the polypeptide is solubilized by polypeptide denaturing agent. This denaturing solution is diluted into denaturing agent-free solution or a dilute solution so that polypeptide denaturing agent concentration is sufficiently low so as to not denature the polypeptide, or dialyzed to constitute the normal three dimensional structure of the polypeptide of the present invention. Thereafter, similar isolation or purification methods are used to obtain a more purified product. Further, when the desired protein is accumulated in a particular organelle such as a protein body inside the cell, such a organelle is separated and thereafter the protein of interest may be purified.

Purification may be conducted by means of normal methods of protein purification (J. Evan. Sadler et al., Methods in Enzymology, 83, 458). For example, a polypeptide such as a gene product of the foreign gene of the present invention may be produced as a fusion protein with another protein, and affinity chromatography having affinity to the protein fused thereto is used to purify the same [Akio Yamakawa, Jikken Igaku (Experimental Medicine), 13, 469-474 (1995)]. For example, a method according to Lowe et al. (Larsen et al., Proc. Natl. Acad. Sci., USA, 86, 8227 (1989), Kukowska-Latallo J F, Genes Dev., 4, 1288 (1990)) is used to produce a fusion protein of the polypeptide of the present invention with Protein A, and purify the same using an affinity chromatography using immunoglobulin G.

Further, the polypeptide of the present invention may be produced as a fusion protein with FLAG peptide and purification may be conducted by means of an affinity chromatography using anti-FLAG antibody (Larsen et al., Proc. Natl. Acad. Sci., USA, 86, 8227 (1989), Kukowska-Latallo J F, Genes Dev., 4, 1288 (1990)).

Further, purification may be conducted using an affinity chromatography using an antibody against the polypeptide of the present invention per se. The polypeptide of the present invention may be produced using in vitro transcription/translation system known in the art [J. Biomolecular NMR, 6, 129-134, Science, 242, 1162-1164, J. Biochem., 110, 166-168 (1991)].

The present invention provides a composition comprising a gene product of a foreign gene produced by the method according to the present invention. Gene product to be comprised in such a composition may vary depending on the actual foreign gene used, but may be a protein.

In another aspect, the present invention is related to use of the nucleic acid molecule of the present invention to reduce the expression level of a protein in a seed of a plant.

In another aspect, the present invention is related to use of the nucleic acid molecule of the present invention for expressing a foreign gene in a seed of a plant. As used herein, in a plant seed expressing a foreign gene, it is preferable that expression of native protein is reduced. Reduction of native protein expression results in the expression of a gene product (in particular, protein) of a target foreign gene, in an extremely efficient manner.

It is to be understood that in each of the above-mentioned uses, each preferable embodiment described herein above for each element, per se may be applied thereto.

Hereinafter, the present invention is described based on the Examples. The following Examples are provided only for the purpose of illustration. Accordingly, the scope of the claims of the present invention is not limited to the description described above or following examples, but only by the appended claims.

EXAMPLES

Example 1

Production of Antisense Constructs

In the present Example, antisense constructs comprising antisense sequences as shown below, and promoters as shown below provide exemplifications of the present invention. Hereinafter, unless otherwise indicated, an antisense construct for reducing prolamin is collectively called "LP gene" or "LP cassette", and a recombinant rice lineage with the same introduced, is collectively called "LP lineage", and a lineage with reduced 13 kDa prolamin, the most abundant prolamin, content, is collectively called "LP13K lineage". For a variant for which a gene is transduced, Nipponbare is represented as H, LGC-1 is represented as LG, and the other variants are represented as such. For example, "H-LP13K" refers to a "Nipponbare with prolamin reduced by the introduction of the LP gene".

Promoter Sequences:

Rice 10 kDa prolamin gene derived sequence (SEQ ID NO: 470;

Rice glutelin B1 gene derived sequence (SEQ ID NO: 48)

CaMV 35S gene derived sequence (SEQ ID NO: 49)

Antisense Sequences:

antisense (SEQ ID NO: 50) of 13 kDa prolamin coding cDNA full length (SEQ ID NO: 1);

antisense (SEQ ID NO: 51) of the N-terminal 67 bp of cDNA encoding 13 kDa prolamin;

antisense (SEQ ID NO: 52) of the N-terminal 15 bp of cDNA encoding 13 kDa prolamin;

Control sequence (SEQ ID NO: 53)

Antisense constructs were constructed as follows:

For selecting the above-mentioned sequence combinations and a transformed rice, those comprising CaMV35S promoter (SEQ ID NO: 49), hygromycin phosphotransferase (SEQ ID NO: 54), and Nos terminator (SEQ ID NO: 55) are used as in an expression cassette to render transformants resistant to hygromycin.

Hereinafter, construction of expression vectors have been conducted by routine molecular biology methodologies using E. coli JM109.

Figure 1:
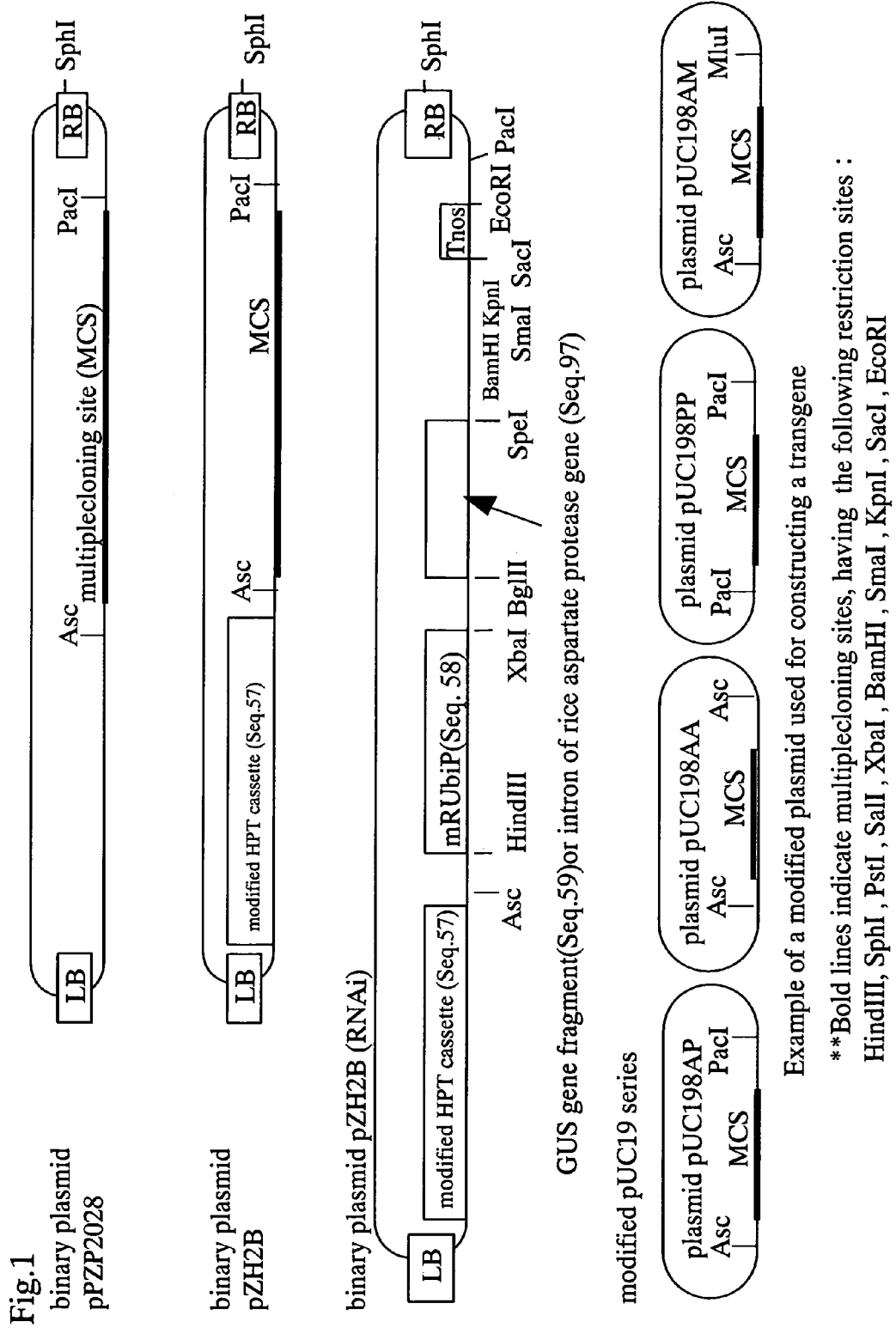
FIG. 1 shows a prolamin antisense gene cassette, an expression cassette of a useful gene and of the present invention, and variant versions of known vectors and promoters for facilitating the construction of a vector using the same. The use of the same allows rapid construction of expression cassettes and expression vectors. Further, a complicated construct of a structural gene can be simultaneously introduced into a plurality of expression cassettes.

Prior to a series of gene manipulation steps, a variant vector has been produced in order to increase efficacy in the construction process. As shown in FIG. 1, binary vector pPZP202 (Plant Molecular Biology 25, 989-994, 1994), pUC19 as a construct support plasmid were used. Other binary vectors or plasmids may be modified in a similar manner. Briefly stating the process: two original vectors pUC19 and binary vector pPZP202 (Plant Molecular Biology 25, 989-994, 1994) used, using known methods (Transgenic Research 4, p 288-290, 1995) to construct the vectors pUC198AP, pUC198AA, pUC198PP and pPZP2028 into which eight base recognition sites for AscI and PacI were introduced. In a similar manner, pUC198AM having respectively AscI and MluI, which is a six base recognition enzyme which is operably linkable to AscI. Further, HPT gene, a selectable marker gene, was used to produce the variant gene mHPT (amino acid SEQ ID NO: 56) by deleting EcoRI, PstI and NcoI sites present by site directed mutagenesis, and was introduced into a cassette to form a selectable marker expression cassette (base SEQ ID NO: 57) in which CaMV 35S promoter and nos terminator are linked so that it is not cleaved by restriction enzymes. This was incorporated into pPZP20208 so as not to be cleaved by restriction enzymes. Further, for rice polyubiquitin promoter fragments, restriction enzyme sites such as XbaI, EcoRI, PacI, PstI, XhoI present in the sequence were eliminated by site-directed mutagenesis to produce a mutated rice polyubiquitin promoter (mRUbiP, SEQ ID NO: 58). The above plasmids were used for the following examples.

Figure 2:
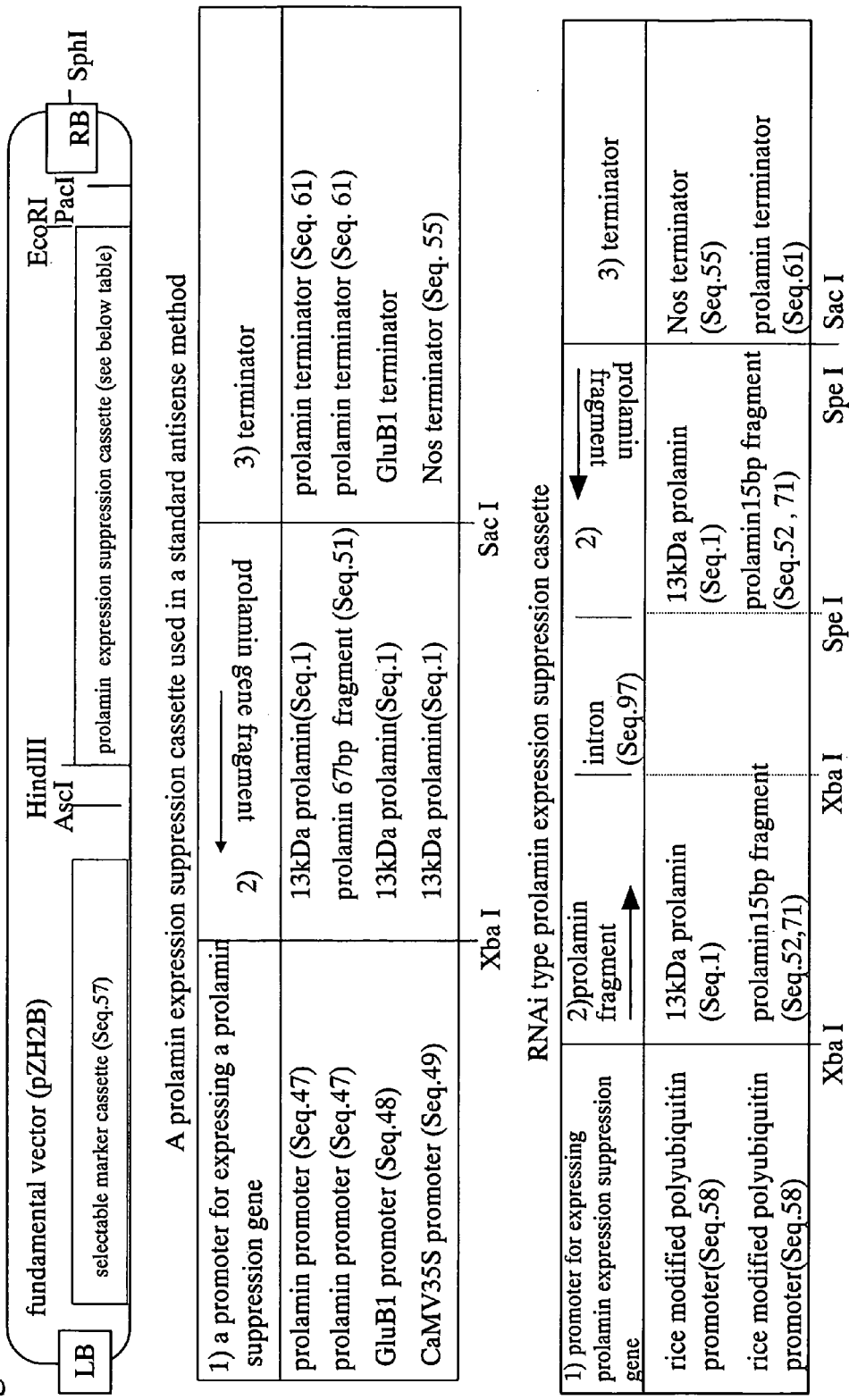
FIG. 2 is a drawing illustrating a schematic of a prolamin antisense gene vector which has been constructed.

Examples of the structure of specific expression vectors are shown in FIG. 2. First, a terminator was ligated into the SacI-EcoRI site of pZH2B vector, and next a promoter was ligated to the HindIII-XbaI site thereof. A gene fragment for antisense was ligated between the XbaI-SacI site. A double-stranded RNA expression vector for RNAi was constructed as follows: a nos terminator was ligated into a SacI-EcoRI site thereof, and a mutated rice polyubiquitin promoter was ligated into an HindIII-XbaI site, and then a GUS gene fragment (SEQ ID NO: 59) in which restriction enzyme sites were ligated (XbaI and BglII at 5' terminus, and SpeI and BamHI ate 3' terminus), or a rice aspartate protease gene intron sequence (SEQ ID NO: 97) was ligated at XbaI-BamHI site to produce a basic RNAi expression vector. Thereafter, one type of an appropriate prolamin gene fragment to be suppressed was selected for ligation, one fragment per XbaI or BglII site, and one fragment per SpeI or BamHI site, in an opposite direction to each other, to complete the vector.

In order to check that the desired antisense expression vector had been constructed, PCR using PCR primers to amplify each fragment, and/or DNA sequencing was conducted.

Vectors were stored at −20° C. until use in the following Examples

Example 2

Transformation of Rice with an Antisense Construct

A vector comprising the antisense construct as produced in Example 1 was used to transform two rice variants (Nipponbare and LGC-1) to produce transgenic rice. Nipponbare was used as a typical variant of rice. LGC-1 was used for more clearly confirming the effects of the present invention on prolamin, which is a rice modified by radiation of Nihonmasari, wherein glutelin expression is greatly decreased and prolamin expression is increased in the seed.

The specific procedure therefor is as follows:

Each of the antisense prolamin gene expression vectors shown in FIG. 2 were subjected to electroporation with Agrobacterium EHA101, and selection of bacteria possessing the vector performed using LB agar medium comprising 100 mg/L spectinomycin. Prior to Agrobacterium infection, the method of Raineri (Raineri D M., Bio/Technology 8, 33-38, 1990) has been used with a partial modification, and after the infection, the culture conditions and media were as described by Toki et al. method (Toki. S., Plant Molecular Biology Reporter 15, 159-164, 1997). Variants which have not been successfully transformed to obtain a transgenic rice by the Toki et al. method, were transformed using a medium composition according to Fukuoka et al. method (Fukuoka H. et al., Plant Cell Reports 19, 815-820, 2000).

Protocols are briefly described, however, unless otherwise noted, a rice cell was cultured at 28° C. Further, base of the medium used was 0.4% gellite (WAKO PURE CHEMICAL). Husked rice seeds were soaked in 70% ethanol, followed by soaking in hypochlorous acid having about 2% effective chlorine concentration to sterilize them. The seeds were then washed with sufficient sterile water, and transferred into callus induction medium containing 2 mg/L 2,4-D (KNO$_3$ 2830 mg/L, (NH$_4$)$_2$SO$_4$ 460 mg, CaCl$_2$.2H$_2$O 166 mg/L, MgSO$_4$.7H$_2$O 185 mg/L, KH$_2$PO$_4$ 400 mg/L, FeSO$_4$.7H$_2$O 27.8 mg/L, EDTA-2Na 37.3 mg/L, MnSO$_4$.4H$_2$O 4.4 mg/L, ZnSO$_4$.7H$_2$O 1.5 mg/L, KI 0.8 mg/L, H$_3$BO$_3$ 1.6 mg/L, nicotinic acid 0.5 mg/L, thiamine hydrochloric acid 1.0 mg/L, pyridoxine hydrochloric acid 0.5 mg/L, glycine 2 mg/L, myoinositol 100 mg/L, proline 2.88 g/L, casamino acid 300 mg/L, sucrose 30 g/L, pH=5.8) to culture the same. Five days later, the seeds were collected and a culture suspension of Agrobacterium containing the target transgene cultured in AAM medium (MnSO$_4$.4H$_2$O 10 mg/L, H$_3$BO$_3$ 3 mg/L, ZnSO$_4$.7H$_2$O 2 mg/L, Na$_2$MoO$_4$.5H$_2$O 0.25 mg/L, CuSO$_4$.5H$_2$O 0.025 mg/L, CoCl$_2$.6H$_2$O 0.025 mg/L, CaCl$_2$.2H$_2$O 150 mg/L, MgSO$_4$.7H$_2$O 250 mg/L, Fe-EDTA 40 mg/L, NaH$_2$PO$_4$.2H$_2$O 150 mg/L, nicotinic acid 1 mg/L, thiamine hydrochloric acid 10 mg/L, pyridoxine hydrochloric acid 1 mg/L, myoinositol 100 mg/L, L-arginine 174 mg/L, glycine 7.5 mg/L, pH=5.2) was inoculated onto the seeds (the culture had an OD$_{600}$ of about 0.03) for two minutes, excess water was removed with a sterile paper towel, and the seeds were placed in a co-culture medium containing 2 mg/L2, 4-D (KNO$_3$ 2830 mg/L, (NH$_4$)$_2$SO$_4$ 460 mg, CaCl$_2$.2H$_2$O 166 mg/L, MgSO$_4$.7H$_2$O 185 mg/L, KH$_2$PO$_4$ 400 mg/L, FeSO$_4$.7H$_2$O 27.8 mg/L, EDTA-2Na 37.3 mg/L, MnSO$_4$.4H$_2$O 4.4 mg/L, ZnSO$_4$.7H$_2$O 1.5 mg/L, KI 0.8 mg/L, H$_3$BO$_3$ 1.6 mg/L, nicotinic acid 0.5 mg/L, thiamine hydrochloric acid 1.0 mg/L, pyridoxine hydrochloric acid 0.5 mg/L, glycine 2 mg/L, myoinositol 100 mg/L, glucose 10 g/L, casamino acid 300 mg/L, sucrose 30 g/L, pH=5.2). The seeds were cultured for three days at 25° C., and thereafter washed with sufficient sterile water, and soaked in sterile water containing 500 mg/L Carbenicillin for five minutes. Seeds from which Agrobacterium was completely thus removed, were cultured in a selective medium containing 50 mg/L hygromycin (KNO$_3$ 2830 mg/L, (NH$_4$)$_2$SO$_4$ 460 mg, CaCl$_2$.2H$_2$O 16 mg/L, MgSO$_4$.7H$_2$O 185 mg/L, KH$_2$PO$_4$ 400 mg/L, FeSO$_4$.7H$_2$O 27.8 mg/L, EDTA-2Na 37.3 mg/L, MnSO$_4$.4H$_2$O 4.4 mg/L, ZnSO$_4$.7H$_2$O 1.5 mg/L, KI 0.8 mg/L, H$_3$BO$_3$ 1.6 mg/L, nicotinic acid 0.5 mg/L, thiamine hydrochloric acid 1.0 mg/L, pyridoxine hydrochloric acid 0.5 mg/L, glycine 2 mg/L, myoinositol 100 mg/L, proline 2.88 g/L, casamino acid 300 mg/L, sucrose 30 g/L, pH=5.8) for two weeks. Thereafter, the resulting cell mass from which albumen and shoots were removed, was cultured on redifferentiation medium containing hygromycin 50 mg/L, and kinetin 2 mg/L, and NAA 0.02 mg/L as hormones (NH$_4$NO$_3$ 1650 mg/L, KNO$_3$ 1900 mg/L, CaCl$_2$.2H$_2$O 440 mg/L, MgSO$_4$.7H$_2$O 370 mg/L, KH$_2$PO$_4$ 1700 mg/L, FeSO$_4$.7H$_2$O 27.8 mg/L, EDTA-2Na 37.3 mg/L, MnSO$_4$.4H$_2$O 22.3 mg/L, ZnSO$_4$.7H$_2$O 8.6 mg/L, CuSO$_4$.5H$_2$O 0.025 mg/L, Na$_2$MoO$_4$.2H$_2$O 0.25 mg/L, CoCl$_2$.6H$_2$O 0.025 mg/L, KI 0.83 mg/L, H$_3$BO$_3$ 6.2 mg/L, nicotinic acid 0.5 mg/L, thiamine hydrochloric acid 0.1 mg/L, pyridoxine hydrochloric acid 0.5 mg/L, glycine 2 mg/L, myoinositol 100 mg/L, casamino acid 2 g/L, sucrose 30 g/L, sorbitol 30 g/L, pH=5.8), and passage was performed using the same medium once a week for three times. In the interim, one cell mass which causes shoot by budding, two shoots presenting significant growth were selected to be transferred to hormone-free medium (NH$_4$NO$_3$ 1650 mg/L, KNO$_3$ 1900 mg/L, CaCl$_2$.2H$_2$O 440 mg/L, MgSO$_4$.7H$_2$O 370 mg/L, KH$_2$PO$_4$ 170 mg/L, FeSO$_4$.7H$_2$O 27.8 mg/L, EDTA-2Na 37.3 mg/L, MnSO$_4$.4H$_2$O 22.3 mg/L, ZnSO$_4$.7H$_2$O 8.6 mg/L, CuSO$_4$.5H$_2$O 0.025 mg/L, Na$_2$MoO$_4$.2H$_2$O 0.25 mg/L, CoCl$_2$.6H$_2$O 0.025 mg/L, KI 0.83 mg/L, H$_3$BO$_3$ 6.2 mg/L, nicotinic acid 0.5 mg/L, thiamine hydrochloric acid 0.1 mg/L, pyridoxine hydrochloric acid 0.5 mg/L, glycine 2 mg/L, sucrose 30 g/L, pH=5.8). After about one month, one shoot having more growth than the other shoot was transferred to a pot, and was grown in an isolated green house or sunlight determined temperature incubator, and it's seeds subsequently harvested. Shoots having been redifferentiated from different cell masses were treated as independent recombinant lineages.

Transformants thus obtained were resistant to hygromycin due to the hygromycin resistance gene encoded by the vector.

Example 3

Growth of Transformants

Commercially available compost (Honensu compost containing trace amounts of nutrition) was put into plastic pots (diameter: 15 cm), and rice, which was grown in a hormone-free medium for one month, was transferred thereto. Usually, seeds were located under natural light in a separate, isolated green house for sprouting seeds. As necessary, the seeds were placed in an artificial climate chamber (Nihon ika FH 301 or the like), cycles of 16-hour light period (15,000 lux or more, 30° C.)—eight-hour dark period (25° C.) were used for growth for two months, followed by cycles of 12-hour light period (15,000 lux or more, 30° C.)—12-hour dark period (25° C.) for two to three months to set seeds.

Example 4

Analysis by Electrophoresis of the Seed Proteins of the Recombinant Plants of the Present Generation The seeds harvested in Example 3 were used to analyze the proteins present in the seed. The details are described as follows:

SDS-PAGE which is well known in the art, was used to analyze seed protein composition using 18% acrylamide gels. Twelve seeds were arbitrarily selected from each independent transgenic rice lineage. Each of selected 12 seeds was individually numbered, then divided into two pieces and marked in order to clarify the relationship between the groups, the half thereof having embryo, was inoculated into hormone-free medium containing hygromycin 50 mg/L. The remaining half thereof was finely ground by sandwiching the grains between aluminum foil and hitting them with hammer, and protein was extracted by locating the seeds in 200 microliters of seed protein extraction buffer (containing 25 mM Tris, pH 6.8, 8M urea, 5% 2-mercaptoethanol, 4% SDS), and vortexing for one minute. After centrifugation, 8 microliters of supernatant were removed therefrom, and mixed with 2 microliters of staining solution (25 mM Tris, pH 6.8, containing 10% glycerol, 0.025% bromophenol blue, and 5% 2-mercaptoethanol), and thereafter electrophoresed and detected with Coommassie brilliant blue. Simple protein quantification was conducted with respect to concentration of protein bands in the gel using OneD/ZeroD Scan (Analysistics Inc.).

(Lineage Selection)

The above mentioned analysis allowed the selection of a lineage in which the content of 13 kDa prolamin is about less than 50%. Seeds of the next generation were harvested, and seeded again into hormone-free medium including hygromycin ($NH_4NO_3$ 1650 mg/L, $KNO_3$ 1900 mg/L, $CaCl_2.2H_2O$ 440 mg/L, $MgSO_4.7H_2O$ 370 mg/L, $KH_2PO_4$ 170 mg/L, $FeSO_4.7H_2O$ 27.8 mg/L, EDTA-2Na 37.3 mg/L, $MnSO_4.4H_2O$ 22.3 mg/L, $ZnSO_4.7H_2O$ 8.6 mg/L, $CuSO_4.5H_2O$ 0.025 mg/L, $Na_2MoO_4.2H_2O$ 0.25 mg/L, $CoCl_2.6H_2O$ 0.025 mg/L, KI 0.83 mg/L, $H_3BO_3$ 6.2 mg/L, nicotinic acid 0.5 mg/L, thiamine hydrochloric acid salt 0.1 mg/L, pyridoxine hydrochloric acid salt 0.5 mg/L, glycine 2 mg/L, sucrose 30 g/L, pH=5.8), and subjected to electrophoresis for validation. This process was repeated for three generations, to investigate in detail lineages in which the content of 13 kDa prolamin was reduced to about less than 50% in a similar manner for all 10 grains randomly selected.

Five grains were milled in a mortar and placed in a 15-ml tube. Five ml of diethylether were added thereto and vigorously vortexed to remove lipids. After centrifugation thereof, the ether was removed and the remaining seed powder was air dried. Next, 5 ml of 25 mM Tris buffer (pH 6.8) was added thereto and vigorously vortexed to extract water soluble proteins, and then centrifuged to collect seed powder. Seed protein extraction buffer (2.5 mL) was added thereto, and then vigorously vortexed and centrifuged. The resultant liquid phase was used as a seed protein extraction solution.

Figure 3:
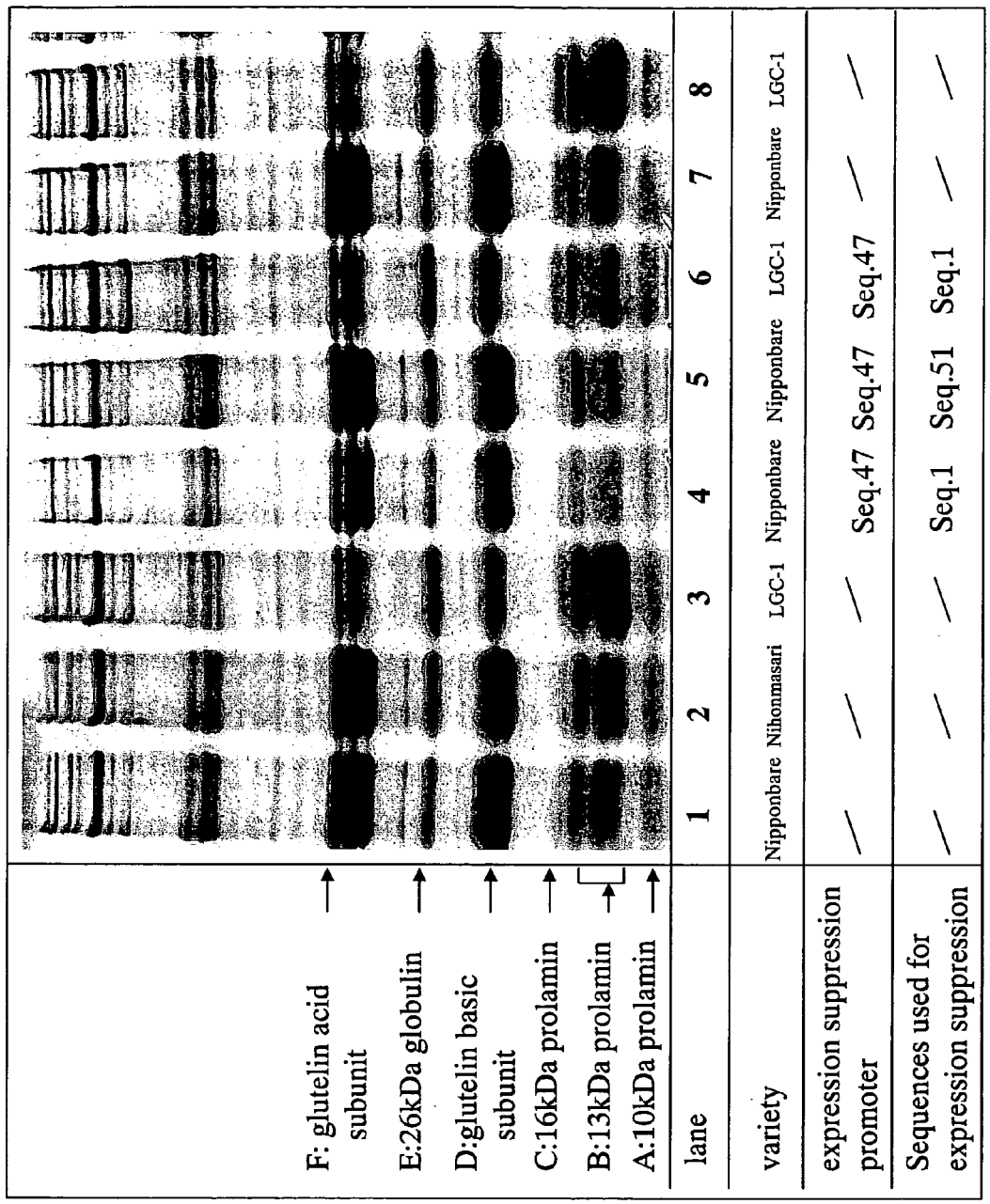
FIG. 3 shows the analysis, by electrophoresis using SDS-PAGE, of a seed protein in a LP13 K lineage (a lineage with 13 kDa prolamin antisense gene cassette introduced therein) of the seed of the present invention. Detection of proteins were visualised by Coommassie Brilliant Blue stain. On the side of the electrogram, bands of the following main storage proteins are depicted: A. 10 kDa prolamin, B: 13 kDa prolamin, C: 16 kDa prolamin, D: glutelin basic subunit, E: 26 kDa globulin, F: gluten acidic subunit. The number shown on the side thereof is an approximate value of molecular weight. This representation is commonly used in the following figures. In Lanes 4, 5 and 6, which are LP13K lineages, concentrations of B bands corresponding to the 13 kDa prolamin are significantly reduced, and thus showing that the 13 kDa prolamin content is reduced therein.

The results of the above experiments are shown in FIG. 3. Major storage proteins are presented in the right hand of the gel photograph. General varieties (Nipponbare, Nihonmasari) such as those in lanes 1, 2 and 7 contained the highest amount of glutelin (D and F), followed by 13 kDa prolamin (B). When prolamin antisense gene was introduced thereto, as shown in lanes 4 and 5, the abundance of 13 kDa prolamin (B) was significantly reduced, and 10 kDa prolamin and 16 kDa prolamin were also reduced to some extent. Glutelin and globulin expression did not change.

Further, lanes 3 and 8 show low-glutelin containing rice (LGC-1), which was produced by radiation mutation of Nihonmasari. As a consequence of homeostasis, prolamin (A-C), and globulin (E) were significantly increased, and most of the reduction of glutelin content was compensated. However, when a prolamin antisense gene was introduced thereto, as shown in lane 6, the prolamin content (A-C) was significantly reduced, while the low-glutelin containing character was retained, and no increase was observed in the expression of globulin. As such, it was demonstrated that the gene of the present invention can be successfully introduced to any variant to reduce prolamin content, and thus the overall seed protein content was also reduced corresponding thereto. Therefore, it was demonstrated that the present invention is very effective for producing low-protein rice.

Figure 4:
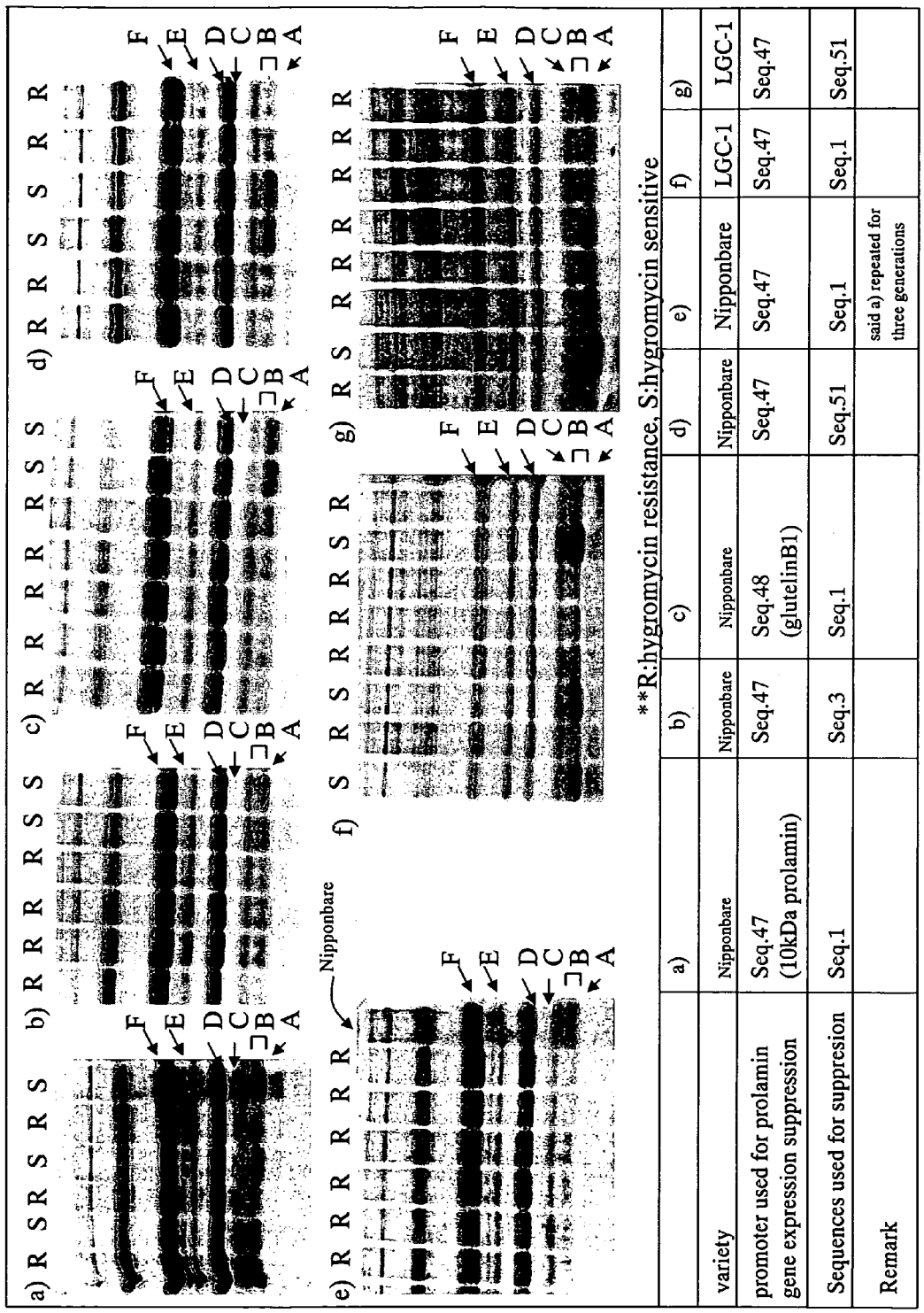
FIG. 4 depicts results of analysis of seed proteins by SDS-PAGE, in which a variety of 13 kDa prolamin antisense gene cassette constructs were introduced therein. Lanes with hygromycin resistance (represented by R in the figure) have a significantly lowered concentration of B band corresponding to the 13 kDa prolamin without exception.

Further, as results of analysis of seeds of lineages with a variety of transgenes introduced are shown in FIG. 4, seeds having hygromycin resistant properties were demonstrated to have reduced prolamin content, and thus it was confirmed that the effect of reduction of prolamin content was actually derived from the transgene.

(Measurement by Densitometer)

Next, SDS-PAGE gels were measured by densitometry to relatively compare the protein amount by digitalization. The above-mentioned extraction solution was aliquoted for an appropriate volume (for example, 5 µl, 15 µl, 30 µl) which was subjected to SDS-PAGE, and similarly, the band concentration was quantified to infer protein amounts thereof. After electrophoresis, proteins in the gel were transferred to a PVDF membrane, and detection of 13 kDa prolamin was conducted using an anti-13 kDa polyclonal antibody and a Western blotting kit (BioRad, or the like). Bands detected were similarly analyzed with SDS-PAGE to determine the concentration of protein content thereof. The results of densitometer are shown in the following Table. The total value of absorbance of storage proteins has been shown to be lower in lineages with prolamin antisense gene introduced therein, than the others, showing that low-protein was achieved. Further, as shown in the Western blotting result in FIG. 5, in comparison with the original variant, absorbance of bands recognizing the 13 kDa prolamin was reduced to 10%-28% of the original, as such, from the results of SDS-PAGE measurements, it was further suggested that further reduction of prolamin occurred therein.

Band concentration results of major storage proteins measured by densitometer are shown in the following tables:

TABLE 1

| Rice lineage | Nipponbare | LP13K | LP13K | LP13K | Nihonmasari | LGC-1 | LG-LP13K |
|---|---|---|---|---|---|---|---|
| Promoter used | | glutelin B1 (Sequence 48) | 10 kDa prolamin (Sequence 47) | 10 kDa prolamin (Sequence 47) | | | 10 kDa prolamin (Sequence 47) |
| Antisense sequence | | Sequence 50 | Sequence 50 | Sequence 51 | | | Sequence 50 |
| glutelin acidic | 1630.4 | 1698.8 | 1636.3 | 1541.3 | 1488.9 | 722.8 | 912.8 |
| globulin 26 KDa | 266.9 | 277.4 | 229.5 | 261.9 | 301.9 | 432.1 | 402.4 |
| glutelin basic | 1227 | 1301.1 | 1236.1 | 1154.9 | 1168.2 | 505.8 | 658.7 |
| prolamin 16 KDa | 310.5 | 278.9 | 297.3 | 304.2 | 364.1 | 478.5 | 343.5 |
| prolamin 13 KDa | 760 | 378.5 | 360.9 | 310.9 | 684.7 | 1453 | 556.1 |
| prolamin 10 KDa | 107.9 | 102.7 | 81.2 | 38.3 | 134.7 | 133.2 | 135.2 |
| total | 4302.7 | 4037.4 | 3841.3 | 3611.5 | 4142.5 | 3725.4 | 3008.7 |

As seen from the above Table, the antisense construct of the present invention not only reduced the expression of prolamin, but also has effects of suppression or neutral towards other storage proteins. This result shows an unexpected result which is totally different from the previous result, in which in low-glutelin plants, prolamin was increased, and as a consequence, no substantial change has been observed in the total amount of seed storage proteins.

(Determination of Nitrogen Content)

Changes of crude protein content were confirmed by determining nitrogen content contained in unhusked rice. In brief, Kjeldahl method, a commonly used chemical analysis of nitrogen content, was used. Ten grains of seeds were placed into a specifically prepared test tube, and degradation enhancer and 2 mL of water were added to heat-degrade at 370° C. Thereafter, after cooling down until the test tube can be handled by naked hand, distilled water was gently poured thereto to dilute it. In this state, nitrogen in the seeds was retained as ammonia-ammonium in a sulfated form. Equal amount of 30% sodium hydroxide was added to this degradation solution (10 mL) and water steam distilled, and the resultant ammonia was trapped into a saturated borate solution. This borate solution was added a pH indicator, and tittered with hydrochloric acid to determine the ammonia content from neutralized point, to calculate nitrogen content. The results thereof are as follows:

Two isolated greenhouses were used to analyze grown rice. It was well known in the art that differences in circumstances of greenhouse have an influence on the nitrogen content, and thus Nipponbare variants in the two separate greenhouses presented different nitrogen content values. However, the lineages which have LP-gene introduced, presented lower nitrogen content than the original variants thereof in any types. Thus, it is understood that crude protein content has been reduced. Thus, the reduction is evidently derived from the reduction of storage proteins.

As is clear from the above Table, the antisense constructs of the present invention were demonstrated to significantly reduce the nitrogen content of the seed proteins, i.e., the seed protein amount. As such, low protein modification has been achieved.

(Results)

In conclusion, the above-mentioned construct of the present invention has been used to significantly reduce the expression amount of 13 kDa prolamin. Other prolamins (10 kDa and 16 kDa) were also shown to be the same or reduced to some extent. Expression of glutelin and globulin was the same as before the introduction of the above-mentioned construct of the present invention. Accordingly, the construct of the present invention can be said to significantly reduce the entire expression amount of the seed proteins.

TABLE 2

| | | Nipponbare | LP13K | Nihonmasari | LGC-1 | LG-LP13K |
|---|---|---|---|---|---|---|
| Isolated Green House A | Unhusked rice nitrogen content (µg/1 grain) | 286.4 | 269.8 | 286.2 | 287 | 257.9 |
| | Relative value | 100 | 94.2 | 100 | 100 | 90.1 |
| Isolated Green House B | Unhusked rice nitrogen content (µg/1 grain) | 389.9 | 330.3 | | | |
| | Relative value | 100 | 84.7 | | | |

Example 5

Electrophoresis Pattern of Seed Proteins Obtained from Independent Lineages

Next, for seeds which fruited in one spike, a plurality of seeds were extracted, and analyzed using electrophoresis according to Example 4. The result is shown in FIG. 4. From this, seeds presenting phenotypes of hygromicin resistance were observed to reduce its prolamin content. Therefore, it has been demonstrated that the insertion into at least one allele of the chromosome of the antisense construct of the present invention is sufficient to suppress prolamin content.

Example 6

Antisense Effects

Next, the antisense's effect of the antisense construct of the present invention was confirmed by independently producing a plurality of types of recombinant rice and analyzing the same. The procedures and results are as follow:

The relationship between the structure of prolamin antisense of the present invention and the prolamin reduction effect caused thereby, was analyzed by producing recombinant rice with a variety of structural genes. Each seeds of 10 or more independent lineages was analyzed according to a method of lineage selection and summarized as follows:

TABLE 3

| No. | variant | promoter | sequence for antisense suppression |
|-----|---------|----------|-------------------------------------|
| A | Nipponbare | 10 kDa prolamin | SEQUENCE 1(13 kDa prolamin) |
| B | Nipponbare | glutelin B1 | SEQUENCE 1(13 kDa prolamin) |
| C | Nipponbare | CaMV35S | SEQUENCE 1(13 kDa prolamin) |
| D | Nipponbare | 10 kDa prolamin | SEQUENCE 51 (a part of prolamin, 67 bp) |
| E | Nipponbare | Glutelin B1 | SEQUENCE 51 (a part of prolamin, 67 bp) |
| F | Nipponbare | CaMV35S | SEQUENCE 51 (a part of prolamin, 67 bp) |
| G | LGC1 | 10 kDa prolamin | SEQUENCE 1(13 kDa prolamin) |
| H | LGC1 | glutelin B1 | SEQUENCE 1(13 kDa prolamin) |

These transformed rice were analyzed for 1) the number of lineages having one or more seeds with 13 kDa prolamin content reduced; 2) the number of lineages having at least seeds having 50% or less 13 kDa prolamin content of that of a non-transformant; and 3) the number of lineages having 13 kDa prolamin content reduced in all the seeds presenting hygromycin resistant.

1) The number of lineages which have one or more seeds with 13 kDa prolamin content reduced, was evaluated with reference in that, 13 kDa prolamin expression content was reduced by 20% or more.

2) Seeds with 13 kDa prolamin content being 50% or less of that of non-transformant, were analyzed by comparing seed extract from non-transformant and seed-extract from comparative reference.

3) With respect to hygromycin resistance, individual which survived in a hygromycin containing medium was selected. With respect to the reduction of prolamin content, the same criteria were employed as for Item 1).

The actual comparison was conducted by reading gel after electrophoresis by means of a gel reader, and the logarithms of the measured values were calculated to absolute value, to calculate the desired sample by making non-transformant as 100%.

The results are shown as follows:

TABLE 4

| No. | No. of rice lineages analyzed | 1) No. of prolamin reduced lineages* | 2) No. of seed lineages with 50% or less** | 3) No. of hygromycin resistant and prolamin reduced lineages*** |
|-----|-------------------------------|--------------------------------------|----------------------------------------------|---------------------------------------------------------------|
| A | 79 | 60 | 45 | 32 |
| B | 56 | 22 | 14 | 6 |
| C | 20 | 2 | 0 | 0 |
| D | 15 | 5 | 3 | 1 |
| E | 68 | 0 | 0 | 0 |
| F | 21 | 0 | 0 | 0 |
| G | 24 | 21 | 12 | 6 |
| H | 18 | 7 | 3 | 0 |

*the number of lineages having one or more seeds with 13 kDa prolamin content reduced;
**the number of lineages having at least seeds having 50% or less 13 kDa prolamin content of that of non-transformant;
***the number of lineages having 13 kDa prolamin content reduced in all the seeds presenting hygromycin resistant.

The results of the above-identified Item 1 and 2 are indicative of how strong a construct has the ability to suppress the expression of 13 kDa prolamin, and that the greater the number becomes, the more efficient the inhibition. The antisense construct according to the present invention is observed to have suppressed its targeted 13 kDa prolamin expression in an efficient way, with some variance in efficiency thereof depending on the structure (in particular, promoter). The results of item 3, the hygroomycin resistance and the phenotype attained by the antisense do not always correspond to each other. This indicates that there may be cases where only one transgene inserted into either of two alleles of chromosome does not sufficiently attain the suppression effect of 13 kDa prolamin. Accordingly, the present invention may preferably have transgenes introduced into two alleles of the chromosome. Generally, in recombinant rice, transgene is randomly incorporated into the chromosome, and thus, it is known that the degree of expression may have an influence on the site of insert. When producing a hundred of individuals with the same gene introduced, it is within common general knowledge of the art that there are great variances in individuals which have well expressed transgene to no expression. Further, regarding individuals with little expression of gene, it is also known that there is some differences in phenotype between individuals with the genes introduced into either one allele of the chromosome and those with the genes introduced into both allele of the chromosome, and between the individuals with one transgene introduced, and those with two transgenes introduced. Originally, when one antisense construct has one introduced into either allele of the chromosome as shown in FIG. 4, antisense effects may be attained. For example, when insertion site on the chromosome is not good, there may be often variance in phenotypes depending on the number of antisense constructs introduced.

As described above, it can be said that the bigger the value shown in 1, 2 and 3 as in these items, the more superior a construct is capable of exerting antisense effect with high probability in a stable manner. In this sense, it turned out that 10 kDa promoter is amenable to obtain lineages with more potent antisense effect than other promoters, and further when gene fragments used for antisense is made shorter (67-

15 bp), these shorter fragments still attained antisense effects. Accordingly, it was demonstrated that the invention has extremely high utility.

Example 7

Antisense Using RNAi-Type Expression Cassette

As another form of antisense gene, RNAi type of LP gene using two fragments complementary to the target gene, has been introduced to verify similar effects. In consideration of the known reference, Nature 407: 319-320 (2000), construction has been carried out, and FIG. 2 shows its gene construct. Amongst these, Table 5 shows a comparison of those with rice polyubiquitin promoter used, which were not presented in Tables 3-4. Table 6 shows its results, in which the method used was in accordance with Table 4.

Further, when sequences derived from 16 kDa prolamin (SEQ ID NO: 31 and 32) are used as prolamin suppression fragments, lineages having 16 kDa prolamin and 13 kDa prolamin simultaneously reduced therein, have been obtained although its appearance probability is low. 16 kDa prolamin and 13 kDa prolamin locally share amino acid sequence with high homology, and the portion thereof are thought to be effective for both prolamins in antisensing activity. This, in addition to the consequence of the earlier results, when generally suppressing expression of multigene family, shows that local consensus in amino acid sequence is important, and thus suggesting that the construct of the present invention is effective in suppressing storage protein suppression of other crops.

Some of the actual results of SDS-PAGE have been shown in FIG. 10.

Generally, antisense gene of RNAi type efficiently and potently inhibit expression of a target gene than an antisense gene using one reverse fragment. Comparing Tables 4 and 6, similar tendency is found in terms of prolamin suppression. In particular, the probability with which lineage with prolamin significantly reduced therein is obtained, is evidently higher for RNAi type antisense, than the other. However, it demonstrates that it is sufficiently possible to obtain a lineage having prolamin significantly reduced with a single reverse fragment. As such, any of the constructs of antisense genes of the present invention is concluded as being highly useful.

TABLE 5

| No. | variant | promoter | spacer | sequence for antisense suppression |
|---|---|---|---|---|
| I | Nipponbare | SEQUENCE 58 | GUS fragment (SEQUENCE 59) | SEQUENCE 1 (13 kDa prolamin) |
| J | Nipponbare | SEQUENCE 58 | intron (SEQUENCE 97) | SEQUENCE 1 (13 kDa prolamin) |
| K | LGC1 | SEQUENCE 58 | GUS fragment (SEQUENCE 59) | SEQUENCE 1 (13 kDa prolamin) |
| L | LGC1 | SEQUENCE 58 | intron (SEQUENCE 97) | SEQUENCE 1 (13 kDa prolamin) |
| M | Nipponbare | SEQUENCE 58 | intron (SEQUENCE 97) | SEQUENCE 65 (a part of prolamin, 45 bp) |
| N | Nipponbare | SEQUENCE 58 | intron (SEQUENCE 97) | SEQUENCE 72 (a part of prolamin, 23 bp) |

TABLE 6

| No. | No. of rice lineages analyzed | 1) No. of prolamin reduced lineages* | 2) No. of seed lineages with 50% or less** | 3) No. of hygromycin resistant and prolamin reduced lineages*** |
|---|---|---|---|---|
| I | 11 | 11 | 9 | 11 |
| J | 11 | 11 | 11 | 11 |
| K | 4 | 4 | 2 | 4 |
| L | 4 | 4 | 4 | 4 |
| M | 4 | 4 | 2 | 4 |
| N | 4 | 4 | 1 | 4 |

*the number of lineages having one or more seeds with 13 kDa prolamin content reduced;
**the number of lineages having at least seeds having 50% or less 13 kDa prolamin content of that of non-transformant;
***the number of lineages having 13 kDa prolamin content reduced in all the seeds presenting hygromycin resistant.

When considering the results, in LP genes of RNAi type, values in items 1) and 3) are consistent with the number of lineages analyzed, and thus it is shown that when the gene is introduced, it certainly reduces prolamin. When comparing GUS fragment and aspartate protease intron as a spacer sequence, aspartate protease intron showed higher value in item 2), and thus demonstrating that it has higher probability of significantly presenting antisense effects. When using short fragments such as 45 bp, 23 bp or the like, it is understood that lineages which significantly present antisense effects can be obtained. Even shorter fragments such as 15 bp have demonstrated their antisense effects.

Example 8

Observation of the Protein Body by Transmission Electron Microscope

Next, protein body in the seed produced in Example 6 was observed. The observation of the protein body was conducted as follows:

Hulls after flowering was marked and sampling was conducted on Days 7, 10, 14 and 21. After seeds have been cut in just upstream and downstream thereof by a blade, and 3% glutaraldehyde solution was placed, and subjected to fixation treatment on ice, in vacuo for 15 minutes, and with a time period of 12 hours at 4° C. Seeds were divided into three pieces, and embedded in LR-White resin (available from Okenshoji Co., Ltd.), and fixed, and diamond knife was used to make segments of about 90 nm. Thereafter, the segments were treated according to normal transmission electron microscope available from JEOL.Ltd to observe cells in albumen surface layers.

FIG. 6 shows observed results fourteen days after flowering. FIG. 6a shows an observed raw photograph. The light gray and smooth globular form, is the Protein Body 1 accumulating prolamin, and the larger with darker color and having less smooth form, is the Protein Body 2 accumulating glutelin and globulin. It was clearly observed that protein granules were tightly loaded. FIG. 6b shows types of protein bodies in the same photographs of FIG. 6a with labels. When observing it with the same area of field of view, LP13K lineage (6b-1) has apparently less number of Protein Body 1 than that of normal variant (6b-2). This indicates that 13 kDa prolamin has an important role in forming Protein Body 1, and thus the regulation of the expression thereof can control the number of the protein body formation. On the other hand, LGC-1 (6b-3) which has the character of low-glutelin and high-prolamin, showed significant reduction in the number and size of Protein Body 2, while the number of Protein Body 1 has increased and thus it can be clearly observed that the reduction of glutelin has been distributed to the increase of prolamin. In LG-LP13K in which prolamin antisense gene has been introduced into LGF-1, it was observed that both Protein Bodies have been reduced. It is known that surface layer of albumen cells are rich in proteins, although it is not as much as bran layer cells, and thus proteins should be removed as much as possible for food or processed food. If the effects of prolamin antisense gene are to significantly reduce the proteins on the surface, there is some merit in obtaining almost the same quality as that with protein removal process, if such process is eliminated. Further, due to the homeostasis of seeds, reduced proteins are to be compensated by other substances, and thus if a gene of a useful protein is forced to express therein, amino acids will be preferentially distributed thereto, and is expected to accumulate such a foreign protein in the surface layer cells.

Example 9

Production of Other Antisense Constructs

Next, antisense of other prolamin gene and promoter, and optional signal sequence have been confirmed in the present Example, whether or not it has similar effects. The promoter sequence and antisense sequence produced in the Examples, are shown as follows: SEQ ID NOs: 63-72 (antisense), 102-105 (antisense), 47 and 58 (promoter), 106-107 (promoter), 108-113 (signal sequences).

Using the sequence and in accordance with the procedure set forth in Examples 1-8 to conduct analysis of effects, it was confirmed that these antisense sequences have similar prolamin and seed protein suppression effects.

This shows that antisense effects were not only shown to the prolamin type per se but also on the other types of prolamins.

As described in Examples 6-7, further analysis were conducted for antisense effects, similar antisense effects were confirmed and in particular, when attempted with RNAi type, a short sequence as short as 15 bp pair and 20 bp pair were shown to be effective.

Example 10

Effects in Other Varieties

In this Example, using the antisense construct of the present invention, it was validated to confirm whether or not the other variants may have similar effects. *Japonica* (general rice, glutinous rice, sake rice, morphological variants such as having dwarfism change), or *indica* variants such as Te Tep, Basmati, IR8, Hunanzao and Kasalath were selected. All the operations after transformation were conducted according to Examples 2-4. FIG. 7 is the results of electrophoresis pattern of seed proteins and those conducted by Western blotting using anti 13 kDa prolamin polyclonal antibody obtained by immunizing a rabbit with prolamin of Nipponbare for some of these variants. Apparently, each variant has extremely similar electrophoresis pattern and crossreacted with the antibody with high response, and thus it explicitly demonstrates that prolamin genes are highly conserved amongst the variants.

When antisense prolamin (LP) gene of the present invention was introduced therein, it was observed that all variants had a significant reduction of prolamin expression. Some of the results of SDS-PAGE are shown in FIG. 10. Rice in which LP gene has been introduced, has significantly less protein band corresponding to prolamin than the normal variants, therefore it reflects the reduction in prolamin protein content. As such, regardless of crossing or gene introduction, rice including the construct of the present invention has decreased prolamin, and thus it can be concluded to have the amount of protein reduced, and thus the utility of the present invention has been proved across the entire rice species. Bands of mochi or glutinous rice variants have been observed to be less concentration than the others, because starch contained therein was significantly expanded during the extraction operation, and thus recovery efficiency of proteins has been significantly reduced, and therefore this is not due to the less amount of proteins contained therein.

Example 11

Expression Example of a Foreign Gene with Low Prolamin Rice

Both seeds of the series of LP13K obtained in the above Examples and the original variant may be compared by introducing useful protein expression cassette. However, when one wishes to attempt verification on a variety of variants, it will be necessary to preliminary produce LP13K types corresponding to the variants, and thus this is not efficient. As in the present example, property of plasmid of FIG. 1 preliminary constructed, should be optimally utilized and thus efficient attempts can be achieved.

In the present Example, as exemplified in FIG. 8, pUC198AM or pUC198AA was used to construct an expression cassette for useful protein and it was inserted into AscI site of a binary vector. This allows the introduction of the expression cassette for useful protein linked with prolamin antisense cassette on the same plasmid, simultaneously and certainly introduced into rice. In particular, when an expression cassette for useful protein with pUC198AM was inserted, MluI from the terminator of the insertion cassette, and the AscI site were ligated to remove such a site, while the AscI derived from the promoter survives and thus an additional expression cassette may be inserted to the AscI site.

Hereinafter, a series of structural genes for expressing useful proteins are produced to verify the utility of prolamin reduced seeds (low protein seed) as a bioreactor.

As described in FIG. 11, genes 1-4 were constructed and introduced into Nipponbare, and fluorescence of GFP was observed. As carried out in Examples 2-4 and 7, SDS-PAGE and Western blotting analysis were conducted. Expression intensity was determined by comparing intensity using fluorescence observation system with Leica microscope. When comparing genes 1 and 2, gene 2 including LP cassette was observed to have evidently higher fluorescence than the other. As for Gene 3, when LP cassette portion of Gene 2 was replaced with GUS, the luminescence intensity thereof was similar level as that of Gene 1, and thus it was determined that the increased intensity of luminescence was derived from the LP cassette. In Gene 4 in which GFP portion of Gene 2 was replaced with GUS, no fluorescence was observed and thus it was determined that the luminescence was originally derived from the GFP. In the Western blotting analysis using anti-GFP antibody, it was estimated that GFP expression amount was about two times or more for Gene 2 than for Gene 1. As such, it was clearly demonstrated that in prolamin reduced seeds, expression of foreign proteins have been clearly increased. However, when any gene has been introduced, GFP proteins may be difficult to observe on SDS-PAGE, and thus the potential as a bioreactor has not been sufficiently attained.

Therefore, as shown in FIG. 12, Genes 5 and 6 with construct having a signal sequence of 13 kDa prolamin was inserted before the GFP, have been constructed and analyzed in the same manner. As a result, the luminescence intensity of GFP in these seeds are increased in the level where comparison of expression amount is difficult. As shown on SDS-PAGE diagram in FIG. 13A, rice with Gene 5 introduced (lane 2), achieved detectable level in which clear band, which was not present in the original variant, was observed, which is expected to be the GFP. In comparison to the case of Gene 5, in the case of Gene 6 in which LP cassette has been introduced (lane 3), the expression amount has been further increased to 1.2 fold of the case of Gene 5, and is estimated to accumulate 50 μg or more per seed. As such, by combining signal sequences, utility as a bioreactor of prolamin reduced seeds have been clearly and more significantly demonstrated.

The unidentified band, which was observed in FIG. 13 and was not present in the original variant, was verified to be GFP by Western blot analysis with anti-GFP antibody. Further, whether or not a protein has the correct primary structure, has been confirmed by amino acid sequence analysis. In FIG. 14A, the structure of the GFP gene introduced is shown, in which 10 kDa prolamin signal sequence is followed by linkage sequences and GFP gene per se, and the deduced amino acid sequence is also shown beneath thereof. In FIG. 14B, in comparison with the original variant (lane 1), recombinant rice with Gene 6 introduced therein (lane 2) has decreased the band concentration (*) corresponding to prolamin, and a clear band surrounded by a box has appeared. This band was transferred to a PVDF membrane, and the N-terminal sequence has been sequence to provide the sequence of Ser-Arg-Ala-Met-Val-Ser-Lys-Gly (SEQ ID NO: 118). Amongst the deduced amino acid sequence, the sequence after the linked portion was identical at 100% identity. As such, 10 kDa prolamin signal sequence was expectedly spliced out and the GFP protein has been correctly expressed. Therefore, it was demonstrated that the construct of the transgene in the present invention has matched in an extremely correct manner.

In order to increase utility, Gene 6 was introduced into LGC-1 to prove its effect. As a result, as shown in FIG. 13B, it was observed that the case where introduction was made into LGC-1 (lane 5), has increased the expression amount of GFP than the case where the introduction was made into Nipponbare (lane 3). Further, the lineage with more reduction of prolamin observed (lane 6) has further increased the expression amount of GFP.

In the case of lane 3, it was estimated that GFP was accumulated to at least 150 μg per grain, resulting in that the foreign protein to be the most abundant protein present in the seed albumen. In comparison of SDS-PAGE pattern of Nipponbare in lane 1, it should be understood that the pattern attained by the present invention is completely different from the original as if it were a completely different plant, and thus the present invention is significant beyond the expectation of the art. By the use of the present invention, it is to be understood that the research and development of creation of recombinant rice variants having completely different properties that the known rice in an accelerated manner.

Example 12

Expression Examples of Useful Foreign Gene Using Low-Prolamin Rice—Cases of Cystatin In this Example, cystatin was used to attempt expression of a foreign gene.

Examples shown in FIG. 15 demonstrated that the system in which GFP was used for investigation, was applied for actually useful protein production. Cystatin used herein has a function of specifically inhibiting cysteine protease. Cysteine protease plays an important role as a digestive enzyme of Coleoptera or Hemiptera insects and an essential agent for propagating a variety of viruses. Accordingly, if enhancement of cystatin in crops suppresses functions of cysteine proteases, insect resistance or viral resistance can be rendered.

Cystatin is originally contained in an edible portion of crops, and thus the human beings have long history in eating the same. Therefore, it is believed that the risk in utilizing the same is extremely low. Accordingly, it is fully possible to use the same by expressing the desired gene at an edible portion which is difficult to be treated with an agent. For example, when expressed in rice, it is useful for preventing *Sitophilus zeamais* which is a harmful insect, and Hemiptera insects which gives damages in rice chaff in ripening rice, and at the same time, functional rice which prevents a virus from infecting the digestive tract.

As such, cystatin gene is highly expected for its availability for utility, no hope has been expected to have a practical application to date. Its major cause is that accumulation thereof in high level in the crop has not been achieved. It has been reported that crops originally contain very low level of cystatin content, and there are some regulatory machineries for suppressing its expression, and there is possibility where protein stability is low (i.e., degradable). There has been a questionable report where expression in rice attained resistance against *Sitophilus zeamais*, its expression level is very low and attained effects where little delay in growth has been achieved, and not reached its practical level.

Thus, the present invention has been applied to maize cystatin to attempt the production and evaluation of cystatin accumulated rice. GFP portions of Genes 5 and 6 are replaced tih maize cystatin to produce Genes 7 and 8, which were introduced into Nipponbare. The present Example were conduced according to Examples 2-4, except for the part of extraction of protein from seeds. The altered portion is that the seed protein extraction solution for evaluation used was prepared by extracting with phosphate buffer, pH 6.0 containing 200 mM sodium chloride after milling the seeds, and treating the extracted supernatant in boiling water for one minute.

The results are shown in FIG. 15. With respect to the level of expression amount, the same pattern was observed for that of GFP, and the lineage with prolamin promoter+signal sequence+cystatin gene was linked and cocurrently introduced with prolamin antisense cassette (Gene 8) accumulated in the most significant manner. In particular, the enhancement effects when prolamin antisense cassette was introduced, was presented much more than that of the GFP case. When cys- Example 13

Application of the Gene Construct of the Present Application to Other Storage Protein Expression suppression cassettes of RNAi type used in the present invention, were constructed, and RNAi genes against glutelin and globulin were introduced therein according to Examples 7 and 9, and analysis and evaluation thereof were carried out according to Examples 2-4. As a result, expression of glutelin and globulin were both suppressed. In combination of this result and the vector system shown in FIG. 1, a vector with all the expression suppression cassettes of glutelin, globulin and prolamin, respectively, was linked with a foreign gene expression cassette, it was demonstrated that in a variety of variants, it was possible to efficiently express a foreign protein while suppressing all the storage proteins. Similarly, three gene fragments of glutelin, globulin and prolamin to produce an artificial fragment, which was preliminarily kinked to all the expression suppression cassette of RNAi type (exemplified in FIG. 17), all the storage protein could be suppressed, while a foreign protein was efficiently expressed.

Further, it was reported that promoters expressing useful proteins in rice seed include glutelin B1 promoter or globulin promoter, which are often used and the signal sequences thereof are effective in increasing expression thereof. As for useful protein cassette portion of GENES 5 and 6, promoter (SEQ ID NOs: 47, 48, 60, 62, 106 and 107) and signal sequences (SEQ ID NOs: 108-117) were investigated with a variety of combinations, and it was found that GENE type 6 was expressed more intensely than type 5. In this case, it was believed that the space in the cell caused by reduction of prolamin was successfully utilized.

As described above, gene construct of the present invention and the structure thereof are shown to demonstrate a general use for making seeds a bioreactor, and thus it can be said that significant effects have been attained which had not been attained to date.

In the regulatory manner in storage protein composition in rice seeds which have been revealed in the course of the present invention (FIG. 16), most excess force of seed protein production are eventually directed to the production of prolamin by homeostasis. Further, it is also well known that prolamin has the property of well expressing in the later stage of seed ripening. Considering the above, it should be understood that the construct of the present invention in which prolamin promoter is used to express a useful protein, is adapted to a greater extent for application of expression of excess production force to a useful protein in an efficient manner. Further, in the present Example, N terminal sequence of the protein actually expressed, has been confirmed as shown in FIG. 14. There has been no such reports to date, in which confirmed to such an extent. In summary, the construct of GENE 6 is presently one of the most superior useful protein expression cassettes for rice seeds amongst others.

Those skilled in the art would have readily understood that the technical concept of the present invention has sufficient universality and extrapolation in other crop seeds in particular in monocotyledonous crop seeds. That is, while suppressing a seed storage protein A by recombination or mutation, introduction of gene promoter of the storage protein A or a construct of promoter+signal sequence+useful protein, its substitute, allows the creation of a dramatic novel crop with a large amount of accumulation of useful protein. As shown in the following Table and FIG. 17, the present invention is a significant consequence of demonstration of specific transgene construct as a bioreactor technology of crop seeds which were vaguely "dreamed" of to date.

TABLE 7

Construction examples of optimum transgenes expected when seeds are considered as a bioreactor.

Schematic structure: [promoter A | C | useful protein E] terminator F ; [promoter B | D] terminator G
C: signal sequence; D: storage protein targeted for suppression

| | promoter A | signal sequence (C) | useful protein E | promoter B | storage protein targeted for suppression (D) |
|---|---|---|---|---|---|
| General examples | storage protein promoter, desirably a storage promoter derived from the same storage promoter as targeted in D | general signadl sequence, desirably a signal sequence of a storage protein | | a promoter of a gene expressed in seeds, desirably a storage protein promoter or a gene promoter expressed in high level in seed, more desirably a storage protein promoter different from A | a storage protein expressed in high level in seed |
| In rice | storage protein promoter, desirably a storage promoter derived from the same storage promoter as targeted in D, or a prolamin promoter, more desirably 13kDa prolamin promoter or 10kDa prolamin promoter | general signadl sequence, desirably a signal sequence of a storage protein, more desirably a prolamin signal sequence | | a promoter of a gene expressed in seeds, desirably a storage protein promoter or a gene promoter expressed in high level in seed, more desirably a prolamin promoter, still more desirably a prolamin promoter different from A | a storage protein expressed in high level in seed |

Examples off optimum combinations: A: 13kDa prolamin promoter; B: polyubuquitine promoter or the like; C: 10kDa prolamin signal sequence; D: glutelin, globulin, 13kDa prolamin are all suppressed; F and G: prolamin terminator

Example 14

Utilization of the Present Invention to Cookery or Processing Foods of Rice

An important operation process in rice processing food production, lies in the sufficient gelatinization by heat after sufficient immersion into water to sufficient imbibitions after rice polishing (or breaking down the same into rice powder). Generally, it is known that rice with large amount of proteins (in particular, prolamin) is poor in imbibitions and thus gelatinization of starch is insufficient, and after heating, imbibitions and viscosity of rice, bloating tendency and extensibility of mochi rice cake dough become poor, and the quality of the product will be derogated. Therefore, for the above mentioned points, low protein rice produced to date in the examples (Nipponbare and Koganemochi with prolamin antisense gene introduced therein) were compared with the original variants thereof, it was observed that the low prolamin rice has almost the same as or even superior to the original variants with respect to viscosity or absorbance property when cooked rice, steamed rice and dough thereof were prepared, even if the time of soaking in water is shortened. As a consequence, the present invention has been demonstrated to be useful when pouch-bagged rice food, or other food processing for catering industry in a large amount, or processed foods such as sembei rice biscuit, arare rice crackers, or dango rice sweet balls or the like.

Example 15

Utilization of the Present Invention in Sake Brewing

Another availability of rice includes brewing of sake. Therefore, LG-LP13K (in which prolamin antisense gene is introduced into LGC-1) was used amongst low-protein rice obtained in the above-mentioned Examples, which was used to conduct brewing test of sake. LGC-1 is not a rice for sake production, but variant for general food may be sufficiently possible to produce sake, and thus LGC-1 per se has been confirmed to be equal to the normal variant in terms of sake production.

In brewery of sake, proteins of raw material rice may be the source of variety of bad taste or odor and thus it is desired to reduce the amount of proteins as low as possible. Bran layer of grains of rice are rich in lipids, minerals and protein, and removal of this is called milling or polishing or rice. How milling is achieved is measured by the indicator of milling percentage by comparing before and after milling. White rice or husked rice which is cooked have about 90% of milling ratio. However, as shown in electron microscopic photograph in FIG. 6, surface layer cells of husked rice is rich in protein. When producing sake, further milling is required, and milling ratio of about 70% or less is generally used, and for the highest rank that can be presented for a competition, is a milling ratio of 30% or less.

When using seeds of the present invention, high ratio of milling ratio of raw material may also be of low-protein, and thus is useful as raw material for allowing simplification of such processes. The present invention also allows deleting washing rice, as protein content is low. Starch is generally good in swelling and gluing because protein content is low, and it is of use in this respect.

LG-LP13K in which rice polishing is simplified, and LGC-1 which was husked as usual, were compared to find no significant difference in taste. Therefore, the low-protein plant of the present invention has been demonstrated to be useful in the food industry.

As described above, although certain preferred embodiments have been described herein, it is not intended that such embodiments be construed as limitations on the scope of the invention except as set forth in the appended claims. Various other modifications will be apparent to and can be readily made by those skilled in the art without departing from the scope and spirit of this invention. It is to be understood that all patents, published patent applications and publications cited herein are incorporated by reference as if set forth fully herein.

EFFECTS OF INVENTION

Rice with the entire protein content in the seed reduced, and the seed thereof were obtained by means of prolamin expression suppression gene of the present invention. As a direct effect, there is a reduction of prolamin, which is low in nutrition, and as a consequence, relative amino acid nutrition value is enhanced, and thus the function of rice as protein may be enriched. Further, particularly in Japan, there are a number of useful cases where low-protein rice is requested, such as for general food, processed rice product, sake production, therapeutic foods for treating diseases which requires limited amino acid ingestion such as renal diseases. Furthermore, the present invention has high potential as a bioreactor efficiently expressing useful foreign protein. As such, the present invention achieved significant effects by giving impacts on a number of fields.

INDUSTRIAL APPLICABILITY

The present invention has applicability in being capable of providing rice enriched in functions as protein source, in which prolamin, having low nutrition values, is reduced and relative amino acid values are enhanced. Alternatively, for a number of cases where low protein rice is required, such as for general food, processed rice product, sake production, therapeutic foods for treating diseases which requires limited amino acid ingestion such as renal diseases. Furthermore, the present invention has high potential as a bioreactor efficiently expressing useful foreign protein. Therefore the present invention greatly contributes to the expansion of industrial application of rice through the creation of novel crops such as rice having novel property. As such, the present invention achieved significant effects by giving impacts on a number of fields.

The Sequence Listing is contained on separately submitted CD-ROM entitled 59150-8035.ST25.TXT (94 KB) created Apr. 12, 2006 which is incorporated in entirety by reference herewith.

What is claimed is:

1. An isolated nucleic acid molecule having antisense or RNA interference activity comprising a promoter that functions in a rice plant operably linked to:
   (i) a nucleic acid sequence having at least 15 contiguous nucleotides complementary to a gene encoding a rice prolamin polypeptide, or
   (ii) a nucleic acid sequence having at least 70% homology to (i),
   wherein, when introduced into a rice cell expressing the prolamin polypeptide, the nucleic acid is effective for reducing the amount of expression of the prolamin polypeptide relative to a rice plant into which the nucleic acid was not introduced.

2. The nucleic acid molecule according to claim 1 comprising said nucleic acid sequence having at least 15 contiguous nucleotides complementary to a gene encoding a prolamin polypeptide.

3. The nucleic acid molecule according to claim 1, wherein the prolamin is of *japonica* rice.

4. The nucleic acid molecule according to claim 1, wherein the nucleic acid sequence having at least 15 contiguous nucleotides complementary to a gene encoding a prolamin polypeptide is at least 50 nucleotides in length.

5. The nucleic acid molecule according to claim 1, wherein the nucleic acid sequence having at least 15 contiguous nucleotides complementary to a gene encoding a prolamin polypeptide comprises a full length sequence encoding the prolamin polypeptide.

6. The nucleic acid molecule according to claim 1, wherein the nucleic acid sequence having at least 15 contiguous nucleotides complementary to a gene encoding a prolamin polypeptide is complementary to the sequence encoding the signal peptide of said prolamin.

7. The nucleic acid molecule according to claim 1, wherein the at least 15 contiguous nucleotides complementary to a gene encoding a prolamin polypeptide is a polynucleotide of 50 nucleotides or less.

8. The nucleic acid molecule according to claim 1, wherein the at least 15 contiguous nucleotides complementary to a gene encoding a prolamin polypeptide is a polynucleotide of 30 nucleotides or less.

9. The nucleic acid molecule according to claim 1, wherein the prolamin is a 13 kDa prolamin.

10. The nucleic acid molecule according to claim 1, wherein said nucleic acid sequence of at least 15 contiguous nucleotides is complementary to:
   (a) a polynucleotide having a nucleic acid sequence set forth in a SEQ ID NO selected from the group consisting of SEQ ID NOs: 1, 3, 5, 7, 9, 11, 13, 15, 17, 19, 21, 23, 25, 27, 29, 31, 33, 35, 37, 39, 41, 43 and 45, or a fragment sequence thereof;
   (b) a polynucleotide encoding a polypeptide having an amino acid sequence set forth in a SEQ ID NO selected from the group consisting of SEQ ID NOs: 2, 4, 6, 8, 10, 12, 14, 16, 18, 20, 22, 24, 26, 28, 30, 32, 34, 36, 38, 40, 42, 44 and 46, or a fragment sequence thereof;
   (c) a polynucleotide encoding a polypeptide variant having at least one mutation selected from the group consisting of one or more amino acid substitution, addition and deletion in an amino acid sequence set forth in a SEQ ID NO selected from the group consisting of SEQ ID NOs: 2, 4, 6, 8, 10, 12, 14, 16, 18, 20, 22, 24, 26, 28, 30, 32, 34, 36, 38, 40, 42, 44 and 46, and having a biological activity;
   (d) a polynucleotide that is an allelic variant of a DNA consisting of a nucleic acid sequence set forth in a SEQ ID NO selected from the group consisting of SEQ ID NOs: 1, 3, 5, 7, 9, 11, 13, 15, 17, 19, 21, 23, 25, 27, 29, 31, 33, 35, 37, 39, 41, 43 and 45;

(e) a polynucleotide encoding a species homolog or an ortholog of a polypeptide consisting of an amino acid sequence set forth in a SEQ ID NO selected from the group consisting of SEQ ID NOs: 2, 4, 6, 8, 10, 12, 14, 16, 18, 20, 22, 24, 26, 28, 30, 32, 34, 36, 38, 40, 42, 44 and 46;

(f) a polynucleotide hybridizing to at least one polynucleotide of any of (a)-(e), and encoding a polypeptide having a biological activity; or (g) a polynucleotide consisting of a base sequence having at least 70% identity with at least one polynucleotide of (a)-(e) or a complementary sequence thereof, and encoding a polypeptide having a biological activity.

11. The nucleic acid molecule according to claim 1, wherein the nucleic acid molecule has RNA interference activity, and wherein said molecule further comprises a polynucleotide complementary to the nucleic acid sequence.

12. The nucleic acid molecule according to claim 9, further comprising a spacer sequence.

13. The nucleic acid molecule according to claim 12, wherein the spacer sequence comprises an intron sequence.

14. The nucleic acid molecule according to claim 12, wherein the spacer sequence is between the nucleic acid sequence and the polynucleotide.

15. A nucleic acid cassette comprising a nucleic acid sequence having antisense or RNA interference activity, comprising:
   (i) a nucleic acid sequence having at least 15 contiguous nucleotides complementary to a gene encoding a rice prolamin polypeptide, or
   (ii) a nucleic acid sequence having at least about 70% homology to (i),
   wherein, when introduced into a rice cell expressing the prolamin polypeptide, the nucleic acid cassette is effective for reducing the amount of expression of the prolamin polypeptide relative to a rice plant into which the nucleic acid cassette was not introduced.

16. The nucleic acid cassette according to claim 15, further comprising a promoter that functions in rice operably linked to a nucleic acid sequence encoding a foreign protein.

17. The nucleic acid cassette according to claim 15, wherein said cassette has RNA interference activity, and wherein said cassette further comprises a polynucleotide complementary to the nucleic acid sequence.

18. The nucleic acid cassette according to claim 17, further comprising a spacer sequence.

19. The nucleic acid cassette according to claim 18, wherein the spacer sequence comprises an intron sequence.

20. The nucleic acid cassette according to claim 18, wherein the spacer sequence is between the nucleic acid sequence and the polynucleotide.

21. The nucleic acid cassette according to claim 16 or claim 17, further comprising a polynucleotide encoding a signal sequence fused, in frame, to the nucleic acid sequence encoding a foreign protein.

22. The nucleic acid cassette according to claim 21, wherein the signal sequence is a signal sequence of a storage protein.

23. The nucleic acid sequence according to claim 21, wherein the signal sequence is a prolamin signal sequence.

24. The nucleic acid cassette according to claim 16, wherein the promoter sequence is operably linked to both the nucleic acid sequence encoding the foreign protein and the polynucleotide.

25. The nucleic acid cassette according to claim 16, wherein separate promoters are independently operably linked to the nucleic acid sequence encoding the foreign protein and the polynucleotide.

26. The nucleic acid cassette according to claim 25, wherein a first promoter sequence is operably linked to the nucleic acid sequence encoding the foreign protein, and a second promoter sequence is operably linked to the polynucleotide, and the first and second promoter sequences are not the same.

27. The nucleic acid cassette according to claim 26, wherein the second promoter sequence promotes expression in a high level in seeds.

28. The nucleic acid cassette according to claim 26, wherein the second promoter sequence is derived from a storage protein promoter.

29. The nucleic acid cassette according to claim 26 wherein the second promoter sequence is derived from a promoter selected from the group consisting of a polyubiquitin promoter, 26 kD globulin promoter, glutelin A promoter, glutelin B promoter, 16 kD prolamin promoter, 13 kD prolamin promoter and 10 kD prolamin promoter.

30. The nucleic acid cassette according to claim 26 wherein the first promoter sequence is derived from a storage protein promoter.

31. The nucleic acid cassette according to claim 26, wherein the first promoter sequence is a promoter sequence naturally associated with the polynucleotide.

32. The nucleic acid cassette according to claim 26 wherein the first promoter sequence is derived from a promoter selected from the group consisting of 26 kD globulin promoter, glutelin A promoter, glutelin B promoter, 16 kD prolamin promoter, 13 kD prolamin promoter and 10 kD prolamin promoter.

33. The nucleic acid cassette according to claim 26, wherein the first promoter sequence is a prolamin promoter.

34. The nucleic acid cassette according to claim 26, wherein the first promoter sequence is derived from a prolamin promoter, and the second promoter sequence is derived from a promoter other than the prolamin promoter.

35. The nucleic acid cassette according to claim 16, comprising a polynucleotide encoding a signal sequence in frame between the nucleic acid encoding the foreign protein and the promoter sequence.

36. The nucleic acid cassette according to claim 17 further comprising a terminator sequence.

37. The nucleic acid cassette according to claim 36, wherein the terminator sequence is a terminator sequence of 10 kD prolamin.

38. The nucleic acid cassette according to claim 17, further comprising a nucleic acid encoding a foreign protein located upstream of both the polynucleotide and the nucleic acid complementary to said polynucleotide.

39. The nucleic acid cassette according to claim 38 comprising a spacer sequence between the polynucleotide and the nucleic acid complementary to said polynucleotide.

40. The nucleic acid cassette according to claim 38 comprising an intron sequence between the polynucleotide and the nucleic acid complementary to said polynucleotide.

41. A method for producing a transgenic rice plant comprising the steps of:
   A) providing the nucleic acid cassette according to claim 15;
   B) transforming a rice plant with the nucleic acid cassette; and
   C) selecting a transformed rice plant having a reduced amount of protein in the seeds compared to an untransformed rice plant.

42. A vector comprising the nucleic acid molecule according to claim 1.

43. The vector according to claim 42, wherein the promoter is a storage protein promoter.

44. The vector according to claim 42 wherein the promoter is a prolamin promoter.

45. The vector according to claim 42, further comprising a terminator.

46. The vector according to claim 42, further comprising a sequence encoding a selectable marker.

47. The vector according to claim 42, further comprising a sequence encoding a foreign protein.

48. A rice plant cell comprising the nucleic acid molecule according to claim 1.

49. The plant cell according to claim 48, further comprising a nucleic acid molecule encoding a foreign protein.

50. The rice plant cell according to claim 48 wherein the plant cell is from the same rice variety from which the prolamin is derived.

51. The rice plant cell according to claim 48, wherein the cell is of a *japonica* rice and the prolamin is from a *japonica* rice.

52. The rice plant cell according to claim 48, wherein the cell is homozygous for the nucleic acid molecule.

53. A plant tissue comprising the plant cell according to claim 48.

54. A starch preparation produced from the rice plant cell according to claim 48, wherein said starch preparation comprises said nucleic acid molecule.

55. A composition comprising a plant tissue comprising the plant cell according to claim 49, wherein said plant cell comprises said foreign protein.

56. A method for reducing the amount of protein in a seed of a rice plant, comprising the steps of:
A) introducing the nucleic acid molecule of claim 1 into a rice plant cell;
B) redifferentiating the cell to produce a transgenic rice plant; and
C) obtaining a seed from the transgenic rice plant.

57. The method according to claim 56, wherein the step of introducing is performed by *Agrobacterium*-mediated transformation.

58. The method according to claim 56, further comprising the step of D) selecting a plant cell with the nucleic acid introduced therein.

59. The method according to claim 58, wherein the step of selecting is performed by determining resistance against an antibiotic.

60. A method for expressing a foreign protein in a rice plant seed, comprising the steps of:
providing the nucleic acid molecule according to claim 1;
providing a nucleic acid encoding the foreign protein;
introducing the nucleic acid molecule according to claim 1 and the nucleic acid encoding the foreign protein into a cell of the rice plant;
redifferentiating the cell to produce a transgenic rice plant; and
obtaining a seed from the transgenic rice plant.

61. The method according to claim 60, wherein the step of introducing is performed by *Agrobacterium*-mediated transformation.

62. The method according to claim 60, further comprising the step of selecting a plant cell with the nucleic acid molecule introduced.

63. The method according to claim 62, wherein the step of selecting is carried out by determining resistance of the plant cell against an antibiotic.

64. The method according to claim 60, further comprising the step of separating the foreign protein from the seed.

* * * * *